US006268369B1

(12) United States Patent
Nagarathnam et al.

(10) Patent No.: US 6,268,369 B1
(45) Date of Patent: *Jul. 31, 2001

(54) 5-(HETEROCYCLIC ALKYL)-6-ARYL-DIHYDROPYRIMIDINES

(75) Inventors: Dhanapalan Nagarathnam, Ramsey; George Chiu, Bridgewater, both of NJ (US); T. G. Murali Dhar, Newark, DE (US); Wai C. Wong, Newark, (US); Mohammad R. Marzabadi, Ridgewood, both of NJ (US); Charles Gluchowski, Danville, CA (US); Bharat Lagu, Maywood, (US); Shou Wu Miao, Edison, both of NJ (US)

(73) Assignee: Synaptic Pharmaceutical Corporation, Paramus, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/836,628

(22) PCT Filed: Nov. 16, 1995

(86) PCT No.: PCT/US95/15025

§ 371 Date: May 16, 1997

§ 102(e) Date: May 16, 1997

(87) PCT Pub. No.: WO96/14846

PCT Pub. Date: May 23, 1996

Related U.S. Application Data

(63) Continuation-in-part of application No. 08/340,611, filed on Nov. 16, 1994, now abandoned.

(51) Int. Cl.[7] .................. C07D 40/04; C07D 403/04; A61K 31/506; A61P 31/08

(52) U.S. Cl. .................. 514/256; 514/269; 514/274; 540/203; 540/461; 540/521; 544/61; 544/117; 544/278; 544/279; 544/280; 544/316; 544/330; 544/331; 544/332

(58) Field of Search .................. 514/256, 269, 514/274; 544/316, 330, 331, 332, 61, 117, 278, 279, 280; 540/203, 461, 521

(56) References Cited

U.S. PATENT DOCUMENTS

| 4,438,117 | 3/1984 | Cherkofsky | 424/251 |
|---|---|---|---|
| 4,684,653 | 8/1987 | Taylor et al. | 514/258 |
| 4,684,655 | * 8/1987 | Atwal | 514/274 |

(List continued on next page.)

FOREIGN PATENT DOCUMENTS

| 0162208 | 11/1985 | (EP) . |
| 0236902 | 9/1986 | (EP) . |
| 0204317 | 12/1986 | (EP) . |
| 0234830 | 9/1987 | (EP) . |

(List continued on next page.)

OTHER PUBLICATIONS

Atwal, K.S., et al., "Dihydropyrimidine Calcium Channel Blockers. 2. 3–Substituted–4aryl–1, 4–dihydro–6–methyl–5–pyrimidinecarboxylic Acid Esters as Potent Mimics of Dihydropyridines," *Journal of Medicinal Chemistry* (1990) vol. 33, pp. 2629–2635;.

Atwal, K.S., et al., Dihydropyrimidine Calcium Channel Blockers. 3. 3–Carbamoyl–4–aryl–1,2,3, 4–tetrahydro–6–methyl–5–pyrimidinecarboxylic Acid, 1991.

Esters As Orally Effective Antihypertensive Agents, *Journal of Medicinal Chemistry* (1991) vol. 34, pp. 806–811;.

Atwal, K.S., et al., "Dihydropyrimidine Calcium Channel Blockers: 2–Heterosubstituted 4–Aryl–1, 4–dihydro–6–methyl–5–pyrimidinecarboxylic Acid Esters as Potent Mimics of Dihydropyridines," *Journal of Medicinal Chemistry* (1990), vol. 33, pp. 1510–1515;.

Atwal, K.S., et al., Substituted 1, 4–Dihydropyrimidines. 3. Synthesis of Selectively Functionalized 2–Hetero–1, 4–Dihydropyrimidines, *Journal of Organic Chemistry* (1989), vol. 54, pp. 5898–5907;.

Atwal, K.S., et al., "Synthesis of Substituted 1,2,3, 4–Tetrahydro–6–methyl–2–Thioxo–5–pyrimidinecarboxylic Acid Esters," (1987), vol. 26, pp. 1189–1192.

Cho, H., et al., "Dihydropyrimidines: Novel Calcium antagonists With Potent and Long–Lasting Vasodilative and Antihypertensive Activity," *Journal of Medicinal Chemistry* (1989), vol. 32, pp. 2399–2406;.

(List continued on next page.)

Primary Examiner—Mark Berch
Assistant Examiner—Thomas C. McKenzie
(74) Attorney, Agent, or Firm—John P. White; Cooper & Dunham LLP

(57) ABSTRACT

This invention is directed to dihydropyrimidine compounds of the following formula:

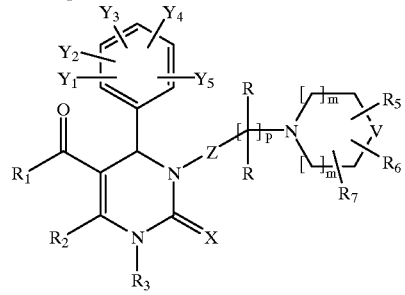

which are selective antagonists for human $\alpha_{1C}$ receptors. This invention is also related to uses of these compounds for lowering intraocular pressure, inhibiting cholesterol synthesis, relaxing lower urinary tract tissue, the treatment of benign prostatic hyperplasia, impotence, cardiac arrhythmia and for the treatment of any disease where antagonism of the $\alpha_{1C}$ receptor may be useful. The invention further provides a pharmaceutical composition comprising a therapeutically effective amount of the above-defined compounds and a pharmaceutically acceptable carrier.

21 Claims, No Drawings

U.S. PATENT DOCUMENTS

| | | | |
|---|---|---|---|
| 4,684,656 | * 8/1987 | Atwal | 514/274 |
| 4,703,120 | 10/1987 | Press | 544/278 |
| 4,728,652 | 3/1988 | Atwal | 514/274 |
| 4,845,216 | 7/1989 | Taylor et al. | 514/279 |
| 4,855,301 | * 8/1989 | Atwal et al. | 514/269 |
| 4,882,334 | 11/1989 | Shih et al. | 514/258 |
| 4,902,796 | 2/1990 | Taylor et al. | 514/279 |
| 4,946,846 | 8/1990 | Nomura et al. | 514/258 |
| 5,134,145 | 7/1992 | Brouwer et al. | 514/274 |
| 5,149,810 | 9/1992 | Perrior et al. | 544/305 |
| 5,202,330 | 4/1993 | Atwal et al. | 514/274 |
| 5,250,531 | 10/1993 | Cooper | 514/256 |
| 5,292,740 | 3/1994 | Burri et al. | 514/256 |
| 5,500,424 | 3/1996 | Nagamine et al. | 514/235.5 |
| 5,521,189 | 5/1996 | Boykin et al. | 514/256 |
| 5,541,186 | 7/1996 | Breu et al. | 514/256 |
| 5,594,141 | 1/1997 | Yuan et al. | 544/242 |
| 5,942,517 | 8/1999 | Nagarathnam et al. | 514/274 |

FOREIGN PATENT DOCUMENTS

| | | |
|---|---|---|
| 0237347 | 9/1987 | (EP) . |
| 0280227 | 8/1988 | (EP) . |
| 0400665 | 12/1990 | (EP) . |
| 0459666 | 12/1991 | (EP) . |
| 0622366 | 11/1994 | (EP) . |
| 0622369 | 11/1994 | (EP) . |
| 0627427 | 12/1994 | (EP) . |
| 2610625 | 8/1988 | (FR) . |
| 56-59778 | 5/1981 | (JP) . |
| 61-282367 | 12/1986 | (JP) . |
| 62-87574 | 4/1987 | (JP) . |
| 62-265271 | 11/1987 | (JP) . |
| 9200741 | 1/1992 | (WO) . |
| WO 92/14453 | 9/1992 | (WO) . |
| 9410989 | 5/1994 | (WO) . |
| 9422829 | 10/1994 | (WO) . |
| 9742956 | 11/1997 | (WO) . |
| 9851311 | 11/1998 | (WO) . |
| 9907695 | 2/1999 | (WO) . |
| 9948530 | 9/1999 | (WO) . |

OTHER PUBLICATIONS

D'Eletto, R.D., and Javitt, N.B., "Effect of Doxazosin on Cholesterol Synthesis in Cell Culture," *Journal of Cardiovascular Pharmacology* (1989), vol. 13.

McGrath, J.C., et al., "Alpha–Adrenoceptors: A Critical Review," *Medicinal Research Reviews* (1989), vol. 9, No. 4, pp. 407–533;.

Rovnyak, G.C., et al., Dihydropyrimidine Calcium Channel Blockers. 4. Basic 3–Substituted–4–aryl–1, 4–dihydropyrimidine–5–carboxylic Acid Esters. Potent 1992.

Antihypertensive Agents, *Journal of Medicinal Chemistry* (1992), vol. 35, pp. 3254–3263;.

Spiers, J.P., et al., "UK–52,046 (a novel ,–Adrenoceptor Antagonist) and the Role of –Adrenoceptor Stimulation and Blockade on Atrioventricular Conduction," *Journal of Cardiovascular Pharmacology* (1990), vol. 16, pp. 824–830;.

Science (1993), vol. 34, Abst. No. 1133–49, p. 928.

Barrio, et al., "A Direct Method For Preparation of 2–Hydroxyethoxymethyl Derivatives of Guanine, Adenine, and Cytosine," *Journal of Medicinal Chemistry* (1980) 23(5) : 572–574 (Exhibit 18);.

Brown, et al., "Inhibitors of Bacillus subtilis DNA Polymerase III. 6–(Arylalkylamino) uracils and 6–Anilinouracils," *Journal of Medicinal Chemistry* (1977) 20(9): 1186–1189 (Exhibit 19);.

Forray, et. et al., "The $\alpha_1$–Adrenergic Receptor That Mediates Smooth Muscle Contraction in Human Prostate Has the Pharmacological Properties of the Cloned Human $\alpha_{1c}$ Subtype," *Molecular Pharmacology* (1994) 45: 703–708 (Exhibit 20);.

Khanina, E.L. et al., Alkylation of derivatives of 2–oxo–4–phenyl–6–methyl–1,2,3, 4–tetrahydropyrimidine–5–carboxlic acid. Chemical Abstracts 89: 43319 (1978) (Exhibit 21); and.

Mamaev, V.P. and Dubovenko, Z.D., Pyrimidines. XXI. 5–Substituted 2–hydroxy–4, 6–diphenylpyrimidines. Chemical Abstracts 73: 77187 (1970) (Exhibit 22).

Boer, R., et al., "(+) –Niguldipine binds with very high affinity to $Ca^{2+}$ channels and to a subtype of $\alpha_1$–adrenoceptors," *European Journal of Pharmacology* –Molecular Pharmacology Section (1989) 172: 131–145 (Exhibit 6).

Wetzel, J.M., et al., "Discovery of $\alpha_{1a}$–Adrenergic Receptor Antagonists Based on the L–Type $Ca^{2+}$ Channel Antagonist Niguldipine" *Journal of Medicinal Chemistry* (1995) 38(10): 1579–1581 (Exhibit 7).

Mamaev, V.P. and Dubovenko, Z. D. Khim. Geterotsikl. Soedin. (4), 541–5, (Russian) 1970. Cited in CA 73:77187. Structures attached.*

Khanina, E. L., et al Latv. PSR Zinat. Akad. Vestis, Kim. Ser. (2), 197–200 (Russian) 1978. Cited in CA 89:43319. Structures attached.*

* cited by examiner-

5-(HETEROCYCLIC ALKYL)-6-ARYL-DIHYDROPYRIMIDINES

This application is the National Stage Application of PCT International Application No. PCT/US95/15025, filed Nov. 16, 1994, which is a continuation-in-part of U.S. Ser. No. 08/340,611, filed Nov. 16, 1994, now abandoned, the contents of which are incorporated by reference. Disclosures of these publications in their entireties are hereby incorporated by reference into this application to more fully describe the state of the art to which this invention pertains.

BACKGROUND OF THE INVENTION

The designation "$\alpha_{1A}$" is the appellation recently approved by the IUPHAR Nomenclature Committee for the previously designated "$\alpha_{1C}$" cloned subtype as outlined in the 1995 Receptor and Ion Channel Nomenclature Supplement (Watson and Girdlestone, 1995). However, the designation $\alpha_{1C}$ is used throughout this application and the supporting tables and figures to refer to the receptor subtype recently renamed "$\alpha_{1A}$". Since in both the old and new nomenclature there has only been one unique receptor subtype which has been designated $\alpha_{1C}$ (i.e., there is no $\alpha_{1C}$ under the current nomenclature), "$\alpha_{1C}$" is an unambiguous description of this unique receptor subtype.

Benign Prostatic Hyperplasia (BPH), also called Benign Prostatic Hypertrophy, is a progressive condition which is characterized by a nodular enlargement of prostatic tissue resulting in obstruction of the urethra. This results in increased frequency of urination, nocturia, a poor urine stream and hesitancy or delay in starting the urine flow. Chronic consequences of BPH can include hypertrophy of bladder smooth muscle, a decompensated bladder and an increased incidence of urinary tract infection. The specific biochemical, histological and pharmacological properties of the prostate adenoma leading to the bladder outlet obstruction are not yet known. However, the development of BPH is considered to be an inescapable phenomenon for the aging male population. BPH is observed in approximately 70% of males over the age of 70. Currently, in the United States, the method of choice for treating BPH is surgery (Lepor, H., Urol. Clinics North Amer., 17, 651 (1990)). Over 400,000 prostatectomies are performed annually (data from 1986). A medicinal alternative to surgery is clearly very desirable. The limitations of surgery for treating BPH include the morbidity rate of an operative procedure in elderly men, persistence or recurrence of obstructive and irritative symptoms, as well as the significant cost of surgery.

α-Adrenergic receptors (McGrath, et. al. Med. Res. Rev., 9, 407–533, 1989) are specific neuroreceptor proteins located in the peripheral and central nervous systems on tissues and organs throughout the body. These receptors are important switches for controlling many physiological functions and, thus, represent important targets for drug development. In fact, many α-adrenergic drugs have been developed over the past 40 years. Examples include clonidine, phenoxybenzamine and prazosin (treatment of hypertension), naphazoline (nasal decongestant), and apraclonidine (treating glaucoma). α-Adrenergic drugs can be broken down into two distinct classes: agonists (clonidine and naphazoline are agonists), which mimic the receptor activation properties of the endogenous neurotransmitter norepinephrine, and antagonists (phenoxybenzamine and prazosin are antagonists), which act to block the effects of norepinephrine. Many of these drugs are effective but also produce unwanted side effects (for example, clonidine produces dry mouth and sedation in addition to its antihypertensive effects).

During the past 15 years a more precise understanding of α-adrenergic receptors and their drugs has evolved through increased scientific scrutiny. Prior to 1977, only one α-adrenergic receptor was known to exist. Between 1977 and 1988, it was accepted by the scientific community that at least two α-adrenergic receptors—$\alpha_1$ and $\alpha_2$—existed in the central and peripheral nervous systems. Since 1988, new techniques in molecular biology have led to the identification of at least six α-adrenergic receptors which exist throughout the central and peripheral nervous systems: $\alpha_{1A}$, $\alpha_{1B}$, $\alpha_{1C}$, $\alpha^{2A}$, $\alpha_{2B}$ and $\alpha_{2C}$ (Bylund, D. B., FASEB J., 6, 832 (1992)). In many cases, it is not known precisely which physiological responses in the body are controlled by each of these receptors. In addition, current α-adrenergic drugs are not selective for any particular α-adrenergic receptor. Many of these drugs produce untoward side effects which may be attributed to their poor α-adrenergic receptor selectivity.

Since the mid 1970's, nonselective α-antagonists have been prescribed to treat BPH. In 1976, M. Caine, et al. (Brit. J. Urol., 48, 255 (1976)), reported that the nonselective α-antagonist phenoxybenzamine was useful in relieving the symptoms of BPH. This drug may produce its effects by interacting with α-receptors located on the prostate. However, this drug also produces significant side effects such as dizziness and asthenia which severely limit its use in treating patients on a chronic basis. More recently, the α-adrenergic antagonists prazosin and terazosin have also been found to be useful for treating BPH. However, these drugs also produce untoward side effects. It has recently been discovered that the $\alpha_{1C}$ receptor is responsible for mediating the contraction of human prostate smooth muscle (Gluchowski, C. et. al., WO 94/10989, 1994; Forray, C. et. al., Mol. Pharmacol. 45, 703, 1994). This discovery indicates that the $\alpha_{1C}$ antagonists may be effective agents for the treatment of BPH with decreased side effects. Further studies have indicated that the aic receptor may also be present in other lower urinary tract tissues, such as urethral smooth muscle (Ford et al. Br. J. Pharmacol., 114, 24P, (1995)).

This invention is directed to dihydropyrimidine compounds which are selective antagonists for cloned human $\alpha_{1C}$ receptors. This invention is also related to uses of these compounds for lowering intraocular pressure (Zhan, et. al. Ophthalmol. Vis. Sci., 34 Abst. #1133, 928, 1993), inhibiting cholesterol synthesis (D'Eletto and Javitt, J. Cardiovascular Pharmacol., 13 (Suppl. 2) S1–S4, 1989), benign prostatic hyperplasia, impotency (Milne and Wyllie, EP 0 459 666 A2, 1991), sympathetically mediated pain (Campbell, WO 92/14453, 1992), cardiac arrhythmia (Spiers, et. al., J. Cardiovascular Pharmacol., 16, 824–830, 1990) and for the treatment of any disease where antagonism of the $\alpha_{1C}$ receptor may be useful.

SUMMARY OF THE INVENTION

This invention is directed to dihydropyrimidine compounds which are selective antagonists for human $\alpha_{1C}$ receptors. This invention is also related to uses of these compounds for lowering intraocular pressure, inhibiting cholesterol synthesis, relaxing lower urinary tract tissue, the treatment of benign prostatic hyperplasia, impotency, cardiac arrhythmia and for the treatment of any disease where antagonism of the $\alpha_{1C}$ receptor may be useful. The invention further provides a pharmaceutical composition comprising a therapeutically effective amount of the above-defined compounds and a pharmaceutically acceptable carrier.

DETAILED DESCRIPTION OF THE INVENTION

The present invention is directed to compounds having the structures:

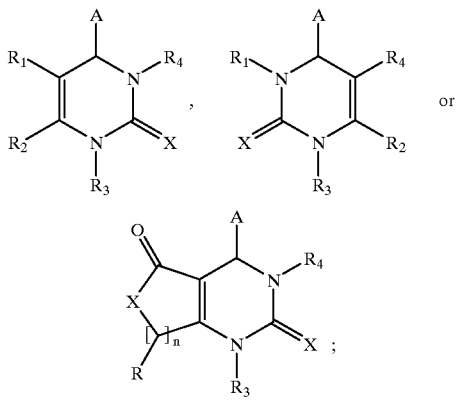

where A is

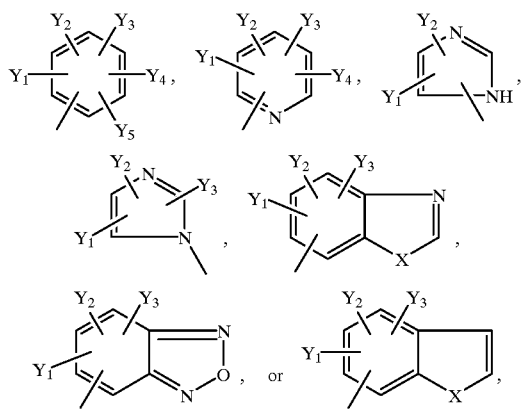

where each of $Y_1$, $Y_2$, $Y_3$, $Y_4$ and $Y_5$ is independently —H; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —F, —Cl, —Br, or —I; —$NO_2$; —$N_3$; —CN; —$OR_3$, —$OCOR_3$, —$COR_3$, —$CONHR_3$, —$CON(R_3)_2$, or —$COOR_3$; or any two of $Y_1$, $Y_2$, $Y_3$, $Y_4$ and $Y_5$ present on adjacent carbon atoms can constitute a methylenedioxy group;

where X is S; O; or $NR_3$;

where $R_1$ is —H; —$NO_2$; —CN; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —$N(R_3)_2$; —$OR_3$; —$(CH_2)_pOR_3$; —$COR_3$; —$CO_2R_3$; or —$CON(R_3)_2$;

where $R_2$ is —H; straight chained or branched $C_1$–$C_7$ alkyl, hydroxyalkyl, alkoxyalkyl, aminoalkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; $C_3$–$C_{10}$ cycloalkyl-$C_1$–$C_{10}$-alkyl, $C_3$–$C_{10}$ cycloalkyl-$C_1$–$C_{10}$-monofluoroalkyl or $C_3$–$C_{10}$ cycloalkyl-$C_1$–$C_{10}$-polyfluoroalkyl; —CN; —$CH_2XR_3$, —$CH_2X(CH_2)_pNHR_3$, —$(CH_2)NHR_3$, —$CH_2X(CH_2)_pN(R_3)_2$, —$CH_2X(CH_2)_pN_3$, or —$CH_2X(CH_2)_pNHCXR_7$; or —$OR_3$;

where each p is independently an integer from 1 to 7;

where each n is independently an integer from 0 to 5;

where each $R_3$ is independently —H; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl;

where $R_4$ is

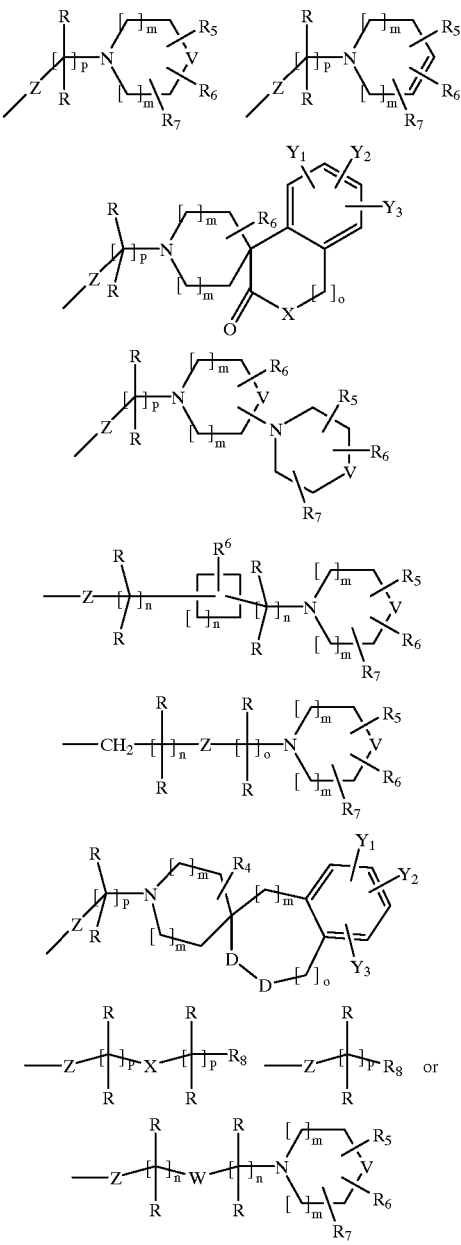

where Z is $C_2$–$C_7$ alkenyl or alkynyl; $CH_2$; O; CO; $C_2$; $CONR_3$; S; SO; $SO_2$; or $NR_3$;

where each D is independently $CH_2$; O; S; $NR_3$; CO; or CS;

where W is C=O; C—$NOR_3$; substituted or unsubstituted phenyl, pyridyl, thiophenyl, furanyl, pyrazinyl, pyrroyl, naphthyl, indolyl, imidazolyl, benzfurazanyl, benzfuranyl or benzimidazoyl, where the phenyl, pyridyl, thiophenyl, furanyl, pyrazinyl, pyrrolyl, naphthyl, indolyl, imidazolyl, benzfurazanyl benzfuranyl or benzimidazolyl is substituted with —H, —F, —Cl, —Br, —I, —NO$_2$, —CN, straight chained or branched C$_1$–C$_7$ alkyl, straight chained or branched C$_1$–C$_7$ monofluoroalkyl, straight chained or branched C$_1$–C$_7$ polyfluoroalkyl, straight chained or branched C$_2$–C$_7$ alkenyl, straight chained or branched C$_2$–C$_7$ alkynyl, C$_3$–C$_7$ cycloalkyl, C$_3$–C$_7$ monofluorocycloalkyl, C$_3$–C$_7$ polyfluorocycloalkyl, C$_3$–C$_7$ cycloalkenyl, —N(R,)$_2$, —OR$_3$, —COR$_3$, —CO$_2$R$_3$, or —CON(R$_3$)$_2$;

where each V is independently O; S; CR$_5$R$_7$; C(R$_7$)$_2$; or NR$_7$;

where each m is independently an integer from 0 to 3;

where o is an integer from 1 to 3;

where each R is independently —H; —F; straight chained or branched C$_1$–C$_7$ alkyl, monofluoroalkyl or polyfluoroalkyl; straight chained or branched C$_2$–C$_7$ alkenyl or alkynyl; —N(R$_3$)$_2$; —NO$_2$; CN; —CO$_2$R$_3$; or —OR$_3$;

where R$_5$ is —H; straight chained or branched C$_1$–C$_7$ alkyl, monofluoroalkyl or polyfluoroalkyl; straight chained or branched C$_2$–C$_7$ alkenyl or alkynyl; C$_3$–C$_7$ cycloalkyl, monofluorocycloalkyl, polyfluorocycloalkyl or cycloalkenyl; phenyl, thiophenyl, pyridyl, pyrrolyl, furanyl, imidazolyl or indolyl; —COOR$_3$, —COR$_3$, —CONHR$_3$, —CN, or —OR$_3$;

where each R, is independently —H; straight chained or branched C$_1$–C$_7$ alkyl, hydroxyalkyl, aminoalkyl, alkoxyalkyl, monofluoroalkyl or polyfluoroalkyl; straight chained or branched C$_2$–C$_7$ alkenyl or alkynyl; C$_3$–C$_7$ cycloalkyl, monofluorocycloalkyl, polyfluorocycloalkyl or cycloalkenyl; or —OR$_3$;

where each R$_7$ is independently —H; substituted or unsubstituted benzyl, benzoyl, phenyl, pyridyl, thiophenyl, furanyl, pyrazinyl, pyrrolyl, naphthyl, indolyl, imidazolyl, benzfurazanyl, benzfuranyl, benzimidazolyl or 2-keto-1-benzimidazolinyl, where the benzyl, benzoyl, phenyl, pyridyl, thiophenyl, furanyl, pyrazinyl, pyrrolyl, naphthyl, indolyl, imidazolyl, benzfurazanyl, benzfuranyl, benzimidazolyl or 2-keto-1-benzimidazolinyl is substituted with —H, —F, —Cl, —Br, —I, —NO$_2$, —CN, straight chained or branched C$_1$–C$_7$ alkyl, straight chained or branched C$_1$–C$_7$ monofluoroalkyl, straight chained or branched C$_1$–C$_7$ polyfluoroalkyl, straight chained or branched C$_2$–C$_7$ alkenyl, straight chained or branched C$_2$–C$_7$ alkynyl, C$_3$–C$_7$ cycloalkyl, C$_3$–C$_7$ monofluorocycloalkyl, C$_3$–C$_7$ polyfluorocycloalkyl, C$_3$–C$_7$ cycloalkenyl, —N(R$_3$)$_2$, —OR$_3$, —COR$_3$, —CO$_2$R$_3$, or —CON(R$_3$)$_2$; substituted or unsubstituted straight chained or branched C$_3$–C$_7$ alkyl, monofluoroalkyl or polyfluoroalkyl; substituted or unsubstituted straight chained or branched C$_2$–C$_7$ alkenyl or alkynyl; C$_3$–C$_7$ cycloalkyl or cycloalkenyl, where the alkyl, monofluoroalkyl, polyfluoroalkyl, alkenyl, alkynyl, cycloalkyl or cycloalkenyl is substituted with —H, phenyl, pyridyl, thiophenyl, furanyl, pyrazinyl, pyrrolyl, naphthyl, indolyl, imidazolyl, benzfurazanyl, benzfuranyl, benzimidazolyl; and where R$_8$ is —H; substituted or unsubstituted benzyl, benzoyl, phenyl, pyridyl, thiophenyl, furanyl, pyrazinyl, pyrryl, naphthyl, indolyl, imidazolyl, benzfurazanyl, benzfuranyl, benzimidazolyl or 2-keto-1-benzimidazolinyl, where the benzyl, benzoyl, phenyl, pyridyl, thiophenyl, furanyl, pyrazinyl, pyrryl, naphthyl, indolyl, imidazolyl, benzfurazanyl, benzfuranyl, benzimidazolyl or 2-keto-1-benzimidazolinyl is substituted with —H, —F, —Cl, —Br, —I, —NO$_2$,—CN, straight chained or branched C$_1$–C$_7$ alkyl, straight chained or branched C$_1$–C$_7$ monofluoroalkyl, straight chained or branched C$_1$–C$_7$ polyfluoroalkyl, straight chained or branched C$_2$–C$_7$ alkenyl, straight chained or branched C$_2$–C$_7$ alkynyl, C$_3$–C$_7$ cycloalkyl, C$_3$–C$_7$ monofluorocycloalkyl, C$_3$–C$_7$ polyfluorocycloalkyl, C$_3$–C$_7$ cycloalkenyl, —N(R$_3$)$_2$, —OR$_3$, —COR$_3$, —CO$_2$R$_3$, or —CON(R$_3$)$_2$; substituted or unsubstituted straight chained or branched C$_1$–C$_7$ alkyl, monofluoroalkyl or polyfluoroalkyl; substituted or unsubstituted straight chained or branched C$_2$–C$_7$ alkenyl or alkynyl; C$_3$–C$_7$ cycloalkyl or cycloalkenyl, where the alkyl, monofluoroalkyl, polyfluoroalkyl, alkenyl, alkynyl, cycloalkyl or cycloalkenyl is substituted with —H, phenyl, pyridyl, thiophenyl, furanyl, pyrazinyl, pyrrolyl, naphthyl, indolyl, imidazolyl, benzfurazanyl, benzfuranyl, benzimidazolyl, —N(R$_3$)$_2$, —NO$_2$, —CN, —CO$_2$R$_3$, —OR$_3$;

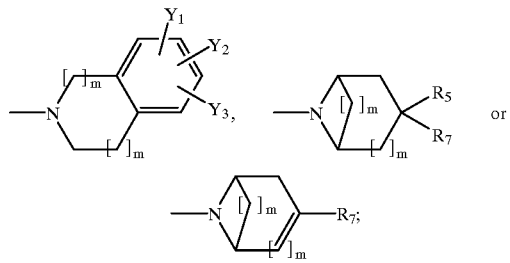

or a pharmaceutically acceptable salt thereof.

The invention also provides for the (−) and (+) enantiomers of the compounds described herein.

In those embodiments having the following structure

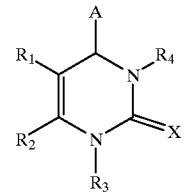

presently preferred compounds include the following:

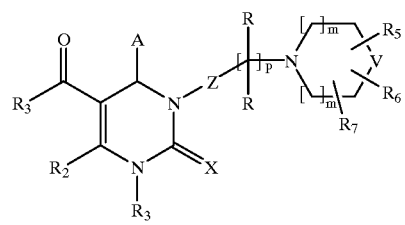

-continued
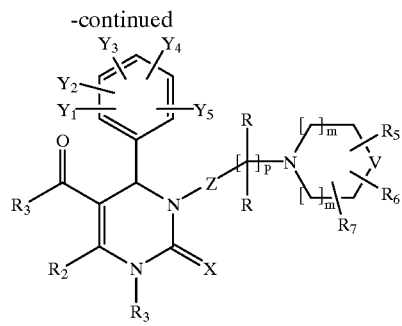
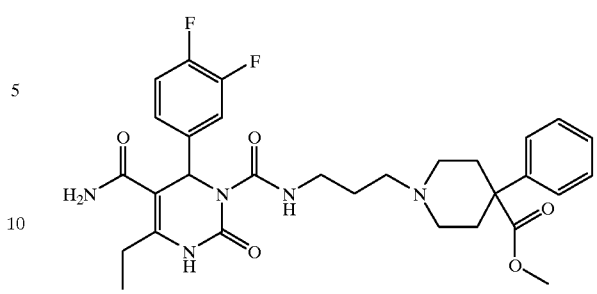
In preferred embodiments, the compounds may have the structures:
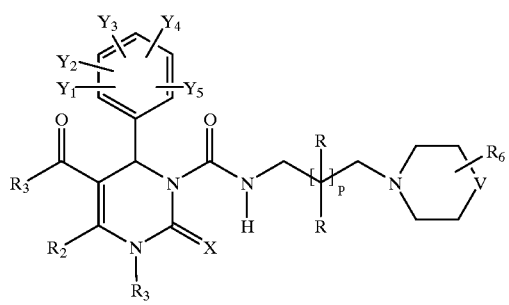
where V is selected from $CR_5R_7$ or $NR_7$ and p is selected from 1–3.
The invention provides for the preferred embodiment having the following structures:
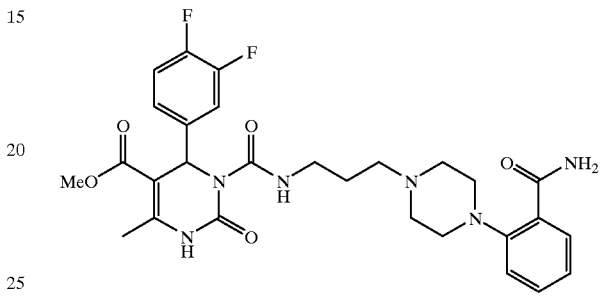
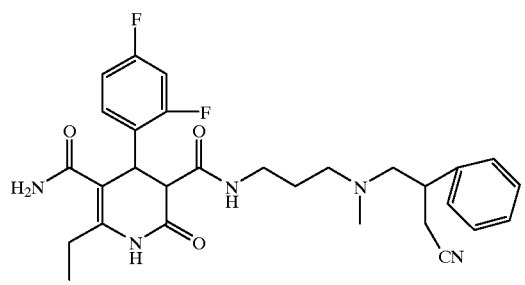
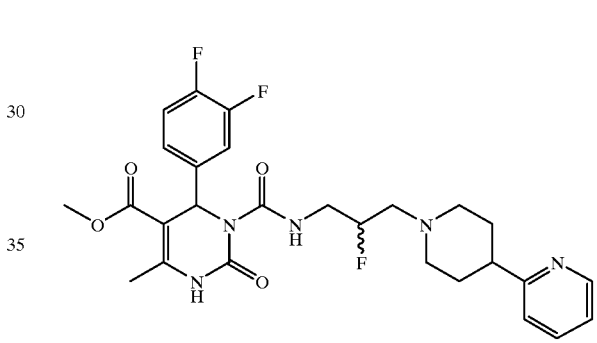
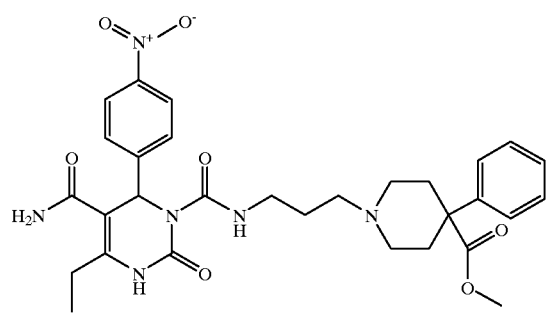
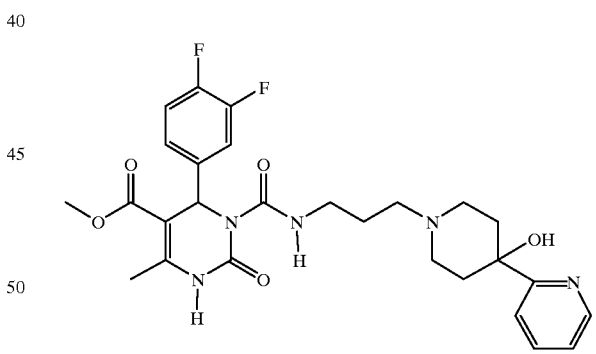
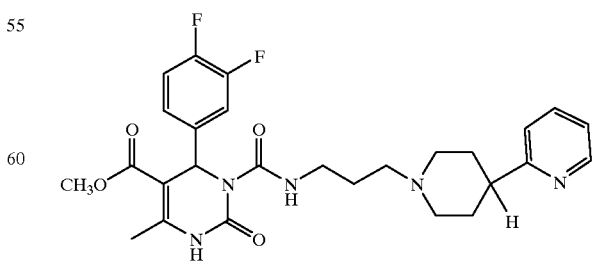

-continued
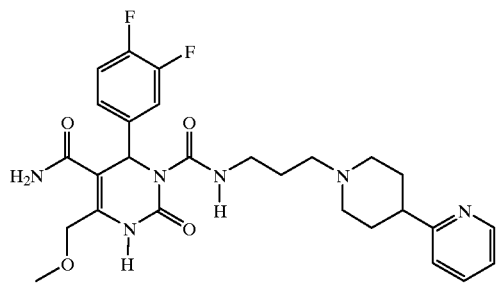
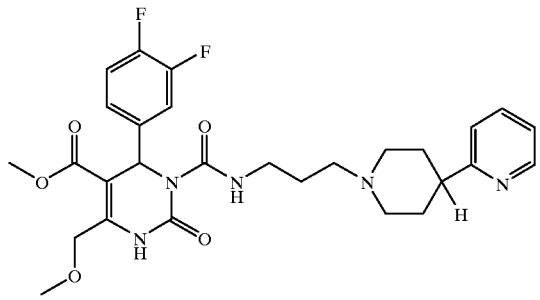
and
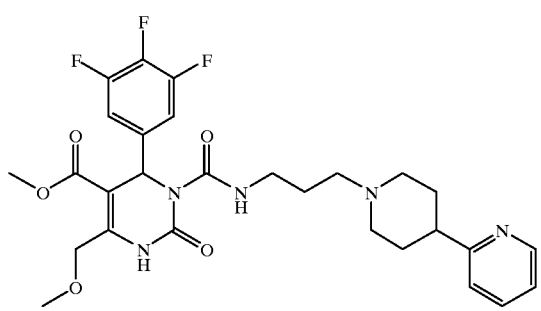
The invention further provides that the compound has the following structures:
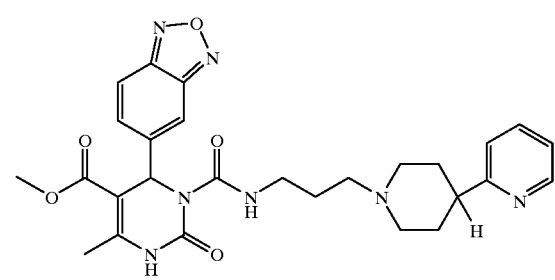
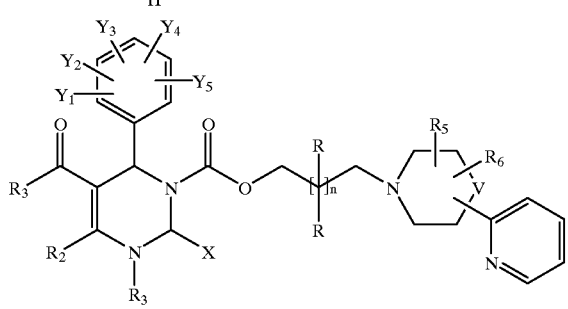
The invention further provides that the compound has the structures:
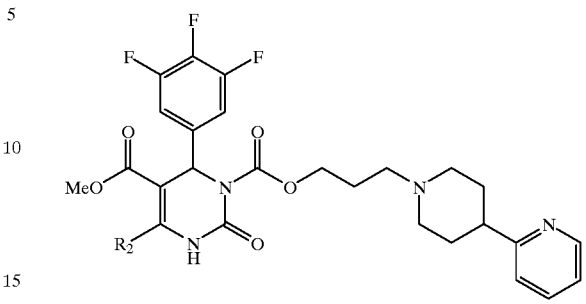
The invention further provides that the compound has the structures:
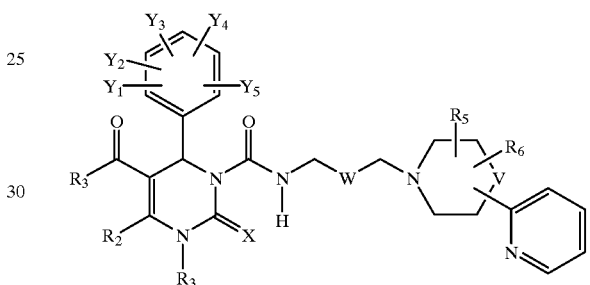
and
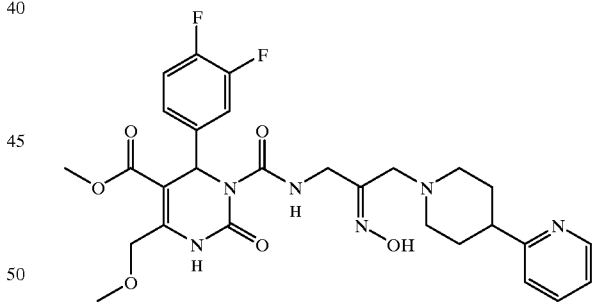
In those embodiments having the following structure
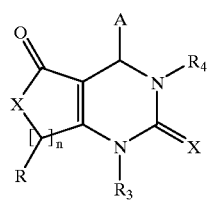

presently preferred compounds include the following:

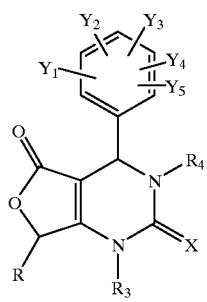

and

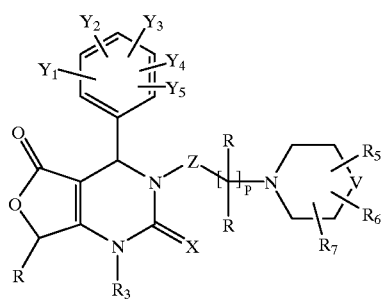

The invention provides for the preferred embodiment having the following structure:

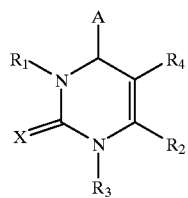

In those embodiments having the following structure

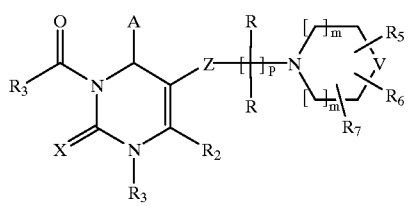

presently preferred compounds include the following:

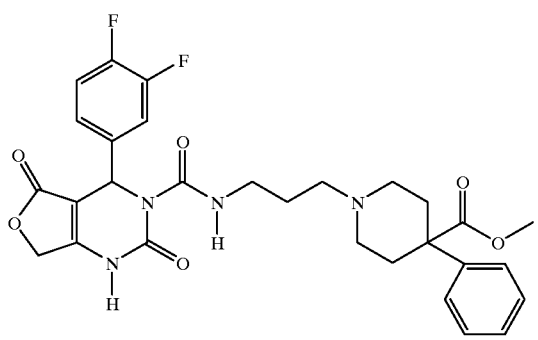

-continued

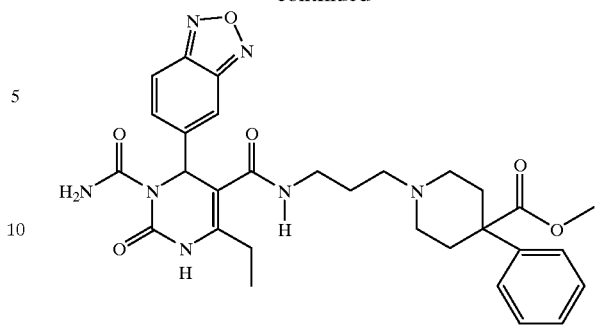

and

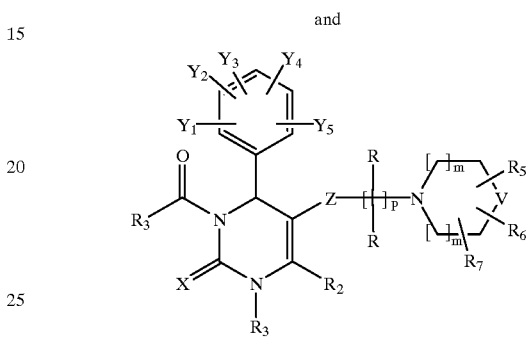

The invention provides for the preferred embodiment having the following structure:

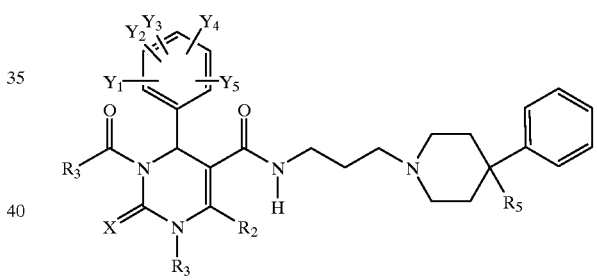

where $R_5$ is selected from —$CO_2CH_3$ or —H.

The present invention is directed to compounds having the structures:

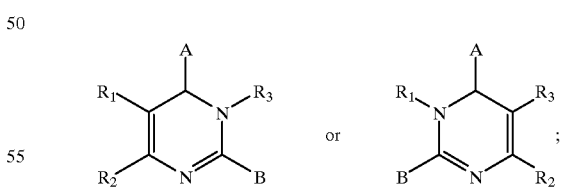

where A is

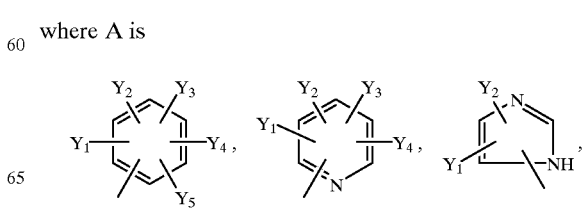

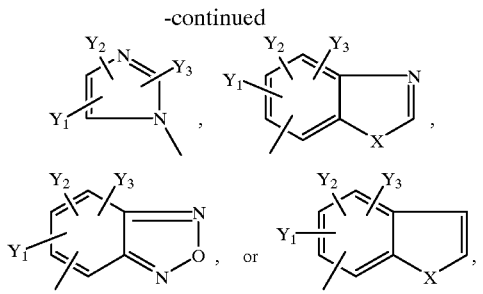

where each of $Y_1, Y_2, Y_3, Y_4$ and $Y_5$ is independently —H; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —F, —Cl, —Br, or —I; —$NO_2$; —$N_3$; —CN; —$OR_4$, —$OCOR_4$, —$COR_4$, —$CONHR_4$, —$CON(R_4)_2$, or —$COOR_4$; or any two of $Y_1, Y_2, Y_3, Y_4$ and $Y_5$ present on adjacent carbon atoms can constitute a methylenedioxy group;

where X is S; O; or $NR_4$;

where B is —H; straight chained or branched $C_1$–$C_7$ alkyl, monofluoroalkyl, polyfluoroalkyl, alkoxy or thioalkyl; straight chained or branched $C_2$–$C_7$ alkenyl; —$SCH_2C_6H_4OR_4$; —$(CH_2)_nC_6H_5$; —$CH_2X(CH_2)_n$ $NHR_4$; —$(CH_2)$ $NHR_4$; or —$OR_4$;

where $R_1$ is —H; —$NO_2$; —CN; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —$N(R_4)_2$; —$OR_4$; —$(CH_2)_pOR_4$; —$COR_4$; —$CO_2R_4$; or —$CON(R_4)_2$;

where $R_2$ is —H; straight chained or branched $C_1$–$C_7$ alkyl, hydroxyalkyl, alkoxyalkyl, aminoalkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; $C_3$–$C_{10}$ cycloalkyl-$C_3$–$C_{10}$-alkyl, $C_3$–$C_{10}$ cycloalkyl-$C_1$–$C_{10}$-monofluoroalkyl or $C_3$–$C_{10}$ cycloalkyl-$C_1$–$C_{10}$-polyfluoroalkyl; —CN; —$CH_2XR_4$, —$CH_2X(CH_2)_pNHR_4$, —$(CH_2)_nNHR_4$, —$CH_2X(CH_2)_pN(R_4)_2$, —$CH_2X(CH_2)_pN_3$, or —$CH_2X(CH_2)_pNHCXR_7$; or —$OR_4$;

where each p is independently an integer from 1 to 7;
where each n is independently an integer from 0 to 5;
where $R_3$ is

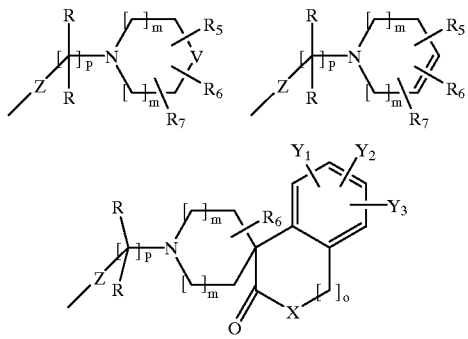

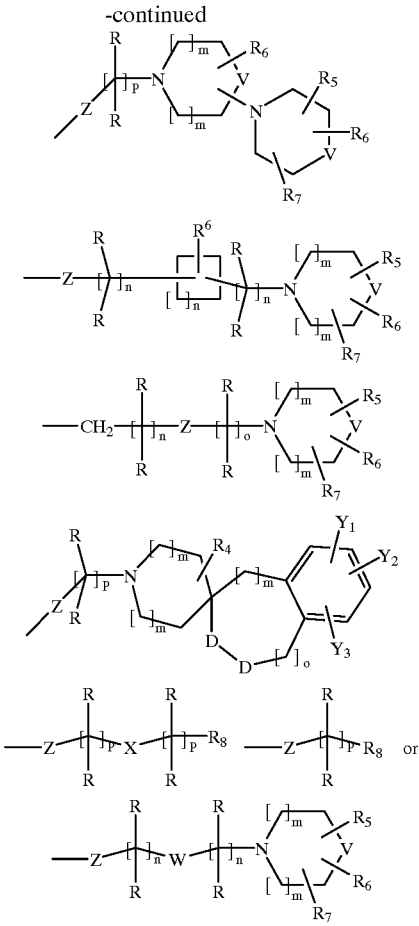

where Z is $C_2$–$C_7$ alkenyl or alkynyl; $CH_2$; O; CO; $CO_2$; $CONR_4$; S; SO; $SO_2$; or $NR_4$;

where each D is independently $CH_2$; O; S; $NR_4$; CO; or CS;

where W is C=O; C=$NOR_4$; substituted or unsubstituted phenyl, pyridyl, thiophenyl, furanyl, pyrazinyl, pyrrolyl, naphthyl, indolyl, imidazolyl, benzfurazanyl, benzfuranyl or benzimidazolyl, where the phenyl, S pyridyl, thiophenyl, furanyl, pyrazinyl, pyrrolyl, naphthyl, indolyl, imidazolyl, benzfurazanyl, benzfuranyl or benzimidazolyl is substituted with —H, —F, —Cl, —Br, —I, —$NO_2$, —CN, straight chained or branched $C_1$–$C_7$ alkyl, straight chained or branched $C_1$–$C_7$ monofluoroalkyl, straight chained or branched $C_1$–$C_7$ polyfluoroalkyl, straight chained or branched $C_2$–$C_7$ alkenyl, straight chained or branched $C_1$–$C_7$ alkynyl, $C_3$–$C_7$ cycloalkyl, $C_3$–$C_7$ monofluorocycloalkyl, $C_3$–$C_7$ polyfluorocycloalkyl, $C_3$–$C_7$ cycloalkenyl, —$N(R_4)_2$, —$OR_4$, —$COR_4$, —$CO_2R_4$, or —$CON(R_4)_2$;

where each V is independently O; S; $CR_5R_7$; $C(R_7)_2$; or $NR_7$;

where each m is independently an integer from 0 to 3;
where o is an integer from 1 to 3;
where each R is independently —H; —F; straight chained or branched $C_1$–$C_7$ alkyl, monofluoroalkyl or polyfluoroalkyl; straight chained or branched $C_2$–$C_7$ alkenyl or alkynyl; —$N(R_4)_2$; —$NO_2$; —CN; —$CO_2R_4$; or —$OR_4$;

where each $R_4$ is independently —H; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl;

where $R_5$ is —H; straight chained-or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; phenyl, thiophenyl, pyridyl, pyrrolyl, furanyl, imidazolyl or indolyl; —COOR$_4$, —COR$_4$, —CONHR$_4$, —CN, or —OR$_4$;

where each $R_6$ is independently —H; straight chained or branched $C_1$–$C_7$ alkyl, hydroxyalkyl, aminoalkyl, alkoxyalkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; or —OR$_4$;

where each $R_7$ is independently —H; substituted or unsubstituted benzyl, benzoyl, phenyl, pyridyl, thiophenyl, furanyl, pyrazinyl, pyrrolyl, naphthyl, indolyl, imidazolyl, benzfurazanyl, benzfuranyl, benzimidazolyl or 2-keto-1-benzimidazolinyl, where the benzyl, benzoyl, phenyl, pyridyl, thiophenyl, furanyl, pyrazinyl, pyrrolyl, naphthyl, indolyl, imidazolyl, benzfurazanyl, benzfuranyl, benzimidazolyl or 2-keto-1-benzimidazolinyl is substituted with —H, —F, —Cl, —Br, —I, —NO$_2$, —CN, straight chained or branched $C_1$–$C_7$ alkyl, straight chained or branched $C_1$–$C_7$ monofluoroalkyl, straight chained or branched $C_1$–$C_7$ polyfluoroalkyl, straight chained or branched $C_2$–$C_7$ alkenyl, straight chained or branched $C_2$–$C_7$ alkynyl, $C_3$–$C_7$ cycloalkyl, $C_3$–$C_7$ monofluorocycloalkyl, $C_3$–$C_7$ polyfluorocycloalkyl, $C_3$–$C_7$ cycloalkenyl, —N(R$_4$)$_2$, —OR$_4$, —COR$_4$, —CO$_2$R$_4$, or —CON(R$_4$)$_2$; substituted or unsubstituted straight chained or branched $C_1$–$C_7$ alkyl, monofluoroalkyl or polyfluoroalkyl; substituted or unsubstituted straight chained or branched $C_2$–$C_7$ alkenyl or alkynyl; $C_3$–$C_7$ cycloalkyl or cycloalkenyl, where the alkyl; monofluoroalkyl, polyfluoroalkyl, alkenyl, alkynyl, cycloalkyl or cycloalkenyl is substituted with —H, phenyl, pyridyl, thiophenyl, furanyl, pyrazinyl, pyrrolyl, naphthyl, indolyl, imidazolyl, benzfurazanyl, benzfuranyl, benzimidazolyl; and where $R_8$ is —H; substituted or unsubstituted benzyl, benzoyl, phenyl, pyridyl, thiophenyl, furanyl, pyrazinyl, pyrrolyl, naphthyl, indolyl, imidazolyl, benzfurazanyl, benzfuranyl, benzimidazolyl or 2-keto-1-benzimidazolinyl, where the benzyl, benzoyl, phenyl, pyridyl, thiophenyl, furanyl, pyrazinyl, pyrrolyl, naphthyl, indolyl, imidazolyl, benzfurazanyl, benzfuranyl, benzimidazolyl or 2-keto-1-benzimidazolinyl is substituted with -H, —F, —Cl, —Br, —I, —NO$_2$, —CN, straight chained or branched $C_1$–$C_7$ alkyl, straight chained or branched $C_1$–$C_7$ monofluoroalkyl, straight chained or branched $C_1$–$C_7$ polyfluoroalkyl, straight chained or branched $C_2$–$C_7$ alkenyl, straight chained or branched $C_2$–$C_7$ alkynyl, $C_3$–$C_7$ cycloalkyl, $C_3$–$C_7$ monofluorocycloalkyl, $C_3$–$C_7$ polyfluorocycloalkyl, $C_3$–$C_7$ cycloalkenyl, —N(R$_4$)$_2$, —OR$_4$, —COR$_4$, —CO$_2$R$_4$, or —CON(R$_4$)$_2$; substituted or unsubstituted straight chained or branched $C_1$–$C_7$ alkyl, monofluoroalkyl or polyfluoroalkyl; substituted or unsubstituted straight chained or branched $C_2$–$C_7$ alkenyl or alkynyl; $C_3$–$C_7$ cycloalkyl or cycloalkenyl, where the alkyl, monofluoroalkyl, polyfluoroalkyl, alkenyl, alkynyl, cycloalkyl or cycloalkenyl is substituted with —H, phenyl, pyridyl, thiophenyl, furanyl, pyrazinyl, pyrrolyl, naphthyl, indolyl, imidazolyl, benzfurazanyl, benzfuranyl, benzimidazolyl, —N(R$_4$)$_2$, —NO$_2$, —CN, —CO$_2$R$_4$, —OR$_4$;

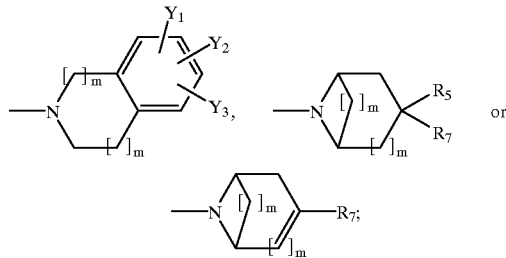

or a pharmaceutically acceptable salt thereof.

The invention further provides for the (−) and (+) enantiomers of the compounds described above.

In those embodiments having the following structure

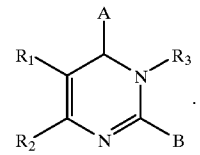

presently preferred compounds include the following:

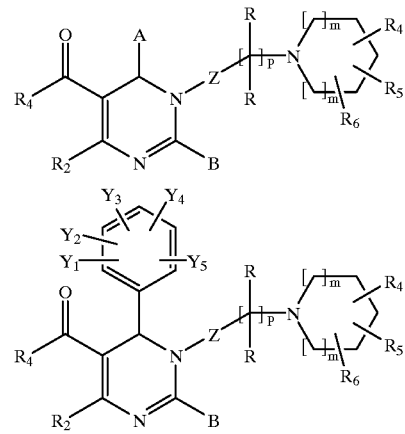

The invention provides for the preferred embodiments having the following structures:

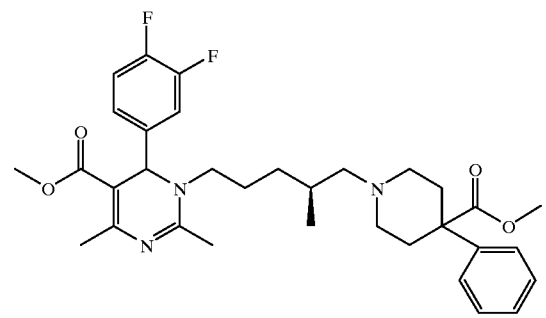

and

-continued

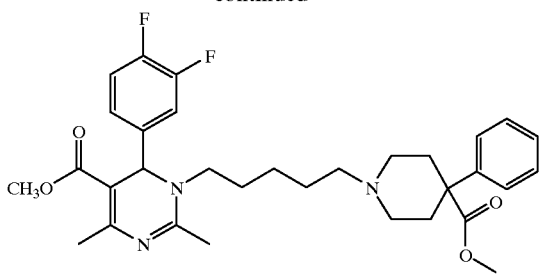

In those embodiments having the following structure

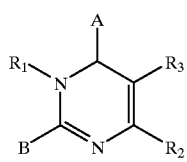

presently preferred compounds include the following:

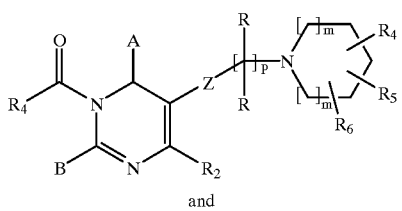

and

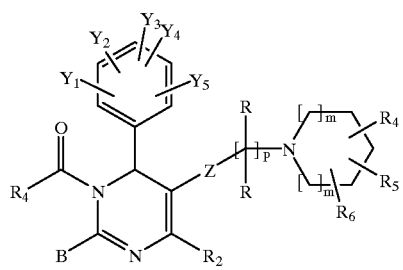

The invention also provides for the following preferred embodiment having the structure:

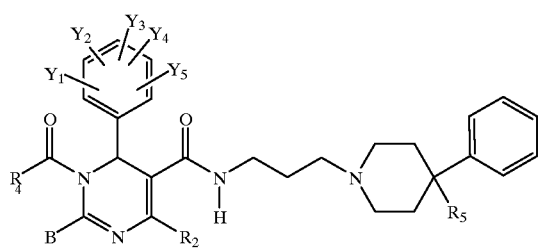

where $R_5$ is selected from —H or —CO$_2$CH$_3$.

The invention further provides for a pharmaceutical composition comprising a therapeutically effective amount of any of the compounds described herein and a pharmaceutically acceptable carrier. In one embodiment the therapeutically effective amount is an amount from about 0.01 mg per subject per day to about 500 mg per subject per day, preferably from about 0.1 mg per subject per day to about 60 mg per subject per day and most preferably from about 1 mg per subject per day to about 20 mg per subject per day. The therapeutically effective amount is an amount from about 0.01 mg to about 500 mg.

In one preferred embodiment the pharmaceutical carrier may be a liquid and the pharmaceutical composition would be in the form of a solution. In another equally preferred embodiment, the pharmaceutically acceptable carrier is a solid and the composition is in the form of a powder or tablet. In a further embodiment, the pharmaceutical carrier is a gel and the composition is in the form of a suppository or cream.

In a preferred embodiment the compound of the pharmaceutical composition additionally does not cause a fall in blood pressure at dosages effective to alleviate benign prostatic hyperplasia. In a further embodiment the compound of the pharmaceutical composition additionally does not cause a fall in blood pressure in rats at a dosage of 10 micrograms of compound per kilogram per rat.

The invention provides a method of treating a subject suffering from benign prostatic hyperplasia which comprises administering to the subject one of the compounds described herein effective to treat benign prostatic hyperplasia. The invention further provides that the compound additionally does not cause a fall in blood pressure at dosages effective to alleviate benign prostatic hyperplasia. In one embodiment the compound additionally does not cause a fall in blood pressure in rats at a dosage of 10 micrograms of compound per kilogram of rat. In one preferred embodiment the compound effects treatment of benign prostatic hyperplasia by relaxing lower urinary tract tissue and in particular where lower urinary tract tissue is urethral smooth muscle.

The invention further provides a method of treating a subject suffering from high intraocular pressure which comprises administering to the subject one of the compounds described herein effective to lower intraocular pressure.

The invention further provides a method of treating a subject suffering from a disorder associated with high cholesterol which comprises administering to the subject one of the compounds described herein effective to inhibit cholesterol synthesis.

The invention also provides a method of treating a disease which is susceptible to treatment by antagonism of the $\alpha_{1C}$ receptor which comprises administering to -the subject one of the compounds described herein effective to treat the disease.

The invention further provides a method of treating a subject suffering from impotency which comprises administering to the subject one of the compounds described herein effective to treat impotency.

The invention further provides a method of treating a subject suffering from sympathetically mediated pain which comprises administering to the subject one of the compounds described herein effective to treat sympathetically mediated pain.

The invention provides a method of treating a subject suffering from cardiac arrhythmia which comprises administering to the subject one of the compounds described herein effective to treat cardiac arrhythmia.

The invention provides a method of treating a subject suffering from benign prostatic hyperplasia which comprises administering to the subject one of the compounds described herein in combination with a 5 alpha-reductase inhibitor effective to treat benign prostatic hyperplasia. In one preferred embodiment the 5-alpha reductase inhibitor is finasteride.

A pharmaceutical composition comprising a therapeutically effective amount one of the compounds described herein in combination with a therapeutically effective amount of finasteride and a pharmaceutically acceptable carrier. In one preferred embodiment the therapeutically effective amount of one of the compounds described herein is an amount from about 0.01 mg to about 500 mg and the therapeutically effective amount of the finasteride is about 5 mg. In a more preferred embodiment the therapeutically effective amount one of the compounds described herein is an amount from about 0.1 mg to about 60 mg and the therapeutically effective amount of finasteride is about 5 mg. In a further embodiment of the invention the therapeutically effective amount of the one of the compounds described herein is an amount from about 1 mg to about 20 mg and the therapeutically effective amount of finasteride is about 5 mg.

The invention further provides a method of relaxing lower urinary tract tissue which comprises contacting the lower urinary tract tissue with an amount of one of the compounds described herein effective to relax lower urinary tract tissue. In one embodiment the lower urinary tract tissue is urethral smooth muscle.

The invention provides a method of relaxing lower urinary tract tissue in a subject which comprises administering to the subject an amount of one of the compounds described herein effective to relax lower urinary tract tissue. In one preferred embodiment the lower urinary tract tissue is urethral smooth muscle.

The invention provides for the use of the compounds described herein for the preparation of a pharmaceutical composition for lowering intraocular pressure, inhibiting cholesterol synthesis, and the treatment of: benign prostatic hyperplasia, impotency, cardiac arrhythmia and any disease where antagonism of the aic receptor may be useful. The invention provides for the use of the compounds described herein for the preparation of a pharmaceutical composition for relaxing lower urinary tract tissue and in particular urethral smooth muscle. The invention further provides for the use of any of compounds described herein for the preparation of a pharmaceutical composition, where the compound additionally does not cause a fall in blood pressure at dosages effective to lower intraocular pressure, to inhibit cholesterol synthesis, and for the treatment of: benign prostatic hyperplasia, impotency, cardiac arrhythmia and any disease where antagonism of the $\alpha_{1C}$ receptor may be useful.

Furthermore the invention provides that the compound used in the preparation of the pharmaceutical composition additionally does not cause a fall in blood pressure in rats at a dosage of 10 micrograms of compound per kilogram per rat.

The invention provides for the use of the compounds described herein in the preparation of a medicament for lowering intraocular pressure, inhibiting cholesterol synthesis, and for the treatment of: benign prostatic hyperplasia, impotency, cardiac arrhythmia and any disease where antagonism of the $\alpha_{1C}$ receptor may be useful. The invention provides for the use of the compounds described herein in the preparation of a medicament for relaxing lower urinary tract tissue and in particular urethral smooth muscle. The invention further provides for the use of any of compounds described herein in the preparation of a medicament, where the compound additionally does not cause a fall in blood pressure at dosages effective to lower intraocular pressure, to inhibit cholesterol synthesis, and for the treatment of: benign prostatic hyperplasia, impotency, cardiac arrhythmia and any disease where antagonism of the $\alpha_{1C}$ receptor may be useful. The invention further provides that the compound in the medicament additionally does not cause a fall in blood pressure in rats at a dosage of 10 micrograms of compound per kilogram per rat.

The invention provides for a drug which is useful for lowering intraocular pressure, inhibiting cholesterol synthesis, and the treatment of: benign prostatic hyperplasia, impotency, cardiac arrhythmia and any disease where antagonism of the $\alpha_{1C}$ receptor may be useful, the effective ingredient of the said drug being any of the compounds described herein. The invention further provides the drug described herein additionally does not cause a fall in blood pressure at dosages effective to lower intraocular pressure, to inhibit cholesterol synthesis, and for the treatment of: benign prostatic hyperplasia, impotency, cardiac arrhythmia and any disease where antagonism of the $\alpha_{1C}$ receptor may be useful. The invention further provides that the drug additionally does not cause a fall in blood pressure in rats at a dosage of 10 micrograms of compound per kilogram per rat.

The invention provides for a drug which is useful for relaxing lower urinary tract tissue and in particular urethral smooth muscle, the effective ingredient of the drug being any of the compounds described herein. The invention further provides the drug which is useful for relaxing lower urinary tract tissue additionally does not cause a fall in blood pressure at dosages effective to relax lower urinary tract tissue. The invention further provides that the drug which is useful for relaxing lower urinary tract tissue additionally does not cause a fall in blood pressure in rats at a dosage of 10 micrograms of compound per kilogram per rat.

The invention also provides for the (−) and (+) enantiomers of all compounds of the subject application described herein. Included in this invention are pharmaceutically acceptable salts and complexes of all of the compounds described herein. The salts include but are not limited to the following acids and bases. The following inorganic acids; hydrochloric acid, hydrofluoric acid, hydrobromic acid, hydroiodic acid, sulfuric acid and boric acid. The organic acids; acetic acid, trifluoroacetic acid, formic acid, oxalic acid, malonic acid, succinic acid, fumaric acid, tartaric acid, maleic acid, citric acid, methanesulfonic acid, trifluoromethanesulfonic acid, benzoic acid, glycolic acid, lactic acid and mandelic acid. The following inorganic bases; ammonia, hydroxyethylamine and hydrazine. The following organic bases; methylamine, ethylamine, propylamine, dimethylamine, diethylamine, trimethylamine, triethylamine, ethylenediamine, hydroxyethylamine, morpholine, piperazine and guanidine. This invention further provides for the hydrates and polymorphs of all of the compounds described herein.

The invention also provides a pharmaceutical composition comprising a therapeutically effective amount of the compounds described above and a pharmaceutically acceptable carrier. In the subject invention a "therapeutically effective amount" is any amount of a compound which, when administered to a subject suffering from a disease against which the compounds are effective, causes reduction, remission, or regression of the disease. In one embodiment the therapeutically effective amount is an amount from about 0.01 mg per subject per day to about 500 mg per subject per day, preferably from about 0.1 mg per subject per day to about 60 mg per subject per day and most preferably from about 1 mg per subject per day to about 20 mg per subject per day. In the practice of this invention the "pharmaceutically acceptable carrier" is any physiological carrier known to those of ordinary skill in the art useful in formulating pharmaceutical compositions.

The invention also provides for pharmaceutical composition comprising a therapeutically effective amount of the any of the compounds described herein in combination with a therapeutically effective amount of finasteride and a pharmaceutically acceptable carrier. In one embodiment the pharmaceutical composition is a therapeutically effective amount from about 0.01 mg per subject per day to about 500 mg per subject per day of any one of the compounds described herein and a therapeutically effective amount of the finasteride of about 5 mg per subject per day. A more preferred embodiment of the pharmaceutical composition is a therapeutically effective amount from about 0.1 mg per subject per day to about 60 mg per subject per day of any one of the compounds described herein and a therapeutically effective amount of the finasteride of about 5 mg per subject per day. The most preferred embodiment of the pharmaceutical composition is a therapeutically effective amount from about 1 mg per subject per day to about 20 mg per subject per day of any one of the compounds described herein and a therapeutically effective amount of the finasteride of about 5 mg per subject per day.

In one preferred embodiment the pharmaceutical carrier may be a liquid and the pharmaceutical composition would be in the form of a solution. In another equally preferred embodiment, the pharmaceutically acceptable carrier is a solid and the composition is in the form of a powder or tablet. In a further embodiment, the pharmaceutical carrier is a gel and the composition is in the form of a suppository or cream. In a further embodiment the compound may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The compound can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The compound can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Optimal dosages to be administered may be determined by those skilled in the art, and will vary with the particular compound in use, the strength of the preparation, the mode of administration, and the advancement of the disease condition. Additional factors depending on the particular subject being treated will result in a need to adjust dosages, including subject age, weight, gender, diet, and time of administration.

The invention further provides a method of treating a subject suffering from benign prostatic hyperplasia which comprises administering to the subject an amount of the one the compounds described above effective to treat benign prostatic hyperplasia.

The invention also provides a method of treating a subject suffering from high intraocular pressure which comprises administering to the subject an amount of any of the compounds described above effective to lower intraocular pressure.

This invention also provides a method of treating a subject suffering a disorder associated with high cholesterol which comprises administering to the subject an amount of any of the compounds described above effective to inhibit cholesterol synthesis.

This invention also provides a method of treating a disease which is susceptible to treatment by antagonism of the $\alpha_{1C}$ receptor which comprises administering to the subject an amount of any the compounds described above effective to treat the disease.

This invention also provides a method of treating a subject suffering from impotency which comprises administering to the subject an amount of any of the compounds described above effective to treat impotency.

This invention also provides a method of treating a subject suffering from sympathetically mediated pain which comprises administering to the subject an amount of any of the compounds described above effective to treat sympathetically mediated pain.

This invention also provides a method of treating a subject suffering from cardiac arrhythmia which comprises administering to the subject an amount of any of the compounds described above effective to treat cardiac arrhythmia.

This invention also provides a method of treating a subject suffering from benign prostatic hyperplasia which comprises administering to the subject an amount of any of the compounds described above in combination with a 5 alpha-reductase inhibitor effective to treat benign prostatic hyperplasia. The 5-alpha reductase inhibitor is finasteride. The dosage administered to the subject is about 0.01 mg per subject day to 50 mg per subject per day of finasteride in combination with an $\alpha_{1C}$ antagonist. A preferred dosage administered to the subject is about 0.2 mg per subject per day to 10 mg per subject per day of finasteride in combination with an $\alpha_{1C}$ antagonist. A more preferred dosage administered to the subject is about 1 mg per subject per day to 7 mg per subject per day of finasteride in combination with an $\alpha_{1C}$ antagonist. The most preferred dosage administered to the subject is about 5 mg per subject per day of finasteride in combination with an $\alpha_{1C}$ antagonist.

One skilled in the art will readily appreciate that appropriate biological assays will be used to determine the therapeutic potential of the claimed compounds for the treating the above noted disorders.

This invention will be better understood from the Experimental Details which follow. However, one skilled in the art will readily appreciate that the specific methods and results discussed are merely illustrative of the invention as described more fully in the claims which follow thereafter.

Experimental Details

For Examples 1–17 Scheme 1 describes the general synthetic preparation. All NMRs were obtained using a 300 MHz GE QEPLUS NMR machine.

EXAMPLE 1

1,6-Dihydro-5-methoxycarbonyl-2-[{(4-methoxyphenyl)methyl}thio]-4-methyl-6-(4-nitrophenyl)-1-{N-[3-(4,4-diphenylpiperidin-1-yl) propyl)}carboxamido pyrimidine.

a. 4,4-Diphenylpiperidine hydrochloride. A mixture of 4-piperidone monohydrate hydrochloride (15.0 g, 0.0976 mol) and $AlCl_3$ (130 g, 0.976 mol, 10.0 eq) in anhydrous benzene (600 mL) were stirred at reflux for 4 hours. The mixture was cooled to room temperature, poured into ice (300 g) and water (50 mL), and filtered. The solid was washed with toluene and dried to afford 19.2 g (72%) of an off-white solid, which was characterized spectroscopically.

b. 3-(4,4-Diphenylpiperidin-1-yl)propionitrile. To a suspension of 4,4-diphenylpiperidine hydrochloride (0.195 g, 0.712 mmol) in EtOH (1.5 mL) was added $Et_3N$ (0.25 mL, 1.8 mmol, 2.6 eq) followed by acrylonitrile (0.13 mL, 2.01 mmol, 2.8 eq). The resulting solution was stirred at room temperature under argon for 15 min and then concentrated. Water was added, and the mixture was extracted with EtOAc (3×10 mL). The combined organic extracts were dried ($MgSO_4$) and concentrated to give 170 mg (87%) of a tan solid, which was characterized spectroscopically and used in the next reaction without purification.

c. 3-(4,4-Diphenylpiperidin-1-yl)propylamine. To a stirred solution of 3-(4,4-diphenylpiperidin-1-yl)propionitrile (2.00 g, 6.89 mmol) in anhydrous THF (20 mL) under argon was added a solution of $BH_3$ in THF (1.0 M, 24.1 mL, 24 mmol, 3.5 eq) at room temperature. The mixture was refluxed for 4.5 hours and then cooled to room temperature. Aqueous HCl (6 N, 50 mL) was added and stirring was continued for 1 hour. The mixture was basified to pH 9 by addition of 6 N aq. NaOH, extracted with $CH_2Cl_2$ (3×10 mL), dried ($MgSO_4$) and concentrated. The residue was purified by flash chromatography ($SiO_2$, EtOAc-MeOH-isopropylamine 9:1:0 to 4:1:0.2) to give 1.35 g (66%) of tan solid, which was characterized spectroscopically.

d. 2-(4-Methoxybenzyl)-2-thiopseudourea hydrochloride.

To a well-stirred suspension of thiourea (7.6 g, 0.1 mol) in THF (50 mL) at 0° C., 4-methoxybenzyl chloride (16 g, 0.1 mol) was added in 10 min and the mixture was allowed to warm to room temperature. After 2 hours the mixture was heated to 65° C. and kept at that temperature for 5 hours. It was cooled to room temperature and diluted with diethyl ether (200 mL). The white precipitate formed was filtered and dried (22.5 g, 96%); m. p. 161–163° C.

e. Methyl 2-{(4-nitrophenyl)methylene}-3-oxobutyrate. A mixture of 4-nitrobenzaldehyde (15.1 g, 0.1 mol), methyl acetoacetate (12.773 g, 0.11 mol), piperidine (0.41 g, 476 mL, 4.8 mmol), and acetic acid (0.288 g, 274 mL, 4.8 mmol) in 2-propanol (400 mL) was stirred at room temperature for 48 hours. The white solid, methyl 2-{(4-nitrophenyl)methylene}-3-oxobutyrate, formed was filtered, washed with 2-propanol (2×50 mL) and dried (21.80 g, 93%).

f. 1,6-Dihydro-5-methoxycarbonyl-2-[{(4-methoxyphenyl)methyl}thio]-4-methyl-6-(4-nitrophenyl)pyrimidine. A mixture of methyl 2-{(4-nitrophenyl)methylene}-3-oxobutyrate (8.96 g, 0.04 mol), 2-(4-methoxybenzyl)-2-thiopseudourea hydrochloride (9.28 g, 0.04 mol), and NaOAc (3.28 g, 0.04 mol) in DMF (100 mL) was stirred and heated at 70–75° C. for 4.5 hours. The mixture was cooled, poured into ice-water (300 mL), extracted with EtOAc (2×400 mL). The combined EtOAc extracts were washed with 10% $NaHCO_3$ solution (2×60 mL), brine (100 mL), and dried ($MgSO_4$). Solvent was evaporated and the crude product was purified by flash column chromatography on silica gel using 10% through 30% EtOAc in hexane as the gradient eluent, to leave the product as an oil, which on trituration with EtOAc/hexane became a yellow solid (11.4 g, 66.7%); m.p. 138–139° C.; $^1$H-NMR ($CDCl_3$): δ 2.15 (s, 3H), 3.62 (s, 3H), 3.72 (s, 3H), 4.05, 5.78 (s, d, J=3 Hz, 1 H), 4.08, 4.20 (AB q, J=12.5 Hz, 2H), 4.21, 6.40 (s, d, J=3 Hz, 1H), 6.66 (2 d, J=8.5 Hz, 2H), 7.08 (2 d, J=8.5 Hz, 2H), 7.37 (2 d, J=8.8 Hz, 2H), 8.7 (2 d, J=8.8 Hz, 2H); Anal. Calcd. for $C_2, H_{21}N_3O_5S$: C, 59.00; H, 4.95; N, 9.83. Found: C, 59.02; H, 4.93; N, 9.77.

g. 1,6-Dihydro-5-methoxycarbonyl-2-[{(4-methoxyphenyl)methyl}thio]-4-methyl-6-(4-nitrophenyl)-1-[(4-nitrophenyloxy)carbonyl]pyrimidine.

To a well-stirred mixture of 1,6-dihydro-5-methoxycarbonyl-2-[{(4-methoxyphenyl)methyl}thio]-4-methyl-6-(4-nitrophenyl)pyrimidine (4.5 g, 0.0105 mol), $NaHCO_3$ (3.69 g, 0.044 mol), $CH_2Cl_2$ (200 mL), and water (50 mL) at 0–5° C., 4-nitrophenyl chloroformate (2.4 g, 0.0119 mol) was added in 5 min and the mixture was allowed to warm to room temperature. After 10 hours, the TLC analysis of the reaction mixture showed the presence of a small amount of starting pyrimidine, therefore, more 4-nitrophenyl chloroformate (0.65 g, 0.0032 mol) was added and the stirring continued for an additional 4 hours. The two layers were separated, the $CH_2Cl_2$ layer was washed with saturated aqueous $NaHCO_3$ solution (3×50 mL), dried ($MgSO_4$), and the solvent evaporated. The residue was recrystallized from $CH_2Cl_2$ and hexane to give the product as white crystals (5.5 g, 88.4%); m.p. 156–157° C.; $^1$H-NMR ($CDCl_3$): δ 2.53 (s, 3H), 3.70 (s, 3 H), 3.81 (s, 3H), 4.06, 4.36 (AB q, J=13.5 Hz, 2H), 6.30 (s, 1H), 6.78 (d, J=8.7 Hz, 2H), 7.17 (d, J=8.5 Hz, 2H), 7.20 (d, J=8.7 Hz, 2H), 7.32 (d, J=8.8 Hz, 2H), 7.97 (d, J 8.8 Hz, 2H), 8.25 (d, J=8.8 Hz, 2H); Anal. Calcd. for $C_2 1H_{24}N_4O_9S$: C, 56.75; H, 4.08; N, 9.45. Found: C, 56.49; H, 4.28; N, 9.25.

h. 1,6-Dihydro-5-methoxycarbonyl-2-[{(4-methoxyphenyl)methyl}thio]-4-methyl-6-(4-nitrophenyl)-1-{N-[3-(4,4-diphenylpiperidin-1-yl)prop-yl]}carboxamido pyrimidine.

To a stirred solution of 1,6-dihydro-5-methoxycarbonyl-2-[{(4-methoxyphenyl)methyl}thio]-4-methyl-6-(4-nitr ophenyl)-1-[(4-nitrophenyloxy)carbonyl]pyrimidine (0.592 g, 1 mmol) in anhydrous THF (10 mL) at room temperature under argon atmosphere, a solution of 3-[4,4-diphenylpiperidin-1-yl]propylamine (0.441 g, 1.5 mmol, 1.5 eq) in THF (5 mL) was added and the stirring continued for 1 hours. Solvent was evaporated from the reaction mixture and the residue was redissolved in $CH_2Cl_2$ (50 mL), washed with 5% $NaHCO_3$ (3×25 mL), brine (50 mL), and dried ($MgSO_4$). Solvent was evaporated and the residue was purified by flash chromatography on silica gel using 10% methanol in EtOAc as the eluent to give the desired product as an oil, which on trituration with hexane and drops of EtOAc became a white powder (0.32 g, 43%); m.p. 79–80° C.; $^1$H-NMR ($CDCl_3$): δ 1.61–1.82 (m, 4H), 2.27 (s, 3H), 2.30–2.51 (m, 8H), 3.19–3.36 (m, 1H), 3.42–3.60 (m, 1H), 3.68 (s, 3H), 3.76 (s, 3H), 3.95, 4.22 (AB q, J=13.6 Hz, 2H), 6.16 (s, 1H), 6.70 (d, J=8.6 Hz, 2H), 7.04 (d, J=8.6 Hz, 2H), 7.11–7.29 (m, 12H), 7.68 (br t, 1 H, NH), 7.91 (d, J=8.8 Hz, 2H); Anal. Calcd. for $C_{42}H_{45}N_5O_6S \cdot 0.33\ CH_2Cl_2$: C, 65.52; H, 5.93; N, 9.03. Found: C, 65.52; H, 6.01; N, 9.20.

EXAMPLE 2

1,6-Dihydro-5-methoxycarbonyl-2-[{(4-methoxyphenyl)methyl}thio]-4-methyl-6-(4-nitrophenyl)-1-{N-[3-(4-phenylpiperidin-1-yl)propyl]}carboxamidopyrimidine.

a. 3-(4-Phenylpiperidin-1-yl)propionitrile. Acrylonitrile (3.1 mL, 44 mmol, 2.5 eq) was added to a solution of 4-phenylpiperidine (3.0 g, 18 mmol) in EtOH (40 mL) and the mixture was stirred at room temperature for 1.5 hours. The volatiles were removed to give 3.8 g of pure product (brown oil, 99%), which was characterized spectroscopically.

b. 3-(4-Phenylpiperidin-1-yl)propylamine. To a stirred solution of 3-(4-phenylpiperidin-1-yl)propionitrile (5.1 g, 24 mmol) in anhydrous THF (20 mL) under argon was added a solution of $BH_3$ in THF (1.0 M, 83 mL, 83 mmol, 3.5 eq) at room temperature. The mixture was refluxed for 4.5 hours and then cooled to room temperature. Aqueous HCl (6 N, 130 mL) was added and stirring was continued for 2 hours at 50–70° C. The mixture was basified to pH 9 by addition of 6 N aq. NaOH and extracted with EtOAc (100 mL) and $CH_2Cl_2$ (3×100 mL). The combined organic extracts were dried ($MgSO_4$) and concentrated. The residue was dissolved in $CH_2Cl_2$ (20 mL) and treated with HCl in ether (1.0 M, 50 mL). The solvents were removed, ether (250 mL) was added, the mixture was filtered, and the filter cake was washed with ether. Water (60 mL) was added to the resulting white solid, the pH was adjusted to 10–11 with 1 N NaOH, and the aqueous phase was extracted with $CH_2Cl_2$ (3×50 mL). The combined extracts were dried ($MgSO_4$) and the solvents evaporated to give 4.5 g (87%) of pure product (light brown solid), which was characterized spectroscopically.

c. 1,6-Dihydro-5-methoxycarbonyl-2-[{(4-methoxyphenyl)methyl}thio]-4-methyl-6-(4-nitrophenyl)-1-{N-[3-(4-phenylpiperidin-1-yl)propyl]}carboxamido pyrimidine. This compound was prepared from 1,6-dihydro-5-methoxycarbonyl-2-[{(4-methoxyphenyl) methyl}thio]-4-methyl-6-(4-nitrophenyl)-1-[(4-nitroph enyloxy)carbonyl] pyrimidine (0.77 g, 1.3 mmol), 3-[4-phenylpiperidin-1-yl] propylamine (0.34 g, 1.56 mmol, 1.2 eq) and purified using similar conditions described in Example 1 (0.63 g, 72-;); m.p. 123–124° C.; $^1$H-NMR ($CDCl_3$): δ 1.65–2.10 (m, 8H), 2.41 (s, 3H), 2.41–2.55 (m, 3H), 2.99–3.06 (m, 2H), 3.2–3.35 (m, 1H), 3.45–3.60 (m, 1H), 3.67 (s, 3H), 3.75 (s, 3H), 4.10, 4.33 (AB q, J=13.6 Hz, 2H), 6.19 (s, 1H), 6.71 (d, J=8.6 Hz, 2H), 7.09 (d, J=8.6 Hz, 2H), 7.20–7.34 (m, 7H), 7.97 (br t, 1 H, NH), 7.97 (d, J=8.8 Hz, 2H); Anal. Calcd. for $C_{36}H_{41}N_5O_6 \cdot 0.25\ CH_2Cl_2$: C, 62.82; H, 6.04; N, 10.11. Found: C, 62.54; H, 6.13; N, 10.03.

EXAMPLE 3

1-{N-[3-(4-Cyano-4-phenylpiperidin-1-yl)propyl]} carboxamido-1,6-dihydro-5-methoxycarbonyl-2-[{(4-methoxyphenyl)methyl}thio]-4-methyl-6-(4-nitrophenyl) pyrimidine.

a. 3-(4-Cyano-4-phenylpiperidinlyl)propylamine. 4-Cyano-4-phenylpiperidine hydrochloride (5.01 g, 22.5 mmol) was added to water (100 mL), and the solution was basified to pH 10–11 by addition of 6 N aqueous NaOH. The mixture was extracted with $CH_2Cl_2$ (3×100 mL). The combined organic extracts were dried ($MgSO_4$) and concentrated. To the residue were added 3-bromopropylamine hydrobromide (4.92 g, 22.5 mmol), anhydrous $K_2CO_3$ (3.42 g, 24.8 mmol, 1.10 eq), and 1,4-dioxane (100 mL). The mixture was stirred at reflux for 24 hours under a $CaSO_4$ drying tube. The solvent was evaporated, and the product was purified by flash chromatography ($SiO_2$, $CHCl_3$/MeOH/2 M $NH_3$ in MeOH (100:8:4 to 100:20:8) to give 3.23 g (59%) of colorless oil, which was characterized spectroscopically.

b. 1-{N-[3-(4-Cyano-4-phenylpiperidin-1-yl)propyl]} carboxamido-1,6-dihydro-5-methoxycarbonyl-2[{(4-methoxy-phenyl)methyl}thio]-4-methyl-6-(4-nitrophenyl) pyrimidine.

This compound was prepared from 1,6-dihydro-5-methoxy carbonyl-2-[{(4-methoxyphenyl) methyl}thio]-4-methyl-6 -(4-nitrophenyl)-1-[(4-nitrophenyloxy)carbonyl] pyrimi dine (0.592 g, 1 mmol), 3-[4-cyano-4-phenyl piperidin-1-yl]propylamine (0.292 g, 1.2 mmol, 1.2 eq) and purified using similar conditions described in Example 1 (0.445 g, 64%); m.p. 143–144° C.; $^1$H-NMR ($CDCl_3$): δ 1.70–1.86 (m, 2H), 2.02–2.09 (m, 4H), 2.38 (s, 3H), 2.41–2.56 (m, 4H), 2.95–3.02 (m, 2H), 3.24–3.40 (m, 1H), 3.42–3.58 (m, 1H), 3.68 (s, 3H), 3.76 (s, 3H), 4.08, 4.23 (AB q, J=13.5 Hz, 2H), 6.23 (s, 1H), 6.72 (d, J=8.6 Hz, 2H), 6.94 (br t, 1 H, NH), 7.08 (d, J=8.6 Hz, 2H), 7.29 (d, J=8.7 Hz, 2H), 7.33–7.49 (m, 5H), 7.94 (d, J=8.8 Hz, 2H); Anal. Calcd. for $C_{37}H_{40}N_6O_6S$: C, 63.78; H, 5.79; N, 12.06. Found: C, 63.86; H, 5.90; N, 11.92.

EXAMPLE 4

1,6-Dihydro-5-methoxycarbonyl-1-{N-[3-(4-methoxycarbonyl-4-phenylpiperidin-1-yl)propyl]} carboxamido-2-[{(4-methoxyphenyl)methyl}thio]-4-methyl-6-(4-nitrophenyl)pyrimidine.

a. 4-Mothoxycarbonyl-4-phenylpiperidine. To a stirred solution of $H_2SO_4$ (16 mL) in MeOH (400 mL), 4-phenyl-4-piperidinecarboxylic acid 4-methyl benzenesulfonate (37.7 g, 0.1 mole) was added and the mixture was stirred and refluxed for 8 hours. Excess methanol was evaporated at reduced pressure and the residue was poured into a mixture of ice and 6 N NaOH. The pH was adjusted to 10–11 by adding more 6 N NaOH and extracted with $CH_2Cl_2$ (3×150 mL). The combined $CH_2Cl_2$ extracts were dried ($MgSO_4$) and the solvent evaporated to leave the desired product as a viscous oil. The product (20.2 g, 92%) was used without further purification.

b. 3-(4-Methoxycarbonyl-4-phenylpiperidin-1-yl) propylazine.

A mixture of 4-methoxycarbonyl-4-phenylpiperidine (8.5 g, 0.039 mol), 3-bromopropylamine hydrobromide (12.7 g, 0.058 mol), potassium carbonate (13.475 g, 0.0957 mole), and KI (3.24 g, 0.0195 mol) in 1,4-dioxane (200 mL) was stirred and refluxed for 24 hours. Dioxane was evaporated at reduced pressure, the residue was treated with ice-cold 6 N NaOH (400 mL) and extracted with $CH_2Cl_2$ (4×120 mL).

Solvent was evaporated from the combined dried ($K_2CO_3$) extracts and the residue was purified by column chromatography on silica gel using $CHCl_3$/MeOH/2 M $NH_3$ in MeOH (20:2:1) as the eluent to afford the product as a viscous oil (7.8 g, 72%).

c. 1,6-Dihydro-5-methoxycarbonyl-1-{N-[3-(4-methoxycarbonyl-4-phenylpiperidin-1-yl)propyl]}carboxamido-2-[{(4-methoxyphenyl)methyl}thio]-4-methyl-6-(4-nitrophenyl)pyrimidine. This compound was prepared from 1,6-dihydro-5-methoxycarbonyl -2-[{(4-methoxyphenyl) methyl}thio]-4-methyl-6-(4-nitr ophenyl)-1-[(4-nitrophenyl-oxy)carbonyl]pyrimidine (1.0 g, 1.69 mmol), 3-[4-methoxycarbonyl-4-phenyl piperidin-1-yl] propylamine (0.56 g, 2.03 mmol, 1.2 eq) and purified using similar conditions described in Example 1 (1.085 g, 88%); m.p. 140–141° C.; $^1$H-NMR ($CDCl_3$): δ 1.62–1.74 (m, 2H), 1.82–2.18 (m, 4H), 2.21 (s,. 3H), 2.35–2.58 (m, 4H), 2.75–2.89 (m, 2H), 3.18–3.30 (m, 1H), 3.42–3.58 (m, 1H), 3.61 (s, 3H), 3.66 (s, 3H), 3.75 (s, 3H), 3.91, 4.15 (AB q, J=13.6 Hz, 2H), 6.14 (s, 1H), 6.69 (d, J=8.6 Hz, 2H), 7.02 (d, J=8.6 Hz, 2H), 7.20–7.37 (m, 7H), 7.56 (br t, 1 H, NH), 7.90 (d, J=8.8 Hz, 2H); Anal. Calcd. for $C_{38}H_{43}N_5O_8S$: C, 62.54; H, 5.94; N, 9.60. Found: C, 62.41; H, 6.06; N, 9.34.

EXAMPLE 5

5-Methoxycarbonyl-4-methyl-6-(4-nitrophenyl) 1-{N-[3-(4,4-diphenyl-piperidin-1-yl)propyl]}carboxamido-1,2, 3,6-tetrahydro-2-thioxo-pyrimidine.

To a stirred solution of 1,6-dihydro-6-methoxycarbonyl-2-[{(4-methoxyphenyl)methyl}thio]-4-methyl-6-(4-nitrophenyl)-1-{N-[3-(4,4-diphenylpiperidin-1-yl)propyl]} carboxamidopyrimidine (0.14 g, 0.187 mmol) and ethanethiol (0.5 mL) in $CH_2Cl_2$ (5 mL) at 5° C. under argon, TFA (0.5 mL) was added and the mixture was allowed to warm to room temperature. After 3 hours, solvents were evaporated completely, the residue was redissolved in EtOAc (10 mL), washed with 5% $NaHCO_3$ (5×1 mL) and dried ($MgSO_4$). Solvent was evaporated and the residue was purified by column chromatography using 1:1 hexane/EtOAc to 100% EtOAc as gradient eluent. The oily product was crystallized from hexane and EtOAc (0.096 g, 82%); m.p. 130–131° C.; $^1$H-NMR ($CDCl_3$): δ 1.65–1.80 (m, 2H), 2.31 (s, 3H), 2.31–2.49 (m, 10H), 3.25–3.55 (m, 2H), 3.76 (s, 3H), 7.01 (s, 1H), 7.09–7.29 (m, 6H), 7.41 (d, J=8.2 Hz, 2H), 8.11 (d, J=8.8 Hz, 2H), 9.76 (br t, 1 H, NH); Anal. Calcd. for $C_{34}H_{37}N_5O_6S\cdot 0.3\ H_2O$: C, 64.50; H, 5.89; N, 11.06. Found: C, 64.45; H, 6.05; N, 10.87.

EXAMPLE 6

5-Methoxycarbonyl-4-methyl-6-(4-nitrophenyl)-1-{N-[3-(4-phenyl-piperidin-1-yl)propyl]}carboxamido-1,2,3,6-tetrahydro-2-thioxo-pyrimidine.

This compound was prepared from 1,6-dihydro-3-{N-[3-(4-phenylpiperidin-1-yl)propyl]}carboxamido-6-methoxycar bonyl-2-[{(4-methoxyphenyl) methyl}thio]-6-(4-nitrophe nyl)-4-methylpyrimidine (0.15 g, 0.223 mmol) using the procedure described in Example 5 and purified by flash column chromatography (0.102 g, 83%); m.p. 134–135° C.; $^1$H-NMR ($CDCl_3$): b 1.72–1.94 (m, 4H), 1.96–2.11 (m, 2 H), 2.36 (s, 3H), 3.0–3.09 (m, 2H), 3.32–3.49 (m, 2 H), 3.76 (s, 3H), 7.06 (s, 1H), 7.17–7.30 (m, 6H), 7.42 (d, J=8.7 Hz, 2H), 8.11 (d, J=8.8 Hz, 2H), 9.80 (br t, 1 H, NH); Anal. Calcd. for $C_{28}H_{33}N_5O_5S$: C, 60.96; H, 6.03; N, 12.70. Found: C, 60.63; H, 5.78; N, 12.55.

EXAMPLE 7

1-{N-[3-(4-Cyano-4-phenylpiperidin-1-yl)propyl]}carboxamido-5-methoxycarbonyl-4-methyl-6-(4-nitrophenyl)-1,2,3,6-tetrahydro-2-thioxo pyrimidine.

This compound was prepared from 1-{N-[3-(4-cyano-4-phenylpiperidin-1-yl) propyl]}carboxamido-1,6-dihydro-6-methoxycarbonyl-2-[{(4-methoxyphenyl)methyl}thio]-6-(4-nitrophenyl)-4-methylpyrimidine (0.15 g, 0.215 mmol) using the procedure described in Example 5 and purified by flash column chromatography (0.118 g, 95%); m.p. 137–138° C.; $^1$H-NMR ($CDCl_3$): b 1.69–1.85 (m, 2H), 2.07–2.20 (m, 4H), 2.37 (s, 3H), 2.37–2.60 (m, 4H), 2.96–3.06 (m, 2H), 3.31–3.86 (m, 2H), 3.76 (s, 3H), 7.09 (s, 1H), 7.31–7.49 (m, 7H), 7.92 (br s, 1 H, NH), 8.12 (d, J=8.8 Hz, 2H), 9.84 (br t, 1 H, NH); Anal. Calcd. for $C_{29}H_{32}N_6O_5S$: C, 60.53; H, 5.74; N, 14.49. Found: C, 60.53; H, 5.74; N, 14.48.

EXAMPLE 8

5-Methoxycarbonyl-1-{N-[3-(4-methoxycarbonyl-4-phenylpiperidin-1-yl)propyl]}carboxamido-4-methyl-6-(4-nitrophenyl)-1,2,3,6-tetrahydro-2-thioxo pyrimidine This compound was prepared from 1,6-dihydro-6-methoxy carbonyl-3-{N-[4-methoxycarbonyl-phenyl-piperidin-1-yl]propyl}carboxamido-2-[{(4-methoxyphenyl)methyl}thio]-6-(4-nitrophenyl)-4-methylpyrimidine (0.730 g, 1 mmol) using the procedure described in Example 5 and purified by flash column chromatography (0.57 g, 94%); m.p. 135–136° C.; $^1$H-NMR ($CDCl_3$): δ 1.62–2.13 (m, 6H), 2.32 (s, 3H), 2.33–2.39 (m, 4H), 2.76–2.84 (m, 2H), 3.34–3.43 (m, 2H), 3.61 (s, 3H), 3.75(s, 3H), 7.04 (s, 1H), 7.21–7.35 (m, 5H), 7.40 (d, J=8.6 Hz, 2H), 7.82 (br s, 1 H, NH), 8.10 (d, J=8.9 Hz, 2H), 9.76 (br t, 1 H, NH); Anal. Calcd. for $C_{30}H_{35}N_5O_7S$: C, 59.10; H, 5.79; N, 11.49. Found: C, 59.08; H, 5.91; N, 11.31.

EXAMPLE 9

1-{N-[3-(4-(4-Methoxyphenyl)-4-phenylpiperidin-1-yl) propyl]}carboxamido-5-methoxycarbonyl-4-methyl-6-(4-nitrophenyl)-1,2,3,6-tetrahydro-2-thioxo pyrimidine.

a. 4-(4-Methoxyphenyl)-4-phenylpiperidine. 4-Hydroxy-4-phenylpiperidine (5.00 g, 28.2 mmol) was added to a suspension of $AlCl_3$ (18.8 g, 0.141 mol, 5.00 eq) in anhydrous anisole (100 mL). The mixture was stirred at room temperature for 1 hours and then heated to 50° C. for 3.5 hours. It was cooled to room temperature and poured cautiously into ice-water. The mixture was basified to pH 11 by addition of 6 N aqueous NaOH, and extracted with EtOAc (3×75 mL). The combined organic extracts were applied directly to a flash chromatography column, which was eluted with $CH_2Cl_2$/0.67 M $NH_3$ in MeOH (4:1) to afford 1.683 g (22%) of light yellow oil, which was characterized spectroscopically.

b. 3-[4-(4-Methoxyphenyl)-4-phenylpiperidin-1-yl] propionitrile. Acrylonitrile (1.03 mL, 15.7 mmol, 2.50 eq) was added at 0° C. to a solution of 4-(4-methoxyphenyl)-4-phenylpiperidine (1.68 g, 6.28 mmol) in EtOH (20 mL) and the resulting solution was stirred for 1.5 hours at room temperature. After removal of the solvent, the residue was purified by flash chromatography ($SiO_2$, EtOAc—$CHCl_3$ 1:3) to give 1.41 g (70%) of colorless oil, which was characterized spectroscopically.

c. 3-[4-(4-Methoxyphenyl)-4-phenylpiperidin-1-yl] propylamine. To a stirred solution of 3-[4-(4-methoxyphenyl)-4-phenylpiperidin-1-yl]pro pionitrile (1.41 g, 4.40 mmol) in anhydrous THF (10 mL) under argon was added a solution of $BH_3$ in THF (1.0 M, 11.0 mL, 2.5 eq) at room temperature. The mixture was refluxed for 4.5 hours and then cooled to room temperature. Aqueous HCl (6 N, 15 mL) was added and stirring was continued for 2 h at 55–60° C. The mixture was basified to pH 9 by addition of 6 N aq. NaOH and extracted with $CH_2Cl_2$ (3×75 mL). The combined organic solutions were dried ($MgSO_4$) and concentrated. The residue was dissolved in $CH_2Cl_2$ (10 mL) and treated with HCl in ether (1.0 M, 9.0 mL, 2.0 eq). The solvents were removed, ether (30 mL) was added, the mixture was filtered, and the filter cake was washed with ether (2×10 mL). Water (20 mL) was added to the resulting white solid, the pH was adjusted to 10 with 1 N NaOH, and the aqueous phase was extracted with $CH_2Cl_2$ (3×40 mL). The combined organic extracts were dried ($MgSO_4$) and concentrated to give 610 mg (43%) of white solid, which was characterized spectroscopically.

d. 1-{N-[3-(4-(4-Methoxyphenyl)-4-phenylpiperidin-1-yl) propyl]}carboxamido-5-methoxycarbonyl-4-methyl-6-(4-nitrophenyl)-1,2,3,6-tetrahydro-2 -thioxopyrimidine.

To a stirred mixture of 1,6-dihydro-5-methoxycarbonyl-2-[{(4-methoxyphenyl)methyl}thio]-4-methyl-6-(4-nitrop henyl)-1-[(4-nitrophenyloxy)carbonyl]pyrimidine (0.592 g, 1 mmol) and $K_2CO_3$ (0.276 g, 2 mmol) in anhydrous THF (10 mL) at room temperature under argon atmosphere, a solution of 3-[4-(4-methoxyphenyl)-4-phenyl piperidin-1-yl]propylamine (0.390 g, 1.2 mmol, 1.2 eq) in THE (10 mL) was added and the stirring was continued for 1 hour. Solvent was evaporated from the reaction -mixture and the residue was redissolved in $CH_2Cl_2$ (50 mL), washed with 5% $NaHCO_3$ (3×25 mL), brine (50 mL), and dried ($MgSO_4$). The $CH_2Cl_2$ solution was filtered and cooled to 5° C. To this, ethanethiol (0.5 mL) and TFA (0.5 mL) were added and the mixture was stirred and allowed to warm to room temperature. After 3 hours, solvents were evaporated completely, the residue was redissolved in EtOAc (10 mL), washed with 5% $NaHCO_3$ (5×1 mL), and dried ($MgSO_4$). Solvent was evaporated and the residue was purified by column chromatography using 1:1 hexane/EtOAc to 100% EtOAc as gradient eluent. The oily product was crystallized from hexane and EtOAc (0.41 g, 62%); m.p. 120–121° C.; $^1$H-NMR ($CDCl_3$): δ 1.60–1.80 (m, 2H), 2.31 (s, 3H), 2.31–2.51 (m, 8H), 3.32–3.43 (m, 2H), 3.75 (s, 3H), 3.76 (s, 3H), 6.77 (d, J=8.8 Hz, 2H), 7.02 (s, 1H), 7.12 (d, J=8.6 Hz, 2H), 7.20–7.27 (m, 6H), 7.41 (d, J=8.6 Hz, 2H), 8.11 (d, J=8.8 Hz, 2H), 9.76 (br t, 1 H, 2H); Anal. Calcd. for $C_{35}H_{39}N_5O_6S$: C, 63.91; H, 5.98; N, 10.65. Found: C, 64.19; H,6.22; N, 10.36.

EXAMPLE 10 a. 4-Ethoxycarbonyl-4-phenylpiperidine. To a stirred solution of $H_2SO_4$ (1.62 g, 16.56 mmol) in EtOH (200 mL), 4-phenyl-4-piperidine-carboxylic acid 4-methyl benzenesulfonate (25 g, 66.23 mmol) was added and the mixture was stirred and refluxed for 12 hours. Excess ethanol was evaporated at reduced pressure and the residue was poured into a mixture of ice and 6 N NaOH. The pH was adjusted to 10–11 by adding more 6 N NaOH and extracted with $CH_2Cl_2$ (3×100 mL). The combined $CH_2Cl_2$ extracts were dried ($MgSO_4$) and the solvent evaporated to leave the desired product as a colorless viscous oil, the $^1$H-NMR showed it to be pure (14.68 g, 95%) and was used without any further purification.

b. 3-(4-Ethoxycarbonyl-4-phenylpiperidin-1-yl) propylamine.

A mixture of 4-ethoxycarbonyl-4-phenylpiperidine (30.5 g, 0.131 mol), 3-bromopropylamine hydrobromide (42.93 g, 0.196 mol), potassium carbonate (36.14 g, 0.241 mole), and KI (10.8 g, 0.065 mol) in 1,4-dioxane (500 mL) was stirred and refluxed for 24 hours. Dioxane was evaporated at reduced pressure, the residue was treated with ice-cold 6 N NaOH (400 mL) and extracted with $CH_2Cl_2$ (4×120 mL) Solvent was evaporated from the combined dried ($K_2CO_3$) $CH_2Cl_2$ extracts and the residue was purified by column chromatography on silica gel using $CHCl_3$/MeOH/2 M $NH_3$ in MeOH (20:2:1) as the eluent to afford the product as a viscous oil (24.2 g, 83.3%).

c. 1-{N-[3-(4-Ethoxycarbonyl-4-phenylpiperidin-1-yl) propyl]}carboxamido-5-methoxycarbonyl-4-methyl-6-(4-nitrophenyl)-1,2,3,6-tetra-hydro-2-thioxopyrimidine. This compound was prepared from 1,6-dihydro-5-methoxycarbonyl-2-[{(4-methoxyphenyl)me thyl}thio]-4-methyl-6-(4-nitrophenyl)-1-[(4-nitrophen yloxy)carbonyl]pyrimidine (0.592 g, 1 mmol), $K_2CO_3$ (0.276 g, 2 mmol), 3-[4-ethoxycarbonyl-4-phenyl piperidin-1-yl]propylamine (0.350 g, 1.2 mmol, 1.2 eq), ethanethiol (0.5 mL), and TFA (0.5 mL) using the procedure described in Example 10 and purified by flash column chromatography (0.295 g, 47%); m.p. 125–126° C.; $^1$H-NMR ($CDCl_3$): δ 1.13 (t, J=7 Hz, 3H), 1.62–1.80 (m, 2H), 1.87–2.0 (m, 2H), 2.06–2.18 (m, 2H), 2.31 (s, 3H), 2.34–2.39 (m, 2H), 2.50–2.55 (m, 2H), 2.79–2.83 (m, 2H), 3.30–3.51 (m, 2H), 3.74 (s, 3H), 4.07 (q, J=7 Hz, 2H), 7.03 (s, 1H), 7.18–7.36 (m, 6H), 7.40 (d, J=8.8 Hz, 2H), 8.08 (d, J=8.8 Hz, 2H), 9.78 (br t, 1 H, NH); Anal. Calcd. for $C_{31}H_{37}N_5O_7S$: C, 59.70; H, 5.98; N, 11.23. Found: C, 59.55; H, 5.99; N, 11.43.

EXAMPLE 11

1,6-Dihydro-1-{N-[3-(4,4-diphenylpiperidin-1-yl)propy l]}carboxamido-2-methoxy-5-methoxycarbonyl-4-methyl-6-(4-nitrophenyl)pyrimidine. To a stirred mixture of 1,6-dihydro-2-methoxy-5-methoxycarbonyl-4-methyl -6-(4-nitrophenyl)-1-[(4-nitrophenyloxy) carbonyl]pyri midine (0.940 g, 2 mmol) and $K_2CO_3$ (0.552 g, 4 mmol) in anhydrous THF (20 mL) at room temperature under argon atmosphere, a solution of 3 [4,4-diphenylpiperidin-1-yl] propylamine (0.882 g, 3 mmol, 1.5 eq) in THF (5 mL) was added and the stirring was continued for 1 hour. Solvent was evaporated from the reaction mixture, the residue was redissolved in $CH_2Cl_2$ (50 mL), washed with 5% $NaHCO_3$ (3×25 mL), brine (50 mL), and dried ($MgSO_4$). Solvent was evaporated and the residue was purified by flash chromatography on silica gel using 10% methanol in EtOAc as the eluent to give the desired product as an oil, which on trituration with hexane and drops of EtOAc became a white powder (1.10 g, 88%); m.p. 95–96 ° C.; $^1$H-NMR ($CDCl_3$): δ 1.61–1.71 (m, 2H), 2.26–2.33 (m, 2H), 2.38 (s, 3H), 2.39–2.50 (m, 8H), 3.20–3.41 (m, 2H), 3.65 (s, 3H), 3.89 (s, 3H), 6.65 (s, 1H), 6.84 (br t, 1 H, NH), 7.08–7.29 (m, 10H), 7.40 (d, J=8.7 Hz, 2H), 8.03 (d, J=8.6 Hz, 2H); Anal. Calcd. for $C_{35}H_{39}N_5O_6$. 0.75 $CH_2Cl_2$: C, 62.28; H, 5.92; N, 10.16. Found: C, 62.23; H, 5.76; N, 10.12.

EXAMPLE 12

5-Methoxycarbonyl-4-methyl-6-(4-nitrophenyl)-1-{N-[3-(4,4-diphenyl-piperidin-1-yl)propyl]}carboxamido-2-oxo-1,2,3,6-tetrahydropyrimid-ine.

a. 1,6-Dihydro-5-methoxycarbonyl-2-methoxy-4-methyl-6-(4-nitro-phenyl) pyrimidine.

A mixture of methyl 2-{(4-nitrophen-yl)methylene}-3-oxobutyrate (12.46 g, 0.05 mol), O-methylisourea hydrogen sulfate (10.32 g, 0.06 mol), and NaOAc (9.84 g, 0.06 mol) in DMF (50 mL) was stirred and heated at 70–75° C. for 4 hours. The mixture was cooled and poured into ice-water (300 mL). The precipitate formed was filtered, washed with water, and dried. The crude product was purified by flash column chromatography on silica gel using 10% through 30% EtOAc in hexane as the gradient eluent (9.8 g, 64%). The $^1$H-NMR analysis of the product showed it to be a 19:1 mixture of the amine/imine tautomers which was used as such in the next step. $^1$H-NMR ($CDCl_3$): δ 2.32, 2.38 (2 s, 3H), 3.59, 3.70 (2 s, 3H), 3.70, 3.85 (2 s, 3H), 5.40, 5.66 (s, d, J=3 Hz, 1H), 5.50, 6.08 (s, d, J=3 Hz, 1H), 7.43, 7.45 (2 d, J=9 Hz, 2H), 8.10, 8.11 (2 d, J=9 Hz, 2H).

b. 1,6-Dihydro-2-methoxy-5-methoxycarbonyl-4-methyl-6-(4-nitrophenyl)-1-[(4-nitrophenyloxy)carbonyl]pyrimidine.

To a well-stirred mixture of 1,6-dihydro-2-methoxy-5-methoxycarbonyl-4-methyl-6-(4-nitrophenyl)pyrimidine (5.7 g, 0.0187 mol), NaHCO$_3$ (6.27 g, 0.074 mol), CH$_2$Cl$_2$ (200 mL), and water (50 mL) at 0–5° C., 4-nitrophenyl chloroformate (3.76 g, 0.0186 mol) was added in 5 min and the mixture was allowed to warm to room temperature. After 10 hours, the TLC analysis of the reaction mixture showed the presence of a small amount of starting pyrimidine, therefore, more 4-nitrophenyl chloroformate (0.65 g, 0.0032 mol) was added and the stirring continued for an additional 4 hours. The two layers were separated, the CH$_2$Cl$_2$ layer was washed with saturated aqueous NaHCO$_3$ solution (3×50 mL), dried (MgSO$_4$), and the solvent evaporated. The residue was recrystallized from CH$_2$Cl$_2$ and hexane to give the product as white crystals (12.8 g, 89%); $^1$H-NMR (CDCl$_3$): δ 2.48 (s, 3H), 3.69 (s, 3H), 3.94 (s, 3H), 6.34 (s, 1H), 7.36 (d, J=9.1 Hz, 2H), 7.46 (d, J=8.7 Hz, 2H), 8.14 (d, J=8.7 Hz, 2H), 8.26 (d, J=9.1 Hz, 2H); m.p. 168–169° C. Anal. Calcd. for C$_{21}$H$_{18}$N$_4$O$_9$: C, 53.62; H, 3.86; N, 11.91. Found: C, 53.69; H, 3.92; N, 11.85.

c. 5-Methoxycarbonyl-4-methyl-6-(4-nitrophenyl)-1-{N-[3-(4,4-di-phenylpiperidin-1-yl)propyl]}carboxamido-2-oxo-1,2,3,6-tetrahydro-pyrimidine.

To a stirred solution of 1,6-dihydro-2-methoxy-6-methoxycarbonyl-4-methyl-6-(4-nitrophenyl)-1-{N-[3-(4,4-diphenylpiperidin-1-yl)propyl]} carboxamidopyrimi dine (0.208 g, 0.33 mmol) in THF (10 mL) at 5° C. under argon, 3 N HCl (6 mL) was added and the mixture was allowed to warm to room temperature. After 2 hours, solvents were evaporated completely, the residue was treated with 40 mL of 10% NaHCO$_3$, the product was extracted with CH$_2$Cl$_2$ (2×15 mL) and the combined extracts were dried (MgSO$_4$). Solvent was evaporated and the residue was crystallized from hexane and EtOAc (0.20 g, 97%); m.p. 197–198° C.; $^1$H-NMR (CDCl$_3$): δ 1.63–1.67 (m, 2H), 2.23–2.28 (m, 2H), 2.34 (s, 3H), 2.37–2.42 (m, 8H), 3.20–3.41 (m, 2H), 3.69 (s, 3H), 6.75 (s, 1H), 7.08–7.26 (m, 11H), 7.46 (d, J=8.7 Hz, 2 H), 8.08 (d, J=8.7 Hz, 2H), 8.77 (br t, 1 H, NH); Anal. Calcd. for C$_{34}$H$_{37}$N$_5$O$_6$: C, 66.76; H, 6.10; N, 11.45. Found: C, 66.48; H, 5.97; N, 11.25.

EXAMPLE 13

1-{N-[3-(4-(4-Methoxyphenyl)-4-phenylpiperidin-1-yl) propyl}]carboxamido-5-methoxycarbonyl-4-methyl-6 -(4-nitrophenyl)-2-oxo-1,2,3,6-tetrahydropyrimidine.

To a stirred mixture of 1,6-dihydro-2-methoxy-5-methoxycarbonyl-4-methyl-6-(4-nitrophenyl) -1-[(4-nitrophenyloxy)carbonyl]pyrimidine (0.47 g, 1 mmol) and K$_2$CO$_3$ (0.552 g, 4 mmol) in anhydrous THF (10 mL) at room temperature under argon atmosphere, a solution of 3-[4-(4-methoxyphenyl)-4-phenyl piperidin-1-yl]propylamine (0.390 g, 1.2 mmol, 1.2 eq) in THF (10 mL) was added and the stirring was continued 6 for 2 hours. The solid was removed by filtration and the solution was cooled to 0–5° C. 6N HCl (2 mL) was added to the solution and stirring was continued. After 3 hours, solvents were evaporated completely, the residue was redissolved in CH$_2$Cl$_2$ (20 mL), washed with 10% NaHCO$_3$ (2×10 mL), and dried (MgSO$_4$). Solvent was evaporated and the residue was purified by column chromatography using 1:1 hexane/EtOAc to 1000 EtOAc as gradient eluent. The oily product was crystallized from hexane and EtOAc (0.55 g, 86%); m.p. 100–102° C.; $^1$H-NMR (CDCl$_3$): δ 1.65–1.80 (m, 2H), 2.26–2.31 (m, 2 H), 2.35 (s, 3H), 2.39–2.44 (m, 6H), 3.18–3.40 (m, 2 H), 3.69 (s, 3H), 3.73 (s, 3H), 6.75 (s, 1H), 7.60 (d, J=8.7 Hz, 2H), 6.84 (br s, 1 H, NH), 7.10 (d, J=8.7 Hz, 2H), 7.18–7.26 (m, 5H), 7.46 (d, J=8.6 Hz, 2H), 8.08 (d, J=8.6 Hz, 2H), 8.78 (br t, 1 H, NH); Anal. Calcd. for C$_{35}$H$_{39}$N$_5$O$_7$. 0.12 CH$_2$Cl$_2$.0.12 EtOAc: C, 64.54; H, 6.12; N, 10.57. Found: C, 64.44; H, 6.12; N, 10.28.

EXAMPLE 14

1-{N-[3-(4-Methoxycarbonyl-4-phenylpiperidin-1-yl) propyl]}carboxamido-5-methoxycarbonyl-4-methyl-6-(4-nitrophenyl)-2-oxo-1,2,3,6-tetrahydropyrimidine (Scheme 2).

To a stirred mixture of 1,6-dihydro-2-methoxy-5-methoxycarbonyl-4-methyl-6-(4-nitrophenyl)-1-[(4-nitrophenyloxy)carbonyl]pyrimidine (0.47 g, 1 mmol), K$_2$CO$_3$ (0.276 g, 2 mmol) in anhydrous THF (10 mL) at room temperature under argon atmosphere, a solution of 3-[4-methoxycarbonyl-4-phenylpiperidin-1-yl]propylamine (0.332 g, 1.2 mmol, 1.2 eq) in THF (10 mL) was added and the stirring was continued for 2 hours. The solid was removed by filtration and the solution was cooled to 0–5° C. To this, 6 N HCl (2 mL) was added and the stirring continued. After 3 hours, solvents were evaporated completely, the residue was redissolved in CH$_2$Cl$_2$ (20 mL), washed with 10% NaHCO$_3$ (2×10 mL), and dried (MgSO$_4$). Solvent was evaporated and the residue was purified by column chromatography using 1:1 hexane/EtOAc to 100% EtOAc as gradient eluent. The oily product was crystallized from hexane and EtOAc (0.55 g, 86%); m.p. 180–181° C.; $^1$H-NMR (CDCl$_3$): δ 1.60–1.80 (m, 2H), 1.85–1.95 (m, 2H), 2.03–2.10 (m, 2H), 2.28–2.33 (m, 2H), 2.35 (s, 3H), 2.48–2.50 (m, 2H), 3.20–3.40 (m, 2H), 3.60 (s, 3H), 3.68 (s, 3H), 6.75 (s, 1H), 7.20–7.34 (m, 6H), 7.46 (d, J=8.8 Hz, 2 H), 8.07 (d, J=8.8 Hz, 2H), 8.78 (br t, 1 H, NH); Anal. Calcd. for C$_{30}$H$_{35}$N$_5$O$_8$: C, 60.70; H, 5.94; N, 11.80. Found: C, 60.71; H, 5.99; N, 11.43.

EXAMPLES 14a & 14b (+)-1-{N-[3-(4-Methoxycarbonyl-4-phenylpiperidin-1-yl) propyl]}carboxamido-5-methoxycarbonyl-4-methyl-6-(4-nitrophenyl)-2-oxo-1,2,3,6-tetrahydropyrimidine and (−)-1-{N-[3-(4-Methoxycarbonyl-4-phenyl-piperidin-1-yl) propyl]}carboxamido-5-methoxycarbonyl-4-methyl-6-(4-nitrophenyl)-2-oxo-1,2,3,6-tetrahydropyrimidine (Scheme 3).

a. (−)-1,6-Dihydro-2-methoxy-5-methoxycarbonyl-4-methyl-6-(4-nitro-phenyl)-1-{N-[(2-phenyl)ethyl]} carboxamidopyrimidine and (+)-1,6-Dihydro-2-methoxy-5-methoxycarbonyl-4-methyl-6-(4-nitrophenyl)-1-{N-[(2-phenyl)ethyl]}carboxamidopyrimidine.

To a stirred solution of (±)-1,6-dihydro-2-methoxy-5-methoxycarbonyl-4-methyl-6-(4-nitrophenyl)-1-[(4-nitrophenyloxy)carbonyl]pyrimidine (2.66 g, 5.6 mmol) in anhydrous THF (80 mL) at room temperature under argon atmosphere, a solution of (S)-(−)-α-methylbenzylamine (0.82 g, 6.78 mmol, 1.2 eq) in THF (5 mL) was added and the stirring was continued for 6 hours. Solvent was evaporated from the reaction mixture, the residue was redissolved in CH$_2$Cl$_2$ (50 mL), washed with 5% NaHCO$_3$ (3'25 mL), brine (50 mL), and dried (MgSO$_4$). Solvent was evaporated and the residue was purified by flash chromatography on silica gel using 5% to 30% EtOAc in hexane as the gradient eluent. The first major product to elute was (−)-1,6-dihydro-2-methoxy-5-methoxy carbonyl-4-methyl-6-(4-nitrophenyl)-1-{N-[(2-phenyl) ethyl]}carboxamidopyrimidine and this compound was crystallized from isopropyl ether (0.85 g, 33.6%); m.p. 119–120° C.; [α]$_D$=−329.32 (CH$_2$Cl$_2$, 10.3 g/100 mL); $^1$H-NMR (CDCl$_3$): δ 1.47 (d, J=7 Hz, 3H), 2.40 (s, 3H), 3.61 (s, 3H), 3.95 (s, 3H), 4.96 (quint, J=6.5 Hz, 2H), 6.66 (s, 1H), 6.82 (d, J=6.8 Hz, 1H, NH), 7.22–7.36 (m, 5H), 7.43 (d, J=8.6 Hz, 2H), 8.09 (d, J=8.6 Hz, 2H); Anal. Calcd. for $C_{23}H_{24}N_4O_6$: C, 61.06; H, 5.35; N, 12.38. Found: C, 60.85; H, 5.13; N, 12.42. The second major compound to elute was (+)-1,6-dihydro-2-methoxy-5-methoxycarbonyl-4-methyl-6-(4-nitrophenyl)-1-{N-[(2-phenyl)ethyl]}carboxamido pyrimidine and this compound was crystallized from isopropyl ether (0.92 g, 36.4%); m.p. 138–140° C.; $[\alpha]_D$=+171.81 ($CH_2Cl_2$, 11.31 g/100 mL); $^1$H-NMR ($CDCl_3$): δ 1.47 (d, J=7 Hz, 3H), 2.42 (s, 3H), 3.644 (s, 3H), 3.917 (s, 3H), 4.989 (quint, J=6.5 Hz, 2H), 6.70 (s, 1H), 6.81 (d, J=6.8 Hz, 1 H, NH), 7.22–7.35 (m, 5H), 7.36 (d, J=8.6 Hz, 2H), 8.04 (d, J=8.6 Hz, 2H); Anal. Calcd. for $C_{23}H_{24}N_4O_6$: C, 61.06; H, 5.35; N, 12.38. Found: C, 60.95; H, 5.20; N, 12.38.

b. (+)-1-{N-[3-(4-Methoxycarbonyl-4-phenyl piperidin-1-yl)propyl]}carboxamido-5-methoxycarbonyl-4-methyl-6-(4-nitrophenyl)-2-oxo-1,2,3,6-tetrahydro pyrimidine.

A solution of (+)-1,6-dihydro-2-methoxy-5-methoxy carbonyl-4-methyl-6-(4-nitrophenyl)-1-{N-[(2-phenyl)ethyl]}carboxamidopyrimidine (0.226 g, 0.5 mmol) and 1,8-diazabicyclo[5.4.0]-unde-7-ene (DBU) (0.076 g, 0.5 mmol) in $CH_2Cl_2$ (10 mL) was stirred and refluxed for 4 hours and the solvent evaporated. The product was purified by column chromatography using 30% EtOAc in hexane as the eluent. The product was found to be a mixture of the amine-imine tautomers (0.120 g, 78.7%); $[\alpha]_D$=+14.5 ($CH_2Cl_2$, 6 g/100 mL)

To a well-stirred solution of (+)-1,6-dihydro-5-methoxy carbonyl-2-methoxy-4-methyl-6-(4-nitrophenyl)pyrimidine (0.12 g, 0.393 mmol) and pyridine (0.5 mL) in $CH_2Cl_2$ (10 In- mL) at 0–5° C., 4-nitrophenyl chloroformate (0.095 g, 0.472 mmol) was added in 5 min and the mixture was allowed to warm to room temperature. After 2 h, saturated aqueous $NaHCO_3$ solution (10 mL) was added and the stirring continued for 30 min. The two layers were separated, the $CH_2Cl_2$ layer was washed with saturated aqueous $NaHCO_3$ solution (3×5 mL), dried ($Na_2SO_4$), and the solvent evaporated. The residue was redissolved in THF (10 mL) and mixed with $K_2CO_3$ (0.11 g, 0.8 mmol). To this, a solution of 3-[4-methoxycarbonyl-4-phenyl piperidin-1-yl]propylamine (0.138 g, 0.5 mmol) in THF (5 mL) was added and the mixture was stirred for 2 hours. The solid was removed by filtration and the solution was cooled to 0–5° C. To this, 6 N HCl (0.5 mL) was added and the stirring continued. After 3 hours, solvents were evaporated completely, the residue was redissolved in $CH_2Cl_2$ (20 mL), washed with 10% $NaHCO_3$ (4×5 mL), and dried ($MgSO_4$). Solvent was evaporated and the residue was purified by column chromatography using 1:1 hexane/EtOAc to 100% EtOAc as gradient eluent. The oily product was crystallized from hexane and EtOAc (0.19 g, 82%); m.p. 138–140° C.; $[\alpha]_D$=+108 ($CH_2Cl_2$, 6.65 g/100 mL); $^1$H-NMR ($CDCl_3$): 1.60–1.80 (m, 2H), 1.85–1.95 (m, 2H), 2.03–2.10 (m, 2H), 2.28–2.33 (m, 2H), 2.35 (s, 3H), 2.48–2.50 (m, 2H), 3.20–3.40 (m, 2H), 3.60 (s, 3H), 3.68 (s, 3H), 6.75 (s, 1H), 7.20–7.34 (m, 5H), 7.46 (d, J=8.8 Hz, 2H), 7.60 (br s, 1 H, N H), 8.07 (d, J=8.8 Hz, 2H), 8.–78 (br t, 1 H, NH); Anal. Calcd. for $C_{30}H_{35}N_5O_8$. 0.2 $CH_2Cl_2$. 0.2 EtOAc: C, 59.27; H, 5.94; N, 11.15. Found: C, 59.07; H, 5.76; N, 10.99.

c. (−)-1-{N-[3-(4-Methoxycarbonyl-4-phenyl piperidin-1-yl)propyl })carboxamido-5-methoxy carbonyl-4-methyl-6-(4-nitrophenyl)-2-oxo-1,2,3,6-tetrahydropyrimidine.

A solution of (−)-1,6-dihydro-2-methoxy-5-methoxy carbonyl-4-methyl-6-(4-nitrophenyl)-1-{N-[(2-phenyl)ethyl]}carboxamidopyrimidine (0.35 g, 0.774 mmol) and 1,8-diazabicyclo[5.4.0]-unde-7-ene (DBU) (0.117 g, 0.774 mmol) in $CH_2Cl_2$ (10 mL) was stirred and refluxed for 8 hours and the solvent evaporated. The product was purified by column chromatography using 30% EtOAc in hexane as the eluent. The product, (−)-1,6-dihydro-5-methoxycarbonyl-2-methoxy-4-methyl-6-(4-nitrophenyl) pyrimidine, was found to be a mixture of the amine-imine tautomers (0.170 g, 72%). To a well-stirred solution of (−)-1,6-dihydro-5-methoxy carbonyl-2-methoxy-4-methyl-6-(4-nitrophenyl)pyrimidine (0.152 g, 0.5 mmol) and pyridine (0.5 mL) in $CH_2Cl_2$ (10 mL) at 0–5° C., 4-nitrophenyl chloroformate (0.121 g, 0.6 mmol) was added in 5 min and the mixture was allowed to warm to room temperature. After 2 hours, saturated aqueous $NaHCO_3$ solution (10 mL) was added and the stirring continued for 30 min. The two layers were separated, the $CH_2Cl_2$ layer was washed with saturated aqueous $NaHCO_3$ solution (3×5 mL), dried ($Na_2SO_4$), and the solvent evaporated. The residue was redissolved in THF (10 mL) and mixed with $K_2CO_3$ (0.165 g, 1.2 mmol). To this, a solution of 3-[4-methoxycarbonyl-4-phenylpiperidin-1-yl]propylamine (0.166 g, 0.6 mmol) in THF (5 mL) was added and the mixture was stirred for 2 hours. The solid was removed by filtration and the solution was cooled to 0–5° C. To this, 6 N HCl (0.5 mL) was added and the stirring continued. After 3 hours, solvents were evaporated completely, the residue was redissolved in $CH_2Cl_2$ (20 mL), washed with 10% $NaHCO_3$ (4×5 mL), and dried ($MgSO_4$). Solvent was evaporated and the residue was purified by column chromatography using 1:1 hexane/EtOAc to 100% EtOAc as gradient eluent. The oily product was crystallized from hexane and EtOAc (0.19 g, 64%); m.p. 138–140° C.; $[\alpha]_D$=−106 ($CH_2Cl_2$, 3.95 g/100 mL); $^1$H-NMR ($CDCl_3$): δ 1.60–1.80 (m, 2H), 1.85–1.95 (m, 2H), 2.03–2.10 (m, 2H), 2.28–2.33 (m, 2H), 2.35 (s, 3H), 2.48–2.50 (m, 2H), 3.20–3.40 (m, 2H), 3.60 (s, 3H), 3.68 (s, 3H), 6.75 (s, 1H), 7.20–7.34 (m, 6H), 7.46 (d, J=8.8 Hz, 2H), 8.07 (d, J=8.8 Hz, 2H), 8.78 (br t, 1 H, NH); Anal. Calcd. for $C_{30}H_{35}N_5O_8$. 0.4 $CH_2Cl_2$: C, 58.18; H, 5.75; N, 11.16. Found: C, 58.25; H, 5.67; N, 10.98.

EXAMPLE 15

1-{N-[3-(4-Ethoxycarbonyl-4-phenylpiperidin-1-yl) propyl]}carboxamido-5-methoxycarbonyl-4-methyl-6-(4-nitrophenyl)-2-oxo-1,2,3,6-tetrahydropyrimidine.

To a stirred mixture of 1,6-dihydro-2-methoxy-5-methoxy carbonyl-4-methyl-6-(4-nitrophenyl)-1-[(4-nitrophenyl oxy)carbonyl]pyrimidine (0.235 g, 0.5 mmol), $K_2CO_3$ (0.138 g, 1 mmol) in anhydrous THF (10 mL) at room temperature under argon atmosphere, a solution of 3-[4 -ethoxycarbonyl-4-phenylpiperidin-1-yl]propylamine (0.174 g, 0.6 mmol, 1.2 eq) in THF (5 mL) was added and the stirring was continued for 4.5 h. The solid was removed by filtration and the solution was cooled to 0–5° C. To this, 6 N HCl (0.5 mL) was added and the stirring continued. After 1 hour, solvents were evaporated completely, the residue was redissolved in $CH_2Cl_2$ (20 mL), washed with 1 N $NaHCO_3$ (2×10 mL), and dried ($MgSO_4$). Solvent was evaporated and the residue was purified by column chromatography using 1:1 hexane/EtOAc to 100% EtOAc as gradient eluent. The oily product was crystallized from hexane and EtOAc (0.182 g, 60%); m.p. 79–80° C.; $^1$H-NMR ($CDCl_3$): δ 1.13 (t, J=7 Hz, 3H), 1.62–1.78 (m, 2H), 1.87–2.0 (m, 2H), 2.06–2.18 (m, 2H), 2.2–2.31 (m, 2H), 2.37(s, 3H), 2.50–2.55 (m, 2H), 2.72–2.80 (m, 2H), 3.25–3.40 (m, 2H), 3.68 (s, 3H), 4.07 (q, J=7 Hz, 2H), 6.75 (s, 1H), 7.18–7.36 (m, 6H), 7.48 (d, J 8.7 Hz, 2H), 8.11 (d, J=8.7 Hz, 2H), 8.79 (br t, 1 H, NH); Anal. Calcd. for $C_{31}H_{37}N_5O_8$. 0.5 $C_6H_{12}$. 1.25 $H_2O$: C, 62.71; H, 7.06; N, 11.55. Found: C, 62.90; H, 7.20; N, 11.33.

EXAMPLE 16

5-Benzyloxycarbonyl-1-{N-[3-(4-methoxycarbonyl-4-phenylpiperidin-1-yl)propyl]}carboxamido-4-methyl-6 -(3,4-methylenedioxyphenyl)-2-oxo-1,2,3,6-tetrahydro pyrimidine.

a. Benzyl 2-{(3,4-methylenedioxyphenyl)methylene}-3-oxobutyrate.

A mixture of 3,4-methylenedioxybenzaldehyde (15.013 g, 0.1 mol), benzyl acetoacetate (20.18 g, 0.105 mol), piperidine (0.41 g, 476 mL, 4.8 mmol), and acetic acid (0.288 g, 274 mL, 4.8 mmol) in 2-propanol (500 mL) was stirred at room temperature for 48 hours. The white solid, benzyl 2-{(3,4-methylenedioxyphenyl)methylene}-3-oxobutyrate, formed was filtered, washed with 2 -propanol (2×50 mL) and dried (29.84 g, 92%); m.p. a , 137–138° C.

b. 5-Benzyloxycarbonyl-1,6-dihydro-2-methoxy-4-methyl-6-(3,4-methylenedioxyphenyl)pyrimidine. A mixture of benzyl 2-{(3,4-methylenedioxyphenyl)methylene}-3-oxobutyrate (16.266 g, 0.05 mol), O-methylisourea hydrogen sulfate (10.32 g, 0.06 mol), and $NaHCO_3$ (8.4 g, 0.1 mol) in EtOH (400 mL) was stirred and heated at 85–90° C. for 48 h. The solid was removed by filtration and ethanol was evaporated from the filtrate. The residue was redissolved in EtOAc (300 mL), washed with water (2×100 mL), dried ($Na_2SO_4$), and the solvent evaporated. The crude product was purified by flash column chromatography on silica gel using 10% through 30% EtOAc in hexane as the gradient eluent, to leave the product as a viscous oil (11.8 g, 62%). The $^1$H-NMR analysis of the product showed it to be a 1:1 mixture of the amine/imine tautomers and was used as such in the next step.

c. 5-Benzyloxycarbonyl-1,6-dihydro-2-methoxy-4-methyl-6-(3,4-methylenedioxyphenyl)-1-[(4-nitrophenyloxy)carbonyl]pyrimidine.

To a well-stirred solution of 5-benzyloxycarbonyl-1,6-dihydro-2-methoxy-4-methyl-6-(3,4-methylenedioxyphenyl) pyrimidine (10.0 g, 0.0263) and pyridine (5 mL) in $CH_2Cl_2$ (500 mL) at 0–5° C., 4-nitrophenyl chloroformate (7.56 g, 0.038 mol) was added in 5 min and the mixture was allowed to warm to room temperature. After 16 hours, saturated aqueous $NaHCO_3$ solution (100 mL) was added and the stirring continued for 30 min. The two layers were separated, the $CH_2Cl_2$ layer was washed with saturated aqueous $NaHCO_3$ solution (3×50 mL), dried ($Na_2SO_4$), and the solvent evaporated. The residue on trituration with isopropyl ether gave the product as white crystals (12.8 g, 89%); m.p. 146–147° C.; $^1$H-NMR ($CDCl_3$): δ 2.46 (s, 3H), 3.93 (s, 3H), 5.19, 5.92 (AB q, J=12.6 Hz, 2H), 5. 92 (s, 2H), 6.22 (s, 1H), 6.68–6.78 (m, 3H), 7.15–7.29 (m, 5H), 7.30 (d, J=9.1 Hz, 2H), 8.22 (d, J=9.1 Hz, 2H); Anal. Calcd. for $C_{28}H_{23}N_3O_9$. 0.25 $H_2O$. 0.25 $CH_2Cl_2$: C, 59.40; H, 4.23; N, 7.36. Found: C, 59.42; H, 4.07; N, 7.30.

d. 5-Benzyloxycarbonyl-1-{N-[3-(4-methoxycarbonyl-4-phenylpiperidin-1-yl)propyl]}carboxamido-4-methyl-6 -(3,4-methylenedioxyphenyl)-2-oxo-1,2,3,6-tetrahydro pyrimidine.

To a stirred mixture of 5-benzyloxycarbonyl-1,6-dihydro -2-methoxy-4-methyl-6-(3,4-methylenedioxyphenyl)-1-[(4-nitrophenyloxy)carbonyl]pyrimidine (1.091 g, 2 mmol), $K_2CO_3$ (0.552 g, 4 mmol) in anhydrous THF (20 mL) at room temperature under argon atmosphere, a solution of 3-[4-methoxycarbonyl-4-phenylpiperidin-1-yl] propylamine (0.663 g, 2.4 mmol, 1.2 eq) in THF (10 mL) was added and the stirring was continued for 2 hours. The solid was removed by filtration and the solution was cooled to 0–5° C. To this, 6 N HCl (2 mL) was added and the stirring continued. After 3 hours, the solvent was evaporated completely, the residue was redissolved in $CH_2Cl_2$ (20 mL), washed with 10% $NaHCO_3$ (2×10 mL), and dried ($MgSO_4$). Solvent was evaporated and the residue was purified by column chromatography using 1:1 hexane/EtOAc to 100% EtOAc as gradient eluent, to afford the pure product as a white foam (0.55 g, 86%); m.p. 100–102° C.; $^1$H-NMR ($CDCl_3$):5 1.64–1.80 (m, 2H), 1.80–1.99 (m, 2H), 2.0–2.09 (m, 2H), 2.24–2.29 (m, 2 H), 2.33 (s, 3H), 2.48–2.50 (m, 2H), 2.76–2.83 (m, 2 H), 3.21–3.37 (m, 2H), 3.60 (s, 3H), 5.02, 5.18 (AB q, J=12.5 Hz, 2H), 5.88 (s, 2H), 6.61–6.78 (m, 3 H), 6.80 (s, 1H), 7.14–7.39 (m, 11H), 8.75 (br t, 1 H, NH); Anal. Calcd. for $C_{37}H_{40}N_4O_8$. 0.3 $H_2O$: C, 65.92; H, 6.07; N, 8.31. Found: C, 65.95; H, 6.00; N, 8.18.

EXAMPLE 17

5-Methoxycarbonyl-1-{N-[3-(4-methoxycarbonyl-4-phenylpiperidin-1-yl)propyl]}carboxamido-4-methyl-6 -(3,4-methylenedioxyphenyl)-2-oxo-1,2,3,6-tetra hydropyrimidine.

To a stirred solution of 5-benzyloxycarbonyl-1-{N-[3-(4-methoxycarbonyl-4-phenylpiperidin-1-yl)propyl]} carboxamido-4-methyl-6-(3,4-methylenedioxyphenyl)-2-oxo-1,2,3,6-tetrahydropyrimidine (0.320 g, 0.48 mmol) in methanol (20 mL) and HCOOH (1 mL) at 0–5° C., 10% Pd—C (0.26 g) was added in portions and the cooling bath was removed. TLC analysis of the reaction mixture at frequent intervals showed the completion of the reaction after 2 hours. The catalyst was removed by filtration and the solvent was evaporated to leave 1-{N-[3-(4-methoxycarbonyl-4-phenylpiperidin-1-yl) propyl]} carboxamido-4-methyl-6-(3,4-methylenedioxy phenyl)-2-oxo-1,2,3,6-tetrahydropyrimidine-5-carboxylic acid as a white solid (0.275 g, 99%). The product was used in the next step without any further purification and characterization. A mixture of 1-{N-[3-(4-methoxycarbonyl-4-phenylpiperidin-1-yl)propyl]}carboxamido-4-methyl-6-(3,4-methylenedioxy phenyl)-2-oxo-1,2,3,6-tetrahydropyrimidine-5-carboxylic acid (0.2 g, 0.346 mmol), 1-(3-dimethylamino propyl)-3-ethylcarbodiimide hydrochloride (0.382 g, 2 mmol), and 4-(N,N-dimethylamino)pyridine (0.488 g, 4 mmol), in methanol (20 mL) was stirred and refluxed for 5 h and the solvent evaporated. The residue was redissolved in $CH_2Cl_2$ (15 mL), washed with saturated aqueous ammonium chloride solution (3×10 mL), and dried ($Na_2SO_4$). Evaporation of the solvent left the pure product as white powder (0.202 g, 99%); m.p. 139–141° C.; $^1$H-NMR ($CDCl_3$): δ 1.62–1.80 (m, 2H), 1.95–2.20 (m, 4H), 2.35 (s, 3H), 2.30–2.55 (m, 4H), 2.76–2.90 (m, 2H), 3.21–3.40 (m, 2H), 3.61 (s, 3H), 3.67 (s, 3H), 5.89 (s, 2H), 6.61–6.82 (m, 3H), 6.63 (s, 1H), 7.21–7.35 (m, 6H), 8.79 (br t, 1 H, NH); Anal. Calcd. for $C_{31}H_{36}N_4O_8$. 0.3 EtOAc: C, 62.47; H, 6.25; N, 9.05. Found: C, 62.64; H, 6.25; N, 8.87.

EXAMPLE 18

5-(2-Cyanoethoxycarbonyl)-4-ethyl-1,6-dihydro-1-{N-[3-(4-methoxycarbonyl-4-phenylpiperidin-1-yl)propyl]} carboxamido-2-methoxy-6-(4-nitrophenyl)pyrimidine.

a. 2-Cyanoethyl 3-{(4-nitrophenyl)methylene}-4 oxopentanoate. A mixture of ethyl propionylacetate (25 g, 0.173 mol) and 3-hydroxypropionitrile (18.48 g, 0.26 mol) was stirred and heated at 200–205° C. for 2 hours and the ethanol formed was removed by distillation. The residue was subjected to high vacuum distillation and the fraction distilling at 120–125° C. at 0.4 mm Hg was collected to get 2-cyanoethyl propionylacetate (21.5 g, 73.4%). A mixture of 4-nitrobenzaldehyde (14.46 g, 0.957 mol), 2-cyanoethyl propionylacetate (17.0 g, 0.1005 mol), piperidine (0.41 g, 476 mL, 4.8 mmol), and acetic acid (0.288 g, 274 mL, 4.8 mmol) in 2-propanol (400 mL) was stirred at room temperature for 24 h. The white solid, 2-cyanoethyl 3-{(4-nitrophenyl)methylene}-4-oxopentanoate, was filtered, washed with 2-propanol (2×50 mL) dried and used without further purification (Yield: 28.34 g, 97%); m.p. 98–100° C.

b. 5-(2-Cyanoethoxycarbonyl)-1,6-dihydro-2-methoxy-4-ethyl-6-(4-nitrophenyl)pyrimidine.

A mixture of 2-cyanoethyl 3-{(4-nitrophenyl) methylene}-4-oxopentanoate (5.00 g, 16.54 mmol), O-methylisourea hydrogen sulfate (3.422 g, 19.85 mmol), and $NaHCO_3$ (2.78 g, 33.08 mol) in EtOH (70 mL) was stirred and heated at 85–90° C. for 5 hours. The solid was removed by filtration and ethanol was evaporated from the filtrate. The residue was redissolved in EtOAc (300 mL), washed with water (2×100 mL), dried ($Na_2SO_4$), and the solvent evaporated. The crude product was purified by flash column chromatography on silica gel using CHCl/methanol (30:1) as the eluent, to leave the product as a white solid (2.95 g, 50%). The $^1$H-NMR analysis of the product showed it to be a 5:1 mixture of the amine/imine tautomers and was used as such in the next step.

c. 5-(2-Cyanoethoxycarbonyl)-4-ethyl-1,6-dihydro-2-methoxy-6-(4-nitrophenyl)-1-(4-nitrophenyloxy) carbonyl] pyrimidine.

To a well-stirred solution of 5-(2-cyanoethoxy carbonyl)-4-ethyl-1,6-dihydro-2-methoxy-6-(4-nitrophenyl) pyrimidine (2.64 g, 7.36 mmol) and pyridine (1.19 mL, 14.72 mmol) in $CH_2Cl_2$ (100 mL) at 0–5° C., 4-nitrophenyl chloroformate (1.485 g, 7.36 mmol) was added in 5 min and the mixture was allowed to warm to room temperature. After 16 h, saturated aqueous $NaHCO_3$ solution (25 mL) was added and the stirring continued for 30 min. The two layers were separated, the $CH_2Cl_2$ layer was washed with saturated aqueous $NaHCO_3$ solution (3×50 mL), dried ($Na_2SO_4$), and the solvent evaporated. The crude product was purified by flash column chromatography on silica gel using $CHCl_3$/EtOAc (25:1) as the eluent to give the product as a viscous oil (1.70 g, 44%); $^1$H-NMR ($CDCl_3$): δ 1.24 (t, J=7 Hz, 3H), 2.61–2.68 (m, 2H), 2.88–2.92 (m, 2H), 3.97 (s, 3H), 4.32 (t, J=7 Hz, 2H), 6.34 (s, 1H), 7.37 (d, J=9.2 Hz, 2H), 7.50 (d, J=8.7 Hz, 2H), 8.18 (d, J=8.7 Hz, 2H), 8.28 (d, J=9.2 Hz, 2H).

d. 5-(2-Cyanoethoxycarbonyl)-4-ethyl-1,6-dihydro-1-{N-[3-(4-methoxycarbonyl-4-phenylpiperidin-1-yl) propyl]} carboxamido-2-methoxy-6-(4-nitrophenyl) pyrimidine.

To a stirred mixture of 5-(2-cyanoethoxycarbonyl)-4-ethyl-1,6-dihydro-2-methoxy-6-(4-nitrophenyl)-1-[(4-nitrophenyloxy)carbonyl)pyrimidine (0.940 g, 2 mmol) and $K_2CO_3$ (0.552 g, 4 mmol) in anhydrous THP (20 mL) at room temperature under argon atmosphere, a solution of 3-[4-methoxycarbonyl-4-phenylpi peridin-1-yl] propylamine (0.882 g, 3 mmol, 1.5 eq) in THF (5 mL) was added and the stirring was continued for 1 h. Solvent was evaporated from the reaction mixture, the residue was redissolved in $CH_2Cl_2$ (50 mL), washed with 5% $NaHCO_3$ (3×25 mL), brine (50 mL), and dried ($MgSO_4$). Solvent was evaporated and the residue was purified by flash chromatography on silica gel using 10% methanol in EtOAc as the eluent to give the desired product as an oil, which on trituration with hexane and drops of EtOAc became a white powder (1.71 g, 80%); m.p. 62–63° C.; $^1$H-NMR ($CDCl_3$):δ 1.16 (t, J=7.5 Hz, 3 H), 1.62–1.78 (m, 2H), 1.80–1.84 (m, 2H), 2.06–2.18 (m, 2H), 2.28–2.36 (m, 2H), 2.50–2.53 (m, 4H), 2.58–2.63 (m, 2H), 2.70–2.84 (m, 4H), 3.25–3.40 (m, 2H), 3.61 (8, 3H), 3.92 (s, 3H), 4.26 (m, 2H), 6.66 (s, 1H), 6.82 (br t, 1 H, NH), 7.22–7.33 (m, 6H), 7.43 (d, J=7.8 Hz, 2H), 8.10 (d, J=7.8 Hz, 2H); Anal. Calcd. for $C_{34}H_{40}N_6O_8$· 0.1 $C_6H_{12}$. 0.5 $H_2O$: C, 61.44; H, 6.27; N, 12.93. Found: C, 61.44; H, 6.27; N, 12.11.

EXAMPLE 19

(+)-5-Carboxamido-4-ethyl-1-{N-[3-(4-methoxycarbonyl-4-phenylpiperidin-1-yl)propyl]}carboxamido-6-(4-nitrophenyl)-2-oxo-1,2,3,6-tetrhydropyrimidine (Scheme 4).

a. 2-Cyanoethyl 3-{(4-nitrophenyl)methylene}-4-oxopentanoate.

A mixture of ethyl propionylacetate (25 g, 0.173 mol) and 3-hydroxypropionitrile (18.48 g, 0.26 mol) was stirred and heated at 200–205° C. for 2 h and the ethanol formed was removed by distillation. The residue was subjected to high vacuum distillation and the fraction distilling at 120–125° C. at 0.4 mm of Hg was collected to get 2-cyanoethyl propionylacetate (21.5 g, 73.4%).

A mixture of 4-nitrobenzaldehyde (14.46 g, 0.957 mol), 2-cyanoethyl propionylacetate (17.0 g, 0.1005 mol), piperidine (0.41 g, 476 mL, 4.8 mmol), and acetic acid (0.288 g, 274 mL, 4.8 mmol) in 2-propanol (400 mL) was stirred at room temperature for 24 h. The white solid, 2-cyanoethyl 3-{(4-nitrophenyl)methylene}-4-oxo pentanoate, formed was filtered, washed with 2-propanol (2×50 mL) and dried (28.34 g, 97%); m.p. 98–100° C.

b. 5-(2-Cyanoethoxycarbonyl)-1,6-dihydro-2-methoxy-4-ethyl-6-(4-nitrophenyl)pyrimidine.

A mixture of 2-cyanoethyl 3-{(4-nitrophenyl) methylene}- 4-oxopentanoate (5.00 g, 16.54 mmol), O-methylisourea hydrogen sulfate (3.422 g, 19.85 mmol), and NaHCO: (2.78 g, 33.08 mol) in EtOH (70 mL) was stirred and heated at 85–90° C. for 5 h. The solid was removed by filtration and ethanol was evaporated from the filtrate. The residue was redissolved in EtOAc (300 mL), washed with water (2×100 mL), dried ($Na_2SO_4$), and the solvent evaporated. The crude product was purified by flash column chromatography on silica gel using $CHCl_3$/methanol (30:1) as the eluent, to leave the product as a white solid (2.95 g, 50%). The $^1$H-NMR analysis of the product showed it to be a 5:1 mixture of the amine/imine tautomers and was used as such in the next step.

c. 5-(2-Cyanoethoxycarbonyl)-4-ethyl-1,6-dihydro-2-methoxy-6-(4-nitrophenyl)-1-[(4-nitrophenyloxy) carbonyl] pyrimidine.

To a well-stirred solution of 5-(2-cyanoethoxy carbonyl)-4-ethyl-1,6-dihydro-2-methoxy-6-(4-nitrophenyl) pyrimidine (2.64 g, 7.36 mmol) and pyridine (1.19 mL, 14.72 mmol) in $CH_2Cl_2$ (100 mL) at 0–5 ° C., 4-nitrophenyl chloroformate (1.485 g, 7.36 mmol) was added in 5 min and the mixture was allowed to warm to room temperature. After 16 h, saturated aqueous $NaHCO_3$ solution (25 mL) was added and the stirring continued for 30 min. The two layers were separated, the $CH_2Cl_2$ layer was washed with saturated aqueous $NaHCO_3$ solution (3×50 mL), dried ($Na_2SO_4$), and the solvent evaporated. The crude product was purified by flash column chromatography on silica gel using $CHCl_3$/EtOAc (25:1) as the eluent to give the product as a viscous oil (1.70 g, 44%); $^1$H-NMR ($CDCl_3$): δ 1.24 (t, J=7 Hz, 3H), 2.61–2.68 (m, 2H), 2.88–2.92 (m, 2H), 3.97 (s, 3H), 4.32 (t, J=7 Hz, 2H), 6.34 (s, 1H), 7.37 (d, J=9.2 Hz, 2H), 7.50 (d, J=8.7 Hz, 2H), 8.18 (d, J=8.7 Hz, 2H), 8.28 (d, J=9.2 Hz, 2H).

d. 5-(2-Cyanoethoxycarbonyl)-4-ethyl-1,6-dihydro-2-methoxy-6-(4-nitrophenyl)-1-{N-[(2-phenyl)ethyl]} carboxamidopyrimidine.

To a stirred solution of 5-(2-cyanoethoxycarbonyl)-4-ethyl-1,6-dihydro-2-methoxy-6(4-nitrophenyl)-1-[(4-nitrophenyloxy)carbonyl]pyrimidine (17.5 g, 33.43 mmol) in anhydrous THF (200 mL) at room temperature under argon atmosphere, (R)-(+)-a-methylbenzylamine (4.86 g, 40.11 mmol) was added and the stirring was continued for 16 h. Solvent was evaporated from the reaction mixture and the residue was purified by flash chromatography on silica gel using toluene/EtOAc (20:3) as the eluent. The first major product to elute was (+)-5-(2-cyanoethoxycarbonyl)-4-ethyl-1,6-dihydro-2 -methoxy-6-(4-nitrophenyl)-1-{N-[(2-phenyl)ethyl]}carboxamidopyrimidine and obtained as a viscous oil (6.11 g, 36.2%); $[\alpha]_D$=+299.5 (c=1.95, CHCl$_3$); $^1$H-NMR (CDCl$_3$): δ 1.18 (t, J=7 Hz, 3H), 1.47 (d, J=7 Hz, 3H), 2.61 (t, 2H), 2.7–2.92 (m, 2H), 3.98 (s, 3H), 4.20–4.32 (m, 2H), 4.96 (quint, J=6.5 Hz, 2H), 6.66 (s, 1H), 6.82 (d, J=6.8 Hz, 1 H, NH), 7.22–7.36 (m, 5H), 7.45 (d, J=8.6 Hz, 2H), 8.11 (d, J=8.6 Hz, 2H). The second major compound to elute was (−)-5-(2-cyanoethoxycarbonyl)-4-ethyl-1,6-dihydro-2-methoxy-6-(4-nitrophenyl)-1-{N-[(2-phenyl)ethyl]}carboxamidopyrimidine and obtained as a viscous oil (5.92 g, 35%); $[\alpha]_D$=−105.1 (c=3.9, CHCl$_3$); $^1$H-NMR (CDCl$_3$): δ 1.20 (t, J=7 Hz, 3H), 1.48 (d, J=7 Hz, 3H), 2.62 (t, 2H), 2.82 (q, 2H), 3.94 (s, 3H), 4.20–4.32 (m, 2H), 4.96 (quint, J=6.5 Hz, 2H), 6.69 (s, 1H), 6.84 (d, J=6.8 Hz, 1 H, NH), 7.22–7.36 (m, 5H), 7.39 (d, J=8.6 Hz, 2H), 8.06 (d, J=8.6 Hz, 2H).

e. (+)—S—(2-Cyanoethoxycarbonyl)-1,6-dihydro-2-methoxy-4-ethyl-6-(4-nitrophenyl)pyrimidine.

To a stirred solution of (+)-5-(2-cyanoethoxycarbonyl)-4-ethyl-1,6-dihydro-2-methoxy-6-(4-nitrophenyl)-1-{N-[(2-phenyl)ethyl]}carboxamido pyrimidine (2.62 g, 5.182 mmol) in toluene (40 mL) was added 1,8-diazabicyclo[5,4,0]-undec-7-ene (0.237,1.55 mmol) at room temperature and the resulting solution was heated at 90° C. for 3.5 minutes. The solvent was evaporated and the residue was purified by flash column chromatography on silica gel using 9:1 CHCl$_3$/EtOAc as the eluent, to give 1.32 g (71%)of (+)-5-(2-cyanoethoxycarbonyl)-1,6-dihydro-2-methoxy-4-ethyl-6-(4-nitrophenyl)pyrimidine; $[\alpha]_D$=+4.0 (c=3.25, CHCl$_3$).

f. (+)-5-(2-Cyanoethoxycarbonyl)-4-ethyl-1,6-dihydro-2-methoxy-6-(4-nitrophenyl)-1-[(4-nitrophenyloxy) carbonyl]pyrimidine.

To a well-stirred solution of 5-(2-cyanoethoxycarbonyl) -4-ethyl-1,6-dihydro-2-methoxy-6-(4-nitrophenyl) pyrimidine (1.62 g, 4.52 mmol) and 4-(N,N-dimethylamino)pyridine (0.663 g, 5.43 mmol) in CH$_2$Cl$_2$ (50 mL) at 0–5° C., 4-nitrophenyl chloroformate (1.094 g, 5.43 mmol) was added in 5 minutes and the mixture was allowed to warm to room temperature. After 3 hours the solvent evaporated and the product was purified by flash column chromatography on silica gel using CHCl$_3$/EtOAc (25:1) as the eluent to give the product as a white solid (2.25 g, 95%); $^1$H-NMR (CDCl$_3$): δ 1.24 (t, J=7 Hz, 3H), 2.61–2.68 (m, 2H), 2.88–2.92 (m, 2H), 3.97 (s, 3H), 4.32 (t, J=7 Hz, 2H), 6.34 (s, 1H), 7.37 (d, J=9.2 Hz, 2H), 7.50 (d, J=8.7 Hz, 2H), 8.18 (d, J=8.7 Hz, 2H), 8.28 (d, J=9.2 Hz, 2H); $[\alpha]_D$=+317.2 (c=3.9, CHCl$_3$)

g. (+)-5-(2-Cyanoethoxycarbonyl)-4-ethyl-1-{N-[3-(4-methoxycarbonyl-4-phenylpiperidin-1-yl)propyl]}carboxamido-6-(4-nitrophenyl)-2-oxo-1,2,3,6-tetrhydro pyrimidine.

To a stirred mixture of (+)-5-(2-cyanoethoxycarbonyl)-4-ethyl-1,6-dihydro-2-methoxy-6-(4-nitrophenyl) -1-[(4-nitrophenyloxy)carbonyl]pyrimidine (3.60 g, 6.878 mmol) in anhydrous THF (100 mL) at room temperature under argon atmosphere, a solution of 3-[4-methoxycarbonyl-4-phenylpiperidin-1-yl]propylamine (2.47 g, 8.94 mmol, 1.3 eq) in THF (10 mL) was added and the stirring was continued for 12 hours. The mixture was cooled to 0° C. and aqueous 6N hydrochloric acid (10 mL). The mixture was allowed to warm to room temperature and the stirring was continued for 5 h. Solvent was evaporated from the reaction mixture, the residue was purified by flash chromatography on silica gel using ethyl acetate (800 mL) followed by chloroform-methanol-2M ammonia in methanol (90/8/4) as the eluent, to obtain the desired product as a white powder (4.40 g, 98.56 );$^1$H-NMR (CDCl$_3$): δ 1.23 (t, J=7.5 Hz, 3H), 2.0–2.1 (m, 2H), 2.40–2.95 (m, 12H), 3.25–3.50 (m, 4H), 3.65 (s, 3H), 4.27–4.32 (m, 2H), 6.64 (s, 1H), 7.20–7.33 (m, 5H), 7.49 (d, J=7.8 Hz, 2H), 8.08 (d, J=7.8 Hz, 2H), 8.70–8.90 (m, 2H); $[\alpha]_D$=+112.1 (c=2.15, CHCl$_3$); This product was used in the next step without any additional analysis.

h. (+)-5-Carboxamido-4-ethyl-1-{N-[3-(4-methoxycarbonyl-4-phenylpiperidin-1-yl)propyl]} carboxamido-6-(4-nitro phenyl)-2-oxo-1,2,3,6-tetrhydropyrimidine.

To a stirred solution of 5-(2-cyanoethoxycarbonyl)-4-ethyl-1-{N-[3-(4-methoxycarbonyl-4-phenyl piperidin-1-yl)propyl]}carboxamido-6-(4-nitrophenyl)-2-oxo-1,2,3,6-tetrahydropyrimidine (4.40 g, 6.8 mmol) in acetone (50 mL) at 0° C., sodium hydroxide solution (1 N, 27.2 mL, 4 eq.) was added drop wise and the stirring was continued until the disappearance of the starting material (1 hour). Most of the acetone from the mixture was evaporated under reduced pressure while 20 keeping the temperature at 0° C. and the residue was adjusted to pH 7.0 by the addition of 1N hydrochloric acid. The white precipitate of (+)-4-ethyl-1-{N-[3-(4-methoxycarbonyl-4-phenylpiperidin-1-yl)propyl]}carboxamido-6-(4-nitrophenyl)-2-oxo-1,2,3,6-tetrhydro pyrimidine-5-carboxylic acid formed was filtered and dried under vacuum (3.59 g, 89%). $^1$H-NMR (CDCl$_3$): δ 1.07 (t, J=7.5 Hz, 3H), 1.55–1.70 (m, 2H), 1.72–1.84 (m, 2H), 1.84–2.15 (m, 2H), 2.20–2.40 (m, 4H), 2.70–2.90 (m, 2H), 3.10–3.40 (m, 4H), 3.51 (s, 3H), 6.54 (s, 1H), 7.18–7.38 (m, 6H), 7.41 (d, J=7.8 Hz, 2H), 8.15 (d, J=7.8 Hz, 2H), 8.79 (br t, 1 H, N H), 10.05 (br S, 1 H, COOH); This product was used in the next step without any additional analysis.

A mixture of (+)-4-ethyl-1-{N-[3-(4-methoxycarbonyl-4-phenylpiperidin-1-yl)propyl]}carboxamido-6-(4-nitro phenyl)-2-oxo-1,2,3,6-tetrhydropyrimidine-5-carboxylic acid (0.350 g, 0.59 mmol), 1-(3-dimethylaminopropyl)-3-ethylcarbodiimide hydrochloride (0.2264 g, 1.181 mmol, 2eq.), and 4-(N,N-dimethylamino)pyridine (0.1443 g, 1.181 mmol, 2 eq) in anhydrous dichloromethane was stirred at room temperature for 2 h. To this, 40% aqueous ammonia (0.6 mL) was added and the stirring was continued for 12 h. The mixture was diluted with 100 mL of dichloromethane and washed with saturated aqueous ammonium chloride solution (3×20 mL). Solvent was evaporated from the dried (magnesium sulfate) dichloromethane solution and the residue was purified by column chromatography on silica gel using chloroform-methanol-2M ammonia in methanol (500/16/8) as the eluent, to obtain the desired product as a white powder (0.24 g, 69%); m.p. 107–109° C.; $^1$H-NMR (CDCl$_3$): δ 1.20 (t, J=7.5 Hz, 3H), 1.66–1.72 (m, 2H), 1.79–2.00 (m, 3H), 2.00–2.20 (m, 2H), 2.29–2.35 (m, 2H), 2.42–2.60 (m, 2H), 2.62–2.82 (m, 3H), 3.20–3.40 (m, 2H), 3.60 (s, 3H), 5.70 (br m, 2 H, NH$_2$), 6.59 (s, 1 H), 7.20–7.39 (m, 6H), 7.52 (d, J=7.8 Hz, 2H), 8.13 (d, J=7.8 Hz, 2H), 8.82 (t, 1H); $[\alpha]_D$=+115.71 (c=1.4, CHCl$_3$); Anal. Calcd. for $C_{30}H_{36}N_6O_7 \cdot 0.8 H_2O$: C, 59.36; H, 6.24; N, 13.84. Found: C, 59.47; H, 6.07; N, 13.64.

EXAMPLE 20

(+)-5-Carboxamido-6-(3,4-difluorophenyl)-4-ethyl-1-{N-[3-(4-methoxycarbonyl-4-phenylpiperidin-1-yl) propyl]} carboxamido-2-oxo-1,2,3,6-tetrhydropyrimidine (Scheme 5).

a. Benzyl 3-[(3,4-difluorophenyl)methylene]-4-oxopentanoate. A solution of benzyl propionylacetate (36.3 g, 176 mmol), 3,4-difluorobenzaldehyde (25.0 g, 176 mmol), piperidine (0.86 mL, 9.0 mmol) and acetic acid (0.49 mL, 9.0 mmol) were refluxed with removal of water using Dean-Stark apparatus for 5 h. The solvent was removed in vacuo and the residue was dissolved in EtOAc. It was washed with water (100 mL) followed by brine (100 mL) and dried over anhydrous $Na_2SO_4$. Solvent was evaporated to get pale yellow syrup (60.2 g). It was used in the next step without further purification.

b. 5-(Benzyloxycarbonyl)-1,6-dihydro-2-methoxy-4-ethyl-6-(3,4-difluorophenyl)pyrimidine. A suspension of benzyl 3-[(3,4-difluorophenyl)methylene]-4-oxopentanoate (16.0 g, 48.0 mmol), O-methylisourea hydrogen sulfate (16.65 g, 97.02 mmol), $NaHCO_3$ (16.3 g, 130.2 mmol) in DMF (190 mL) was stirred at 70° C. for 20 h. After cooling to room temperature, the mixture was filtered and the filtrate was diluted with EtOAc (300 mL) and then washed with water (4×100 mL), brine (200 mL) and dried over $Na_2SO_4$. After removal of solvent, the residue was purified by column chromatography ($SiO_2$, EtOAc/Hexane, 10%–30%) to get 5-(benzyloxycarbonyl)-1,6-dihydro-2-methoxy-4-methyl-6-(3,4-difluorophenyl)pyrimidine as a colorless oil (10.6 g, 58%). The NMR analysis showed it to be a mixture of amine/imine tautomers and was used as is in the next step.

c. 5-(Benzyloxycarbonyl)-4-ethyl-1,6-dihydro-2-methoxy-6-(3,4-difluorophenyl)—1-[(4-nitrophenyloxy)carbonyl] pyrimidine. To a well stirred solution of 5-(benzyloxy carbonyl)-1,6-dihydro-2-methoxy-4-ethyl-6-(3,4-difluoro phenyl)pyrimidine (17.0 g, 44.04 mmol) and 4-dimethyl aminopyridine (6.99 g, 57.25 mmol) in $CH_2Cl_2$ (200 mL) was added a powder of 4-nitrophenyl chloroformate 11.54 g, 57.25 mmol) at room temperature. The reaction mixture was stirred for 12 hours and then the solvent was removed in vacuo. The residue was purified by chromatography (SiO2, EtOAc/Hexane 10–30%) to get 5-(benzyloxycarbonyl)-4-ethyl-1,6-dihydro-2-methoxy-6 -(3,4-difluorophenyl)-1-[(4-nitrophenyloxy)carbonyl]pyrimidine as a colorless viscous oil(12.6 g, 50%).$^1$H NMR ($CDCl_3$): δ 1.24 (t, J=7.2 Hz, 3H), 2.81–2.98 (m, 3H), 3.97 (s, 3H), 5.14 ($AB_q$, $δ_A$=5.08, $δ_B$=5.20, J=12.3 Hz, 2H), 6.28 (s, 1H), 7.03–7.29 (m, 8H), 7.35 (d, J=9.2 Hz, 2H), 8.26 (d, J=9.2 Hz, 2H).

d. 5-(Benzyloxycarbonyl)-4-ethyl-1,6-dihydro-1-{N-[2-phenyl)ethyl]}carboxamido-2-methoxy-6-(3,4-difluoro phenyl)pyrimidine. To a stirred mixture of 5-(benzyloxycarbonyl)-4-ethyl-1,6-dihydro-2-methoxy-6-(3,4-difluorophenyl)-1-[(4-nitrophenyloxy) carbonyl] pyrimidine (12.6 g, 22.86 mmol) in THF (150 mL) was added a solution of R-(+)-a-methyl benzylamine (3.53 mL, 27.44 mmol) at room temperature. The stirring was continued for 12 hours. Solvent was removed in vacuo. The yellow residue was dissolved in chloroform (200 mL) and was washed with 10% $K_2CO_3$ solution (2×30 mL). The organic layer was dried over $Na_2SO_4$, filtered and solvent was removed in vacuo. The resulting mixture of diastereomers was separated by column chromatography over silica gel with 9:1 Pet. ether:Ether to 4:1 Pet. ether:Ether. First major product to elute was 5-(benzyloxycarbonyl)-4-ethyl-1,6-dihydro-1-{N-[2-phenyl)ethyl]}carboxamido-2-methoxy-6-(3,4-difluorophenyl)pyrimidine. Colorless oil, Rf=0.31(4:1 Pet ether:ether), wt.=3.8 g (60%), $[α]_D$=+267.05 (c=0.76, $CHCl_3$) $^1$H NMR: δ 1.22 (t, J=7.5 Hz, 3H), 1.52 (d, J=6.9 Hz, 3H),2.88 (q, J=6.0 Hz, 2H), 3.99 (s, 3H), 4.99 (m, 1H), 5.09 ($AB_q$, $δ_A$=5.00, $δ_B$=5.19, J=12.6 Hz, 2H), 6.66 (s, 1H), 6.99–7.36 (m, 13H).; Second major product to elute was (−)-5-(benzyloxycarbonyl)-4-ethyl-1,6-dihydro-1-{N-[2-phenyl)ethyl]}carboxamido-2-methoxy-6-(3,4-difluorophenyl)pyrimidine. Colorless oil. Rf=0.22(4:1 Pet ether:ether), wt.=3.2 g (51.2%), $[α]_D$=−146.89 (c=0.38, $CHCl_3$), $^1$H NMR: δ 1.22 (t, J=7.2 Hz, 3H), 1.49 (d, J=6.9 Hz, 3H),2.88 (q, J=6.0 Hz, 2H), 3.94 (s, 3H), 5.03 (m, 1H), 5.11 ($AB_q$, $δ_A$=5.02,$δ_B$=5.19, J=12.6 Hz, 2H), 6.68 (s, 1H), 6.91–7.34 (m, 13H).

e. (+)-5-(Benzyloxycarbonyl)-1,6-dihydro-2-methoxy-4-ethyl-6-(3,4-difluorophenyl)pyrimidine. To a stirred solution of (+)-5-(benzyloxycarbonyl)-4-ethyl-1,6-dihydro-1-{N-(2-phenyl) ethyl]}carboxamido-2-methoxy-6-(3,4-diflurophenyl)pyrimidine (1.83 mmol, 1.0 g) in toluene (10 mL) was added 1,8-diazabicyclo[5,4,0]-undec-7-ene (0.81 mmol,0.12 mL) at room temperature and the resulting solution was heated to reflux for 5 h and then stirred for 12 h at room temperature. The solvent was evaporated and the residue was purified by flash column chromatography on silica gel with 3:1 EtOAc/Hexanes as the eluting system. 0.56 g of the (+)-5-(benzyloxycarbonyl)-1,6-dihydro-2-methoxy-4-ethyl-6-(3,4-diflurophenyl)pyrimidine was obtained (77%).

f. (+)-5-(Benzyloxycarbonyl)-4-ethyl-1,6-dihydro-2-methoxy-6-(3,4-diflurophenyl)-1-[(4-nitrophenyloxy) carbonyl]pyrimidine. To a well stirred solution of (+)-5-(benzyloxycarbonyl)-1,6-dihydro-2-methoxy-4-ethyl-6-(3, 4-diflurophenyl)pyrimidine (17.0 g, 44.04 mmol) and 4-dimethylaminopyridine (6.99 g, 57.25 mmol) in $CH_2Cl_2$ (200 mL) was added a powder of 4-nitrophenyl chloroformate 11.54 g, 57.25 mmol) at room temperature. The reaction mixture was stirred for 12 hours and then the solvent was removed in vacuo. The residue was purified by chromatography (SiO2, EtOAc/Hexane 10–30%) to get (+)-5-(benzyloxycarbonyl)-4-ethyl-1,6-dihydro-2-methoxy-6-(3,4-diflurophenyl)-1-[(4-nitrophenyloxy) carbonyl] pyrimidine as a colorless viscous oil(19.3 g, 76%).

g. (+)-5-(Benzyloxycarbonyl)-6-(3,4-difluorophenyl)-4-ethyl-1-{N-[3-(4-methoxycarbonyl-4-phenyl piperidin-1-yl) propyl]}carboxamido-2-oxo-1,2,3,6-tetrhydropyrimidine. To a stirred mixture of (+)-5-(benzyloxycarbonyl)-4-ethyl-1,6-dihydro-2-methoxy-6-(3,4-difluorophenyl)-1-[(4-nitrophenyloxy) carbonyl]pyrimidine (0.55 g, 1.12 mmol) in THF (5 mL) was added a solution of 3-[4-methoxycarbonyl-4-phenylpiperidin-1-yl]propylamine (0.31 g, 1.12 mmol) in THF (5 mL) at room temperature. The stirring was continued for 12 hours. A solution of 10% HCl in water (2 mL) was added and stirred for 2 h. The solvent was then removed in vacuo and the residue was extracted with ethyl acetate (3×10 mL). It was washed with 10% aq. KOH solution, dried over $Na_2SO_4$ and solvent was removed in vacuo to obtain (+)-5-(benzyloxycarbonyl)-6-(3,4-difluorophenyl)-4-ethyl—{N-[3-(4-methoxycarbonyl-4-phenylpiperidin-1-yl) propyl]} carboxamido-2-oxo-1,2,3,6-tetrhydropyrimidine as a white foamy compound (0.73 g, 96.6%) the purity of which was characterized as its HCl salt. It was used in the next step without further purification. Anal. Calcd. for $C_{37}H_{41}ClF_2N_4O_6 \cdot 0.5CHCl_3$:C, 58.43; H, 5.43; N, 7.27. Found: C, 58.11, H; 5.85; N, 7.64.

h. 6-(3,4-Difluorophenyl)-4-ethyl-1-{N-[3-(4-methoxy carbonyl-4-phenylpiperidin-1-yl)propyl]}carboxamido-1,2, 3,6-tetrhydro-2-oxopyrimidine-5-carboxylic acid. To a suspension of 10% Pd—C (0.14 g, 20% by wt.) in MeOH (3 mL) was added the solution of (+)-5-(benzyloxycarbonyl)-6-(3,4-difluorophenyl)-4-ethyl-1-{N-[3-(4-methoxycarbonyl-4-phenylpiperidin-1-yl) propyl]}carboxamido-2-oxo-1,2,3,6-tetrhydropyrimidine at room temperature with constant stirring. A balloon filled with $H_2$ was attached and the reaction mixture was stirred for 48 hours. The black suspension was filtered through a pad of celite and the filtrate was concentrated in vacuo. The residue was purified by column chromatography ($SiO_2$, 10% MeOH in EtOAc) to obtain (+)-6-(3,4-difluorophenyl)-4-ethyl-1-{N-[3-(4-methoxycarbonyl-4-phenylpiperidin-1-yl) propyl]}carboxamido-1,2,3,6-tetrhydro-2-oxopyrimidine-5-carboxylic acid as a white solid. M.P. 184–186° C.; $[\alpha]_D$=+142.2 (c=0.25, $CHCl_3$) The purity was checked by combustion analysis as a HCl salt. Anal. Calcd. for $C_{30}H_{35}ClF_2N_4O_6$. $0.3CHCl_3$:C, 55.40; H, 5.42; N, 8.53. Found: C, 55.34; H; 5.80; N, 8.13.

i. (+)-5-Carboxamido-6-(3,4-difluorophenyl)-4-ethyl-1-{N-[3-(4-methoxycarbonyl-4-phenylpiperidin-1-yl) propyl]} carboxamido-2-oxo-1,2,3,6-tetrhydro pyrimidine.

To a solution of (+)-6-(3,4-difluorophenyl)-4-ethyl-1-{N-[3-(4-methoxycarbonyl-4-phenylpiperidin-1-yl) propyl]} carboxamido-1,2,3,6-tetrhydro-2-oxopyrimidine-5-carboxylic acid (0.22 g, 0.375 mmol) in $CH_2Cl_2$ (3 mL) was added 4-N,N-dimethylamino pyridine (0.14 g, 1.12 mmol) and 1-(3-dimethylaminopropyl)-3-ethylcarbodiimide hydrochloride (0.21 g, 1.12 mmol) under argon and the resulting solution was stirred at room temperature for 2h. Three drops of saturated $NH_4OH$ was then added and the solution was stirred for 48 h. The solution was washed with water (5 ml) and dried over $Na_2SO_4$. The solvent was removed in vacuo and the residue was purified by column chromatography ($SiO_2$, 10% MeOH in $CHCl_3$) to obtain 5-carboxamido-6-(3,4-difluorophenyl)-4-ethyl -1-{N-[3-(4-methoxycarbonyl-4-phenylpiperidin-1-yl)propyl]}carboxamido-2-oxo-1,2,3, 6-tetrhydropyrimidine as a beige solid (0.1 g, 45%). Characterized as HCl salt. M.P. 136–138° C., $[\alpha]_D$=+111.44 (c=0.18, MeOH): δ 1.21 (t, J=7.5 Hz, 3H), 1.60–1.75 (m, 2H), 1.92–2.1 (m, 8H), 2.33 (t, J=6.6 Hz, 2H), 2.44–2.52 (m, 2H), 2.53–2.84 (m, 4H), 3.27–3.32 (m, 2H), 3.60 (s, 3H), 5.60 (br s,2H), 6.47 (s, 1H), 7.05–7.33 (m, 8H), 8.80 (br t, 1H), Anal. Calcd. for $C_{30}H_{35}ClF_2N_4O_6$. 1.0 $CHCl_3$:C, 50.35; H. 5.04; N, 9.47. Found: C, 50.40; H; 5.33; N, 9.13.

EXAMPLE 21

6-(3,4-Difluorophenyl)-5-methoxycarbonyl-4-methyl-2-oxo-1-{N-[4-(2-pyridyl)-piperidine-1-yl] propyl}carboxamido-1,2,3,6-tetrahydropyrimidine dihydrochloride (Scheme 7).

a. 1-Benzyl-4-cyano-4-(2-pyridyl)piperidine. To a mixture of N,N-bis-(2-chloroethyl)benzylamine (E.Szarvasi, Eur. J. Med. Chem. Chim. Ther. 11(2), 115–124, 1976) (60 g, 22 mmol), 2-pyridylacetonitrile (2.51 ml, 22 mmol) and tetrabutylammonium hydrogen sulfate (0.26 g, 0.7 mmol) in toluene (10 ml), sodium hydroxide solution (2.43 g in 4.86 ml $H_2O$) was added over a 20 minute period. The reaction mixture was heated at 65 ° C. for 4 hours. The reaction mixture was cooled to room temperature, 10 ml of water was added and the solution partitioned between ethyl acetate (45 ml) and water. The organic layer was dried over sodium sulfate, filtered and concentrated. Purification of the crude product by column chromatography (hexane:EtOAc,2:3) gave 6.2 g (87%) of the title compound as a red solid; $^1$H-NMR ($CDCl_3$): a 2.05 (d, J 13.1 Hz, 2H), 2.30 (t, J=13.2 Hz, 2H), 2.48 (t, J=13.2 Hz, 2H), 2.97 (d, J=12.1 Hz, 2H), 3.57 (s, 2H), 7.19–7.27 (m, 6H), 7.30 (d, J=7.6 Hz, 1H), 7.60 (t, J=7.6 Hz, 1H), 8.58 (d, J=4.6 Hz,1H).

b. 1-Benzyl-4-carboxamido-4-(2-pyridyl)piperidine. To 1-benzyl-4-cyano-4-(2-pyridyl)piperidine (4.5 g, 14.3 mmol), 10 ml of conc.$H_2SO_4$ was added and the solution was stirred at room temperature for 24 hours. It was cooled to 0° C., diluted with ice pieces and poured into crushed ice. The mixture was then carefully neutralized with 50% NaOH solution. The reaction mixture was repeatedly extracted with chloroform (3×25 ml), dried over sodium sulfate, filtered and concentrated to give 4.5 g (95%)of the crude product which was used as such for the subsequent step; $^1$H-NMR ($CDCl_3$): δ 2.21–2.28 (m, 2H), 2.47 (s, 6H), 3.41 (s, 2H), 5.23 (s, 1H), 6.40 (s, 1H), 7.12–7.29 (m, 6H), 7.33 (d, J=7.6 Hz, 1H), 7.63 (t, J=7.6 Hz, 1H), 8.55 (d, J=4.6 Hz, 1H).

c. 1-Benzyl-4-(2-pyridyl)-piperidine. To 1-benzyl-4-carboxamido-4-(2-pyridyl)piperidine (4.5 g, 13.5 mmol) in anhydrous methanol (100 ml), HCl gas was bubbled through the solution at 0° C. for 15 minutes. The reaction mixture was then refluxed for 24 hours. It was cooled to room temperature, concentrated, neutralized with 50% NaOH and repeatedly extracted with chloroform (3×25 ml). The combined organic layer was then dried over sodium sulfate, filtered and concentrated. Flash chromatography (hexane:ethylacetate, 1:4) of the crude product yielded 1.72 g (50%) of the product as a syrup; $^1$H-NMR ($CDCl_3$) δ 1.8–1.94 (m, 4H), 2.11 (t, J=11.4 Hz, 2H), 2.70–2.72 (m, 1H),3.02 (d, J=11.4 Hz, 2H), 3.54 (s, 2 H), 7.07–7.36 (m, 7H), 7.58 (t, J=7.6 Hz, 1H), 8.52 (d, J=4.6 Hz, 1H).

d. 3-[4-(2-Pyridyl)-piperidine-1-yl]propylamine (Scheme 6). To 1-Benzyl -4-(2-pyridyl)-piperidine (3. 2 6 g, 12.9 mmol) in dry methanol (25 ml), 10% palladium hydroxide (1.9 g) was added and the solution was hydrogenated at 200 psi for 24 hours. The solution was filtered over celite, concentrated to give 2.1 g (99%) of 4-(2-pyridyl)-piperidine which was used as such for the subsequent step. A mixture of 3-bromopropylamine hydrobromide (20 g, 91.3 mmol), potassium carbonate (37.85 g, 273.9 mmol) and di-tert-butyldicarbonate (21.90 g, 100 mmol) in methanol was stirred at room temperature for 24 hours. The reaction mixture was concentrated and partitioned between 250 ml EtOAc and 50 ml water, dried over sodium sulfate, filtered and concentrated. Purification of the crude product by column chromatography (Hexane: EtOAc, 4.5:0.5) gave 17.5 g (80%) of the product as a pale yellow oil. To a stirred solution of the 4-(2-pyridyl)-piperidine (1.86 g, 11.4 mmol) in dioxane (20 ml), N-(tert-butoxycarbonyl)-3-bromopropylamine (2.82 g, 11.4 mmol) and potassium carbonate (3.16 g, 22.9 mmol) were added and the solution refluxed for 24 hours. The reaction mixture was cooled to room temperature, concentrated and partitioned between 40 ml chloroform and 5 ml water. The organic layer was dried over sodium sulfate, filtered and concentrated. The crude product was purified by column chromatography (ethyl acetate: methanol, 4:1) to yield 1.86 g (49%) of the required product as a colorless oil; $^1$H-NMR ($CDCl_3$): δ 1.45 (s, 9H),1.54–1.69 (m, 8H), 2.21–2.68 (m, 2H), 2.74–2.80 (m, 1H), 3.02–3.22 (m, 4H), 5.41 (s, 1H), 7.13–7.17 (m, 1H), 7.33 (d, J=7.93 Hz, 1H).7.63 (t, J=7.6 Hz, 1H), 8.54 (d, J=4.6 Hz, 1H). To N-(tert-butoxycarbonyl)-3-[4-(2-pyridyl)-piperidin-1-yl]propylamine (0.15 g, 0.45 mmol) in 5 ml of dichloromethane, 1 ml of trifluoroacetic acid was added and the solution stirred at room temperature for 1 hour. The solution was concentrated, neutralized with 10% KOH solution and extracted into 25 ml of dichloromethane. The organic layer was dried over sodium sulfate, filtered and concentrated to give 0.098 g (100%) of 3-[4-(2-pyridyl)-piperidin-1-yl]propylamine which was used as such for the subsequent step (step h).

e. Methyl 2-{(3,4-difluorophenyl)methylene}-3-oxobutyrate. A mixture of 3,4-difluorobenzaldehyde (14.2 g, 0.1 mol), methyl acetoacetate (12.2 g, 0.105 mol), piperidine (0.430 g, 5 mmol), and acetic acid (0.30 g, 5 mmol) in benzene (150 mL) was stirred and refluxed with a Dean-Stark trap for 8 hours. Benzene was. evaporated, the residue was dissolved in ethyl acetate (200 mL) and washed with brine (50 mL), saturated potassium bisulfate solution (50 mL), and saturated sodium bicarbonate solution in sequence. The ethyl acetate solution was dried (magnesium sulfate), solvent removed under reduced pressure and the residue was purified by column chromatography (SiO2, EtOAc/hexane, 10%–15%). The product, methyl 2-{(3,4-difluorophenyl)methylene}-3-oxobutyrate, was obtained as a yellow oil (0.98 g, 98.3%) and was used in the next step without any further characterization.

f. 6-(3,4-Difluorophenyl)-1,6-dihydro-2-methoxy-5-methoxycarbonyl-4-methylpyrimidine. A mixture of methyl 2-{(3,4-difluorophenyl) methylene} 3-oxobutyrate (8.8 g, 36.6 mmol), O-methylisourea hydrogen sulfate (9.4 g, 55 mmol), and $NaHCO_3$ (12.3 g, 0.146 mol) in DMF (30 mL) was stirred and heated at 70° C. for 16 hours. The mixture was cooled, diluted with EtOAc (300 mL) and washed with water (5×300 mL), brine (300 mL), and dried ($MgSO_4$). Solvent was evaporated and the crude product was purified by flash column chromatography on silica gel using 10% through 20% EtOAc in hexane as the gradient eluent, to leave the product as an oil (3.82 g, 30.2%); $^1$H-NMR ($CDCl_3$): δ 2.32,2.39 (2 s, 3H), 3.58, 3.64 (2 s, 3H), 3.72, 3.85 (2 s, 3H), 5.55 (s, 1H), 6.13–7.8 (m, 4H).

g. 6-(3,4-Difluorophenyl)-1,6-dihydro-2-methoxy-5-methoxycarbonyl -4-methyl-1-[(4-nitrophenyloxy)carbonyl]pyrimidine.

To a solution of 6-(3,4-difluorophenyl)-1,6-dihydro-2-methoxy-5-methoxycarbonyl-4-methylpyrimidine (2.82 g, 9.52 mmol) and 4-dimethylaminopyridine (1.16 g, 9.52 mmol) in $CH_2Cl_2$ (50 mL),at 0–5° C., 4-nitrophenyl chloroformate (1.82 g, 9.04 mmol) was added and the mixture was allowed to warm to room temperature. After 12. hours solvent was evaporated and the residue was purified by flash column chromatography ($SiO_2$, EtOAc/hexane, 10%–15%) to obtain the product as white crystals (3.72, 84.7%); m.p. 172–174° C.; $^1$H-NMR ($CDCl_3$):b 2.51 (s, 3H), 3.72 (s, 3H), 3.97 (s, 3H), 6.26 (s, 1H), 7.0–7.3 (m, 3H), 7.38 (d, J=9.3 Hz, 2H), 8.32 (d, J=9.3 Hz, 2H).

h. 6-(3,4-Difluorophenyl)-5-methoxycarbonyl-4-methyl-2-oxo-1-{N-[4-(2-pyridyl)-piperidine-1-yl]propyl}carboxamido-1,2,3,6-tetrahydropyrimidine dihydrochloride. To 6-(3,4-difluorophenyl)-1,6-dihydro-2-methoxy-5-methoxycarbonyl-4-methyl-1-(4-nitrophenoxy)carbonylpyrimidine (0.04 g,0.086 mmol) in 10 ml of dry dichloromethane, 3-[4-(2-pyridyl)-piperidine-1-yl]propylamine (0.038 g, 0.17 mmol) was added and the solution was stirred at room temperature for 24 hours. The reaction mixture was stirred for another 1 hour after addition of 2 ml of 6N HCl. After neutralization with 10% aqueous KOH solution, the reaction mixture was extracted into dichloromethane (3×10 ml). The organic layer was dried over sodium sulfate, filtered and concentrated. The crude product was purified by flash chromatography (EtOAc: MeOH, 4.5:0.5) to give 0.040 g (89%) as a syrup ; $^1$H-NMR ($CDCl_3$): δ 1.73–2.11 (m, 7H), 2.41 (s, 6H), 2.69 (m, 1H), 3.04 (d, J=12.1 Hz, 2H), 3.31–3.48 (m, 2H), 3.71 (s, 3H), 6.70 (s, 1H), 7.24–7.27 (m, 5H), 7.61 (t, J=8.0 Hz, 2H), 8.51 (d, J=4.6 Hz, 1H), 8.89 (t, J=5.1 Hz, 2H).

To the free base (0.04 g, 0.07 mmol) in 4 ml of dichloromethane, 5 ml of 1N HCl in ether was added, and the solution concentrated under reduced pressure. Recrystallization from ether gave 0.04.6 g (98%) of 6-(3,4-difluorophenyl)-5-methoxycarbonyl-4-methyl-2-oxo-1-{N-[4-(2-pyridyl)-piperidine-1-yl]propyl}carboxamido-1,2,3,6-tetrahydropyrimidine dihydrochloride as a white solid; m.p. 170–174° C.; Anal. Calcd. for $C_{27}H_{33}Cl_2F_2N_5O_4$. 1.0 $H_2O$: C, 52.43; H,5.70, N 11.30. Found: C, 52.16; H 5.35; N 11.10.

EXAMPLE 22

6-(3,4-Benzofurazan-5-yl)-5-methoxycarbonyl-4-methyl-2-oxo-1-{N-[4-(2-pyridyl)-piperidin-1-yl]propyl}carboxamido-1,2,3,6-tetrahydropyrimidine dihydrochloride (Scheme 8).

5-Methylbenzfuroxan. 4-Methyl-2-nitroaniline (100 g, 0.650 mol) was suspended in saturated alcoholic sodium hydroxide solution (1.50 1). To this suspension was added with cooling (5° C.) commercial aqueous sodium hypochlorite till the red color disappeared. The fluffy yellow precipitate formed was filtered, washed with cold water and recrystallized from ethanol to get 5-Methylbenzfuroxan (88.2 g, 89 0% yield) as a pale solid.

5-Methylbenzofurazan. To 5-Methylbenzfuroxan (88.2 g, 0.59. mol) in refluxing EtOH (75 ml) was added dropwise $P(OEt)_3$ (150 ml ). When addition was complete, refluxing was continued for 1 more hour. The solvent was removed by rotary evaporation and the residue shaken with water (200 mL) and allowed to stand overnight at (0~5° C.). The brown solid so obtained was filtered, washed with water and chromatograghed on silica gel to yield 5-Methylbenzofurazan (70 g, 87%) as white needle.

5-Dibromomethylbenzofurazan. 5-Methylbenzofurazan (70 g, 0.52 mol), NBS (325 g), and benzoyl peroxide (0.5 g) were refluxed with stirring in carbon tetrachloride (1.5 L) with exclusion of moisture for 30 hours. The reaction mixture was washed with water (2×0.5L), dried ($NaSO_4$), and the solvent was removed in vacuo. The residue was chromatographed (silica, EtOAc-hexane, 1:150) to give 122 g (80%) of the title compound. The resulting white solid was used in the next step without any further characterization.

5-Formylbenzofurazan. To a refluxing mixture of the dibromomethylbenzofurazan (122 g, 418 mmol) in EtOH (1 L) was added $AgNO_3$ (163 g) in 2 L of water. Refluxing was continued for 2 hours. The mixture was cooled and the AgBr was removed by filtration through Celite, and the solvent was concentrated to a small volume. The resulting solution was extracted with toluene (10×100 mL), dried ($MgSO_4$), and the solvent was removed in vacuo. The residue was chromatographed on silica (EtOAc-hexane, 8:1000) to give 48.2 g of the title aldehyde (78%) as a white solid.

a. Methyl 2-{(benzofuran-5-yl)methylene}-3-oxobutyrate.

A mixture of 5-Formylbenzofurazan (0.6 g, 4.1 mmol), methyl acetoacetate (0.52 g, 4.5 mmol), piperidine (0.019 g, 0.225 mmol), and acetic acid (0.014 g, 0.225 mmol) in benzene (30 mL) was stirred and refluxed with a Dean-Stark trap for 8 h. Benzene was evaporated, the residue was dissolved in ethyl acetate (80 mL) and washed with brine (50 mL), saturated potassium bisulfate solution (50 mL), and saturated sodium bicarbonate solution in sequence. The ethyl acetate solution was dried (magnesium sulfate), solvent removed under reduced pressure and the residue was purified by column chromatography (SiO2, EtOAc/hexane, 10%–15%). The product, methyl 2-{(benzofuran-5-yl) methylene}-3 -oxobutyrate, was obtained as an oil (0.98 g, 98.3%) and was used in the next step without any further characterization.

b. 6-(Benzofurazan-5-yl)-1,6-dihydro-2-methoxy-5-methoxycarbonyl-4-methylpyrimidine. A mixture of methyl 2-{(benzofuran-5-yl)methylene}-3-oxobutyrate (1.02 g, 4.1 mmol), O-methylisourea hydrogen sulfate (1.06 g, 6.2 mmol), and NaHCO$_3$ (1.3 g, 16.4 mmol) in DMF (15 mL) was stirred and heated at 70° C. for 16 h. The mixture was cooled, diluted with EtOAc (50 mL) and washed with water (5×50 mL), brine (50 mL), and dried (MgSO$_4$). Solvent was evaporated and the crude product was purified by flash column chromatography on silica gel using 10% through 20% EtOAc in hexane as the gradient eluent, to leave the product as an oil (0.52 g, 43%); $^1$H-NMR (CDCl$_3$): δ 2.38,2.42 (2 s, 3H), 3.60, 3.66 (2 s, 3H), 3.74, 3.82 (2 s, 3H), 5.53, 5.68 (2 s, 1H), 6.31, 6.32 (br s, 1H), 7.0–7.8 (m, 3H).

c. 6-(Benzofurazan-5-yl)-1,6-dihydro-2-methoxy-5-methoxycarbonyl-4-methyl-1-[(4-nitrophenyloxy) carbonyl]pyrimidine.

To a solution of 6-(benzofuran-5-yl)-1,6-dihydro-2-methoxy-5-methoxycarbonyl-4-methylpyrimidine (0.485 g, 1.6 mmol) and 4-dimethylaminopyridine (0.2 g, 1.6 mmol) in CH$_2$Cl$_2$ (20 mL),at 0–5° C., was added 4-nitrophenyl chloroformate (0.307 g, 1.52 mmol) and the mixture was allowed to warm to room temperature. After 12 hours solvent was evaporated and the residue was purified by flash column chromatography (SiO2, EtOAc/hexane, 10%–15%) to obtain the product as white crystals (0.665 g, 89%); m.p. 180–183° C.; $^1$H-NMR (CDCl$_3$): 2.54 (s, 3H), 3.75 (s, 3H), 3.98 (s, 3H), 6.37 (s, 1H), 7.40 (d, J=9.3 Hz, 2H), 7.52 (d, J=9.0 Hz, 1H), 7.68 (s, 1H), 7.84 (d, J=9.0 Hz, 1H), 8.32 (d, J=9.3 Hz, 2H).

d. 6-(3,4-Benzofurazan-5-yl)-5-methoxycarbonyl-4-methyl-2-oxo-1-{N-[4-(2-pyridyl)-piperidin-1-yl]propyl}carboxamido-1,2,3,6-tetrahydropyrimidine dihydrochloride. To 6-(benzofurazan-5-yl)-1,6-dihydro-2-methoxy-5-methoxycarbonyl-4-methyl-1-(4-nitrophenoxy) carbonylpyrimidine (0.04 g,0.085 mmol) in 10 ml of dry dichloromethane, 3-[4-(2-pyridyl)-piperidine-1-yl] propylamine (0.037 g, 0.17 mmol) was added and the solution was stirred at room temperature for 24 hours. The reaction mixture was stirred for another 1 hour after addition of 2 ml of 6N HCl. After neutralization with 10% aqueous KOH solution, the reaction mixture was extracted into dichloromethane (3×10 ml). The organic layer was dried over sodium sulfate, filtered and concentrated. The crude product was purified by flash chromatography (EtOAc: MeOH, 4.5:0.5) to give 0.040 g (89%) as a syrup ; $^1$H-NMR (CDCl$_3$): δ 1.74–2.10 (m, 7H), 2.46 (s, 6H), 2.70–2.72 (m, 1H), 3.05 (d, J=12.1 Hz, 2H), 3.34–3.48 (m, 2 H), 3.76 (s, 3H), 6.82 (s, 1H), 7.11–7.32 (m, 3H), 7.54–7.78 (m, 4H), 8.53 (d, J=4.6 Hz, 1H), 8.89 ( t, J=5.16 Hz, 2H).

To the free base (0.04 g, 0.07 mmol)in 4 ml of dichloromethane, 5 ml of 1N HCl in ether was added, and the solution concentrated under reduced pressure. Recrystallization from ether gave 0.040 g (87%) of 6-(3,4-benzofurazan-5-yl)-5-methoxycarbonyl-4-methyl-2-oxo-1-{N-[4-(2-pyridyl)-piperidine-1-yl]propyl}carboxamido-1,2,3,6-tetrahydropyrimidine dihydrochloride as a white solid; m.p. 200–204° C.; Anal. Calcd. for C$_{27}$H$_{33}$Cl$_2$N$_7$O$_5$. 2.5 H$_2$O: C, 49.77; H,5.88. Found: C, 49.41; H 5.20.

EXAMPLE 23

6-(3,4-Difluorophenyl)-1,6-dihydro-5-methoxycarbonyl-1-(5-(4-methoxycarbonyl-4-phenylpiperidin-1-yl)-pentyl)-2,4-dimethylpyrimidine (Scheme 9). a. 6-(3,4-Difluorophenyl)-1,6-dihydro-2,4-dimethyl-5-methoxycarbonylpyrimidine. To a solution of acetamidine hydrochloride (1.53 g, 16.2 mmol.) in DMF (10 mL) were added a solution of potassium tert-butoxide (1.33 g, 11.8 mmol.) in DMF (10 mL) and a solution of methyl {2-(3,4-difluorophenyl) methylene}-3-oxobutanoate (2.6 g, 10.8 mmol.) in DMF (10 mL) at 0° C. After the mixture was stirred for 0.5 hour at 0° C., p-toluenesulfonic acid monohydrate (4.1 g, 21.5 mmol.) was added. The mixture was heated at 100–120° C. for 2 hrs. The reaction mixture was cooled to room temperature, quenched with aqueous NaOH solution (2N, 60 mL), and extracted with ether. The organic layer was dried over Na$_2$SO$_4$ and evaporated. The residue was flash chromatographed over silica gel (eluent: ethyl acetate) to give the product in 59% yield (1.8 g) as a yellow solid: $^1$H NMR (300 MHz, CDCl$_3$): δ 1.98 (3H, s), 2.31 (3H, s), 3.59 (3H, s), 5.47 (1H, s), 7.03–7.05 (3H, m).

b. 1-(5-Chloropentyl)-6-(3,4-difluorophenyl)-1,6-dihydro-2,4-dimethyl-5-methoxycarbonylpyrimidine. To a suspension of NaH (90 mg, 60% dispersion in mineral oil, 2.25 mmol.) in THF (7 mL) was added a solution of the above yellow solid (0.6 g, 2.14 mmol.) in THF (8 mL) at 0° C. After 20 min, 1-bromo-5-chloropentane (1 mL, d 1.408, 7.59 mmol.) was added. The reaction mixture was then refluxed overnight. After the removal of the solvent, the residue was flash chromatographed over silica gel (eluent: ethyl acetate) to give the product in 75% yield (0.614 g) as a yellow oil: $^1$H NMR (300 MHz, CDCl$_3$): δ 1.42–1.75 (6H, m), 2.17 (3H, s), 2.28 (3H, s), 3.05–3.45 (2H, m), 3.49 (2H, t, J=5.88 Hz), 3.63 (3H, s), 5.23 (1H, s), 7.01–7.15 (3H, m)

c. 6-(3,4-Difluorophenyl)-1,6-dihydro-5 -methoxycarbonyl-1-(5-(4-methoxycarbonyl-4-phenylpiperidin-1-yl)-pentyl)-2,4-dimethylpyrimidine.

A mixture of the above yellow oil (0.667 g, 1.73 -mmol.), 4-methoxycarbonyl-4-phenyl piperidine (0.76 g, 3.47 mmol.), potassium carbonate (0.96 g, 6.95 mmol.), sodium iodide (0.52 g, 3.47 mmol.) and 1,4-dioxane (15 mL) was refluxed overnight. The undissolved solid was then filtered off and the solvent was evaporated. The residue was flash chromatographed over silica gel (eluent: 80:20 v/v ethyl acetate-2M ammonia in methanol) to give the title compound in 78% yield (0.768 g) as a yellow oil: CIMS, m/z 568 (MH$^+$); $^1$H NMR 7. (300 MHz, CDCl$_3$): δ 1.23–1.28 (2H, m), 1.43–1.51 (2H, m), 1.77–2.13 (8H, m), 2.16 (3H, s), 2.28 (3H, s), 2.47–2.55 (2H, m), 2.74–2.81 (2H, m), 3.00–3.12 (1H, m), 3.22–3.38 (1H, m), 3.613 (3H, s), 3.615 (3H, s), 5.22 (1H, s), 6.99–7.35 (3H, m).

Treatment of the free base with 2 equivalents of 1M HCl in ether gave the HCl salt as a yellow foam: m.p. 170–176° C. Anal. Calc. for C$_{32}$H$_{39}$F$_2$N$_3$O$_4$.2HCl.2.3H$_2$O: C, 56.35; H, 6.74; N, 6.16; Found: C, 56.34; H, 6.62; N, 5.86.

EXAMPLE 24

(+)-6-(3,4-Difluorophenyl)-5-methoxycarbonyl-4-methyl-2-oxo-1-{N-[3-(4-(2-pyridyl)-4-hydroxypiperidin-1-yl) propyl]}carboxamido-1,2,3,6-tetrahydropyrimidine dihydrochloride.

A solution of (+)-6-(3,4-difluorophenyl)-1,6-dihydro-2-methoxy-5-methoxycarbonyl-4-methyl-1-(4-nitrophenoxy) carbonylpyrimidine (0.894 g, 2 mmol), 3-[4-(2-pyridyl)-4-hydroxypiperidin-1-yl]propylamine (0.517 g, 2.2 mmol) in tetrahydrofuran (100 mL) was stirred at room temperature for 24 hours. The reaction mixture was stirred for another 1 hour after addition of 2 ml of 6N HCl. Solvent was evaporated at reduced pressure and the residue was basified by treatment with 10% aqueous KOH solution, extracted with dichloromethane (3×10 mL). The combined extracts were dried over potassium carbonate, and solvent evaporated. The crude product was purified by flash chromatography on silica gel (dichloromethane:MeOH:2M ammonia in MeOH, 90:8:4) to give 1.20 g (97%) as a syrup. The free base was dissolved in 20 mL anhydrous ether, cooled to 0–5° C. and treated with 10 mL of 1N HCl in ether. The white powder was filtered and dried to give 6-(3,4-difluorophenyl)-5-methoxycarbonyl-4-methyl-2-oxo-1-{N-[3-(4-(2-pyridyl)-4-hydroxypiperidin-1-yl)propyl]}carboxamido-1,2,3,6-tetrahydropyrimidine dihydrochloride; m.p. 200–206° C.; $[\alpha]_D$=+91 (c=1.15 g, in 100 mL of chloroform). Anal. Calcd. for $C_{27}H_{33}Cl_2F_2N_5O_4$. $0.4CHCl_3$: C, 48.18; H, 4.92; N, 10.18. Found: C, 48.34; H, 5.01; N, 10.08.

EXAMPLE 25

(+)-1,2,3,6-Tetrahydro-1-{N-[4-(2-pyridyl)-piperidin-1-yl]-(2-hydroxypropyl)}carboxamido-5-methoxycarbonyl-2-oxo-6-(3,4-difluorophenyl)-4-methylpyrimidine dihydrochloride a) 3-[4-(2-Pyridyl)-piperidin-1-yl] (2-hydroxypropyl) phthalimide A mixture of 4-(2-pyridyl)piperidine (3.25 g, 19.90 mmol) and 2,3-epoxypropylphthalimide (4.449 g, 21.89 mmol) in DMF (20 mL) was stirred and heated at 70° C. for 48 h. The solvent was evaporated under reduced pressure and the residue was purified by column chromatography on silica gel using chloroform-methanol-2M ammonia in methanol (1000/28/14) as the eluent, to obtain the desired product as a viscous oil (6.15 g, 84%).

b) 3-[4-(2-Pyridyl)-piperidin-1-yl]-2-hydroxy propylamine

A mixture of 3-[4-(2-pyridyl)-piperidin-1-yl](2-hydroxypropyl)phthalimide (1.35 g, 3.68 mmol) and hydrazine (0.588 g, 18.4 mmol) in methanol (15 mL) was stirred and refluxed for 4.5 h. It was cooled, filtered, and the solid was washed with methanol (30 mL). Evaporation of solvent from the filtrate gave the product as a viscous oil (0.85 g, 98%).

c) (+)-1,2,3,6-Tetrahydro-1-{N-[4-(2-pyridyl)-piperidi n-1-yl]-(2-hydroxypropyl) )carboxamido-5-methoxycarbon yl-2-oxo-6-(3,4-difluorophenyl)-4-methylpyrimidine dihydrochloride A solution of (+)-6-(3,4-difluorophenyl)-1,2,3,6-tetrahydro-2-oxo-5-methoxycarbonyl-4-methyl-1-(4-nitrophenoxy) carbonylpyrimidine (105 mg, 0.23 mmol), 3-[4-(2-pyridyl)piperidin-1-yl]-2-hydroxypropylamine (50 mg, 0.23 mmol) in tetrahydrofuran (20 mL) was stirred at room temperature for 24 hours. Solvent was evaporated at reduced pressure and the residue was basified by treatment with 10% aqueous KOH solution, extracted with dichloromethane (3×10 mL). The combined extracts were dried over potassium carbonate, and solvent evaporated. The crude product was purified by flash chromatography (dichloromethane:MeOH:2M ammonia in MeOH,90:8:4) to give 120 mg (97%5) as a syrup; The HCl salt was prepared by treatment with 1N HCl in ether; m.p. 215–220° C.; $[\alpha]_D$=+41 (c=1.15 g, in 100 mL of methanol). Anal. Calcd. for $C_{27}H_{33}N_5O_6F_2Cl_2$. 0.8 MeOH: C, 52.00; H, 5.68; N, 10.90. Found: C, 52.08; H; 5.70; N, 10.53.

EXAMPLE 26 AND EXAMPLE 27

(+)-1,2,3,6-Tetrahydro-1-{N-[3-(4-(2-pyridyl)-piperidin-1-yl)-(2-fluoro)propyl]}carboxamido-5-metho xycarbonyl-2-oxo-6-(3,4-difluorophenyl)-4-methylpyrim idine dihydrochloride A mixture of (+)-1,2,3,6-tetrahydro-1-{N-[3 -(4-(2-pyridyl)-piperidine-1-yl)-(2-hydroxy)propyl]}ca rboxamido-5-methoxycarbonyl-2-oxo-6-(3,4-difluorophenyl)-4-methylpyrimidine (0.50 g, 0.92 mmol), diethylaminosulfur trifluoride (DAST, 0.222 g, 1.38 mmol, 1.5 eq.), and benzene (50 mL) was stirred at 70 ° C. under dry argon atmosphere for 24 h. The TLC analysis of reaction mixture showed the complete disappearance of the starting material. Solvent was evaporated under reduced pressure and the residue was purified by column chromatography on silica gel (20 g), using chloroform/methanol/2 M ammonia in methanol (500/16/8) as the eluent to give two products as a mixture of two diastereomers. These diastereomers were purified by chiral HPLC separation on Chiralpak A3, 4.6× 250 mm column, using isocratic condition (90% hexane and 10% ethanol containing 0.5% DEA). The retention time for the first product (example 26) was 12.97 minutes and for the second product (example 27) was 16.18 minutes. The combined yield of these products is (65 mg +65 mg) 24%. The HCl salt was prepared by treatment with 1N HCl in ether; Example 26: m.p. 132–134° C.; $[\alpha]_D$=+108 (c=0.715 g, in 100 mL of chloroform). Anal. Calcd. for $C_{28}H_{32}N_5O_4F_3Cl_2$. 2.0 $H_2O$: C, 53.38; H, 5.60; N, 11.12. Found: C, 53.28; H; 5.89; N, 10.96. Example 27: m.p. 130–132° C.; $[\alpha]_D$=+100 (c=0.7 g, in 100 mL of chloroform). Anal. Calcd. for $C_{28}H_{32}N_5O_4F_3Cl_2$.1.5 $H_2O$: C, 54.15; H, 5.52; N, 11.28. Found: C, 54.17; H; 5.57; N, 11.00.

Note: Examples 26 and 27 are two diastereomeric products derived from the (+)enantiomer at the pyrimidine part and the two possible enantiomeric compounds with respect to the fluoromethylene chiral center.

EXAMPLE 28

(+)-5-Carboxamido-6-(2,4-difluorophenyl)-4-ethyl-1-{N-[3-(4-cyano-4-phenylpiperidin-1-yl)propyl]}carboxamido-2-oxo-1,2,3,6-tetrahydropyrimidine.

a) 3-(4-Cyano-4-phenylpiperidin-1-yl)propylphthalimide.

A mixture of 4-cyano-4-phenylpiperidine hydrochloride (111 g, 0.5 mol), 3-bromopropylphthalimide (135.39 g, 0.505 mol), potassium carbonate (276.42 g, 2 mol), and potassium iodide (5.4 g) in DMF (1 L) was stirred and heated at 100–110° C. for 8 h. About 80% of the solvent was evaporated at reduced pressure, the residue was diluted with dichloromethane (1 L) and washed with brine (3×300 mL) and dried ($Na_2SO_4$). Solvent was evaporated from the dichloromethane solution and the residue was treated with isopropanol (400 mL) and cooled. The pale yellow crystalline product formed was filtered, washed with ice-cold isopropanol and dried (168.6 g, 90%); M.p. 96–98° C.

b) 3-(4-Cyano-4-phenylpiperidin-1-yl)propylamine.

To a solution of 3-(4-cyano-4-phenylpiperidin-1-yl) propylphthalimide (112 g, 0.3 mol) in methanol (1.5 L), hydrazine (30 mL) was added and the mixture was stirred and refluxed for 20 h. It was cooled, the white solid formed was filtered and washed with more methanol (200 mL). Solvent was evaporated from the filtrate and residue was dried under vacuum for 4 h. Chloroform (500 mL) was added to this, stirred for 1 h and filtered. The white solid was washed with more chloroform (200 mL), the solvent was evaporated from the combined filtrates to leave the product as an oil (70 g, 96%).

c) Benzyl 2-[(2,4-difluorophenyl)methylene]-3-oxopentanoate. A solution of benzyl propionylacetate (157 g, 0.758 mol), 2,4-difluorobenzaldehyde (107.65 g, 0.758 mol), and piperidinium acetate (5.49 g, 38 mmol) in benzene (1 L) were stirred at room temperature for 96 h. The mixture was washed with water (2×100 mL), dried (magnesium sulfate) and the solvent evaporated under reduced pressure to get the product as a pale yellow syrup (251.2 g). It was used in the next step without further purification.

d) 5-(Benzyloxycarbonyl)-1,6-dihydro-2-methoxy-4-ethyl-6-(2,4-difluorophenyl)pyrimidine.

A suspension of benzyl 2-[(2,4-difluorophenyl) methylene]-3-oxopentanoate (80.0 g, 0.241 mol), 0-methylisourea hemisulfate (63.8 g, 0.362 mol, 1.5 eq.), $NaHCO_3$ (60.48 g, 0.72 mol) in ethanol (800 mL) was stirred at 60–70 (C for 20 h. After cooling to room temperature, the mixture was filtered, and the solid was washed with ethanol (200 mL). The solvent was evaporated from the combined filtrates and the residue was purified by column chromatography (SiO$_2$, EtOAc/Hexane, 10%–30%) to get 5-(benzyloxycarbonyl)-1,6-dihydro-2-methoxy-4-ethyl-6-(2,4-difluorophenyl) pyrimidine as a pale yellow oil (39 g, 42%). The $^1$H-NMR analysis showed it to be a mixture of amine/imine tautomers and was used as is in the next step.

e) 5-(Benzyloxycarbonyl)-4-ethyl-1,6-dihydro-2-methoxy-6-(2,4-difluorophenyl)-1-[(4-nitrophenyloxy) carbonyl] pyrimidine.

To a well stirred solution of 5-(benzyloxycarbonyl)-1,6-dihydro-2-methoxy-4-ethyl-6-(2,4-difluorophenyl) pyrimidine (22.5 g, 59.3 mmol) and 4-(N,N-dimethyl amino) pyridine (9.3 g, 75.8 mmol) in CH$_2$Cl$_2$ (200 mL) was added a powder of 4-nitrophenyl chloroformate (15.3 g, 75.8 mmol) at 0° C. The reaction mixture was stirred for 12 h at room temperature and then water (50 mL) was added. The pH of the aqueous layer was adjusted to 10–11 by the addition of 6 N sodium hydroxide. The dichloromethane layer was separated and dried (Na$_2$SO$_4$). Solvent was evaporated in vacuo and the residue was purified by column chromatography (SiO$_2$, dichloromethane /hexane, 20%–50%) to give the product as a viscous oil (32.0 g, 98%).

f) 5-(Benzyloxycarbonyl)-4-ethyl-1,6-dihydro-1-{N-[2-phenyl) ethyl]}carboxamido-2-methoxy-6-(2,4-difluorophenyl) pyrimidine.

To a stirred solution of 5-(benzyloxycarbonyl)-4-ethyl-1,6-dihydro-2-methoxy-6-(2,4-difluorophenyl)-1-[(4-nitrophenyloxy)carbonyl]pyrimidine (32 g, 58.17 mmol) in dichloromethane (200 mL) was added R-(+)-(-methylbenzylamine (9.16, 75.6 mmol) at room temperature and the stirring was continued for 12 h. The mixture was diluted with more dichloromethane (200 mL) and washed with 0.5 N NaOH solution (2×60 mL). The organic layer was dried over Na$_2$SO$_4$, filtered and solvent was evaporated. The resulting mixture of diastereomers was separated by column chromatography(SiO$_2$, 3% EtOAc in toluene). The first major product to elute was (+)-5-(benzyloxycarbonyl)-4-ethyl-1,6-dihydro-1-{N-[2-phenyl) ethyl]}carboxamido-2-methoxy-6-(2,4-difluorophenyl)pyrimidine (12.15 g, 38%). $[\alpha]_D$=+214 (c=1.5 g in 100 mL CHCl$_3$); The second major product to elute was the other diastereomer and no effort was made to isolate it.

g) (+)-5-(Benzyloxycarbonyl)-1,6-dihydro-2-methoxy-4-ethyl-6-(2,4-difluorophenyl)pyrimidine.

To a stirred solution of (+)-5-(benzyloxycarbonyl)-4-ethyl-1,6-dihydro-1-{N-[2-phenyl)ethyl]}carboxamido-2-methoxy-6-(2,4-difluorophenyl)pyrimidine (11.15 g, 20.41 mmol) in toluene (250 mL) was added 1,8-diazabicyclo[5,4,01-undec-7-ene (4.04 g, 26.53 mmol) and the mixture was stirred at room temperature for 14 h. The solvent was evaporated and the residue was purified by flash column chromatography on silica gel with 3:1 EtOAc/hexane as eluent to give (+)-5-(benzyloxycarbonyl)-1,6-dihydro-2-methoxy-4-ethyl-6 -(2,4-difluorophenyl)pyrimidine as a viscous oil (6.15 g, 78%).

h) (+)-5-(Benzyloxycarbonyl)-4-ethyl-1,6-dihydro-2-methoxy-6-(2,4-difluorophenyl)-1-[(4-nitrophenyloxy) carbonyl]pyrimidine.

To a well stirred solution of (+)-5-(benzyloxycarbonyl) -1,6-dihydro-2-methoxy-4-ethyl-6-(2,4-difluorophenyl) pyrimidine (4.1 g, 10.62 mmol) and 4-(N,N-dimethylamino) pyridine (1.69 g, 13.80 mmol) in CH$_2$Cl$_2$ (200 mL) was added a powder of 4-nitrophenyl chloroformate (2.78 g, 13.80 mmol) at room temperature. The reaction mixture was stirred for 12 h and washed with 0.5 N NaOH solution (2×50 mL). The organic layer was separated and dried (Na$_2$SO$_4$). The solvent was evaporated and the residue was purified by column chromatography on silica gel using dichloromethane/hexane (20%–50%) as the eluent to give (+)-5-(benzyloxycarbonyl)-4-ethyl-1,6-dihydro-2-methoxy-6-(2,4-difluorophenyl)-1-[(4-nitrophenyloxy)carbonyl] pyrimidine (5.37 g, 92%) as a viscous oil.

i) (+)-5-(Benzyloxycarbonyl)-6-(2,4-difluorophenyl)-4-ethyl-1-{N-[3-(4-cyano-4-phenylpiperidin-1-yl)propyl]} carboxamido-2-oxo-1,2,3,6-tetrahydropyrimidine.

A mixture of (+)-5-(benzyloxycarbonyl)-4-ethyl-1,6-dihydro-2-methoxy-6-(2,4-difluorophenyl)-1-[(4-nitrophenyloxy) carbonyl]pyrimidine (6.50 g, 11.81 mmol) and 3-[4-cyano-4-phenylpiperidin-1-yl]propylamine (3.60 g, 15.36 mmol) in THF (500 mL) was stirred at room temperature for 18 h. It was cooled to 0° C. and 10% HCl in water (2 mL) was added and stirred for 2 h. The mixture was washed with 0.5 N aq. NaOH solution (30 mL), dried over Na$_2$SO$_4$ and the solvent evaporated. The residue was purified by column chromatography on SiO$_2$ using CHCl$_3$/MeOH/2M NH$_3$ in MeOH (100/2/1) as eluent to obtain (+)-5-(benzyloxycarbonyl)-6-(2,4-difluorophenyl)-4-ethyl-1-{N [3-(4-cyano-4-phenylpiperidin-1-yl)propyl]} carboxamido-2-oxo-1,2,3,6-tetrahydropyrimidine as a white foamy solid (7.05 g, 93%).

j) 6-(2,4-Difluorophenyl)-4-ethyl-1-{N-[3-(4-cyano-4-phenylpiperidin-1-yl)propyl]}carboxamido-1,2,3,6-tetrahydro-2-oxopyrimidine-5-carboxylic acid.

To a suspension of 10% Pd—C (2.1 g) in MeOH (100 mL) and H$_2$O (20 mL) was added a solution of (+)-5-(benzyloxycarbonyl)-6-(2,4-difluorophenyl)-4-ethyl-1-{N-[3-(4-cyano-4-phenylpiperidin-1-yl)propyl]}carboxamido-2-oxo-1,2,3,6-tetrahydropyrimidine (7.55 g, 11.2 mL) in methanol (100 mL) and the mixture was hydrogenated at 80 psi for 14 h. The black suspension was filtered through a pad of celite and washed thoroughly with MeOH (2.0 L) and methanol/chloroform (1:2, 200 mL). Solvent was evaporated from the combined filtrate to leave the product (+)-6-(2,4-difluorophenyl)-4-ethyl-1-{N-[3-(4-cyano-4-phenylpiperidin-1-yl)propyl]}carboxamido-1,2,3,6-tetrahydro-2-oxopyrimidine-5-carboxylicacidas a white solid (6.06 g, 98%). It was used in the next step without further purification.

k) (+)-5-Carboxamido-6-(2,4-difluorophenyl)-4-ethyl-1-{N-[3-(4-cyano-4-phenylpiperidin-1-yl)propyl]} carboxamido-2-oxo-1,2,3,6-tetrahydropyrimidine.

A mixture of (+)-6-(2,4-difluorophenyl)-4-ethyl-1-{N-[3-(4-cyano-4-phenylpiperidin-1-yl)propyl]}carboxamido-1,2,3,6-tetrahydro-2-oxopyrimidine-5-carboxylic acid (6.30 g, 11.18 mmol), 1-(3-dimethylaminopropyl)-3-ethylcarbodiimide hydrochloride (4.29 9, 22.36 mmol, 2 eq.), and 4-(N,N-dimethylamino)pyridine (3.41 g, 27.95 mmol, 2.5 eq) in anhydrous dichloromethane (400 mL) was stirred at room temperature for 2 h. To this, 40% aqueous ammonia (6.13 g, 5 eq) was added and the stirring was continued for 12 h. The mixture was diluted with 200 mL of dichloromethane and washed with saturated aqueous ammonium chloride solution (3×200 mL). Solvent was evaporated from the dried (sodium sulfate) dichloromethane solution and the residue was purified by column chromatography on silica gel using chloroform-methanol-2M ammonia in methanol (100/2/1) as the eluent, to obtain the desired product as a white powder (5.45 g, 87%); m.p. 210–211° C.; Part of the compound (300 mg) was dissolved in dichloromethane (3 mL), cooled to 0–5° C. and treated with 1N HCl in ether (10 mL) followed by anhydrous ether (20 mL). The white powder formed was filtered, washed with ether (100 mL) and dried (320 mg, 100%); m.p. 196–97° C.; [α]$_D$=+126 (c=0.505 g, in 100 mL of 1:1 chloroform/MeOH). Anal. Calcd. for $C_{29}H_{33}N_6O_3F_2Cl$: C, 59.27; H, 5.78; N, 14.24. Found: C, 59.33; H; 5.67; N, 14.32.

EXAMPLE 29

(+)-5-Carboxamido -6-(3,4-difluorophenyl)-4-methoxymethyl-1-{N-[3-(4 (2-pyridyl)piperidin-1-yl)propyl]}carboxamido-2-oxo-1,2,3,6-tetrahydropyrimidine dihydrochloride.

a) 2-Cyanoethyl 4-methoxyacetoacetate.

A mixture of methyl 4-methoxyacetoacetate (50 g, 0.342 mol) and 3-hydroxypropionitrile (31.61 g, 0.444 mol) was heated to 160–180° C. in a distillation set-up. It was kept at that temperature for 2 h until the distillation of the methanol stopped. The residual yellow oil of 2-cyanoethyl 4-methoxyacetoacetate (56.4 g, 90%) was used as is without any further purification.

b) 2-Cyanoethyl 2-[(3,4-difluorophenyl)methylene]-3-oxo-4-methoxybutyrate.

A solution of 2-cyanoethyl 4-methoxyacetoacetate (17.8 g, 0.125 mol), 3,4-difluorobenzaldehyde (25.5 g, 6.26 mmol), acetic acid (0.3769, 6.26 mmol), and piperidine (0.533 g, 6.26 mmol) in benzene (500 mL) were added molecular sieves (200 g) and the mixture was stirred at room temperature for 24 h. Then the solvent was evaporated under reduced pressure and the residue was purified by column chromatography using chloroform/ethyl acetate (100:5) to get the product as an oil (29 g, 75%).

c) 5-(2-Cyanoethoxycarbonyl)-1,6-dihydro-2-methoxy-4-methoxymethyl-6-(3,4-difluorophenyl)pyrimidine.

A suspension of 2-cyanoethyl 2-[(3,4-difluorophenyl)methylene]-3-oxo-4—methoxybutyrate (29 g, 0.094 mol), O-methylisourea hemisulfate (21 g, 0.121 mol, 1.3 eq.), dimethylaminopyridine (29.67 g, 0.243 mol, 2.5 eq.) in ethanol (400 mL) was stirred at 50–55 ° C. for 6 h. The solvent was evaporated from the combined filtrates and the residue was purified by column chromatography (SiO$_2$, EtOAc/hexane, 10%–30%) to get 5-(2-cyanoethoxycarbonyl)-1,6-dihydro-2-methoxy-4-methoxymethyl-6-(3,4-difluorophenyl)pyrimidine as a pale yellow oil (10.5 g, 31%). The $^1$H-NMR analysis showed it to be a mixture of amine/imine tautomers and was used as is in the next step.

d) 5-(2-Cyanoethoxycarbonyl)-4-methoxymethyl-1,6-dihydro-2-methoxy-6-(3,4-difluorophenyl)-1-[(4-nitrophenyloxy)carbonyl]pyrimidine.

To a well stirred solution of 5-(2-cyanoethoxy carbonyl)-1,6-dihydro-2-methoxy-4-methoxymethyl-6-(3,4-difluorophenyl)pyrimidine (10.5 g, 28.74 mmol) and 4-(N,N-dimethylamino)pyridine (6.95 9, 34.49 mmol) in CH$_2$Cl$_2$ (100 mL) was added a powder of 4-nitrophenyl chloroformate (4.21 g, 34.49 mmol) at 0° C. The reaction mixture was stirred for 12 h at room temperature and then the solvent was evaporated. The residue was purified by column chromatography (SiO$_2$, dichloromethane/hexane, 20%–50%) to give the product as a viscous oil (6.5 g, 43%).

e) 5-(2-Cyanoethoxycarbonyl)-4-methoxymethyl-1,6-dihydro-1-{N-[2-phenyl) ethyl]}carboxamido-2-methoxy-6-(3,4-difluorophonyl)pyrimidine.

To a stirred solution of 5-(2-cyanoethoxycarbonyl)-4-methoxymethyl-1,6-dihydro-2-methoxy-6-(3,4-difluorophenyl)-1-[(4-nitrophenyloxy)carbonyl]pyrimidine (6.5 g, 12.25 mmol) in dichloromethane (150 mL) was added R-(+)-α-methylbenzylamine (1.78 g, 14.7 mmol) at room temperature and the stirring was continued for 12 h. Solvent was evaporated and the residue was purified by column chromatography (SiO$_2$, 10–20% EtOAc in hexane). The first major product to elute was (+)-5-(2-cyanoethoxycarbonyl)-4-methoxymethyl-1,6-dihydro-1-{N-[2-phenyl) ethyl]}carboxamido-2-methoxy-6-(3,4-difluorophenyl)pyrimidine (2.54 g, 44.5%) [α]$_D$=+177.8 (c=9.2 g in 100 mL CHCl$_3$); The second major product to elute was the other diastereomer and no effort was made to isolate it.

f) (+)-5-(2-Cyanoethoxycarbonyl)-1,6-dihydro-2-methoxy-4-ethyl-6-(3,4-difluorophenyl)pyrimidine.

To a stirred solution of (+)-5-(2-cyanoethoxycarbonyl)-4-methoxymethyl-1,6-dihydro-1-{N-[2-phenyl)ethyl]}carboxamido-2-methoxy-6-(3,4-difluorophenyl)pyrimidine (2.80 g, 5.46 mmol) in toluene (80 mL) was added 1,8-diazabicyclo[5,4,0]-undec-7-ene (0.250 g, 1.64 mmol) and the mixture was stirred at 75° C. for 1 h. The solvent was evaporated and the residue was purified by flash column chromatography on silica gel with 3:1 EtOAc/hexane as eluent to give (+)-5-(2-cyanoethoxycarbonyl)-1,6-dihydro-2-methoxy-4 -methoxymethyl-6-(3,4-difluorophenyl) pyrimidine as a viscous oil (0.82 g, 40.5%).

g) (+)-5-(2-Cyanoethoxycarbonyl)-4-methoxymethyl-1,6-dihydro-2-methoxy-6-(3,4-difluorophenyl)-1-[(4-nitrophenyloxy)carbonyl]pyrimidine.

To a well stirred solution of (+)-5-(2-cyanoethoxycarbonyl)-1,6-dihydro-2-methoxy-4-methoxymethyl-6-(3,4-difluorophenyl)pyrimidine (0.82 g, 2.24 mmol) and 4-(N,N-dimethylamino)pyridine (0.329 g, 2.69 mmol) in CH$_2$Cl$_2$ (200 mL) was added a powder of 4-nitrophenyl chloroformate (0.543 g, 2.69 mmol) at room temperature. The solvent was evaporated and the residue was purified by column chromatography on silica gel using dichloromethane/hexane (20%–50%) as the eluent to give (+)-5-(2-cyanoethoxycarbonyl)-4-methoxymethyl-1,6-dihydro-2-methoxy-6-(3,4-difluorophenyl)-1-[(4-nitrophenyloxy)carbonyl] pyrimidine (0.80 g, 67%) as a viscous oil.

h) (+)-5-(2-Cyanoethoxycarbonyl)-6-(3,4-difluorophenyl)-4-methoxymethyl-1-{N-[3-(4-(2-pyridyl)piperidin-1-yl)propyl]}carboxamido-2-oxo-1,2,3,6-tetrahydropyrimidine.

A mixture of (+)-5-(2-cyanoethoxycarbonyl)-4-methoxymethyl-1,6-dihydro-2-methoxy-6-(3,4-difluorophenyl)-1-[(4-nitrophenyloxy)carbonyl]pyrimidine (0.44 g, 0.83 mmol) and 3-[4-(2-pyridyl)piperidin-1-yl]propylamine (0.218 g, 0.996 mmol) in THF (15 mL) was stirred at room temperature for 12 h. It was cooled to 0° C. and 10% HCl in water (2 mL) was added and stirred for 2 h. Solvent was evaporated and the residue was purified by column chromatography on SiO$_2$ using CHCl$_3$/MeOH/2M NH$_3$ in MeOH (100/2/1) as eluent to obtain (+)-5-(2-cyanoethoxycarbonyl)-6-(3,4-difluorophenyl)-4-methoxymethyl-1-{N-(3-(4-(2-pyridyl)piperidin-1-yl)propyl]}carboxamido-2-oxo-1,2,3,6-tetrahydropyrimidine as a white foamy solid (0.41 g, 83%).

i) 6-(3,4-Difluorophenyl)-4-methoxymethyl-1-{N-[3-(4-(2-pyridyl)piperidin-1-yl)propyl]}carboxamido-1,2,3,6-tetrahydro-2-oxopyrimidine-5-carboxylic acid.

To a stirred solution of (+)-5-(2-cyanoethoxycarbonyl)-6-(3,4-difluorophenyl)-4-methoxymethyl-1-{N-[3-(4-(2-pyridyl)piperidin-1-yl)propyl]}carboxamido-2-oxo-1,2,3,6-tetrahydropyrimidine (0.34 g, 0.57 mmol) in acetone (5 mL) at 0° C., sodium hydroxide solution (1 N, 1.71 mL) was added drop wise and the stirring was continued until the disappearance of the starting material (1 hour). Most of the acetone from the mixture was evaporated under reduced pressure while keeping the temperature at 0° C. and the residue was adjusted to pH 7.0 by the addition of 1N hydrochloric acid. The white precipitate of 6-(3,4-difluorophenyl)-4-methoxymethyl-1-{N-[3-(4-(2-pyridyl)piperidin-1-yl)propyl]}carboxamido-1,2,3,6-tetrahydro-2-oxopyrimidine-5-carboxylic acid formed was filtered and dried under vacuum (0.30 g, 96%).

j) (+)-5-Carboxamido-6-(3,4-difluorophenyl)-4-methoxymethyl-1-{N-[3-(4-(2-pyridyl)piperidin-1-yl)propyl]}carboxamido-2-oxo-1,2,3,6-tetrahydropyrimidine.

A mixture of (+)-6-(3,4-difluorophenyl)-4-methoxymethyl-1-{N-[3-(4-(2-pyridyl)piperidin-1-yl)propyl]}carboxamido-1,2,3,6-tetrahydro-2-oxopyrimidine-5-carboxylic acid (0.30 g, 0.55 mmol), 1-(3-dimethylaminopropyl)-3-ethylcarbodiimide hydrochloride (0.212 9, 1.1 mmol, 2 eq.), and 4-(N,N-dimethylamino) pyridine (0.134 g, 1.1 mmol, 2 eq) in anhydrous dichloromethane (20 mL) was stirred at room temperature for 2 h. To this, 40% aqueous ammonia (0.64 g, 10 eq) was added and the stirring was continued for 12 h. The mixture was diluted with 20 mL of dichloromethane and washed with saturated aqueous ammonium chloride solution (3×200 mL). Solvent was evaporated from the dried (sodium sulfate) dichloromethane solution and the residue was purified by column chromatography on silica gel using chloroform-methanol-2M ammonia in methanol (100/2/1) as the eluent, to obtain the desired product as a white powder (0.232 g, 78%); The HCl salt of this compound was prepared by treatment with 1 N HCl in ether. m.p. 95–97° C.; $[\alpha]_D$=+139 (c=2.1 g, in 100 mL of chloroform). Anal. Calcd. for $C_{27}H_{34}N_6O_4F_2Cl_2$. 2.2 $H_2O$: C, 49.50; H, 5.91; N, 12.83. Found: C, 49.50; H, 5.89; N, 12.43.

EXAMPLE 30

(+)-5-Methoxycarbonyl-6-(3,4-difluorophenyl)-4-methoxymethyl-1-{N-[3-(4-(2-pyridyl)piperidin-1-yl)propyl]}carboxamido-2-oxo-1,2,3,6-tetrahydropyrimidine.

A mixture of (+)-6-(3,4-difluorophenyl)-4-methoxymethyl-1-{N-[3-(4-(2-pyridyl)piperidin-1-yl)propyl]}carboxamido-1,2,3,6-tetrahydro-2-oxopyrimidine-5-carboxylic acid (0.30 g, 0.55 mmol), 1-(3-dimethylaminopropyl)-3-ethylcarbodiimide hydrochloride (0.212 g, 1.1 mmol, 2 eq.), and 4-(N,N-dimethylamino) pyridine (0.134 g, 1.1 mmol, 2 eq) in methanol (20 mL) was stirred at room temperature for 20 h. Solvent was evaporated and the residue was dissolved in 20 mL of dichloromethane and washed with saturated aqueous ammonium chloride solution (3×200 mL). Solvent was evaporated from the dried (sodium sulfate) dichloromethane solution and the residue was purified by column chromatography on silica gel using chloroform-methanol-2M ammonia in methanol (100/2/1) as the eluent, to obtain the desired product as a white powder (278 mg, 91%); The HCl salt of this compound was prepared by treatment with 1 N HCl in ether. m.p. 180–184° C.; $[\alpha]_D$=+122 (c=1.25 g, in 100 mL of methanol) Anal. Calcd. for $C_{28}H_{31}N_5O_5F_2Cl_2$. 1.0 $H_2O$: C, 51.86; H, 5.75; N, 10.80. Found: C, 52.14; H, 5.72; N, 10.53.

EXAMPLE 31

(+)-1,2,3,6-Tetrahydro-1-{N-[3-(4-(2-pyridyl)-piperidine-1-yl)-(2-oxo)propyl]}carboxamido-5-methoxy carbonyl-2-oxo-6-(3,4-difluorophenyl)-4-methoxymethyl pyrimidine dihydrochloride a) Methyl 2-[(3,4-difluorophenyl) methylene]-3-oxo-4-methoxybutyrate.

A solution of methyl 4-methoxyacetoacetate (84.32 g, 0.577 mol), 3,4-difluorobenzaldehyde (82 g, 0.577 mmol), and piperidinium acetate (5.86 g, 0.068 mol) in benzene (1.5 L) were added molecular sieves (400 g) and the mixture was stirred at room temperature for 48 h. The molecular sieves were removed by filtration and the solvent was evaporated from the filtrate under reduced pressure. The residue was purified by column chromatography on silica gel using chloroform/ethyl acetate (100:3) to get the product as an oil (67 g, 47%).

b) 5-Methoxycarbonyl-1,6-dihydro-2-methoxy-4-methoxymethyl-6-(3,4-difluorophenyl)pyrimidine.

A suspension of methyl 2-[(3,4-difluorophenyl) methylene]-3-oxo-4-methoxybutyrate (7.50 g, 27.75 mmol), O-methylisourea hemisulfate (7.17 g, 41.63 mmol, 1.5 eq.), sodium bicarbonate (6.99 g, 83.25 mmol, 3 eq.) in ethanol (400 mL) was stirred at 50–55° C. for 6 h. The solvent was evaporated from the combined filtrates and the residue was purified by column chromatography ($SiO_2$, EtOAc/hexane, 10%–30%) to get 5-methoxycarbonyl-1,6-dihydro-2-methoxy-4-methoxymethyl-6-(3,4-difluorophenyl) pyrimidine as a pale yellow oil (4.3 g, 47%). The $^1$H-NMR analysis showed it to be a mixture of amine/imine tautomers and was used as is in the next step.

c) 5-Methoxycarbonyl-4-methoxymethyl-1,6-dihydro-2-methoxy-6-(3,4-difluorophenyl)-1-[(4-nitrophenyloxy)carbonyl]pyrimidine.

To a well stirred solution of 5-methoxycarbonyl-1,6-dihydro-2-methoxy-4-methoxymethyl-6-(3,4-difluorophenyl)pyrimidine (4.3 g, 13.18 mmol) and 4-(N,N-dimethylamino)pyridine (2.09 g, 17.13 mmol) in $CH_2Cl_2$ (100 mL) was added a powder of 4-nitrophenyl chloroformate (3.45 g, 17.13 mmol) at 0° C. The reaction mixture was stirred for 12 h at room temperature and the solid formed was removed by filtration. Solvent was evaporated from the filtrate and the residue was purified by column chromatography ($SiO_2$, dichloromethane/hexane, 20%–50%) to give the product as a viscous oil (3.85 g, 59%).

d) 5-Methoxycarbonyl-4-methoxymethyl-1,6-dihydro-1-(N-[2-phenyl)ethyl]}carboxamido-2-methoxy-6-(3,4-difluorophenyl)pyrimidine.

To a stirred solution of 5-methoxycarbonyl-4-methoxymethyl-1,6-dihydro-2-methoxy-6-(3,4-difluorophenyl)-1-[(4-nitrophenyloxy)carbonyl] pyrimidine (3.82 g, 7.77 mmol) in THF (140 mL) was added R-(+)-α-methylbenzylamine (1.13 g, 9.33 mmol, 1.2 eq.) at room temperature and the stirring was continued for 12 h. Solvent was evaporated and the residue was purified by column chromatography ($SiO_2$, 10–20% EtOAc in hexane). The first major product to elute was (+)-5-methoxycarbonyl-4-methoxmethyl-1,6-dihydro-1-{N-[2-phenyl)ethyl]} carboxamido-2-methoxy-6-(3,4-difluorophenyl)pyrimidine (1.74 g, 44.5). $[\alpha]_D$=+205.5 (c=5.1 g in 100 mL $CHCl_3$); The second major product to elute was the other diastereomer and no effort was made to isolate it.

e) (+)-5-Methoxycarbonyl-1,6-dihydro-2-methoxy-4-methoxymethyl-6-(3,4-difluorophenyl)pyrimidine.

To a stirred solution of (+)-5-methoxycarbonyl-4-methoxymethyl-1,6-dihydro-1-{N-[2-phenyl)ethyl]} carboxamido-2-methoxy-6-(3,4-difluorophenyl)pyrimidine (1.74 g, 3.67 mmol) in toluene (40 mL) was added 1,8-diazabicyclo[5,4,0]-undec-7-ene (0.250 g, 1.64 mmol) and the mixture was stirred at 70–80° C. for 1.5 h. The solvent was evaporated and the residue was purified by flash column chromatography on silica gel with 9:1 $CHCl_3$/EtOAc as eluent to give (+)-5-methoxycarbonyl-1,6-dihydro-2-methoxy-4-methoxymethyl-6-(3,4-difluorophenyl) pyrimidine as a viscous oil (1.11 g, 92.5%).

f) (+)-5-Methoxycarbonyl-4-methoxymethyl-1,6-dihydro-2-methoxy-6-(3,4-difluorophenyl)-1-[(4-nitrophenyloxy)carbonyl]pyrimidine.

To a well stirred solution of (+)-5-methoxycarbonyl-1,6-dihydro-2-methoxy-4-methoxymethyl-6-(3,4-difluorophenyl)pyrimidine (1.11 g, 3.4 mmol) and 4-(N,N-dimethylamino)pyridine (0.54 g, 4.42 mmol) in $CH_2Cl_2$ (200 mL) was added a powder of 4-nitrophenyl chloroformate (0.891 g, 4.42 mmol) at room temperature. The solvent was evaporated and the residue was purified by column chromatography on silica gel using $CHCl_3$/EtOAc (20%–50%) as the eluent to give (+)-5-methoxycarbonyl-4-methoxymethyl-1,6-dihydro-2-methoxy-6-(3,4-difluorophenyl)-1-[(4-nitrophenyloxy)carbonyl] pyrimidine (1.30 g, 78%) as a viscous oil. $[\alpha]_D$=+262.2 (c=2.3 g in 100 mL $CHCl_3$).

g) (+)-1,2,3,6-Tetrahydro-1-{N-[3-(4-(2-pyridyl)-piperidine- 1-yl)-(2-hydroxy)propyl]}carboxamido-5-methoxycarbonyl-2-oxo-6-(3,4-difluorophenyl)-4-methoxymethylpyrimidine.

A solution of (+)-6-(3,4-difluorophenyl)-1,6-dihydro-2-methoxy-5-methoxycarbonyl-4-methoxymethyl-1-(4-nitrophenoxy)carbonylpyrimidine (0.450 g, 0.91 mmol), 3-[4-(2-pyridyl)piperidin-1-yl]-2-hydroxypropylamine (0.280 g, 1.19 mmol) in tetrahydrofuran (100 mL) was stirred at room temperature for 24 hours. The reaction mixture was stirred for another 1 hour after addition of 2 ml of 6N HCl. Solvent was evaporated at reduced pressure and the residue was basified by treatment with 10% aqueous KOH solution, extracted with dichloromethane (3×10 mL). The combined extracts were dried over potassium carbonate, and solvent evaporated. The crude product was purified by flash chromatography (dichloromethane:MeOH:2M ammonia in MeOH,90:8:4) to give 0.514 g (98%) as a syrup.

h) (+)-1,2,3,6-Tetrahydro-1-{N-[3-(4-(2-pyridyl)-piperidine-1-yl)-(2-oxo)propyl]}carboxamido-5-methoxycarbonyl-2-oxo-6-(3,4-difluorophenyl)-4-methoxymethyl pyrimidine dihydrochloride To a stirred solution of DMSO (0.174 g, 2.23 mmol) in dichloromethane (5 mL) at −78° C., oxalyl chloride (0.135 g, 1.07 mmol) in dichloromethane (5 mL) was added and the mixture was stirred for 3 min. To this, a solution of (+)-1,2,3,6-tetrahydro-1-{N-[3-(4-(2-pyridyl)-piperidine-1-yl)-(2-hydroxy)propyl]}carboxamido-5-met hoxycarbonyl-2-oxo-6-(3,4-difluorophenyl)-4-methoxyme thylpyrimidine (0.51 g, 0.889 mmol) in dichloromethane (5 mL) was added and the stirring was continued for 15 min. It was warmed to room temperature and added 5 mL of water. The pH of the mixture was adjusted to 10–11 by adding 1N NaOH and the dichloromethane layer was separated. The aqueous layer was extracted with more dichloromethane (3×10 mL). The combined dichloromethane extracts were dried (magnesium sulfate), solvents evaporated, and the residue was purified by flash chromatography (dichloromethane:MeOH:2M ammonia in MeOH,90:8:4) to give 0.32 g (63%) of the product as a syrup. $[\alpha]_D$=+122 (c=0.55 g in 100 mL $CHCl_3$); Anal. Calcd. for $C_{29}H_{33}N_5O_6F_2Cl_2$. 2.5 $H_2O$: C, 48.77; H, 5.55; N, 10.16. Found: C, 48.71; H, 5.72; N, 9.87.

EXAMPLE 32 AND EXAMPLE 33

Syn and anti isomers of (+)-1,2,3,6-tetrahydro-1-{N-[3-(4-(2-pyridyl)-piperidine-1-yl)-(2-hydroximino)propyl ]}carboxamido-5-methoxycarbonyl-2-oxo-6-(3,4-difluorophenyl)-4-methoxymethylpyrimidine dihydrochloride A solution of (+)-1,2,3,6-tetrahydro-1-{N-[3-(4-(2-pyridyl)-piperidin-1-yl)-(2-oxo)propyl]}carboxa mido-5-methoxycarbonyl-2-oxo-6-(3,4-difluorophenyl)-4-methoxymethylpyrimidine (0.14 g, 0.22 mmol), hydroxylamine hydrochloride (19.6 mg, 0.28 mmol), and sodium acetate (74.8 mg, 0.55 mmol) in methanol (5 mL) was stirred at room temperature for 24 h. Solvent was evaporated at reduced pressure, the residue was mixed with dichloromethane (30 mL) and washed with water. The dichloromethane solution was dried (sodium sulfate) and the solvent evaporated. The residue was purified by column chromatography on silica gel (chloroform:MeOH:2M ammonia in MeOH,90:8:4). The first product to elute was Example 32, syn isomer with respect to oxime hydroxyl and piperidine (30 mg); $[\alpha]_D$=+94.1 (c=0.528 g in 100 mL $CHCl_3$); The HCl salt was prepared by treatment with 1N HCl in ether; m.p. 90–92 ° C.; Anal. Calcd. for $C_{28}H_{34}N_6O_6F_2Cl_2$. 1.5 $H_2O$.0.6 $CH_2Cl_2$: C, 47.65; H, 5.35; N, 11.26. Found: C, 47.67; H; 5.56; N, 11.36.

The second product to elute was example 33, anti isomer with respect to oxime hydroxyl and piperidine (70 mg); $[\alpha]_D$=+104 (c=0.3 g in 100 mL $CHCl_3$); The HCl salt was prepared by treatment with 1N HCl in ether; m.p. 103–105° C.; Anal. Calcd. for $C_{28}H_{34}N_6O_6F_2Cl_2$.2.2 $H_2O$.0.22 $CH_2Cl_2$: C, 47.74; H, 5.51; N, 11.84. Found: C, 48.01; H,. 5.72; N, 11.57.

EXAMPLE 34

(+)-1,2,3,6-Tetrahydro-1-{N-[3-(4-(2-pyridyl)-piperidine-1-yl)-(2-methoximino)propyl]}carboxamido-5-methoxycarbonyl-2-oxo-6-(3,4-difluorophenyl)-4-methoxymethylpyrimidine dihydrochloride A solution of (+)-1,2,3,6-tetrahydro-1-{N-[3-(4-(2-pyridyl)-piperidine-1-yl)-(2-oxo)propyl]}carbox amido-5-methoxycarbonyl-2-oxo-6-(3,4-difluorophenyl)-4-methoxymethylpyrimidine (30 mg, 0.047 mmol), O-methoxylamine hydrochloride (7.78 mg, 0.093 mmol), and sodium acetate (32 mg, 0.24 mmol) in methanol (5 mL) was stirred at room temperature for 24 h. Solvent was evaporated at reduced pressure, the residue was mixed with dichloromethane (30 mL) and washed with water. The dichloromethane solution was dried (sodium sulfate) and the solvent evaporated. The residue was purified by column chromatography on silica gel (chloroform:MeOH:2M ammonia in MeOH,90:8:4). Only one isomeric product was detected by this purification (20 mg, 71%); $[\alpha]_D$=+98 (c=0.4 g in 100 mL $CHCl_3$); The HCl salt was prepared by treatment with 1N HCl in ether; m.p. 109–112° C.; Anal. Calcd. for $C_{29}H_{36}N_6O_6F_2Cl_2$. 2.3$H_2O$. 0.46 $CH_2Cl_2$: C, 46.93; H, 5.55; N, 11.15. Found: C, 47.08; H, 5.66; N, 10.88.

EXAMPLE 35

(±)-1,2,3,6-Tetrahydro-1-{N - [3-(4-(2-carboxamidophenyl)-piparazin-1-yl)-propyl]}carboxamido-5-acetyl-2-oxo-6-(3,4,5-trifluorophenyl)-4-methylpyrimidine dihydrochloride a) 3-{(3,4,5-Trifluorophenyl)methylene}-2,4-pentanedione.

A mixture of 3,4,5-trifluorobenzaldehyde (4.2 g, 26.2 mmol), 2,4-pentanedione (2.62 g, 26.2 mmol), piperidine (0.430 g, 5 mmol)in benzene (150 mL) was stirred and refluxed with a Dean-Stark trap for 8 hours. Benzene was evaporated, the yellow oily residue, 2-{(3,4,5-trifluorophenyl)methylene}-2,4-pentanedione, was used in the next step without any further purification.

b) 6-(3,4,5-Trifluorophenyl)-1,6-dihydro-2-methoxy-5-acetyl-4-methylpyrimidine.

A mixture of 2-{(3,4,5-trifluorophenyl)methylene}-2,4-pentanedione (26.2 mmol), O-methylisourea hydrogen sulfate (3.22 g, 39.3 mmol), and $NaHCO_3$ (6.6 g, 78.6 mmol) in EtOH (400 mL) was stirred and heated at 95–100 ° C. for 6 hours. The mixture was filtered, the solid residue was washed with ethanol (100 mL). Solvent was evaporated from the combined filtrate and the crude product was purified by flash column chromatography on silica gel using 10% through 25% EtOAc in hexane as the gradient eluent, to leave the product as an oil (2.80 g, 36%).

c) 6-(3,4,5-Trifluorophenyl)-1,6-dihydro-2-methoxy-5-acetyl-4-methyl-1-[(4-nitrophenyloxy) carbonyl]pyrimidine To a solution of 6-(3,4,5-trifluorophenyl)-1,6-dihydro-2-methoxy-5-acetyl-4-methylpyrimidine (2.8 g, 9.38 mmol) and pyridine (10 mL) in $CH_2Cl_2$ (200 mL) at 0–5° C., 4-nitrophenyl chloroformate (1.886 g, 9.38 mmol) was added and the mixture was allowed to warm to room temperature. After 12 hours solvent was evaporated and the residue was purified by flash column chromatography ($SiO_2$, dichloromethane/EtOAc, 10%–15%)to obtain the product as a white powder (4.0 g, 92%).

d) 6-(3,4,5-Trifluorophenyl)-1,2,3,6-tetrahydro-2-oxo-5-acetyl-4-methyl-1-[(4-nitrophenyloxy) carbonyl]pyrimidine.

To a well-stirred solution of 6-(3,4,5-trifluorophenyl)-1,6-dihydro-2-methoxy-5-acetyl-4-methyl-1-[(4-nitrophenyloxy) carbonyl]pyrimidine (4.0 g, 8.63 mmol) in THF (100 mL) at 0–5° C., 6N aqueous HCl (4 mL) was added and the mixture was allowed to warm to room temperature. After 2 h, solvent was evaporated and the product dried under vacuum. The product was obtained as a pure single component and no need for further purification (3.88 g, 100%).

e) (±)-1,2,3,6-Tetrahydro-1-{N-[3-(4-(2-carboxamidophenyl)-piperazin-1-yl)-propyl]}carboxamido-5-acetyl-2-oxo-6-(3,4,5-trifluorophenyl)-4-methylpyrimidine dihydrochloride A mixture of 6-(3,4,5-difluorophenyl)-1,2,3,6-tetra hydro-2-oxo-5-acetyl-4-methyl-1-[(4-nitrophenyloxy) carbonyl] pyrimidine (44.9 mg, 0.1 mmol) and 3-[4-(2-carboxamidophenyl)-piperazin-1-yl]-propylamine (26.2 mg, 0.1 mmol) in THF (10 mL) was stirred at room temperature for 10 h and the solvent evaporated. It was redissolved in dichloromethane (10 mL), washed with ice-cold 0.5 N NaOH (2×5 mL), dried and solvent evaporated. The residue was purified by preparative thin layer chromatography on silica gel using chloroform-methanol-2M ammonia in methanol (100/2/1) as the eluent to afford the product as a white powder (60 mg, 93%); The HCl salt was prepared by treatment with 1N HCl in ether to give the product as a dihydrochloride salt. Anal. Calcd. for $C_{28}H_{33}N_6O_4Cl_2F_3$.0.4 $H_2O$: C, 51.52; H. 5.22; N, 12.88. Found: C, 51.70; H, 5.25; N, 12.53.

EXAMPLE 36

1,2,3,6-Tetrahydro-1-{N-[3-(4-(4-fluorobenzoyl) piperidin-1-yl) ethyl]}carboxamido-5-methoxycarbonyl-4 -methyl-6-(3,4-difluorophenyl)-2-oxopyrimidine hydrochloride a). 6-(3,4-Difluorophenyl)-1,2,3,6-tetrahydro-2-oxo-5-methoxycarbonyl-4-methyl-1-(4-nitrophenoxy) carbonylpyrimidine.

A well stirred solution of 6-(3,4-difluorophenyl)-1,6-dihydro-2-methoxy-5-methoxycarbonyl-4-methyl-1-(4-nitrophenoxy)carbonylpyrimidine (10 g) in THF (200 mL) at room temperature, aqueous 6N hydrochloric acid (10 mL) was added and the stirring was continued for 3 h. Solvent was evaporated and the residue was dried under vacuum to obtain the product as a white powder (9.7 g, 100%); m.p. 185–186° C.

b) 6-(3,4-Difluorophenyl)-1,2,3,6-tetrahydro-2-oxo-5-methoxycarbonyl-4-methyl-1-(2-bromoethylamino carbonyl)pyrimidine.

A mixture of 6-(3,4-difluorophenyl)-1,2,3,6-tetrahydro-2-oxo-5-methoxycarbonyl-4-methyl-1-(4-nitrophenoxy) carbonylpyrimidine (0.5 g, 1.118 mmol), 2-bromoethylamine hydrobromide (0.458 g, 2.237 mmol), and potassium carbonate (2.0 g) in THF/water (50 mL/5 mL) were stirred at room temperature for 1 h. Then most of the solvent was evaporated at reduced pressure. The residue was partitioned between dichloromethane and water (100 mL and 100 mL). The dichloromethane layer was separated, washed with ice-cold 0.5 N NaOH (2×50 mL) and dried (sodium sulfate). Evaporation of the solvent gave the product as a single product (0.48 g, 100%) as a white powder; m.p. 159–160° C.

c) 1,2,3,6-Tetrahydro-1-{N-[2-(4-(4-fluorobenzoyl) piperidin-1-yl)ethyl]}carboxamido -5-methoxycarbonyl-4-methyl-6-(3,4-difluorophenyl)-2 -oxopyrimidine hydrochloride A mixture of 6-(3,4-difluorophenyl)-1,2,3,6-tetrahydro-2-oxo-5-methoxycarbonyl-4-methyl-1-(2-bromoethylamino carbonyl)pyrimidine (43 mg, 0.1 mmol), 4-(4-fluorobenzoyl)piperidine p-toluene sulfonate (57 mg, 0.15 mmol), potassium carbonate (300 mg), and potassium iodide (30 mg) in THF(10 mL) was stirred at room temperature for 20 h. The solid material was removed by filtration, the solvent from the filtrate was evaporated, and the residue was purified by preparative thin layer chromatography on silica gel using chloroform-methanol-2M ammonia in methanol (100/2/1) as the eluent to afford the product as a viscous oil which was converted to the HCl salt by treatment with 1N HCl in ether; m.p. 159–160° C.; Anal. Calcd. for $C_{29}H_{29}N_4O_5F_3$.1HCl.0.8$Et_2O$: C, 57.27; H, 5.85; N, 8.56. Found: C, 57.31; H; 5.75; N, 8.79.

EXAMPLE 37

1,2,3,6-Tetrahydro-1-{N-[3-(4-(4-fluorophenyl)-4-hydroxypiperidin-1-yl)propyl]}carboxamido-5-methoxycarbonyl-4-methyl -6-(3,4-difluorophenyl)-2-oxopyrimidine hydrochloride a) 6-(3,4-Difluorophenyl)-1,2,3,6-tetrahydro-2-oxo-5-methoxycarbonyl-4-methyl-1-(3-bromopropylamino carbonyl)pyrimidine.

A mixture of 6-(3,4-difluorophenyl)-1,2,3,6-tetrahydro-2-oxo-5-methoxycarbonyl-4-methyl-1-(4-nitrophenoxy) carbonylpyrimidine (1.0 g, 2.237 mmol), 3-bromopropylamine hydrobromide (0.979 g, 4.474 mmol), and potassium carbonate (4.0 g) in THF/water (100 mL/10 mL) were stirred at room temperature for 1 h. Then most of the solvent was evaporated at reduced pressure. The residue was partitioned between dichloromethane and water (100 mL and 100 mL). The dichloromethane layer was separated, washed with ice-cold 0.5 N NaOH (2×50 mL) and dried (sodium sulfate). Evaporation of the solvent gave the product as a single product (0.98 g, 100%) as a white powder and confirmed by $^1$H-NMR.

b) 1,2,3,6-Tetrahydro-1-{N-[3-(4-(4-fluorophenyl)-4-hydroxypiperidin-1-yl)propyl]}carboxamido-5-methoxycarbonyl-4-methyl-6-(3,4-difluorophenyl)-2-oxopyrimidine hydrochloride A mixture of 6-(3,4-difluorophenyl)-1,2,3,6-tetrahydro-2-oxo-5-methoxycarbonyl-4-methyl-1-(3-bromopropylamino carbonyl)pyrimidine (44.6 mg, 0.1 mmol), 4-(4-fluorophenyl)-4-hydroxypiperidine (28.7 mg, 0.15 mmol), potassium carbonate (300 mg), and potassium iodide (30 mg) in THF(10 mL) was stirred at room temperature for 20 h. The solid material were removed by filtration, the solvent from the filtrate was evaporated, and the residue was purified by preparative thin layer chromatography on silica gel using chloroform-methanol-2M ammonia in methanol (100/2/1) as the eluent to afford the product as a viscous oil which was converted to the HCl salt by treatment with 1N HCl in ether; m.p. 160–164° C.; Anal. Calcd. for $C_{29}H_{29}N_4O_5F_3 \cdot 1HCl \cdot 0.8Et_2O$: C, 57.27; H, 5.85; N, 8.56. Found: C, 57.31; H; 5.75; N, 8.79.

EXAMPLE 38 a) (−)-5-(Benzyloxycarbonyl)-4-ethyl-1,6-dihydro-2-methoxy-6-(3,4-difluorophenyl)-1-methoxy-carbonyl]pyrimidine.

To a well stirred solution of (benzyloxycarbonyl)-1,6-dihydro-2-methoxy-4-ethyl-6-(3,4-diflurophenyl) pyrimidine (0.6 g, 1.5 mmol) and 4-(N,N-dimethylamino) pyridine (0.32 g, 2.66 mmol) in $CH_2Cl_2$ (6 mL) was added methyl chloroformate (0.2 mL, 2.66 mmol) at room temperature. The solvent was removed in vacuo and the residue was purified by column chromatography on silica gel with 3:1 Petroleum ether/EtOAC as the eluting system to obtain 0.45 g (78% yield) of (−)-5-(benzyloxycarbonyl)-4-ethyl-1,6 -dihydro-2-methoxy-6-(3,4-difluorophenyl)-1-[methoxy-carbonyl]pyrimidine as a colorless oil.

b) (−)-1,2,3,6-Tetrahydro-4-ethyl-2-oxo-6-(3,4-difluorophenyl)-1-[methoxycarbonyl]pyrimidine-5-carboxylic acid.

To a solution of (−)-5-(benzyloxycarbonyl)-4-ethyl-1,6-dihydro-2-methoxy-6-(3,4-difluorophenyl)-1-[methoxycarbonyl]pyrimidine (0.45 g, 1.18 mmol) in 20 mL of MeOH was added 0.05 g of 10% Pd on carbon and the resulting suspension was hydrogenated under 100 psi for 12 h. The catalyst was then filtered through a pad of celite and was washed thoroughly with MeOH. All the MeOH washings were collected and the solvent was removed in vacuo to obtain 0.42 g (99% yield) of (−)-1,2,3,6-tetrahydro-4-ethyl-2-oxo-6-(3,4-difluorophenyl)-1-[methoxycarbonyl]pyrimidine-5-carboxylic acid as a white solid which was used in the next reaction without further purification.

c) (−)1,2,3,6-Tetrahydro-5-{N-[3-(4-methoxycarbonyl)-4-phenyl-piperidin-1-yl]propyl}-carboxamido-1-methoxycarbonyl-4-ethyl-6-(3,4-difluorophenyl)-2-oxo-pyrimidine.

To a solution of (−)-1,2,3,6-tetrahydro-4-ethyl-2-oxo-6-(3,4-difluorophenyl)-1-[methoxycarbonyl]pyrimidine-5-carboxylic acid (1.18 mmol, 0.4 g) and 3-[4-methoxycarbonyl-4-phenylpiperidin-1-yl)propylamine (1.23 mmol, 0.34 g) in 20 mL $CH_2Cl_2$ was added 4-(N,N-dimethylamino)-pyridine (1.16 mmol, 0.15 g), followed by 1-(3-dimethylaminopropyl)-3-ethylcarbodiimide (1.84 mmol, 0.54 g) and the resulting solution was stirred at room temperature under argon for 2 days. The solution was then transferred into a separatory funnel, extracted with $CH_2Cl_2$, washed with sat. $NH_4Cl$ solution (2×20 mL) and then with brine (20 mL). The organic layer was separated and dried over $Na_2SO_4$, filtered and the solvent was evaporated in vacuo to obtain an off-white solid. It was purified by column chromatography on silica gel with 10% MeOH in EtOAc as the solvent system to obtain (−)1,2,3,6-tetrahydro-5-{N-[3-(4-methoxycarbonyl)-4-phenyl-piperidin-1-yl]propyl}-carboxamido-1-methoxycarbonyl-4-ethyl-6-(3,4-difluorophenyl)-2-oxo-pyrimidine as a white solid (0.55 g, 79% yield). M.P. 53–55° C.; $[\alpha]_D$=−48.5 (c=0.43, $CHCl_3$). It was characterized as HCl salt. Anal. Calcd. For $C_{31}H_{37}N_4O_6F_2Cl \cdot 0.4$ $CHCl_3$: C, 55.23; H, 5.52; N, 8.20. Found: C, 55.29; H, 5.35; N, 7.99.

EXAMPLE 39

(+)-1-3-{[4-(3,4-Difluorophenyl)-2,5-dioxo-1,2,5,7-tetrahydro-4H-furo[3,4-d]-pyrimidine-3-carbonyl]amino}-propyl-4-phenyl-piperidine-5-carboxylic acid methyl ester.

a) (+)-6-(3,4-Difluorophenyl)-1,6-dihydro-2-oxo-5-methoxy-carbonyl-4-bromomethyl-1-[(4-nitrophenyl-oxy) carbonyl]pyrimidine.

To a well stirred solution of (+)-6-(3,4-difluorophenyl)-1,6-dihydro-2-methoxy-5-methoxycarbonyl-4-methyl-1-[(4-nitrophenyloxy) carbonyl]pyrimidine (1.5 mmol, 0.66 g) in 5 mL of chloroform was added a solution of bromine (1.5 mmol, 0.09 mL) in 3 mL of chloroform at 0° C. and the solution was allowed to attain room temperature over 1.5 h. The solvent was removed in vacuo and the residue was again dissolved in $CHCl_3$ (20 mL) and washed with brine. The organic layer was separated, dried over $Na_2SO_4$, filtered and the solvent was removed in vacuo to get 0.81 g of (+)-6-(3,4-difluorophenyl)-1,2,3,6-tetrahydro-2-oxo-5-methoxycarbonyl-4-bromomethyl-1-[(4-nitrophenyloxy) carbonyl]pyrimidine as a yellow foam. It was used in the next step without any purification.

b)(+)-4-(3,4-Difluorophenyl)-2,5-dioxo-1,2,4,5,6,7-hexahydro-cyclopentapyrimidine-3-carboxylic acid-4-nitrophenyl eater.

(+)-6-(3,4-Difluorophenyl)-1,6-dihydro-2-oxo-5-methoxy-carbonyl-4-bromomethyl-1-[(4-nitrophenyloxy) carbonyl] pyrimidine (1.5 mmol, 0.81 g) was heated in oil bath for 3 h (bath temperature 130° C.). The brown residue thus obtained was washed with $CHCl_3$ and (+)-4-(3,4-difluorophenyl)-2,5-dioxo-1,2,4,5,6,7-hexahydro-cyclopenta pyrimidine-3-carboxylic acid-4-nitrophenyl ester was obtained as a pale brown solid which was used in the next step without further purification (crude wt. 0.51 g).

c) (+)-1-3-{[4-(3,4-Difluorophenyl)-2,5-dioxo-1,2,5,7-tetrahydro-4H-furo[3,4-d]-pyrimidine-3-carbonyl]amino}-propyl-4-phenyl-piperidine-5-carboxylic acid methyl ester.

A solution of (+)-4-(3,4-difluorophenyl)-2,5-dioxo-1,2,4,5,6,7-hexahydro-cyclopenta pyrimidine-3-carboxylic acid-4-nitrophenyl ester ((0.30 mmol, 0.13 g) and 3-[4-methoxycarbonyl-4-phenylpiperidin-1-yl)propylamine (0.32 mmol, 0.09 g) in 10 mL of anhydrous THF was stirred overnight at room temperature. The solvent was removed in vacuo and the residue was purified by column chromatography ($CH_2Cl_2$ followed by 9:1 $CH_2Cl_2$/MeOH) to obtain (+)-1-3-{[4-(3,4-difluorophenyl)-2,5-dioxo-1,2,5,7-tetrahydro-4H-furo[3,4-d]-pyrimidine-3-carbonyl]amino}-propyl-4-phenyl-piperidine-5-carboxylic acid methyl ester as a pale yellow solid (0.12 g, 70%). $[\alpha]_D$=128.1 (c=0.525, $CHCl_3$). It was characterized as HCl salt. M.P. 142–145° C.; Anal. Calcd. For $C_{29}H_{31}N_4O_6F_2Cl \cdot 0.23$ $CHCl_3$: C, 55.55; H, 4.98; N, 8.87. Found: C, 55.25; H. 5.03; N, 8.52.

EXAMPLE 40

(−)-1-3-{[4-(3,4-Difluorophenyl)-2,5-dioxo-1,2,5,7-tetrahydro-4H-furo[3,4-d]-pyrimidine-3-carbonyl]amino}-propyl-4-phenyl-piperidine-5-carboxylic acid methyl ester.

In a similar way, (−)-1-3-{[4-(3,4-difluorophenyl)-2,5-dioxo-1,2,5,7-tetrahydro-4H-furo[3,4-d]-pyrimidine-3-carbonyl]amino}-propyl-4-phenyl-piperidine-5-carboxylic acid methyl ester was prepared starting with (−)-6-(3,4-difluorophenyl)-1,6-dihydro-2-methoxy-5-methoxycarbonyl-4-methyl-1-[(4-nitrophenyloxy) carbonyl]pyrimidine (overall yield 27%). M.P. 162–165° C. $[\alpha]_D$=−121.3 (c=0.52, $CHCl_3$)

EXAMPLE 41

(+)-1,2,3,6-Tetrahydro -1-{N-[14-(2-carboxamidophenyl) piperazin-1yl]propyl}-carboxamido-4-methyl-6-(3,4-difluorophenyl)-2-oxo-pyrimidine a)1-(2-Carboxamidophenyl)piperazine Concentrated sulfuric acid (15 mL) was added to 1-(2-cyanophenyl)piperazine (1.5 g, 8.0 mmol) placed in a round bottom flask and the resulting slurry was stirred at room temperature for 48 h. The reaction mixture was poured on crushed ice very slowly and then basified (pH 9) with 50% solution of NaOH. The aqueous layer was extracted several times with EtOAc, dried over $K_2CO_3$, filtered and the solvent was evaporated. 1-(2- carboxamidophenyl)piperazine was obtained as an off-white solid (1.2 g, 73%). It was used in the next step without further purification. Mass spectrum 206 (M+1, 100%); Combustion analysis was obtained on its hydrochloride salt. Anal. Calcd. for $C_{11}H_{17}N_3OCl.0.3$ $CHCl_3$: C, 43.23; H, 5.55; N, 13.30. Found: C, 43.58; H, 5.70; N, 12.79.

b) (+)-1,2,3,6-Tetrahydro -1-{N-[4-(2-carboxamidophenyl) piperazin-1yl]propyl}-carboxamido-4-methyl-6-(3,4-difluorophenyl)-2-oxo-pyrimidine.

To a solution of (+)-6-(3,4-difluorophenyl)-1,2,3,6 - tetrahydro-2-oxo-5-methoxycarbonyl-4-methyl-1-(3-bromopropylaminocarbonyl)pyrimidine (0.435 g, 1.0 mmol) and 1-(2-carboxamidophenyl)piperazine (0.4 g, 2.0 mmol) in 25 mL of anhydrous acetone was added powdered $K_2CO_3$ (0.69 g, 5.0 mmol) and KI (0.17 g, 1.0 mmol) and the resulting suspension was heated to reflux for 10 h. TLC indicated complete formation of the product ($R_f$=0.4, 3:0.5 EtOAc/MeOH). The solvent was evaporated and the residue was dissolved in water (10 mL). The aqueous layer was extracted in EtOAc (3×30 mL), the separated organic extract was dried over $Na_2SO_4$ and the solvent was removed in vacuo. The residue thus obtained was purified by column chromatography on silica gel with EtOAc/MeOH (5:1) as the eluting system. (+)-1,2,3,6-tetrahydro-1-{N-[4-(2-carboxamido phenyl)piperazin-1yl]propyl}-carboxamido-4-methyl-6-(3,4-difluorophenyl)-2-oxo-pyrimidine was obtained as light yellow powder (0.48 g, 84% yield). The product was analyzed as its dihydrochloride salt. M.P. 190–193 ° C.; $[\alpha]_D$=98.8 (c=0.31, MeOH); Anal calcd. for $C_{28}H_{34}N_6F_2O_5Cl_2.0.35$ EtOAc: C, 52.16; H, 5.50; N, 12.46. Found: C, 51.84; H, 5.67; N, 12.05.

EXAMPLE 42

1,2,3,6-Tetrahydro-1{N-[4-(N-benzimidazolyl)-piperidin-1-yl]propyl}-carboxamido-4-methyl-6-(3,4-difluorophenyl)-2-oxo-pyrimidine.

To a solution of 6-(3,4-difluorophenyl)-1,2,3,6-tetrahydro-2-oxo-5-methoxycarbonyl-4-methyl-1-(3-bromopropylaminocarbonyl)pyrimidine (43 mg, 0.1 mmol) in 10 mL of anhydrous acetone was added 4-(N-benzimidazolyl)-piperidine (32.6 mg, 0.15 mmol) followed by $NaHCO_3$ (41 mg, 0.3 mmol) and KI (16 mg, 0.1 mmol). The resulting suspension was heated to reflux for 10 h and then cooled to room temperature. The solvent was removed in vacuo and the residue was purified by flash column chromatography on silica gel with EtOAc followed by 10% MeOH in EtOAc to obtain 1,2,3,6-tetrahydro-1{N-[4-(N-benzimidazolyl)-piperidin-1-yl]propyl}-carboxamido-4-methyl-6-(3,4-difluorophenyl)-2-oxo-pyrimidine as an oil (15 mg, 26% yield). The product thus obtained was then dissolved in 2 mL of chloroform and 0.5 mL of HCl in $Et_2O$ (1 M) was added at room temperature. The solvent was removed in vacuo and the HCl salt was characterized by combustion analysis. M.P. 168–172° C. Anal calcd. for $C_{29}H_{33}N_6F_2O_5Cl:0.75$ $CHCl_3$: C, 50.43; H, 4.90; N, 11.86. Found: C, 50.84; H, 5.44; N, 11.46.

EXAMPLE 43

(−)-6-(Benzo[1,2,5]oxadiazol-5-yl)-1-carboxamido-4-ethyl-5-{N-[3-(4-methoxycarbonyl-4-phenylpiperidin-1-yl )propyl]}carboxamido-2-oxo-1,2,3,6-tetrahydro pyrimidine.

a) 5-Methylbenzfuroxan.

4-Methyl-2-nitroaniline (100 g, 0.650 mol) was suspended in saturated alcoholic sodium hydroxide solution (1.50 l). To this suspension was added with cooling (5° C.) commercial aqueous sodium hypochlorite until the red color disappeared. The fluffy yellow precipitate formed was filtered, washed with cold water and recrystallized from ethanol to get 5-methylbenzfuroxan (88.2 g, 89% yield) as a pale solid.

b) 5-Methylbenzofurazan.

To 5-methylbenzfuroxan (88.2 g, 0.59 mol) in refluxing EtOH (75 ml) was added dropwise $P(OEt)_3$ (150 ml). When addition was complete, refluxing was continued for 1 more hour. The solvent was removed by rotary evaporation and the residue shaken with water (200 ml) and allowed to stand overnight at (0–5° C.). The brown solid so obtained was filtered, washed with water and chromatographed on silica gel to yield 5-methylbenzofurazan (70 g, 87%) as white needles.

c) 5-Dibromomethylbenzofurazan.

5-Methylbenzofurazan (70 g, 0.52 mol), NBS (325 g), and benzoyl peroxide (0.5 g) were refluxed with stirring in carbon tetrachloride (1.5 l) with exclusion of moisture 5 for 2 days. The reaction mixture was washed with water (2×0.5 l), brine, dried ($Na_2SO_4$), and the solvent removed in vacuo. The residue was chromatographed on silica (hexane/EtOAc=150/1) to get 122 g (80%) of the title compound as a pink solid. 5-Tribromomethylbenzofurazan (17 g, 9%) was also isolated as a pink solid.

d) 5-Formylbenzofurazan.

To a refluxing mixture of 5-dibromo methylbenzofurazan (122 g, 418 mmol) in EtOH (1 l) was added $AgNO_3$ (163 g) in 2 l of water. When addition was complete, refluxing was continued for 2 hours. The mixture was cooled and the AgBr formed was removed by filtration. The resulting solution was concentrated to a small volume and extracted with toluene (10×300 ml). The extract was concentrated and the residue collected was chromatographed on silica gel (3 kg), (EtOAc/hexane=8/1000) to get the title compound (48.2 g, 78%) as a white solid.

e) 2-Cyanoethyl 3-benzo[1,2,5]oxadiazol-5-yl-2-propionyl-acrylate.

A mixture of 5-formylbenzofurazan (25.0 g, 168.8 mmol), 2-cyanoethyl 3-oxo-pentanoate (31.4 g, 203 mmol), and piperidinium acetate (1.22 g, 8.40 mmol) in benzene (1.5 l) was refluxed with a Dean-Stark trap for 24 hours. Benzene was evaporated, and the residue was chromatographed on silica (200 g) (EtOAc/$CHCl_3$=5/100) to get the title compound (32.36, 62.1% yield) as a orange oil.

f) 2-Cyanoethyl 6-benzo[1,2,5]oxadiazol-5-yl-4-ethyl-2 -methoxy-1,6-dihydropyrimldine-5-carboxylate.

A mixture of 2-cyano-ethyl 3-benzo[1,2,5]oxadiazol-5-yl-2-propionyl-acrylate (19 g, 63.48 mmol), O-methylisourea hydrogen sulfate (15.3 g, 88.9 mmol), and 4-dimethylaminopyridine (21.3 g, 175 mmol) in THF (200 ml) was stirred at 65° C. for 6 hours. The solvent was evaporated and the residue was chromatographed on silica gel (~300 g) (hexane/EtOAc=2/1) to get 8 g of the title compound as an orange oily solid. This reaction was repeated for many times and the yields were between 5% and 38%.

g) 6-Benzo[1,2,5]oxadiazol-5-yl-4-ethyl-2-methoxy-6H-pyrimidine-1,5-dicarboxylic acid 5-(2-cyan-ethyl) eater 1-(4-nitro-phenyl) ester.

To a solution of 2-cyanoethyl 6-benzo [1,2,5]oxadiazol-5-yl-4-ethyl-2-methoxy-1,6-dihydropyrimidine-5-carboxylate (3.62 g, 10.19 mmol) and 4-dimethylaminopyridine (1.49 g, 12.2 mmol) in $CH_2Cl_2$ (75 ml), at 0° C., was added 4-nitrophenylchloroformate (2.46 g, 12.22 mmol). The reaction mixture was slowly warmed to r.t. at which it was stirred for 20 hours. Then, the solvent was evaporated and the residue was purified by flash column chromatography (~60 g of $SiO_2$, $CHCl_3$/EtOAc= 100/3) to get the title compound (1.96 g, 37% yield) as a yellow solid.

h)2-Cyanoethyl ester 6-benzo[1,2,5]oxadiazol-5-yl-4-ethyl-2-methoxy-1-(1-phenyl-ethyl carbamoyl)-1,6-dihydro-pyrimidine-5-carboxylate.

A solution of 6-benzo[1,2,5]oxadiazol-5-yl-4-ethyl-2-methoxy-6H-pyrimidine-1,5-dicarboxylic acid 5-(2-cyanoethyl) ester 1-(4-nitrophenyl) ester (2.2 g, 4.22 mmol ) and (R)-(+)-α- methylbenzylamine (1.36 ml, 10.6 mmol) in $CH_2Cl_2$ (30 ml) was stirred at room temperature for 10 hours. The solvent was evaporated, and the residue was chromatographed on silica gel (100 g) ($CHCl_3$ /EtOAc=30/1) to get the two diasteromers of the title compound (1.03 g in total, 49%).

i) (−)-2-Cyanoethyl 6-benzo[1,2,5]oxadiazol-5-yl-4-ethyl-2-methoxy-1,6-dihydropyrimidine-5-carboxylate.

A mixture of (−)-2-cyanoethyl ester 6-benzo[1,2,5]oxadiazol-5-yl-4-ethyl-2-methoxy-1-(1-phenyl- ethyl carbamoyl)-1,6-dihydro-pyrimidine-5-carboxylate (557 mg, 1.11 mmol) and 1,8-diazabicyclo[5,4,0]undec-7-ene (82.5 ml, 0.55 mmol) in benzene (15 ml) was stirred at 50° C. for 1 hour. The solvent was evaporated, and the residue was chromatographed on silica gel (~30 g) ($CHCl_3$/EtOAc/2 N $NH_3$ in MeOH=40/10/1) to get the title compound (270 mg, 68.5% yield) as a yellow solid. No rotation was observed for this compound.

j) (−)-6-Benzo[1,2,5]oxadiazol-5-yl-4-ethyl-2-methoxy-6H-pyrimidine-1,5-dicarboxylic acid 5-(2-cyanoethyl) ester 1-(4-nitro-phenyl) ester.

To a solution of (−)-2-cyanoethyl 6-benzo[1,2,5] oxadiazol-5-yl-4-ethyl-2-methoxy-1,6-dihydropyrimidine-5-carboxylate (220 mg, 0.62 mmol) and 4-dimethylaminopyridine (99 mg, 0.81 mmol) in $CH_2Cl_2$ (12 ml), at 0° C., was added 4-nitrophenylchloroformate (164 mg, 0.81 mmol). The reaction mixture was slowly warmed to r.t. at which it was stirred for 24 hours. The solvent was evaporated and the residue was purified by flash column chromatography (~30 g of $SiO_2$, $CHCl_3$/EtOAc=38/1) to get the title compound (301 mg, 93% yield) as a yellow solid.

k) (−)-6-(Benzo[1,2,5]oxadiazol-5-yl)-1-carboxamido-4-ethyl-5-{N-[3-(4-methoxycarbonyl-4-phenylpiperidin-1-yl) propyl]}carboxamido-2-oxo-1,6-dihydropyrimidine.

To (−)-6-benzo[1,2,5]oxadiazol-5-yl-4-ethyl-2-methoxy-6H-pyrimidine-1,5-dicarboxylic acid 5-(2-cyanoethyl) ester 1-(4-nitrophenyl) ester (100 mg, 0.19 mmol) in dry THF (10 ml) ammonia (gas) was introduced with a balloon at room temperature. It was stirred at room temperature for 14 hours. TLC and $^1H$ NMR of the reaction mixture showed that the reaction was complete. NaOH (1 N, 3 ml) was added at room temperature. After it was stirred for 6 hours, HCl solution (6 N, 4 ml) was added. It was stirred at room temperature for 14 hours. The solvent was evaporated to get a white solid which was used directly in the next step.

A mixture of the crude product from the above step, 4-dimethyl aminopyridine (61mg, 0.5 mmol), 1-(3-dimethylaminopropyl)-3-ethylcarbodiimide hydrochloride (96 mg, 0.5 mmol) in $CH_2Cl_2$ (15 ml) was stirred at room temperature for 4 hours. Methyl 1-(3-amino-propyl)-4-phenyl-piperidine-4-carboxylate (140 mg, 0.5 mmol) was added. The reaction mixture was stirred at room temperature for 16 hours. The solvent was evaporated and the residue was chromatographed on silica gel (5 g) ($CHCl_3$/MeOH/2 N $NH_3$ in MeH=250/2/1) to get the title compound as a white solid (10.8 mg, 10% yield over 3 steps). $[\alpha]_D$=−303.9. Hydrochloride of the title compound was made with HCl in ether. M.P. of the salt: 140–143° C. Calculated for $C_{30}H_{35}N_7O_6$+1.0HCl+0.6 ether: C, 58.03%; H, 6.31%; N, 14.62%. Found: C, 58.07%; H, 6.08%; N,14.66%.

EXAMPLE 44

6-(3,4-Difluoro-phenyl)-1-[3-(3',6'-dihydro-[2,4']bipyridinyl-1'-yl)-propylcarbamoyl]-4-methyl-5-methoxycarbonyl-2-oxo-1,2,3,6-tetrahydropyrimidine hydrochloride.

a) 1-(3-Aminopropyl)-4-[pyrid-2-yl]pyridinium bromide hydrobromide.

A solution of 2,4'-dipyridyl (5.0 g, 32.0 mmol) and 3-bromopropylamine hydrobromide (7.0 g, 32.0 mmol) in DMF (50.0 mL) and acetonitrile (50.0 mL) was heated at 90–95° C. for 1 h. After cooling, the white solid that came out was filtered, washed with $Et_2O$ and dried. The mother liquor was concentrated to remove $Et_2O$ and then heated to 90–95° C. for 4 h. The solvent was evaporated and the white residue was triturated with $Et_2O$ (100.0 mL) and filtered. The combined weight of the salt was 11.6 g (97%).

b) 3-(3',6'-Dihydro-2'-H-[2,4']bipyridinyl-1'-yl)-propylamine.

To a solution of 1-(3-aminopropyl)-4-[pyrid-2-yl] pyridinium bromide hydrobromide (0.66 g, 1.75 mmol) in 20.0 mL MeOH was added $NaBH_4$ (0.101 g, 2.62 mmol) in small portions. The reaction mixture was stirred for 30 min and then quenched with 6M HCl solution. The solution was concentrated to 20.0 mL and basified with 50% NaOH solution to pH 12. Extracted with $CHCl_3$ (5×30.0 mL), dried over $MgSO_4$ and the solvent was removed to give 3-(3',6'-dihydro-2'-H-[2,4']bipyridinyl-1'-yl)-propylamine as an oil (0.37 g, 96% yield). It is used in the next step immediately without purification.

c)6-(3,4-Difluoro-phenyl)-1-[3-(3',6'-dihydro-[2,4']bipyridinyl-1'-yl)-propylcarbamoyl]-4-methyl-5-methoxycarbonyl-2-oxo-1,2,3,6-tetrahydro-pyrimidine hydrochloride.

A solution of 6-(3,4-difluorophenyl)-4-methyl-5-methoxycarbonyl-1-(4-nitrophenoxy)carbonyl-2-oxo-1,2,3,6-tetrahydro-pyrimidine (20 mg, 0.045 mmol) and 3-(3',6'-dihydro-2'H-[2,4']bipyridyl-1-yl)propylamine (9.7 mg, 0.045 mmol) in $CH_2Cl_2$ (10 ml) was stirred at room temperature for 3 days. The solvent was removed in vacuum. The residue was separated on preparative TLC ($CHCl_3$/MeOH=100/15) to get the title compound (21mg, 89% yield) as a yellow solid. Hydrochloride salt was made with HCl in ether. M.P. of the salt: 242–244° C. Calcd for $C_{27}H_{29}N_5O_4F_2$+2.0 HCl+1.05 $CHCl_3$+1.05 ether: C, 48.32%; H, 5.35%; N, 8.74%. Found: C, 48.10%; H, 5.13%; N, 8.72%.

EXAMPLE 45

6-(3,4-Difluorophenyl)-1-(3-imidazol-1-yl-propylcarbamoyl)-4-methyl-2-oxo-1,2,3,6-tetrahydro-pyrimidine-5-carboxylic acid methyl ester.

A solution of 6-(3,4-difluorophenyl)-4-methyl-5-methoxycarbonyl-1-(4-nitrophenoxy)carbonyl-2-oxo-1,2,3, 6-tetrahydro-pyrimidine (100 mg, 0.22 mmol) and 1-(3-aminopropyl)imidazole (40 ml, 0.34 mmol) in $CH_2Cl_2$ (10 ml) was stirred at room temperature for 3 hours. The solvent was removed in vacuum. The residue was separated on preparative TLC ($CHCl_3$/MeOH=100/15) to get the title compound (80 mg, 84% yield) as a white solid. Hydrochloride of title compound was made with HCl in ether. Calcd for $C_{20}H_{21}N_5O_4F_2$+0.3 $H_2O$: C, 54.74%; H, 4.99%; N, 15.89%. Found: C, 54.92%;H, 4.65%; N, 15.77%. M.P. of the salt: 221–224° C.

EXAMPLE 46

6-(3,4-Difluorophenyl)-1-{N-[3-(2-phenylimidazol-1-yl)propyl]}carboxamido-4-methyl-5-methoxycarbonyl-2-oxo-1,2,3,6-tetrahydropyrimidine hydrochloride.

A mixture of 6-(3,4-difluorophenyl)-1,2,3,6-tetrahydro-2-oxo-5-methoxycarbonyl-4-methyl-1-(3-bromopropylamino carbonyl)pyrimidine (100 mg, 0.22 mmol), 2-phenylimidazole (32.3 mg, 0.22 mmol), and $CsCO_3$ (358 mg, 1.1 mmol) in DMF (10 ml) was stirred at room temperature for 2 days. The solid was filtered out. The solution was concentrated and separated on preparative TLC (EtOAc/hexane=3/1) to get the title compound (41 mg, 37% yield) as a white oily solid. Hydrochloride of title compound was made with HCl in ether. M.P. of the salt: 278–282° C. Calculated for $C_{26}H_{25}N_5O_4F_2+2.0$ HCl+0.25 $H_2O$: C, 52.23%; H, 4.60%; N, 11.60%. Found: C, 52.21%; H, 4.69%; N, 11.11%.

EXAMPLE 47 AND EXAMPLE 48

(+)-, and (−)-3,6-Dihydro-1-{N-[4-(2-pyridyl)-piperidine-1-yl]propyl}carboxamido-5-methoxy carbonyl-2-oxo-6-(3,4,5-trifluorophenyl)-4-methyl pyrimidine dihydrochloride.

a) 4Methyl 2-acetyl-3-(3,4,5-trifluoro-phenyl)-acrylate.

A mixture of 3,4,5-trifluorobenzaldehyde (1.0 g, 6.3 mmol), methyl acetoacetate (0.81 ml, 7.5 mmol), and piperidinium acetate (45 mg, 0.31 mmol) in benzene (10 ml) was refluxed with a Dean-Stark trap for 12 hours. The solvent was evaporated, and the residue was chromatographed on silica gel (~50 g) (EtOAc/hexane=1/6) to get the title compound (825 mg, 51% yield) as a mixture of cis and trans isomers (yellow oil).

b) Methyl 2-methoxy-4-methyl-6-(3,4,5-trifluoro-phenyl)-1,6-dihydro-pyrimidine-5-carboxylate.

A mixture of methyl 2-acetyl-3-(3,4,5-trifluoro-phenyl)-acrylate (670 mg, 2.60 mmol), O-methylisourea hydrogen hemisulfate (448 mg, 3.63 mmol), and 4-dimethylaminopyridine (407 mg, 3.63 mmol) in ethanol (20 ml) was stirred at 65° C. for 2 days. The solid formed was filtered out. The filtrate was concentrated and chromatographed on silica gel (30 g) ($CH_2Cl_2$/EtOAc=9/1) to get the title compound (390 mg, 48% yield) as a pale yellow oil. Calculated for $C_{14}H_{13}N_2O_3F_3$: C, 53.50%; H, 4.20%; N, 8.90%. Found: C, 53.24%; H, 4.20%; N, 8.60%.

c) 1,6-Dihydro-5-methoxycarbonyl-2-methoxy-4-methyl-1-(4-nitro phenyloxy)carbonyl -6-(3,4,5-trifluorophenyl)-pyrimidine.

To a solution of methyl 1,6-dihydro-2-methoxy-4-methyl-6-(3,4,5-trifluoro-phenyl)-pyrimidine-5-carboxylate (385 mg, 1.23 mmol) and 4-dimethylaminopyridine (195 mg, 1.60 mmol) in $CH_2Cl_2$ (15 ml), at room temperature, was added 4-nitrophenyl chloroformate (322 mg, 1.60 mmol). The reaction solution was stirred at room temperature for 2 days. The white solid formed was filtered out. The filtrate was concentrated and chromatographed on silica gel (~20 g) ($CHCl_3$/$CH_3OH$=9/1) to get the titled compound (206 mg, 35% yield) as a white solid. Calculated for $C_{21}H_{16}N_3O_7F_3$+1.0 $H_2O$: C, 50.71%; H, 3.65%; N, 8.45%. Found: C, 50.83%; H, 3.29%; N, 8.33%.

d) 1,6-Dihydro-2-methoxy-5-methoxycarbonyl-4-methyl-1-{N-[4-(2-pyridyl)-piperidin-1-yl]-propyl}carbamoyl-6-(3,4,5-trifluoro-phenyl)-pyrimidine.

A mixture of 1,6-dihydro-5-methoxycarbonyl-2-methoxy-(4-nitrophenyloxy) carbonyl-6-(3,4,5-trifluorophenyl)-4-methyl-pyrimidine (25 mg, 0.05 mmol) and 3-[4-(2-pyridyl)-piperidin-1-yl]-propylamine (16 mg, 0.078 mmol) was stirred at room temperature for 12 hours. The solvent was evaporated and the residue chromatographed on silica gel (~5 g) ($CHCl_3$/EtOAc=30/1) to get the title compound (16 mg, 57% yield) as a pale solid.

e) 1,2,3,6-Tetrahydro-5-methoxycarbonyl-4-methyl-2-oxo-1-{N-[4-(2-pyridyl)-piperidine-1-yl]-propyl}carboxamido-6-(3,4,5-trifluorophenyl)-pyrimidine dihydrochloride.

1,6-Dihydro-2-methoxy-5-methoxycarbonyl-4-methyl-1-{N-[4-(2-pyridyl)-piperidin-1-yl]-propyl}carbamoyl-6-(3,4,5-trifluoro-phenyl)-pyrimidine from the previous step was dissolved in $CH_2Cl_2$ (5 ml) and concentrated HCl solution (0.5 ml) was added. The reaction mixture was stirred at room temperature for 1 hour. NaOH solution (1 N) was added to neutralized the reaction mixture. It was extracted with $CH_2Cl_2$. The extractant was dried ($Na_2SO_4$) and concentrated to get the title compound (16 mg, quantitative) as a pale solid. Hydrochloride of the title compound was made with HCl in ether. Calculated for $C_{27}H_{29}N_5O_4F_3$+2.0 HCl+4.0 THF+0.8 $CH_2Cl_2$: C, 54.02%; H, 6.69%; N. 7.19%. Found: C, 54.00%; H, 6.48%; N, 7.42%.

f) (+)-, and (−)-3,6-Dihydro-1-{N-[4-(2-pyridyl)-piperidine-1-yl]propyl}carboxamido-5-methoxy carbonyl-2-oxo-6-(3,4,5-trifluorophenyl)-4-methyl pyrimidine dihydrochloride.

The enantiomers were separated by chiral HPLC separation (column: chiralpak AS) of the racemic 1,2,3,6-tetrahydro-1-{N-[4-(2-pyridyl)-piperidine-1-yl]propyl}carboxamido-5-methoxycarbonyl-2-oxo-6-(3,4,5-trifluorophenyl)-4-methylpyrimidine dihydrochloride which was synthesized in the previous step. The (+) isomer: $[\alpha]_D$=+80.4 (c=0.2 g in 100 ml dichloromethane): The (−) isomer: $[\alpha]_D$=−82.2. Hydrochloride salts of the title compounds was made with HCl in ether.

EXAMPLE 49

(+)-1,2,3,6-Tetrahydro-5-methoxycarbonyl-4-methoxymethyl-2-oxo-1-{N-[4-(2-pyridyl)-piperidine-1-yl]-propyl}carboxamido-6-(3,4,5-trifluorophenyl)-pyrimidine dihydrochloride.

a) Methyl 2-methoxyacetyl-3-(3,4,5-trifluoro-phenyl)-acrylate.

A mixture of 3,4,5-trifluoro benzaldehyde (10 g, 62.5 mmol), methyl 4-methoxyacetoacetate (9.7 ml, 75.0 mmol), and piperidinium acetate (450 mg, 3.1 mmol) in benzene (100 ml) was refluxed with a Dean-Stark trap for 8 hours. The white solid formed (some side product) was filtered out. The solvent was evaporated, and the residue was chromatographed on silica gel (~1 Kg) (toluene/t-butyl methyl ether=8/1) to get the title compound (4.5 g, 25% yield) as a mixture of cis and trans isomers (white solid).

b) 1,6-Dihydro-2-methoxy-5-methoxycarbonyl-4-methoxymethyl-6-(3,4,5-trifluoro-phenyl)-pyrimidine.

A mixture of methyl 2-methoxyacetyl-3-(3,4,5-trifluoro-phenyl)-acrylate (6.0 g, 20.8 mmol), O-methylisourea hydrogen hemisulfate (3.6 g, 29.2 mmol), and 4-dimethylaminopyridine (3.6 g, 29.2 mmol) in ethanol (20 ml) was stirred at 65° C. for 12 hours. The solid formed was filtered out. The filtrate was concentrated and chromatographed on silica gel (~1 kg) (hexane/ether=2/1) to get the title compound (4.0 g, 56% yield) as a pale colorless oily solid.

c) 1,6-Dihydro-2-methoxy-5-methoxycarbonyl-4-methoxymethyl-1-(4-nitrophenyloxy)carbonyl -6-(3,4,5-trifluorophenyl)-pyrimidine.

To a solution of 1,6-dihydro-2-methoxy-5-methoxycarbonyl-4-methoxymethyl-6-(3,4,5-trifluorophenyl)-pyrimidine (3.24 g, 9.41 mmol) and 4-dimethylaminopyridine (1.38 g, 11.3 mmol) in $CH_2Cl_2$ (20 ml), at room temperature, was added 4-nitrophenyl chloroformate (2.28 g, 11.3 mmol). The reaction solution was stirred at room temperature for 2 days. The white solid formed was filtered out. The filtrate was concentrated and chromatographed on silica gel (hexane/ether=1/1) to get the title compound (3.70 g, 77% yield) as a yellow solid.

d)(+)-, and (−)-1,6-Dihydro-2-methoxy-5-methoxycarbonyl-4-methoxymethyl-1-[N-(2-methylbenzyl)]carbamoyl-6-(3,4,5-trifluoro-phenyl)-pyrimidine.

A mixture of 1,6-dihydro-2-methoxy-5-methoxycarbonyl-4-methoxymethyl-1-(4-nitrophenyloxy)carbonyl-6-(3,4,5-trifluorophenyl)-pyrimidine (3.80 g, 7.46 mmol) and (R)-(+)-α-methylbenzylamine (2.02 mg, 16.4 mmol) in $CH_2Cl_2$ was stirred at room temperature for 2 days. The solvent was evaporated and the residue chromatographed on silica gel (toluene/t-butyl methyl ether=5/1) to get the title compound as yellow oil solids. For the less polar isomer (1.81 g, 50% yield): $[\alpha]_D$=+164.3. For the more polar isomer (1.79 g, 50% yield): $[\alpha]_D$=−86.2.

e)(+)-1,6-dihydro-2-methoxy-5-methoxycarbonyl-4-methoxymethyl-6-(3,4,5-trifluoro-phenyl)-pyrimidine.

A mixture of (+)-1,6-dihydro-2-methoxy-5-methoxycarbonyl-4-methoxymethyl-1-[N-(2-methylbenzyl )]carbamoyl-6-(3,4,5-trifluoro-phenyl)-pyrimidine (1.81 g 3.81 mmol) and 1,8-diazabicyclo[5,4,0]undec-7-ene (0.28 ml, 1.90 mmol) in benzene (10 ml) was stirred at room temperature for 4 days. The solvent was evaporated, and the residue was chromatographed on silica gel (~500 g) (hexane/ether=2.5/1) to get the title compound (1.2 g, 91% yield) as a yellow oil. No rotation was observed for this compound.

f) (+)-1,6-Dihydro-2-methoxy-5-methoxycarbonyl-4-methoxymethyl-1-(4-nitrophenyloxy) carbonyl -6-(3,4,5-trifluorophenyl)-pyrimidine.

To a solution of 1,6-dihydro-2-methoxy-5-methoxycarbonyl-4-methoxymethyl-6-(3,4,5-trifluorophenyl)-pyrimidine (1.20 g, 3.49 mmol) and 4-dimethylaminopyridine (0.51 g, 4.18 mmol) in $CH_2Cl_2$ (20 ml), at room temperature, was added 4-nitrophenyl chloroformate (0.84 g, 11.3 mmol). The reaction solution was stirred at room temperature for 12 hours. The white solid formed was filtered out. Trials to purify the crude product on silica gel only hydrolyzed the desired product to the start materials. The crude product was used in the next step without any further purification.

g) (+)-1,6-Dihydro-2-methoxy-5-methoxycarbonyl-4-methoxymethyl-1-{N-[4-(2-pyridyl)-piperidin-1-yl]-propyl}carbamoyl-6-(3,4,5-trifluoro-phenyl)-pyrimidine.

A mixture of (+)-1,6-dihydro-2-methoxy-5-methoxy carbonyl-4-methoxymethyl-1-(4-nitrophenyloxy) carbonyl-6-(3,4,5-trifluorophenyl)-pyrimidine and 3-[4-(2-pyridyl)-piperidin-1-yl]-propylamine (215 mg, 1.05 mmol) was stirred at room temperature for 12 hours. The solvent was evaporated and the residue chromatographed on prep. TLC ($CHCl_3$/MeOH=100/15) to get the title compound (115 mg, 22% yield over 2 steps) as a yellow oil.

h) (+)-1,2,3,6-Tetrahydro-5-methoxycarbonyl-4-methoxymethyl-2-oxo-1-{N-[4-(2-pyridyl)-piperidine-1-yl]-propyl}carboxamido-6-(3,4,5-trifluorophenyl)-pyrimidine dihydrochloride.

1,6-Dihydro-2-methoxy-5-methoxycarbonyl-4-methoxymethyl-1-{N-[4-(2-pyridyl)-piperidin-1-yl]-propyl}carbamoyl-6-(3,4,5-trifluoro-phenyl)-pyrimidine from the previous step was dissolved in $CH_2Cl_2$ (5 ml) and HCl solution (6 N,0.5 ml) was added. The reaction mixture was stirred at room temperature for 4 hour. KOH solution (1 N) was added to neutralize the reaction mixture. It was extracted with $CH_2Cl_2$. The extractant was dried ($Na_2SO_4$) and concentrated to get the title compound (106 mg, 94% yield) as a pale oily solid. $[\alpha]_D$=+78.6 (c=0.5 g in 100 ml dichloromethane) Hydrochloride of the title compound was made with HCl in ether. Calculated for $C_{28}H_{32}N_5O_5F_3$+3.8 HCl+1.8 EtOAc: C, 48.44%; H, 5.80%; N, 8.02%. Found: C, 48.19%; H, 5.38%; N, 8.32%.

EXAMPLE 50

(−)-1,2,3,6-Tetrahydro-5-methoxycarbonyl-4-methoxymethyl-2-oxo-1-{N-[4-(2-pyridyl)-piperidine-1-yl]-propyl}carboxamido-6-(3,4,5-trifluorophenyl)-pyrimidine dihydrochloride.

a) (−)-1,6-Dihydro-2-methoxy-5-methoxycarbonyl-4-methoxymethyl-6-(3,4,5-trifluoro-phenyl)-pyrimidine.

A mixture of (−)-1,6-dihydro-2-methoxy-5-methoxycarbonyl-4-methoxymethyl-1-[N-(2-methylbenzyl)]carbamoyl-6-(3,4,5-trifluoro-phenyl)-pyrimidine (1.79 g, 3.80 mmol) and 1,8-diazabicyclo[5,4,0]undec-7-ene (0.28 ml, 1.90 mmol) in benzene (10 ml) was stirred at room temperature for 4 days. The solvent was evaporated, and the residue was chromatographed on silica gel (~500 g) (hexane/ether=2.5/1) to get the title compound (0.92 g,70%) as a yellow oil. No rotation was observed for this compound.

b) (−)-1,6-Dihydro-2-methoxy-5-methoxycarbonyl-4-methoxymethyl -1-(4-nitrophenyloxy)carbonyl -6-(3,4,5-trifluorophenyl)-pyrimidine.

To a solution of 1,6-dihydro-2-methoxy-5-methoxycarbonyl -4-methoxymethyl -6-(3,4,5-trifluorophenyl)-pyrimidine (0.92 g, 2.67 mmol) and 4-dimethylaminopyridine (0.46 g, 3.74 mmol) in $CH_2Cl_2$ (20 ml), at room temperature, was added 4-nitrophenyl chloroformate (0.75 g, 3.74 mmol). The reaction solution was stirred at room temperature for 2 days. The white solid formed was filtered out. The filtrate 4 was concentrated and chromatographed on silica gel (hexane/ether=3/1) to get the title compound (1.01 g, 79% yield) as a yellow solid.

c) (−)-1,6-Dihydro-2-methoxy-5-methoxycarbonyl-4-methoxymethyl-1-{N-[4-(2-pyridyl)-piperidin-1-yl]-propyl}carbamoyl-6-(3,4,5-trifluorophenyl)-pyrimidine.

A mixture of (−)-1,6-dihydro-2-methoxy-5-methoxycarbonyl-4-methoxymethyl-1-(4-nitrophenyloxy)carbonyl-6-(3,4,5-trifluorophenyl)-pyrimidine (300 mg, 0.59 mmol) and 3-[4-(2-pyridyl)-piperidin-1-yl]-propylamine (160 mg, 0.77 mmol) was stirred at room temperature for 12 hours. The solvent was evaporated and the residue chromatographed on prep. TLC ($CHCl_3$/MeOH/2 N $NH_3$ in MeOH=20/2/1) to get the title compound (290 mg, 83% yield) as a yellow oil.

d) (−)-1,2,3,6-Tetrahydro-5-methoxycarbonyl-4-methoxymethyl-2-oxo-1-{N-[4-(2-pyridyl)-piperidine-1-yl]-propyl}carboxamido-6-(3,4,5-trifluorophenyl)-pyrimidine dihydrochloride.

(−)1,6-dihydro-2-methoxy-5-methoxycarbonyl-4-methoxymethyl-1-{N-[4-(2-pyridyl)-piperidin-1-yl]-propyl}carbamoyl-6-(3,4,5-trifluoro-phenyl)-pyrimidine (290 mg, 0.49 mmol) was dissolved in $CH_2Cl_2$ (5 ml) and 9 HCl solution (6 N, 2 ml) was added. The reaction mixture was stirred at room temperature for 10 hour. KOH solution (1 N) was added to neutralized the reaction mixture. It was extracted with $CH_2Cl_2$. The extractant was dried ($Na_2SO_4$) and concentrated to get the title compound (180 mg, 64% yield) as a pale oily solid. $[\alpha]_D$=−31.4 (c=0.44 g in 100 ml dichloromethane). Hydrochloride of the title compound was made with HCl in ether. Calculated for $C_{28}H_{32}N_5O_5F_3$+2.0 HCl+0.8 ether+0.8 $CH_2Cl_2$: C, 50.59%; H, 5.78%; N, 9.22%. Found: C, 50.86%; H, 5.82%; N, 8.75%.

EXAMPLE 51

1,2,3,6-Tetrahydro-5-methoxycarbonyl-4-methyl- 2-oxo-1-{N-[4-(2-pyridyl)- piperidine-1-yl]-propyl}carboxamido-6-(2,4,5-trifluorophenyl- pyrimidine dihydrochloride.

a) Methyl 2-acetyl-3-(2,4,5-trifluoro-phenyl)-acrylate.

A mixture of 2,4,5-trifluorobenzaldehyde (1.0 g, 6.3 mmol), methyl acetoacetate (0.81 ml, 7.4 mmol), and piperidinium acetate(38 mg, 0.26 mmol) in benzene (10 ml) was stirred at room temperature for 2 days. The solvent was evaporated, and the residue was chromatographed on silica gel (~50 g) (hexane/ether=5/1) to get the title compound (1.60 g, quantitative ) as a mixture of cis and trans isomers (colorless oil).

b) 1,6-Dihydro-2-methoxy-5—methoxycarbonyl-4-methyl-6-(2,4,5-trifluoro-phenyl)-pyrimidine.

A mixture of methyl 2-acetyl-3-(2,4,5-trifluoro-phenyl)-acrylate (1.60 g, 6.20 mmol), O-methylisourea hydrogen hemisulfate (1.07 g, 8.68 mmol), and 4-dimethylaminopyridine (1.06 g, 8.68 mmol) in ethanol (10 ml) was stirred at 65° C. for 2 days. The solid formed was filtered out. The filtrate was concentrated and chromatographed on silica gel (~50 g) ($CH_2Cl_2$/EtOAc=9/1) to get the title compound (982 mg, 50% yield) as a pale colorless oily solid.

c) 1,6-Dihydro-5-methoxycarbonyl-2-methoxy-4-methyl-1-(4-nitro phenyloxy) carbonyl -6-(2,4,5-trifluorophenyl)-pyrimidine.

To a solution of 1,6-dihydro-2-methoxy-5-methoxycarbonyl-4-methyl-6-(2,4,5-trifluoro-phenyl)-pyrimidine (600 mg, 1.91 mmol) and 4-dimethylaminopyridine (280 mg, 2.29 mmol) in $CH_2Cl_2$ (8 ml), at room temperature, was added 4-nitrophenyl chloroformate (462 mg, 2.29 mmol). The reaction solution was stirred at room temperature for 18 hours. The white solid formed was filtered out. The filtrate was concentrated and chromatographed on silica gel (~50 g) (hexane/ether=4/1) to get the title compound (143 mg, 16 t yield) as a white solid.

d) 1,6-Dihydro-2-methoxy-5-methoxycarbonyl-4-methyl-1-{N-[4-(2-pyridyl)-piperidin-1-yl]-propyl}carbamoyl-6-(2,4,5-trifluoro-phenyl)-pyrimidine.

A mixture of 116-dihydro-5-methoxycarbonyl-2-methoxy-4-methyl-1-(4-nitrophenyloxy)carbonyl-6-(2,4,5-trifluorophenyl)-pyrimidine (70 mg, 0.146 mmol) and 3-[4-(2-pyridyl)-piperidin-1-yl]propylamine (46 mg, 0.220 mmol) was stirred at room temperature for 12 hours. The solvent was evaporated and the residue separated on preparative TLC ($CHCl_3$/MeOH/2 N $NH_3$ in MeOH=20/2/1) to get the title compound (59 mg, 72% yield ) as a yellow oil.

e) 1,2,3,6-Tetrahydro-5-methoxycarbonyl-4-methyl-2-oxo-1-{N-[4-(2-pyridyl)- piperidine-1-yl]- propyl}carboxamido-6-(2,4,5-trifluorophenyl- pyrimidine dihydrochloride.

1,6-Dihydro-2-methoxy-5methoxycarbonyl-4-methyl-1-{N-[4-(2-pyridyl)-piperidin-1-yl]-propyl}carbamoyl-6-(2,4,5-trifluoro-phenyl)-pyrimidine (59 mg, 0.11 mmol) was dissolved in THF (3 ml) and HCl solution (6 N, 2 ml) was added. The reaction mixture was stirred at room temperature for 6 hour. KOH solution (1 N) was added to neutralized the reaction mixture. It was extracted with $CH_2Cl_2$. The extractant was dried ($Na_2SO_4$) and concentrated to get the title compound (50 mg, 87% yield) as a white solid. Hydrochloride of the title compound was made with HCl in ether. Calculated for $C_{27}H_{30}N_5O_4F_2$+2.0 HCl+1.0 $C_6H_{12}$+1.0 $CHCl_3$ C, 49.68%; H, 5.52%; N, 8.52%. Found: C, 49.22%; H, 6.11%; N, 8.59%. M.P. of the salt: 239–243° C.

EXAMPLE 52

4-(3,4-Difluorophenyl)-3-[3-(3-hydroxy-3-phenyl-8-aza bicyclo[3.2.1]oct-8-yl)propylcarbamoyl]-6-methyl-2-oxo-1,2,3,6-tetrahydro-pyrimidine-5-carboxylic acid methyl ester a) 8-Benzyl-3-phenyl-8-azabicyclo[3.2.1]octan-3-ol:

N-benzyltropinone (14.4 g, 66.7 mmol) was added dropwise (neat) to a solution of phenyl magnesium bromide (100 mL, 0.1 M in THF). The addition was continued as such a rate to maintain a gentle reflux. Once the addition was complete, the reaction mixture was heated at reflux temperature for 19 hours, cooled to room temperature, poured over 200 mL of crushed ice, saturated with ammonium chloride, and extracted with 3×100 mL of ethyl acetate. The combined organic extracts were dried ($K_2CO_3$), solvent removed in Vacuo, and the crude product was chromatographed on 500 g of silica packed with $CHCl_3$. The column was eluted with $CHCl_3$ (1 L), 5%EtOAc—$CHCl_3$ (1 L), 10% (1 L), 20%, (1 L), 30% (1 L), 50% (1 L), 100% EtOAc (1 L), and 10% MeOH-EtOAc (2 L), to give 11.8 g (40%) of the desired product as a slightly yellow oily solid. Anal. Calc. for $C_{20}H_{23}N_1O_1$: C, 81.87; H, 7.90; N, 4.77. Found: C, 81.63; H, 8.01; N, 4.70.

b) 3-Phenyl-8-azabicyclo[3.2.1]octan-3-ol:

A mixture of 5.10 g of 8-benzyl-3-phenyl-8-azabicyclo [3.2.1]octan-3-ol (17.4 mmol), 3.15 g of 10% Pd/C in 50 mL of 95% ethanol was hydrogenated in a pressurized bomb (200 psi) at 60–70° C. (bath temperature) for 16 hours. The reaction mixture was filtered through a pad *of Celite, and the solids were washed with 5×30 mL of methanol. The combined organic extracts were concentrated, and the crude product was chromatographed on 300 g of silica packed with EtOAc-MeOH-isopropanol (30:2:1). The column was eluted with EtOAc-MeOH-isopropanol 25:2:1 (1 L), 20:2:1 (1 L), and 15:2:1 (1 L) to give 3.16 g (89%) of the desired product as a slightly yellow oily solid. Anal. Calc. for $C_{13}H_{17}N_1O_1$: C, 76.81; H, 8.43; N, 6.89. Found: C, 76.57; H, 8.53; N, 6.80.

c)4-(3,4-Difluorophenyl)-3-[3-(3-hydroxy-3-phenyl-8-a zabicyclo [3.2.1]oct-8-yl) propylcarbamoyl]-6-methyl-2-oxo-1,2,3,6-tetrahydro-pyrimidine-5-carboxylic acid methyl ester.

A mixture of 243 mg of 3-phenyl-8-azabicyclo[3.2.1] octan-3-ol (1.2 mmol), 640 mg of 1,2,3,6-tetra hydro-1-{3-bromopropyl}carboxamido-5-methoxy carbonyl-4-methyl-6-(3,4-difluorophenyl)-2-oxo pyrimidine (1.44 mmol), 197 mg of $K_2CO_3$ (1.44 mmol), catalytic amounts (a few crystals) of KI in 10 mL of ethanol were heated at reflux temperature for 4 hours. The reaction mixture was cooled to room temperature, and the crude product was purified with preparative TLC (2000 microns, 10% MeOH-EtOAc) to give 290 mg (43%) of the desired product as a slightly yellow viscous oil. Anal. Calc. For $C_{30}H_{34}F_2N_4O_5$+1.0 Methanol: C, 61.99; H, 6.38; N, 9.33. Found: C, 62.12; H, 6.02; N, 9.58. The hydrochloride salt was prepared by dissolving 150 mg of the free base in minimum EtOAc and excess 1N HCl in ether was added. The solvent was decanted and the separated oil was triturated with ether to give the hydrochloride as a slightly yellow powder: Anal. Calc. for $C_{30}H_{34}F_2N_4O_5$+1.0 HCl+1.2 $H_2O$: C, 57.50; H, 6.01; N, 8.94. Found: C, 57.76; H, 5.82; N, 8.50.

EXAMPLE 53 AND EXAMPLE 54

1,2,3,6-Tetrahydro-1-(N-(3-(3-imidazol-1-yl)propyl)amino)propylcarboxamido-5-methoxycarbonyl-2-oxo-6-(3,4-difluorophenyl)-4-methylpyrimidine dihydrochloride and 1,2,3,6-Tetrahydro-1-(N-(3-(2-indol-3-yl))ethyl)amino) propylcarboxamido-5-methoxycarbonyl-2 -oxo-6-(3,4-difluorophenyl)-4-methylpyrimidine hydrochloride In two separate reaction vessels, a mixture of 89 mg of 1,2,3,6-tetrahydro-1-{3-bromopropyl}carboxamido-5-methoxy carbonyl-4-methyl-6-(3,4-difluorophenyl)-2-oxo pyrimidine (0.200 mmol), 0.200 mmol of the following nucleophiles (25.0 mg of 1-(3-aminopropyl)imidazole, 25 mg of tryptamine), 89 mg of $K_2CO_3$, in 1 mL of acetonitrile were heated at reflux temperature for 2–5 days, applied to the preparative-TLC and eluted with $CHCl_3$—MeOH—2N $NH_3$ in MeOH (10:1:1) to give the title compounds. The hydrochlorides were prepared by dissolving the title compounds in minimum EtOAc, and excess 1N HCl in ether was added until no more precipitate was apparent. The solids were filtered, washed with ether, and dried under high vacuum. 1,2,3,6-Tetrahydro-1-(N-(3-(3-imidazol-1-yl)propyl) amino) propylcarboxamido-5-methoxycarbonyl-2-oxo-6-(3,4-difluorophenyl)-4-methylpyrimidine dihydrochloride (12 mg): Anal. Calc. for $C_{23}H_{28}F_2N_2O_4$+2.0 HCl+0.6 ether+0.3 $CH_2Cl_2$: C, 49.31; H, 5.76; N, 13.12. Found: C, 49.07; H, 5.78; N, 13.28.

1,2,3,6-Tetrahydro-1-(N-(3-(2-indol-3-yl))ethyl)amino) propylcarboxamido-5-methoxycarbonyl-2 -oxo-6-(3,4-difluorophenyl)-4-methylpyrimidine hydrochloride (23 mg); Anal. Calc. for $C_{27}H_{29}F_2N_5O_4$+1.0 HCl +3.7 THF: C, 60.58; H, 7.25; N, 8.45. Found: C, 60.84; H, 7.21; N, 8.48.

EXAMPLE 55

6-(3,4-Difluorophenyl)-1,6-dihydro-1-methoxycarbonyl-5-(3-(4-methoxycarbonyl-4-phenylpiperidin-1-yl)-propylaminocarbonyl)-2,4-dimethylpyrimidine a) Benzyl 3-oxo-2-(3,4-difluorobenzylidenyl)butanoate.

A mixture of 3,4-difluorobenzaldehyde (7.1 g, 50 mmol.), benzyl acetoacetate (12.48 g, 65 mmol.), acetic acid (0.15 g, 2.5 mmol.), piperidine (0.212 g, 2.5 mmol.) and benzene (300 mL) was refluxed under a dean-stark trap overnight. After the removal of solvent, the residue was then dissolved in ethyl acetate and washed with saturated $KHSO_4$, saturated $NaHCO_3$, water and then dried over $Na_2SO_4$. The solvent was evaporated, and the residue was flash chromatographed over silica gel (eluent: 1:1 v/v ethyl acetate-hexane) to give the product in 87% yield (13.7 g) as a yellow solid.

b) 5-Benzyloxycarbonyl-6-(3,4-difluorophenyl)-1,6-dihydro-2,4-dimethylpyrimidine.

To a stirred solution of acetamidine hydrochloride (1.42 g, 15 mmol.) in DMF (10 mL) were added a solution of potassium tert-butoxide (1.23 g, 11 mmol.) in DMF (10 mL) and a solution of the above yellow solid (3.16 g, 10 mmol.) in DMF (10 mL) at 0° C. After the mixture was stirred for 15 min at 0° C., p-toluenesulfonic acid monohydrate (3.8 g, 20 mmol.) was added. The mixture was heated at 100–110° C. for 2 hrs. After cooling, it was quenched with 2N aqueous NaOH solution and extracted with ether. The organic layer was dried over $Na_2SO_4$ and evaporated. The residue was flash chromatographed over silica gel (eluent: 100:5 v/v ethyl acetate-2M ammonia in methanol) to give the product in 42% yield (1.5 g) as an off-white solid.

c) 5-Benzyloxycarbonyl-6-(3,4-difluorophenyl)-1,6-dihydro-1-methoxycarbonyl-2,4-dimethylpyrimidine.

To a stirred slurry of NaH (59 mg, 60% in mineral oil, 1.47 mmol.) in THF (5 mL) was added a solution of the above off-white solid (0.5 g, 1.4 mmol.) in THF (10 mL) at 0° C. After 5 min, methyl chloroformate (0.16 g, 1.7 mmol.) was added at 0° C. Stirring was continued at room temperature for 30 min. The mixture was quenched with brine and extracted with ethyl acetate. The organic layer was dried over $Na_2SO_4$ and evaporated to give a quantitative yield of the product as a yellow solid.

d) 5-Carboxy-6-(3,4-difluorophenyl)-1,6-dihydro-1-methoxycarbonyl-2,4-dimethylpyrimidine.

A solution of the above yellow solid (0.63 g, 1.52 mmol) in methanol (20 mL) was subjected to hydrogenation with a $H_2$ balloon in the presence of palladium (63 mg, 5% on C). The reaction was carried out at room temperature for 30 min. The catalyst was then filtered off and the solvent was removed in vacuo to give the product in 99% yield (0.487 g) as an off-white solid.

e) 6-(3,4-Difluorophenyl)-1,6-dihydro-1-methoxycarbonyl-5-(3-(4-methoxycarbonyl-4-phenylpiperidin-1-yl)-propylaminocarbonyl)-2,4-dimethylpyrimidine.

A mixture of the above off-white solid (0.070 g, 0.22 mmol.), 4-dimethylaminopyridine (0.040 g, 0.33 mmol.), 1-(3-dimethylaminopropyl)-3-ethylcarbodiimide hydrochloride (0.060 g, 0.30 mmol.) and $CH_2Cl_2$ (5 mL) was stirred at room temperature for 0.5 hr. After the addition of 3-(4-methoxycarbonyl-4-phenylpiperidin-1-yl)propylamine (0.075 g, 0.27 mmol.), the mixture was refluxed overnight. To the mixture was added another 25 mL of $CH_2Cl_2$ and washed with saturated $NH_4Cl$ solution. After the removal of the solvent, the residue was flash chromatographed over silica gel (eluent: 85:15 v/v ethyl acetate-methanol) to give the title compound in 42% yield (0.052 g) as a white solid: mp 55–57° C. Anal. Calcd. for $C_{31}H_{36}F_2N_4O_5 \cdot 0.5CH_2Cl_2$: C, 60.52; H, 5.97; N, 8.96. Found: C, 60.61; H, 6.09; N, 8.94.

EXAMPLE 56

6-(3,4-Difluorophenyl)-1,6-dihydro-5-(3-(4-methoxycarbonyl-4-phenylpiperidin-1-yl) propylaminocarbonyl)-1-methoxymethyl-2,4-dimethylpyrimidine a) 5-Benzyloxycarbonyl-6-(3,4-difluorophenyl)-1,6-dihydro-1-methoxymethyl-2,4-dimethylpyrimidine.

To a stirred slurry of NaH (24 mg, 60% in mineral oil, 0.6 mmol.) in THF (5 mL) was added a solution of 5-benzyloxycarbonyl-6-(3,4-difluorophenyl)-1,6-dihydro-2,4-dimethylpyrimidine (0.2 g, 0.56 mmol.) in THF (10 mL) at 0° C. After 10 min, chloromethyl methyl ether (0.043 mL, 0.57 mmol.) was added at 0° C. Stirring was continued at room temperature for 3 hrs. The mixture was quenched with brine and extracted with ethyl acetate. The organic layer was dried over $Na_2SO_4$ and evaporated to give the product in 44.5% yield as a yellow oil.

b) 5-Carboxy-6-(3,4-difluorophenyl)-1,6-dihydro-1-methoxymethyl-2,4-dimethylpyrimidine.

A solution of the above yellow oil (0.17 g, 0.43 mmol) in methanol (20 mL) was subjected to hydrogenation with a $H_2$ balloon in the presence of palladium (34 mg, 5% on C). The reaction was carried out at room temperature for 0.5 hr. The catalyst was then filtered off and the solvent was removed in vacuo to give the product in 100% yield (0.13 g) as an off-white solid.

c) 6-(3,4-Difluorophenyl)-1,6-dihydro.-5-(3-(4-methoxycarbonyl-4-phenylpiperidin-1-yl) propylaminocarbonyl)-1-methoxymethyl-2,4-dimethylpyrimidine.

A mixture of 5-carboxy-6-(3,4-difluoro-phenyl)-1,6-dihydro-1-methoxymethyl-2,4-dimethylpyrimidine (0.13 g, 0.42 mmol.), 4-dimethylaminopyridine (0.1 g, 0.84 mmol.), 1-(3-dimethylaminopropyl)-3-ethylcarbodiimide hydrochloride (0.16 g, 0.82 mmol.) and $CH_2Cl_2$ (5 mL) was stirred at room temperature for 0.5 hr. After the addition of 3-(4-methoxycarbonyl-4-phenylpiperidin-1-yl)propylamine (0.17 g, 0.62 mmol.), the mixture was refluxed overnight. To the mixture was added another 25 mL of $CH_2Cl_2$ and washed with saturated $NH_4Cl$ solution. After removal of the solvent, the residue was flash chramotographed over silica gel (eluent: 80:20 v/v ethyl acetate- methanol) to give the title compound in 32% yield (0.075 g) as a pale yellow solid: mp 53–57° C. Anal. Calcd. for $C_{31}H_{38}F_2N_4O_4 \cdot 0.25CHCl_3$: C, 62.71; H, 6.44; N, 9.36. Found: C, 62.62; H, 6.79; N, 9.19.

EXAMPLE 57

1,6-Dihydro-5-methoxycarbonyl-1-(5-(4-methoxycarbonyl-4-phenylpiperidin-1-yl)pentyl)-4-methyl-6-(4-nitrophenyl)-pyrimidine a) 1,6-Dihydro-5-methoxycarbonyl-4-methyl-6-(4-nitrophenyl)-pyrimidine.

Sodium (0.55 g, 23.9 mmol) was allowed to react with anhydrous EtOH (100 mL). Then the solution was cooled by an ice water bath when formamidine acetate (2.29 g, 22.0 mmol) and methyl 2-(4-nitrobenzylidenyl)acetoacetate (5.00 g, 20.1 mmol) were added. The mixture was stirred at room temperature for 3 h. The product was filtered off as a yellow powder (4.68 g, 80%). It was mixed with p-toluenesulfonic acid monohydrate (6.7 g, 35.2 mmol) in dry DMSO (125 mL) and heated at 110° C. for 3 h. Ice water (450 mL) was added and the product as a tosylate was filtered off as an off-white solid (5.55 g, 78%).

b) 1-(5-Chloropentyl)-1,6-dihydro-5-methoxycarbonyl-4-methyl-6-(4-nitrophenyl)pyrimidine.

The above solid (2.44 g, 5.45 mmol) was added to dry THF (50 mL) containing sodium hydride (60% oil dispersion, 480 mg, 12.0 mmol) and cooled by an ice water bath. Then 1-bromo-5-chloropentane (3 mL, 22.8 mmol) was added. The mixture was stirred at room temperature for 7 h before ice water was added. Extraction with EtOAc gave a dark oil (4.455 g) which was flash chromatographed over silica gel (120 g) eluting with $EtOAc/hexane/Et_3N$ (15:15:1) to afford a brown oil (1.43 g, 69%).

c) 1,6-Dihydro-5-methoxycarbonyl-1-(5-(4-methoxycarbonyl-4-phenyl-piperidin-1-yl)pentyl)-4-methyl-6-(4-nitrophenyl)-pyrimidine.

The above oil (220 mg, 0.58 mmol) was mixed with 4-methoxy-carbonyl-4-phenylpiperidine (127 mg, 0.58 mmol) and potassium iodide (106 mg, 0.64 mmol) in dry glyme (4 mL) cooled by an ice water bath. Then sodium hydride (24 mg, 60% oil dispersion, 0.60 mmol) was added. The mixture was heated at reflux overnight and more KI (106 mg) was added. Reflux was continued for two more days. Ice water was added. Extraction with EtOAc (3×3 mL) gave a brown oil (158 mg). It was dissolved in $CHCl_3/EtOAc$ and flash chromatographed over silica gel (16 g) eluting with $EtOAc/MeOH/Et_3N$ (20:1:1) to afford a yellow oil (89 mg, 27%). Anal. Calcd. for $C_{31}H_{38}N_4O_6 \cdot 3/4H_2O$: C, 64.62; H, 6.91; N, 9.72. Found: C, 64.56; H, 6.84; N, 9.76.

EXAMPLE 58

6-(2,4-Difluorophenyl)-1,6-dihydro-1-(5-(4-methoxycarbonyl-4-phenylpiperidin-1-yl)-pentyl)-2,4-dimethyl-5-methylaminocarbonyl-pyrimidine a) Benzyl 3-oxo-2-(2,4-difluorobenzylidenyl)butanoate.

A mixture of 2,4-difluorobenzaldehyde (7.1 g, 50 mmol.), benzyl acetoacetate (12.48 g, 65 mmol.), acetic acid (0.15 g, 2.5 mmol.), piperidine (0.212 g, 2.5 mmol.) and 2-propanol (300 mL) was stirred at room temperature for two days. After the removal of solvent, the residue was then dissolved in ethyl acetate and washed with saturated $KHSO_4$, saturated $NaHCO_3$, water and then dried over $Na_2SO_4$. The solvent was evaporated, and the residue was flash chromatographed over silica gel (eluent: 1:5 v/v ethyl acetate-hexane) to give the product in 91% yield (14.3 g) as a yellow solid.

b) 5-Benzyloxycarbonyl-6-(2,4-difluorophenyl)-1,6-dihydro-2,4-dimethylpyrimidine. To a stirred solution of acetamidine hydrochloride (2.84 g, 30 mmol.) in DMF (20 mL) were added a solution of potassium tert-butoxide (2.46 g, 22 mmol.) in DMP (20 mL) and a solution of the above yellow solid (6.32 g, 20 mmol.) in DMF (20 mL) at 0° C. After the mixture was stirred for 15 min at 0° C., p-toluenesulfonic acid monohydrate (7.6 g, 40 mmol.) was added. The mixture was heated at 100–110° C. for 2 hrs. After cooling, it was quenched with 2N aqueous NaOH solution and extracted with ether. The organic layer was dried over $Na_2SO_4$ and evaporated. the residue was flash chromatographed over silica gel (eluent: 100:5 v/v ethyl acetate-2M ammonia in Methanol) to give the product in 42% yield (1.5 g) as an off-white solid.

c) 5-Benzyloxycarbonyl-1-(5-bromopentyl)-6-(2,4-difluorophenyl)-1,6-dihydro-2,4-dimethylpyrimidine. To a suspension of NaH (123 mg, 60% dispersion in mineral oil, 3.08 mmol.) in THF (5 mL) was added a solution of the above off-white solid (1.0 g, 2.8 mmol.) and HMPA (0.5 g, 2.8 mmol.) in THF (5 mL) at 0° C. After 15 min, 1,5-dibromopentane (1.53 mL, 11.2 mmol.) was added. The mixture was then refluxed for 30 min. The solid was filtered off. After the removal of the solvent, the residue was flash chromatographed over silica gel (eluent: ethyl acetate) to give the product in 78% yield (1.1 g) as a yellow oil.

d) 5-Benzyloxycarbonyl-6-(2,4-difluorophenyl)-1,6-dihydro-1-(5-(4-methoxycarbonyl-4-phenylpiperidin-1-yl) pentyl)-2,4-dimethyl-pyrimidine. A mixture of the above yellow oil (1.62 g, 3.2 mmol.), 4-methoxycarbonyl-4-phenyl piperidine (1.4 g, 6.4 mmol.), potassium carbonate (1.76 g, 12.7 mmol.), sodium iodide (0.45 g, 3.0 mmol.) and 1,4-dioxane (15 mL) was refluxed overnight. The undissolved solid was then filtered off and the solvent was evaporated. The residue was flash chromatographed over silica gel (eluent: 80:20 v/v ethyl acetate-2M ammonia in methanol) to give the product in 66% yield (1.36 g) as a yellow oil.

e) 5-Carboxy-6-(2,4-difluorophenyl)-1,6-dihydro-1-(5-(4-methoxycarbonyl-4-phenylpiperidin-1-yl)pentyl)-2,4-dimethyl-pyrimidine. A solution of the above yellow oil (0.36 g, 0.56 mmol) in methanol (20 mL) was subjected to hydrogenation with a $H_2$ balloon in the presence of palladium (36 mg, 5% on C). The reaction was carried out at room temperature for 30 min. The catalyst was then filtered off and the solvent was removed in vacuo to give the product in quantitative yield (0.31 g) as an off-white solid.

f) 6-(2,4-Difluorophenyl)-1,6-dihydro-1-(5-(4-methoxycarbonyl-4-phenylpiperidin-1-yl)-pentyl)-2,4-dimethyl-5-methylaminocarbonyl-pyrimidine. A mixture of the above off-white solid (0.244 g, 0.44 mmol.), 4-dimethylaminopyridine (0.26 g, 2.12 mmol.), 1-(3-dimethylaminopropyl)-3-ethylcarbodiimide hydrochloride (0.13 g, 0.66 mmol.) and $CH_2Cl_2$ (10 mL) was stirred at room temperature for 2 hrs. After the addition of methyl amine hydrogen chloride (0.089 g, 1.32 mmol.), the mixture was stirred at room temperature overnight. To the mixture was added another 25 mL of $CH_2Cl_2$ and washed with saturated $NH_4Cl$ solution. After removal of the solvent, the residue was flash chramotographed over silica gel (eluent: 100:20 v/v ethyl acetate-2M ammonia in methanol) to give the title compound in 22% yield (0.055 g) as a yellow oil. Treatment of the free base with 2 equivalents of 1M HCl in ether gave the HCl salt as a pale yellow solid: mp 152–155° C. Anal. Calcd. for $C_{32}H_{40}F_2N_4O_3 \cdot 2HCl \cdot 1.6H_2O \cdot 0.8CHCl_3$: C, 51.57; H, 6.07; N, 7.33. Found: C, 51.38; H, 5.91; N, 7.27.

EXAMPLE 59

6 (R,S)-(3,4-Difluorophenyl)-1,6-dihydro-5-methoxycarbonyl-1-(5-(4-methoxycarbonyl-4-phenylpiperidin-1-yl)-4(S)-methyl)pentyl-2,4-dimethylpyrimidine a) (S)-(+)-3-Methylpiperidine. A mixture of (+)-mandelic acid (45.64 g, 0.3 mol) in ethyl acetate (300 mL) was heated to solution and treated with 3-methylpiperidine (29.75 g, 0.3 mol). The mixture was allowed to come to room temperature before filtration. The crystalline material was washed with 1:1 ethyl acetate-ether (400 mL). Two recrystallizations of this salt from ethyl acetate gave the optically pure salt in 56% yield (21.7 g).

b) (S)-(+)-N-Benzoyl-3-methylpiperidine. The above salt (21 g, 0.088 mol) was dissolved in sodium hydroxide solution (1.0 N, 200 mL). The solution was cooled to 3° C., and benzoyl chloride (12.5 g, 0.089 mol) was added dropwise over 10 min. After the addition was complete, the mixture was transferred to a separatory funnel and extracted with ether. The combined extracts were dried ($Na_2SO_4$) and concentrated to give the pure amide in 98% yield (17.2 g): $[\alpha]_D$+45.9 (c=1.00, $CH_3OH$)

c) (S)-(−)-2-Methyl-1,5-dibromopentane. To the above amide powder was added phosphorus tribromide (7.81 mL, : d 2.85, 0.082 mol) at 5° C. over 20 min with vigorous stirring. After the addition, the mixture was warmed to room temperature, and $Br_2$ (4 mL, 0.082 mol) was added dropwise over 10 min. The mixture was then allowed to stand at room temperature overnight and distilled under vacuum (0.5–1 mm Hg) until the head temperature reached 80° C. The distillate was dissolved in hexane (100 mL) and washed successively with water (20 mL), concentrated sulfuric acid (4×30 mL), water (20 mL), NaOH solution (1N, 2×40 mL), and water (20 mL). The hexane solution was then dried ($Na_2SO_4$) and concentrated to give the product in 31% yield (6.4 g) as a light yellow liquid.

d) 1-(5-Bromo-4(S)-methylpentyl)-6(R,S)-(3,4-difluorophenyl)-1,6-dihydro-5-methoxycarbonyl-2,4-dimethylpyrimidine. To a suspension of NaH (47 mg, 60% dispersion in mineral oil, 1.17 mmol.) in THF (3 mL) was added a solution of 6-(3,4-difluoro-phenyl)-1,6-dihydro-5-methoxycarbonyl-2,4-dimethylpyrimidine (0.3 g, 1.07 mmol.) and HMPA (0.193 g, 1.07 mmol.) in THF (4 mL) at 0° C. After 10 min, a solution of (−)-2-methyl-1,5-dibromopentane (0.86 g, 3.53 mmol.) in THF (5 mL) was added. The mixture was then refluxed for 10 min. The solid formed was filtered off. After the removal of the solvent, the residue was flash chromatographed over silica gel (eluent: 100:5 v/v ethyl acetate-2.0M ammonia in methanol) to give the product in 36% yield (0.169 g) as a yellow oil.

e) 6(R,S)-(3,4-Difluorophenyl)-1,6-dihydro-5-methoxycarbonyl1--(5-(4-methoxycarbonyl-4—phenylpiperidin-1-yl)-4(S)-methyl)pentyl-2,4-dimethylpyrimidine. A mixture of the above yellow oil (0.169 g, 0.38 mmol.), 4-methoxycarbonyl-4-phenyl piperidine (0.167 g, 0.76 mmol.), potassium carbonate (0.21 g, 1.52 mmol.), sodium iodide (0.057 g, 0.38 mmol.) and 1,4-dioxane (8 mL) was refluxed overnight. The undissolved solid was then filtered off and the solvent was evaporated. The residue was flash chromatographed over silica gel (eluent: 100:5 v/v ethyl acetate-2M ammonia in methanol) to give the title compound in 11% yield (0.025 g) as a yellow oil. Treatment of the free base with 2 equivalents of 1M HCl in ether gave the HCl salt as a light yellow solid: mp 155–158° C. Anal. Calcd. for $C_{33}H_{41}F_2N_3O_4 \cdot 2HCl \cdot 0.5H_2O$: C, 59.72; H, 6.64; N, 6.33. Found: C, 59.47; H, 6.66; N, 6.10.

EXAMPLE 60

6-(3,4-Difluorophenyl)-1,6-dihydro-5-methoxycarbonyl-1-(3-(4-methoxycarbonyl-4-phenylpiperidin-1-yl)methyl)benzyl-2,4-dimethylpyrimidine a) 1-(3-Bromomethylbenzyl)-6-(3,4-difluorophenyl)-1,6-dihydro-5-methoxycarbonyl-2,4-dimethylpyrimidine. To a suspension of NaH (31 mg, 60% dispersion in mineral oil, 0.77 mmol.) in THF (5 mL) was added a solution of 6-(3,4-difluorophenyl)-1,6-dihydro-5-methoxycarbonyl-2,4-dimethylpyrimidine (0.3 g, 1.07 mmol.) and HMPA (0.193 g, 1.07 mmol.) in THF (5 mL) at 0° C. After 15 min, α,α'-dibromo-m-xylene (0.99 g, 3.75 mmol.) was added. The mixture was then refluxed for 15 min. The solid was filtered off. After the removal of the solvent, the residue was flash chromatographed over silica gel (eluent: ethyl acetate) to give the product in 91% yield (0.45 g) as a yellow oil.

b) 6-(3,4-Difluorophenyl)-1,6-dihydro-5-methoxycarbonyl-1-(3-(4-methoxycarbonyl-4-phenyl-4-phenylpiperidin-1-yl)methyl)benzyl-2,4-dimethylpyrimidine.

A mixture of the above yellow oil (0.45 g, 0.97 mmol.), 4-methoxycarbonyl-4-phenyl piperidine (0.42 g, 1.9 mmol.), potassium carbonate (0.67 g, 4.86 mmol.), sodium iodide (0.14 g, 0.97 mmol.) and 1,4-dioxane (10 mL) was refluxed overnight. The undissolved solid was then filtered off and the solvent was evaporated. The residue was flash chromatographed over silica gel (eluent: 100:5 v/v ethyl acetate-2M ammonia in methanol) to give the title compound in 17% yield (0.10 g) as a yellow oil. Treatment of the free base with 2 equivalents of 1M HCl in ether gave the HCl salt as an off-white solid: mp 181–183° C. Anal. Calcd. for $C_{35}H_{37}F_2N_3O_4 \cdot 2HCl \cdot 1.0H_2O$: C, 60.69; H, 5.97; N, 6.07. Found: C, 60.73; H, 5.77; N, 5.94.

EXAMPLE 61

6-(3,4-Difluorophenyl)-1,6-dihydro-5-methoxycarbonyl-2,4-dimethyl-1-(5-(3-phenylpropylamino)pentyl)-pyrimidine A mixture of 1-(5-bromopentyl)-6-(3,4-difluorophenyl)-1,6-dihydro-5-methoxycarbonyl-2,4-dimethylpyrimidine (0.186 g, 0.433 mmol.), 3-phenyl-1-propylamine (0.12 g, 0.89 mmol.), potassium carbonate (0.3 g, 2.17 mmol.), sodium iodide (70 mg, 0.46 mmol.) and 1,4-dioxane (8 mL) was refluxed overnight. The undissolved solid was then filtered off and the solvent was evaporated. The residue was flash chromatographed over silica gel (eluent: 100:20:10 v/v/v $CHCl_3$-methanol-2M ammonia in methanol) to give the product in 54% yield (0.114 g) as a yellow oil. Treatment of the free base with 2 equivalents of 1M HCl in ether gave the HCl salt as a white solid: mp 95–97° C. Anal. Calcd. for $C_{28}H_{35}F_2N_3O_2 \cdot 2HCl \cdot 0.5CH_2Cl_2$: C, 57.15; H, 6.39; N, 7.02. Found: C, 57.09; H, 6.65; N, 6.85.

EXAMPLE 62

(+)-6-(3,4-Difluorophenyl)-1,6-dihydro-1-(4-hydroxy-5-(4-(2-pyridyl)piperidin-1-yl)pentyl)-5-methoxycarbonyl-2,4-dimethylpyrimidine a) 3-Bromopropylepoxide.

To a solution of 5-bromo-1-pentene (2.15 g, 14.4 mmol.) in $CH_2Cl_2$ (40 mL) was added MCPBA (3.0 g, 17.3 mmol.) at 0° C. slowly. After stirred at room temperature overnight, the mixture was poured into a mixture of ice and 2N NaOH solution. The separated aqueous layer was extracted with $CH_2Cl_2$. The combined organic layer was then washed with water, brine and dried over $Na_2SO_4$. The concentrated mixture was flash chromatographed over silica gel (eluent: $CH_2Cl_2$) to give the product in 92% yield (2.19 g) as a pale yellow liquid.

b) 1-(4,5-Epoxypentyl)-6-(3,4-difluorophenyl)-1,6-dihydro-5-methoxycarbonyl-2,4-dimethylpyrimidine.

To a suspension of NaH (78 mg, 60% dispersion in mineral oil) in THF (10 mL) was added a solution of 6-(3,4-difluorophenyl)-1,6-dihydro-5-methoxycarbonyl-2,4-dimethylpyrimidine (0.5 g, 1.78 mmol.) and HMPA (0.3 mL, 1.78 mmol.) in THF (5 mL) at 0° C. After 20 min, the above pale yellow liquid (0.6 g, 3.6 mmol.) was added. The mixture was then refluxed 2hrs. After the removal of the solvent, the residue was flash chromatographed over silica gel (eluent:100:5 v/v ethyl acetate-2.0M ammonia in methanol) to give the product in 62% yield (0.4 g) as a yellow oil.

c) 6-(3,4-Difluorophenyl)-1,6-dihydro-1-(4-hydroxy-5-(4-(2-pyridyl)piperidin-1-)ylpentyl)-5-methoxycarbonyl-2,4-dimethylpyrimidine.

A mixture of the above yellow oil (0.48 g, 1.32 mmol.). 4-(2-pyridyl)piperidine (0.32 g, 1.98 mmol.) and 1,4-dioxane (10 mL) was refluxed overnight. The concentrated mixture was then flash chromatographed over silica gel (eluent: 80:20 v/v ethyl acetate-2.0M ammonia in methanol) to give all four diastereomers in 43% yield (0.3 g). Chiral HPLC separation gave the title enantiomer which was converted to a HCl salt: $[\alpha]_D$=120.6 (c=0.7, MeOH); mp 163–165° C. Anal. Calcd. for $C_{29}H_{36}F_2N_4O_3 \cdot 3HCl \cdot 0.7CHCl_3$: C, 49.57; H, 5.56; N, 7.79. Found: C, 49.41; H, 5.96; N, 7.38.

EXAMPLE 63

6-(3,4-Difluorophenyl)-1,6-dihydro-5-methoxycarbonyl-2,4-dimethyl-1-(5-(4-(2-pyridyl)piperidin-1-yl)-4 -oxo)pentyl pyrimidine To a solution of oxalyl chloride (8 mg, 0.06 mmol.) in $CH_2Cl_2$ (0.25 mL) was added a solution of DMSO (10 mg, 0.14 mmol.) in $CH_2Cl_2$ (0.3 mL) at −78° C. After 3 min, a solution of 6-(3,4-difluorophenyl)-1,6-dihydro-1-(4-hydroxy-5-(4-(2-pyridyl)-piperidin-1-yl)pentyl)-5-methoxycarbonyl-2,4-dimethylpyrimidine (30 mg, 0.057 mmol.) in $CH_2Cl_2$ (1 mL) was added to the mixture which was stirred for another 15 min. The mixture was treated with triethylamine (0.04 mL) and stirred for another 5 min. Then it was allowed to warm up to room temperature. After the addition of water, it was washed with 1N NaOH and water. The organic layer was dried over $Na_2SO_4$ and concentrated. The residue was purified by preparative TLC (eluent: 100:20 v/v ethyl acetate-2.0M ammonia in methanol) to give the title compound in 43% yield (13 mg) as a yellow oil. Treatment of the free base with 3 equivalents of 1M HCl in ether gave the HCl salt as a pale yellow solid: mp 135–137° C. Anal. Calcd. for $C_{19}H_{34}F_2N_4O_3 \cdot 3HCl_2H_2O$ $0.9CH_2Cl_2$: C, 48.11; H, 5.78; N, 7.51. Found: C, 47.99; H, 6.08; N, 7.35.

EXAMPLE 64

(+)-4-(3,4,5-Trifluorophenyl)-3,4-dihydro-5-methoxycarbonyl-6-methyl-3-(5-(4-(2-pyridyl)piperidin-1-yl)-pentyl-2(1H)-pyrimidone a) 3-(5-Bromopentyl)-4-(3,4,5-trifluorophenyl)-3,4-dihydro-5-methoxycarbonyl-6-methyl-2(1H)-pyrimidone.

To a suspension of NaH (0.23 g, 60% dispersion in mineral oil, 5.8 mmol.) in THF (40 mL) was added a solution of 6-(3,4,5-trifluorophenyl-1,6-dihydro-2-methoxy-5-methoxycarbonyl-4-methyl-pyrimidine (0.6 g, 1.9 mmol.) and HMPA (0.33 mL, 1.9 mmol.) in THF (10 mL) at 0° C. After 20 min, 1,5-dibromopentane (1.75 g, 9.4 mmol.) was added. The mixture was then refluxed for 2 hrs and quenched by water. The mixture was partitioned between ethyl acetate and water. The organic layer was separated, treated with 6N HCl (10 mL) solution and stirred at room temperature for 1 hr. It was then separated and dried over $Na_2SO_4$. After the removal of solvent, the residue was flash chromatographed over silica gel (eluent: 80:20 v/v hexane-ethyl acetate) to give the product in 73% yield (0.62 g) as a yellow oil.

b)(+)-4-(3,4,5-Trifluorophenyl)-3,4-dihydro-5-methoxycarbonyl-6-methyl-3-(5-(4-(2-pyridyl) piperidin-1-yl)-pentyl-2(1H)-pyrimidone. A mixture of 3-(5-bromopentyl)-4-(3,4,5-trifluorophenyl)-3,4-dihydro-5-methoxycarbonyl-6-methyl-2(1H)-pyrimidone (0.3 g, 0.7 mmol.), 4-(2-pyridyl) piperidine (0.22 g, 1.4 mmol.), potassium carbonate (0.5 g, 3.6 mmol.), sodium iodide (0.1 g, 0.7 mmol.) and acetone (20 mL) was refluxed overnight. The undissolved solid was then filtered off and the solvent was evaporated. The residue was flash chromatographed over silica gel (eluent: 80:20 v/v ethyl acetate-2.0M ammonia in Methanol) to give the racemic product in 85% yield (0.3 g) as a yellow oil. Chiral HPLC separation afforded the title enantiomer which was converted to a HCl salt: $[\alpha]_D$=122 (c=4.1, MeOH); mp 125–127° C. Anal. Calcd. for $C_{28}H_{33}F_3N_4O_3 \cdot 2HCl \cdot 2H_2O \cdot 0.2Et_2O$: C, 52.86; H, 6.32; N, 8.56. Found: C, 52.66; H, 6.37; N, 8.15.

EXAMPLE 65

4-(3,4,5-Trifluorophenyl)-3,4-dihydro-5-methoxycarbonyl-6-methyl-3-(3-(4-(2-pyridyl)piperidin-1-yl)propyloxycarbonyl)-2(1H)-pyrimidone.

a) 1-(3-Hydroxypropyl)-4-(2-pyridyl)piperidine.

A mixture of 4-(2-pyridyl)piperidine (200 mg, 1.23 mmol), 3-bromopropanol (135 mL, 1.49 mmol), potassium carbonate (620 mg, 4.49 mmol) and a catalytic amount of sodium iodide in acetone (10 mL) was heated at reflux overnight. Filtration followed by evaporation of the solvent gave a light brown oil (324 mg) which was dissolved in $CHCl_3$ and flash chromatographed over silica gel (20 g) eluting with $EtOAc/MeOH/Et_3N$ (20:1:1) to afford a light brown solid (166 mg, 61%).

b) 4-(3,4,5-Trifluorophenyl)-3,4-dihydro-5-methoxycarbonyl-6-methyl-3-(3-(4-(2-pyridyl)piperidin-1-yl)propyloxycarbonyl)-2(1H)-pyrimidone.

A mixture of 1-(3-hydroxypropyl)-4-(2-pyridyl)-piperidine (72 mg, 0.33 mmol) and 4-(3,4,5-trifluorophenyl)-3,4-dihydro-5-methoxycarbonyl-6-methyl-3-(4-nitrophenoxycarbonyl)-2(1H)-pyrimidine (152 mg, 0.33 mmol) in dry THF (8 mL) was heated at reflux overnight. The residue obtained after evaporation of the solvent was dissolved in EtOAc and flash chromatographed over silica gel (18 g) eluting with $EtOAc/MeOH/Et_3N$ (100:3:3) to afford an off-white solid (133 mg, 75%). It was dissolved in $CH_2Cl_2$ and treated with 1M HCl in ether (0.6 mL) to give an off-white solid: mp 154° C. (dec.). Anal. Calcd. for $C_{27}H_{29}F_3N_4O_5 \cdot 2HCl \, 2H_2O$: C, 49.47; H, 5.38; N, 8.55. Found: C, 49.48; H, 5.16; N, 8.35.

EXAMPLE 66

(+)-1,2,3,6-Tetrahydro-1-{N-[4-cyano-4-(phenyl)cyclohex-1-yl]ethyl}carboxamido-5-methoxy carbonyl-4-methoxymethyl-6-(3,4-difluorophenyl)-2-oxopyrimidine hydrochloride.

a) 2-[4-Cyano-4-(phenyl)cyclohex-1-yl]ethylamine.

A mixture of 4-phenyl-4-cyanocyclohexanone (5.00 g, 25.09 mmol) and ethylenediamine (5.58) and p-toluene sulfonic acid in benzene (200 mL) were refluxed for 4 h in a Dean-Stork set-up to remove the water formed. Solvent was evaporated and the residue was redissolved in methanol and cooled to 0° C. To this, sodium borohydride (1.5 g) was added in portions and the mixture was stirred at room temperature for 3 h. Solvent was evaporated, the residue was dissolved in dichloromethane (300 mL), washed with-brine (2×200 mL) and dried (sodium sulfate). Solvent was evaporated and the residue was dried under vacuum to leave the product as an oil (5.2 g). The $^1$H-NMR showed this product to be pure and found to contain the cis/trans isomers in the ratio of about 9:1. It was used as was in the next step.

b) (+)-1,2,3,6-Tetrahydro-1-{N-[4-cyano-4-(phenyl)cyclohex-1-yl]ethyl}carboxamido-5-methoxycarbonyl-4-methoxy methyl-6-(3,4-difluorophenyl)-2-oxopyrimidine hydrochloride.

A solution of (+)-6-(3,4-difluorophenyl)-1,6-dihydro-2-methoxy-5-methoxycarbonyl-4-methoxymethyl-1-(4-nitrophenoxy)carbonylpyrimidine (0.220 91 0.448 mmol), 2-[4-cyano-4-(phenyl) cyclohex-1-yl]ethylamine (0.130 g, 0.538 mmol) in tetrahydrofuran (100 mL) was stirred at room temperature for 24 hours. The reaction mixture was stirred for another 1 hour after addition of 2 mL of 6N HCl. Solvent was evaporated at reduced pressure and the residue was basified by treatment with 10% aqueous KOH solution, extracted with dichloromethane (3×10 mL). The combined extracts were dried over potassium carbonate, and solvent evaporated. The crude product was purified by preparative thin layer chromatography (dichloromethane:MeOH:2M ammonia in MeOH,90:8:4). The two possible isomer were obtained in the order of less polar compound as the minor product and the more polar compound as the major component (yields: 16 mg minor and 160 mg major isomer). The HCl salts were obtained by treatment with 1N HCl in ether. The minor isomer HCl salt:m.p. 124–126° C.; $[\alpha]_D$=+112 (c=0.21 g in 100 mL $CHCl_3$); Anal. Calcd. for $C_{30}H_{34}N_5O_5F_2Cl.0.5$ chloroform. 0.5 ether: C, 54.61; H, 5.57; N, 9.80. Found: C, 54.43; H, 5.29; N, 9.54. The major isomer HCl salt: m. p. 136–138° C.; $[\alpha]_D$=+142 (c=0.21 g in 100 mL $CHCl_3$) Anal. Calcd. for $C_{30}H_{34}N_5O_5F_2Cl.0.4$ chloroform: C, 54.84; H, 5.21; N, 10.52. Found: C, 55.16; H, 5.39; N, 10.42.

EXAMPLE 67

As a specific embodiment of an oral composition of a compound of this invention, 100 mg of one of the compounds described herein is formulated with sufficient finely divided lactose to provide a total amount of 580 to 590 mg to fill a size O hard gel capsule.

Pharmacological Profiles of the Compounds in Cloned Human Adrenergic Receptors.

Binding affinities were measured for selected compounds of the invention at six cloned human alpha-1 and alpha-2 receptor subtypes, as well as at the L-type calcium channel. The protocols for these experiments are given below.

Protocol for the Determination of the Potency of $\alpha_1$ Antagonists

The activity of compounds at the different human receptors was determined in vitro using cultured cell lines that selectively express the receptor of interest. These cell lines were prepared by transfecting the cloned cDNA or cloned genomic DNA or constructs containing both genomic DNA and cDNA encoding the human α-adrenergic receptors as follows:

$\alpha_{1A}$ Human Adrenergic Receptor: The entire coding region of α1A (1719 bp), including 150 base pairs of 5' untranslated sequence (5' UT) and 300 bp of 3' untranslated sequence (3' UT), was cloned into the BamHI and ClaI sites of the polylinker-modified eukaryotic expression vector pCEXV-3, called EXJ.HR. The construct involved the ligation of partial overlapping human lymphocyte genomic and hippocampal cDNA clones: 5' sequence were contained on a 1.2 kb SmaI-XhoI genomic fragment (the vector-derived BamHI site was used for subcloning instead of the internal insert-derived SmaI site) and 3' sequences were contained on an 1.3 kb XhoI-ClaI cDNA fragment (the ClaI site was from the vector polylinker). Stable cell lines were obtained by cotransfection with the plasmid α1A/EXJ (expression vector containing the α1A receptor gene) and the plasmid pGCcos3neo (plasmid containing the aminoglycoside transferase gene) into LM(tk-), CHO, and NIH3T3 cells, using calcium phosphate technique. The cells were grown, in a controlled environment (37° C., 5% $CO_2$), as monolayers in Dulbecco's modified Eagle's Medium (GIBCO, Grand Island, N.Y.) containing 25 mM glucose and supplemented with 10% bovine calf serum, 100 units/ml penicillin g, and 100 μg/ml streptomycin sulfate. Stable clones were then selected for resistance to the antibiotic G-418 (1 mg/ml), and membranes were harvested and assayed for their ability to bind [$^3$H]prazosin as described below (see "Radioligand Binding assays").

$\alpha_{1B}$ Human Adrenergic Receptor: The entire coding region of α1B (1563 bp), including 200 base pairs and 5' untranslated sequence (5' UT) and 600 bp of 3' untranslated sequence (3' UT), was cloned into the EcoRI site of pCEXV-3 eukaryotic expression vector. The construct involved ligating the full-length containing EcoRI brainstem cDNA fragment from λ ZapII into the expression vector. Stable cell lines were selected as described above.

$\alpha_{1C}$ Human Adrenergic Receptor: The entire coding region of α1C (1401 bp), including 400 base pairs of 5' untranslated sequence (5' UT) and 200 bp of 3' untranslated sequence (3' UT), was cloned into the KpnI site of the polylinker-modified pCEXV-3-derived eukaryotic expression vector, EXJ.RH. The construct involved ligating three partial overlapping fragments: a 5' 0.6 kb HincII genomic clone, a central 1.8 EcoRI hippocampal cDNA clone, and a 3' 0.6 Kb PstI genomic clone. The hippocampal cDNA fragment overlaps with the 5' and 3' genomic clones so that the HincII and PstI sites at the 5' and 3' ends of the cDNA clone, respectively, were utilized for ligation. This full-length clone was cloned into the KpnI site of the expression vector, using the 5' and 3' KpnI sites of the fragment, derived from vector (i.e., pBluescript) and 3'-untranslated sequences, respectively. Stable cell lines were selected as described above.

Radioligand Binding Assays: Transfected cells from culture flasks were scraped into 5 ml of 5 mM Tris-HCl, 5 mM EDTA, pH 7.5, and lysed by sonication. The cell lysates were centrifuged at 1000 rpm for 5 min at 4° C., and the supernatant was centrifuged at 30,000× g for 20 min at 4° C. The pellet was suspended in 50 mM Tris-HCl, 1 mM $MgCl_2$, and 0.1% ascorbic acid at pH 7.5. Binding of the α1 antagonist [$^3$H]prazosin (0.5 nM, specific activity 76.2 Ci/mmol) to membrane preparations of LM(tk-) cells was done in a final volume of 0.25 ml and incubated at 37° C. for 20 min. Nonspecific binding was determined in the presence of 10 μM phentolamine. The reaction was stopped by filtration through GF/B filters using a cell harvester. Inhibition experiments, routinely consisting of 7 concentrations of the tested compounds, were analyzed using a non-linear regression curve-fitting computer program to obtain Ki values.

$\alpha_2$ Human Adrenergic Receptors: To determine the potency of c antagonists at the $\alpha_2$ receptors, LM(tk-) cell lines stably transfected with the genes encoding the $\alpha_{2A}$, $\alpha_{2B}$, and $\alpha_{2C}$ C receptors were used. The cell line expressing the $\alpha_{2A}$ receptor is designated L-$\alpha_{2A}$, and was deposited on Nov. 6, 1992 under ATCC Accession No. CRL 11180. The cell line expressing the $\alpha_{2B}$ receptor is designated L-NGC-$\alpha_{2B}$, and was deposited on October 25, 1989 under ATCC Accession No. CRL10275. The cell line expressing the $\alpha_{2C}$ receptor is designated L-$\alpha_{2C}$, and was deposited on Nov. 6, 1992 under ATCC Accession No. CRL-11181. Cell lysates were prepared as described above (see Radioligand Binding Assays), and suspended in 25 mM glycylglycine buffer (pH 7.6 at room temperature). Equilibrium competition binding assay were performed using [3H]rauwolscine (0.5 nM), and non-specific binding was determined by incubation with 10 $\mu$M phentolamine. The bound radioligand was separated by filtration through GF/B filters using a cell harvester.

Determination of the Activity of $\alpha_1$ Antagonists at Calcium Channels

The potency of $\alpha_1$ antagonists at calcium channels was determined in competition binding assays of [3H] nitrendipine to membrane fragments of rat cardiac muscle, essentially as described by Glossman and Ferry (Methods in Enzymology 109:513–550, 1985). Briefly, the tissue was minced and homogenized in 50 mM Tris-HCl (pH 7.4) containing 0.1 mM phenylmethylsulfonyl fluoride. The homogenates were centrifuged at 1000 g for 15 minutes, the resulting supernatant was centrifuged at 45,000 g for 15 minutes. The 45,000 g pellet was suspended in buffer and centrifuged a second time. Aliquots of membrane protein were incubated for 30 minutes at 37° C. in the presence of [3H]nitrendipine (1 nM), and nonspecific binding was determined in the presence of 10 $\mu$M nifedipine. The bound radioligand was separated by filtration through GF/B filters using a cell harvester.

The compounds described above were assayed using cloned human alpha adrenergic receptors and the rat calcium channel. The preferred compounds were found to be selective $\alpha_{1C}$ antagonists. The binding affinities of compounds 19–23 are illustrated in the following table. Binding affinities of compounds 19–23 at cloned human $\alpha$1a, $\alpha$1b and $\alpha$1c receptors.

| Example | h$\alpha$1a | | | h$\alpha$1b | | | h$\alpha$1c | | |
| --- | --- | --- | --- | --- | --- | --- | --- | --- | --- |
| | pKi | SEM | n | pKi | SEM | n | pKi | SEM | n |
| 19 | 6.14 | 0.02 | 3 | 6.21 | 0.09 | 3 | 9.74 | 0.02 | 3 |
| 20 | 6.46 | 0.04 | 3 | 6.59 | 0.08 | 3 | 9.68 | 0.05 | 3 |
| 21 | 6.01 | 0.03 | 3 | 6.33 | 0.06 | 3 | 9.41 | 0.09 | 3 |
| 22 | 6.24 | 0.06 | 3 | 6.37 | 0.06 | 3 | 9.54 | 0.09 | 3 |
| 23 | 6.17 | 0.04 | 4 | 6.32 | 0.06 | 4 | 8.99 | 0.12 | 4 | h = human

Scheme 1
General synthetic schemes for the synthesis of the piperidine sidechains.

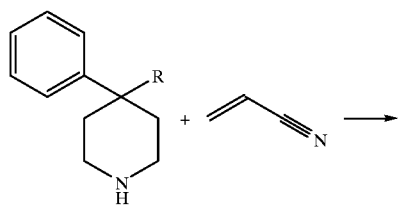

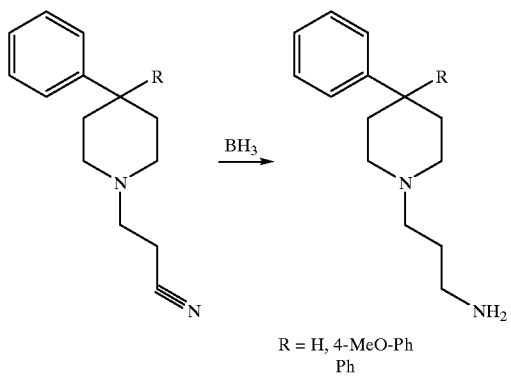

R = H, 4-MeO-Ph
Ph

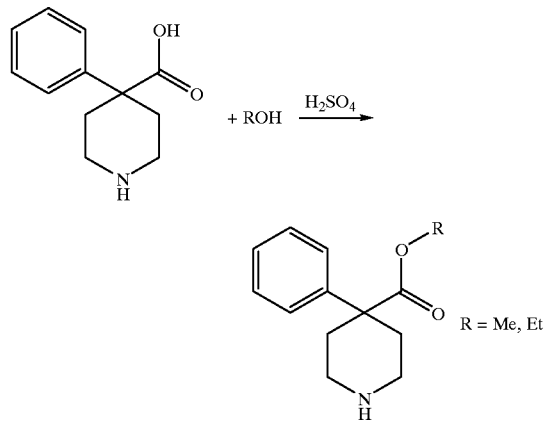

R = Me, Et

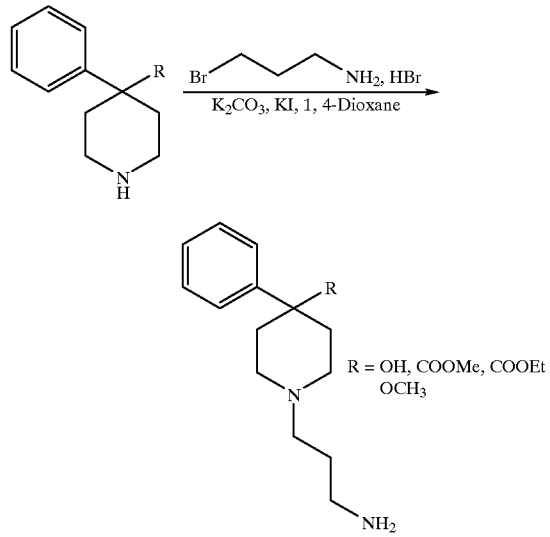

R = OH, COOMe, COOEt
OCH$_3$

Scheme 1 (continued)
General synthetic scheme for examples 1–17.

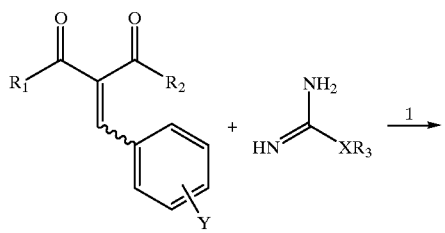

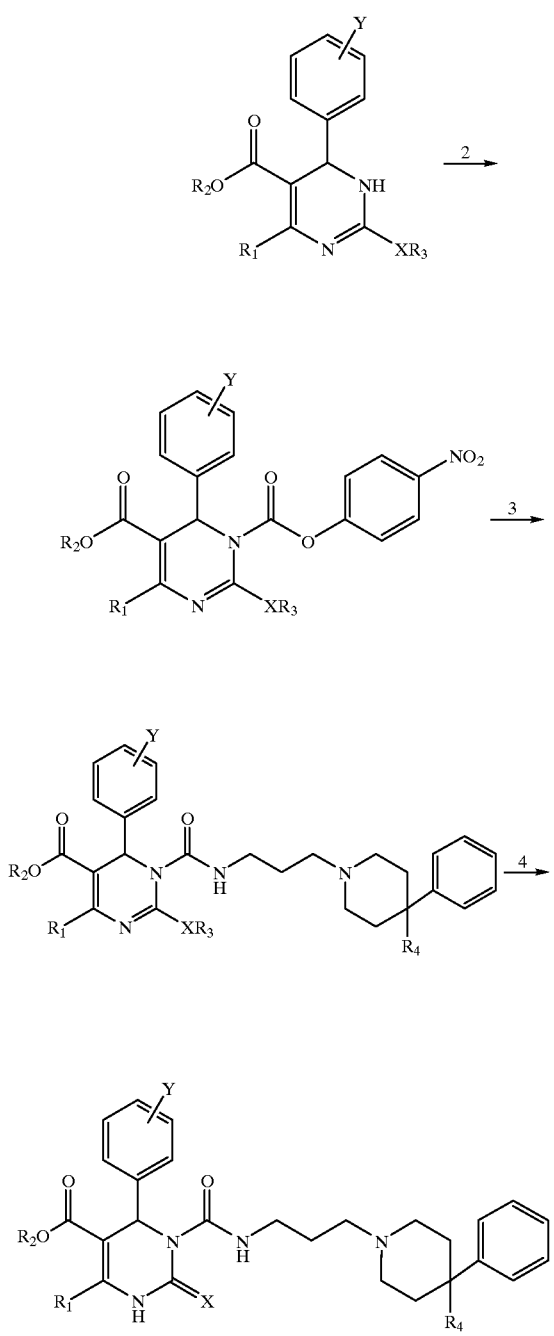
1. NaOAc, DMF.
2. 4-Nitrophenyl chloroformate, NaHCO$_3$, CH$_2$Cl$_2$, H$_2$O.
3.
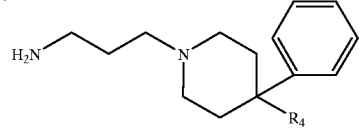
4. HCl/THF or EtSH/TFA.
Scheme 2
Synthetic scheme for example 14.
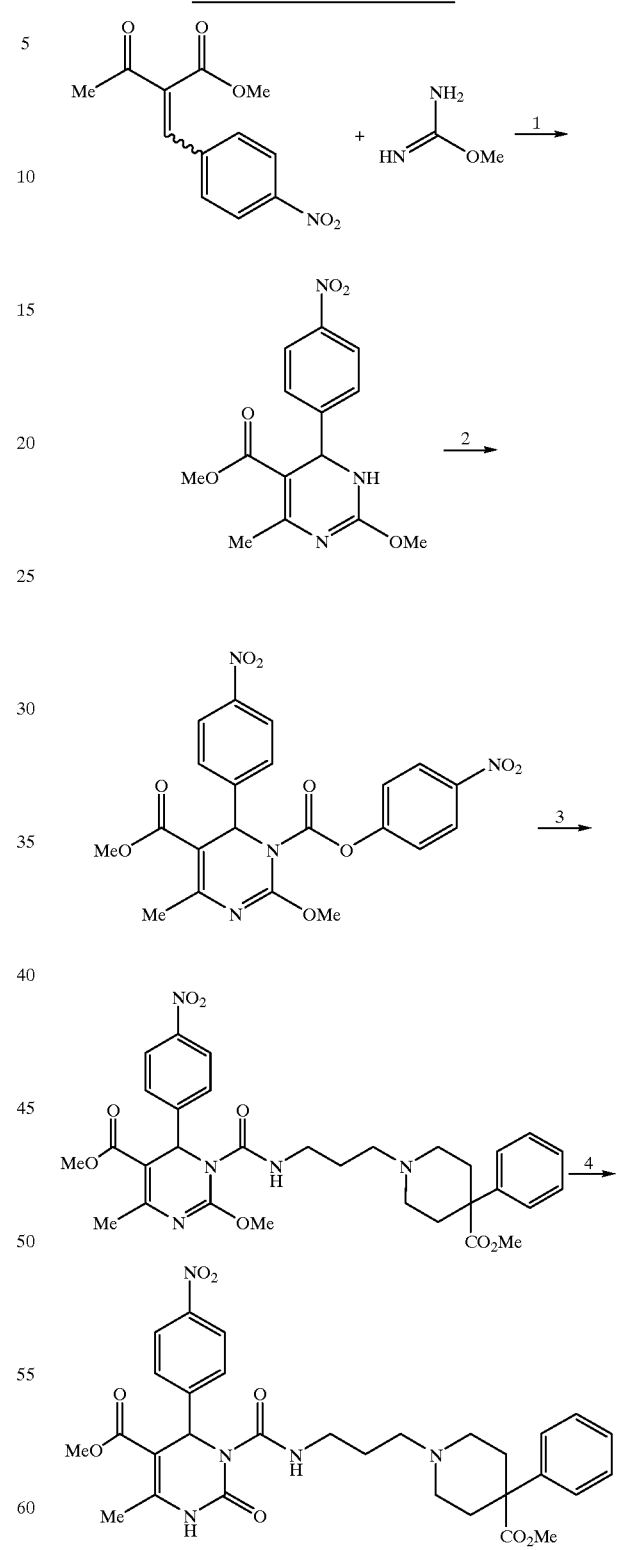
1. NaOAc, DMF.
2. 4-Nitrophenyl chloroformate, NaHCO$_3$, CH$_2$Cl$_2$, H$_2$O.
3. 3 [(4-Methoxycarbonyl-4-phenyl) piperidine-1-yl] propylamine, THF.
4. 6N HCl/THF.

Scheme 3
Synthetic scheme for examples 14a and 14b.
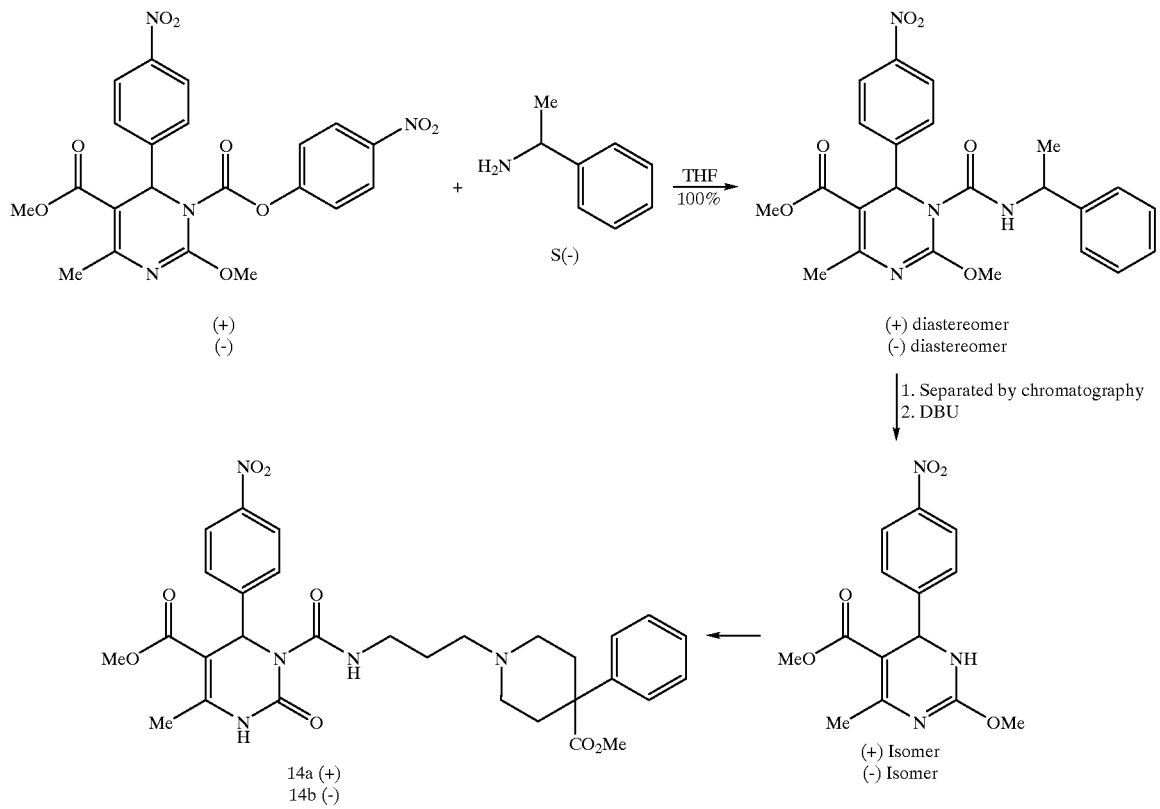
Scheme 4
Synthetic scheme for example 19.
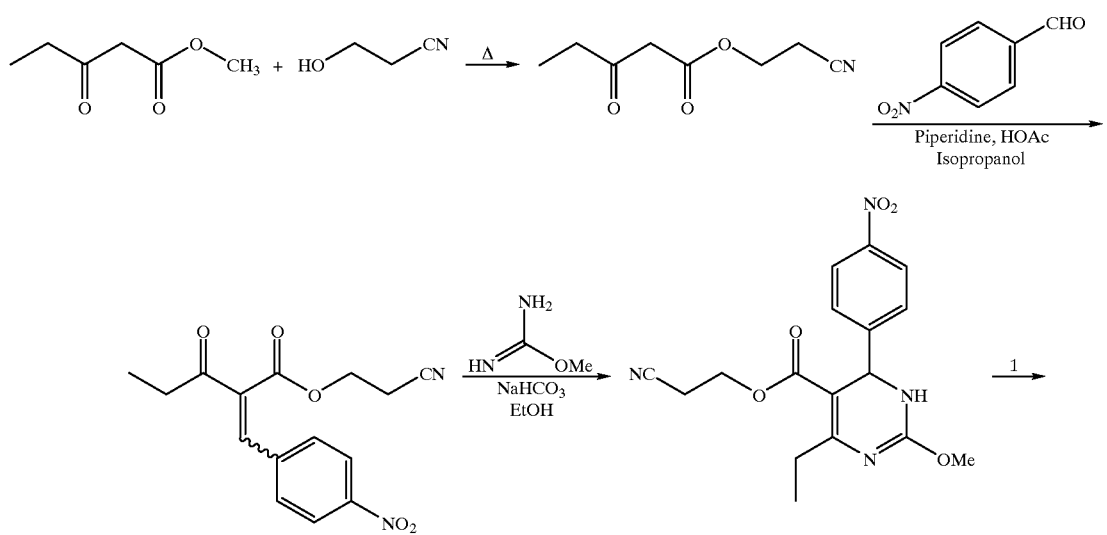

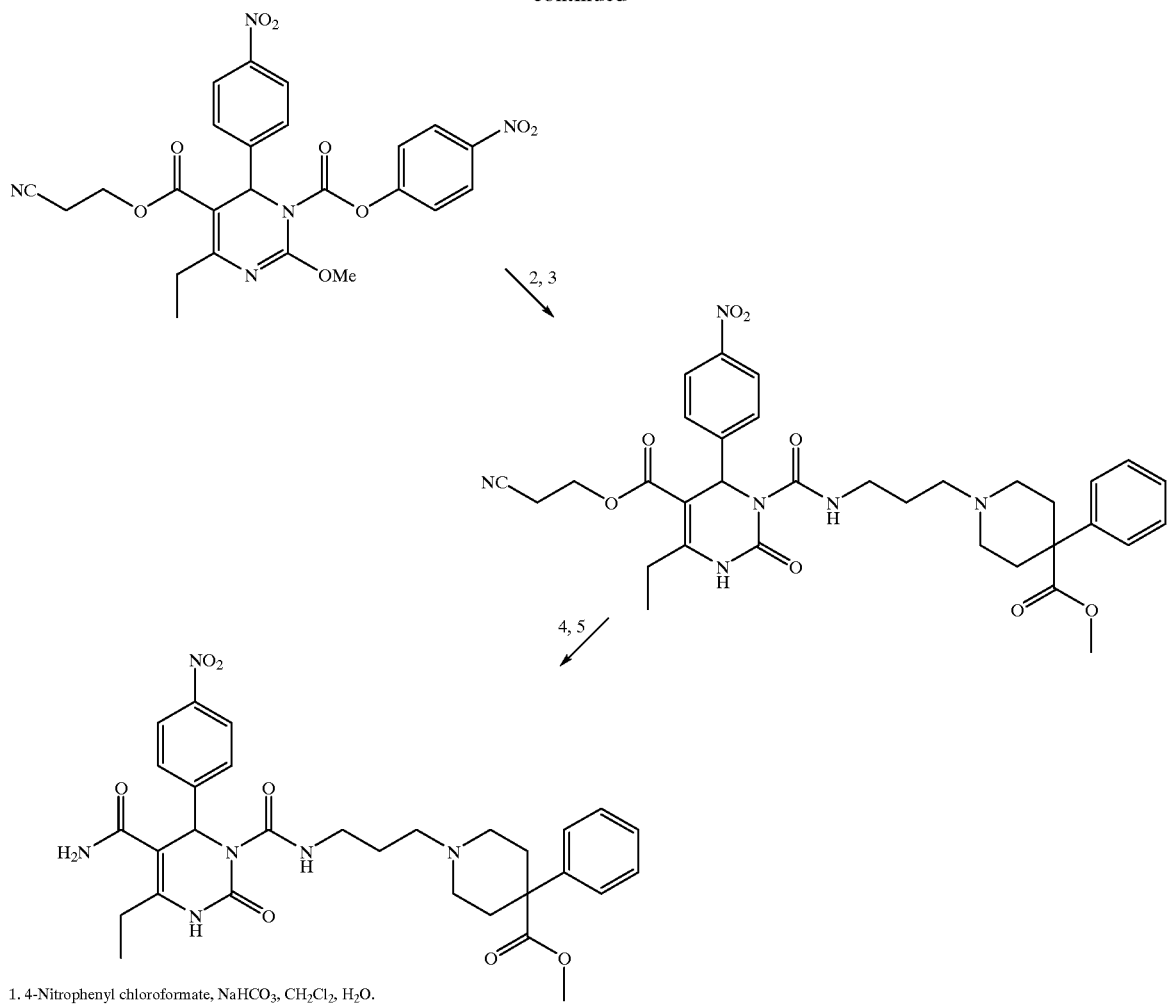
1. 4-Nitrophenyl chloroformate, NaHCO₃, CH₂Cl₂, H₂O.
2. 3-[(4-Methoxycarbonyl-4-phenyl) piperidin-1-yl] propylamine.
3. 6N HCl.
4. NaOH, Acetone.
5. DMAPECD, DMAP, NH₃, CH₂Cl₂.
Scheme 5
Synthetic scheme for example 20.
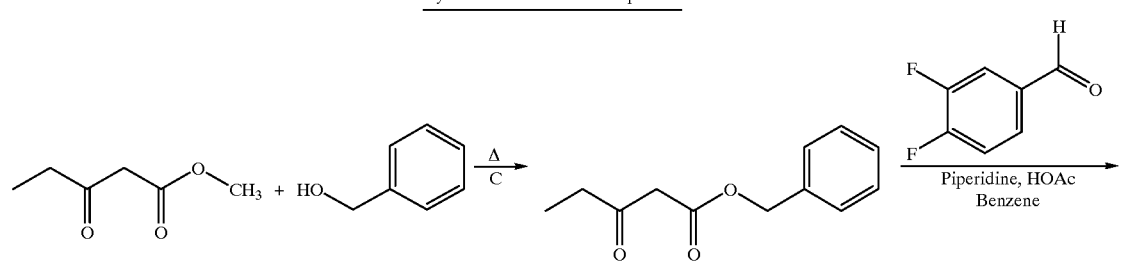

91 92
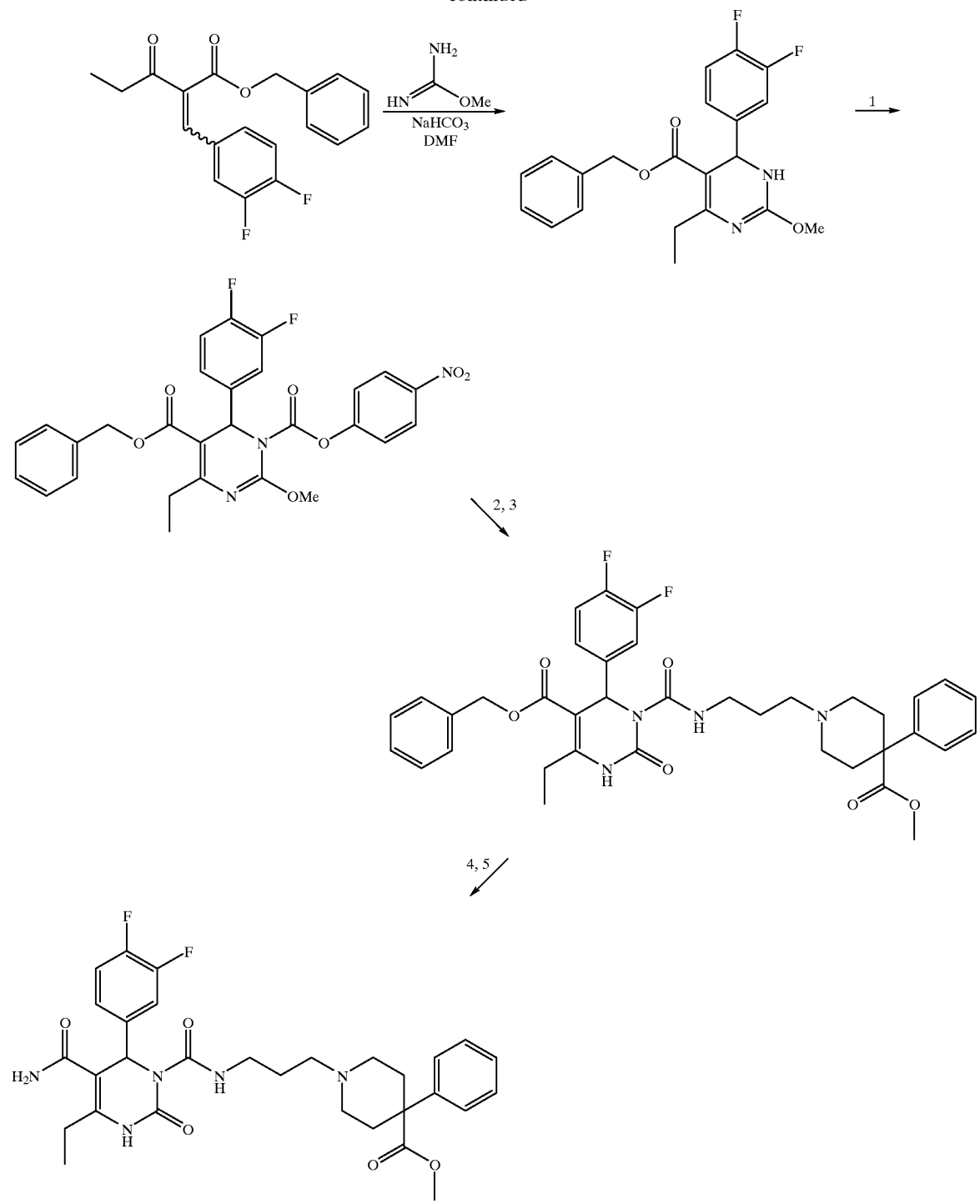
1. 4-Nitrophenyl chloroformate, DMAP, THF
2. 3-[(4-Methoxycarbonyl-4-phenyl)piperidin-1-yl]propylamine.
3. 6N HCl.
4. H₂, Pd—C, MeOH.
5. DMAPECD, DMAP, NH₄OH, CH₂Cl₂.

Scheme 6
Synthetic scheme for the preparation of 3-[4-(2-Pyridyl)-piperidin-1-yl]propylamine (Example 21 part d).
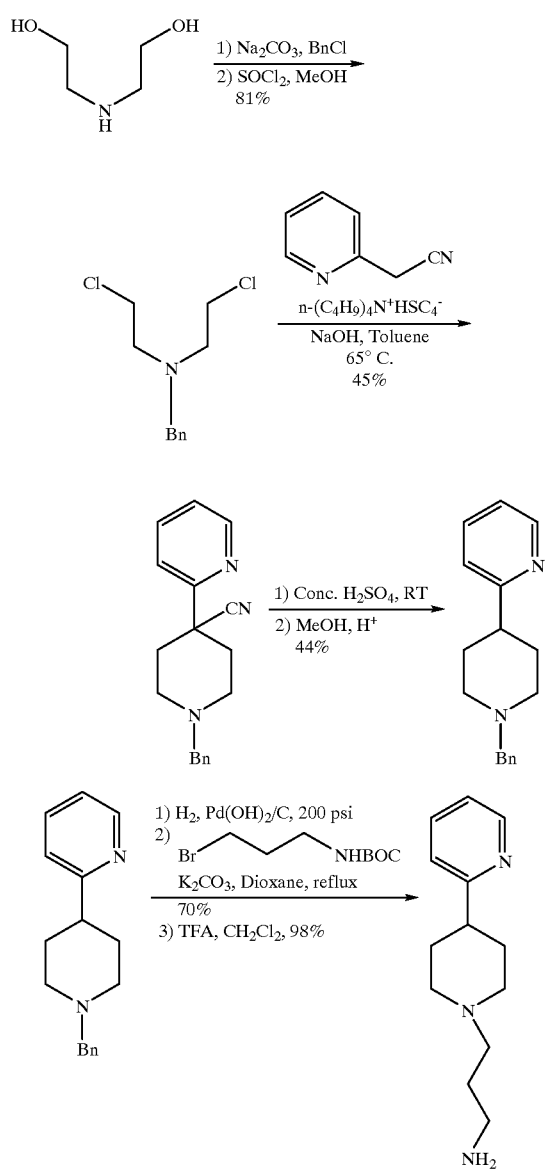
Scheme 7
Synthetic scheme for example 21.
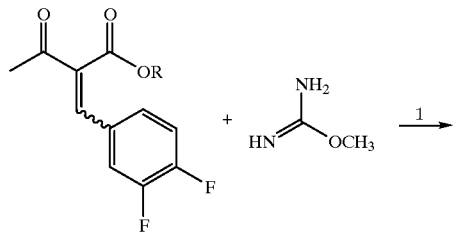
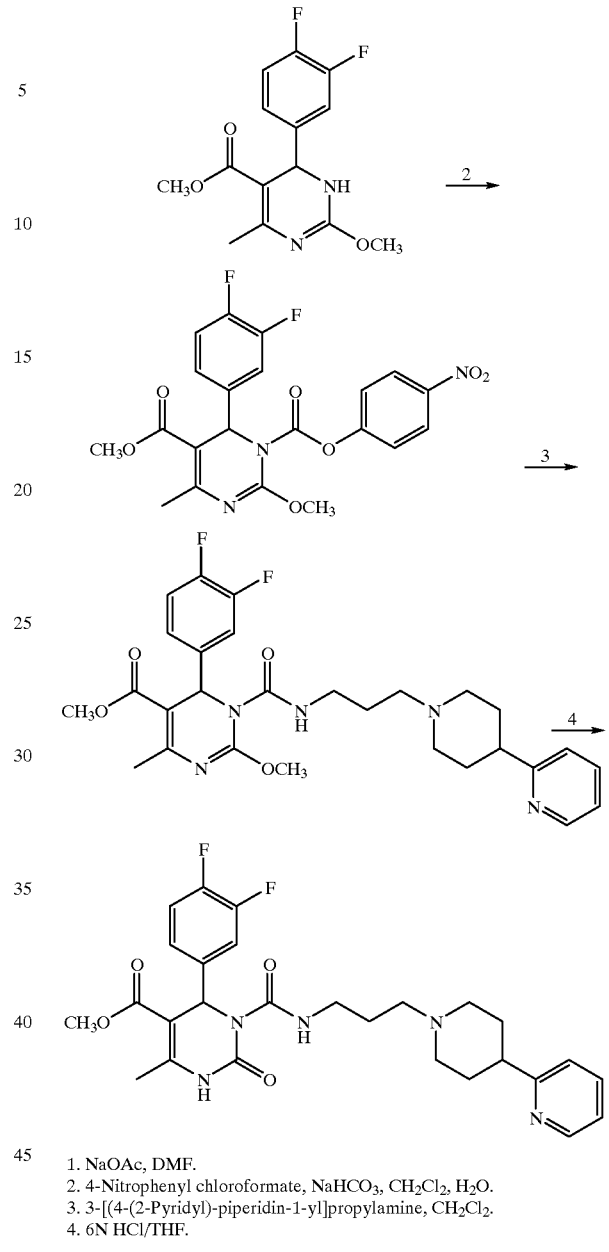
1. NaOAc, DMF.
2. 4-Nitrophenyl chloroformate, NaHCO$_3$, CH$_2$Cl$_2$, H$_2$O.
3. 3-[(4-(2-Pyridyl)-piperidin-1-yl]propylamine, CH$_2$Cl$_2$.
4. 6N HCl/THF.
Scheme 8
Synthetic scheme for example 22.
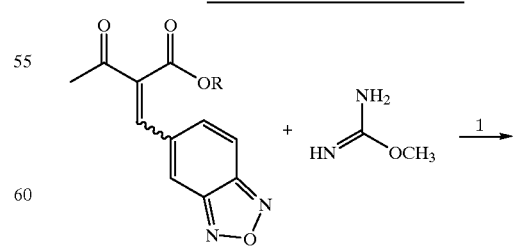

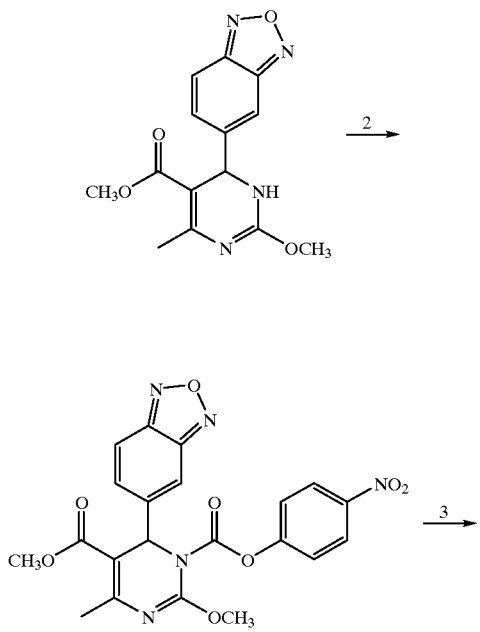
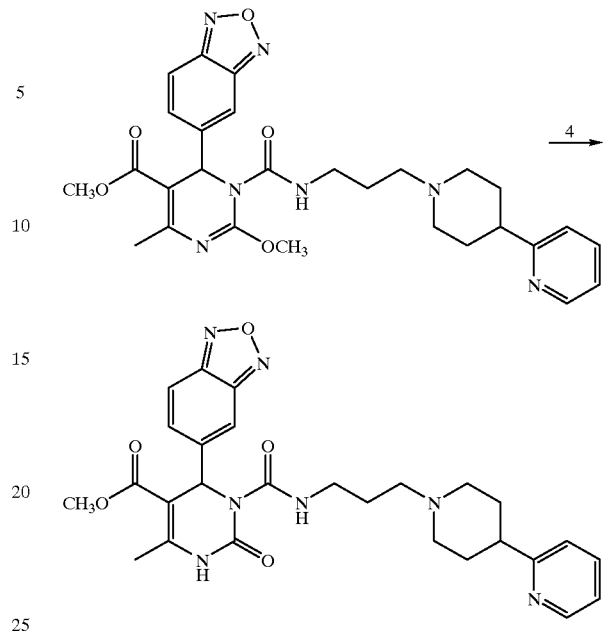
1. NaOAc, DMF.
2. 4-Nitrophenyl chloroformate, NaHCO₃, CH₂Cl₂, H₂O.
3. 3-[(4-(2-Pyridyl)-piperidin-1-yl]propylamine, CH₂Cl₂.
4. 6N HCl/THF.
Scheme 9
Synthetic scheme for example 23.
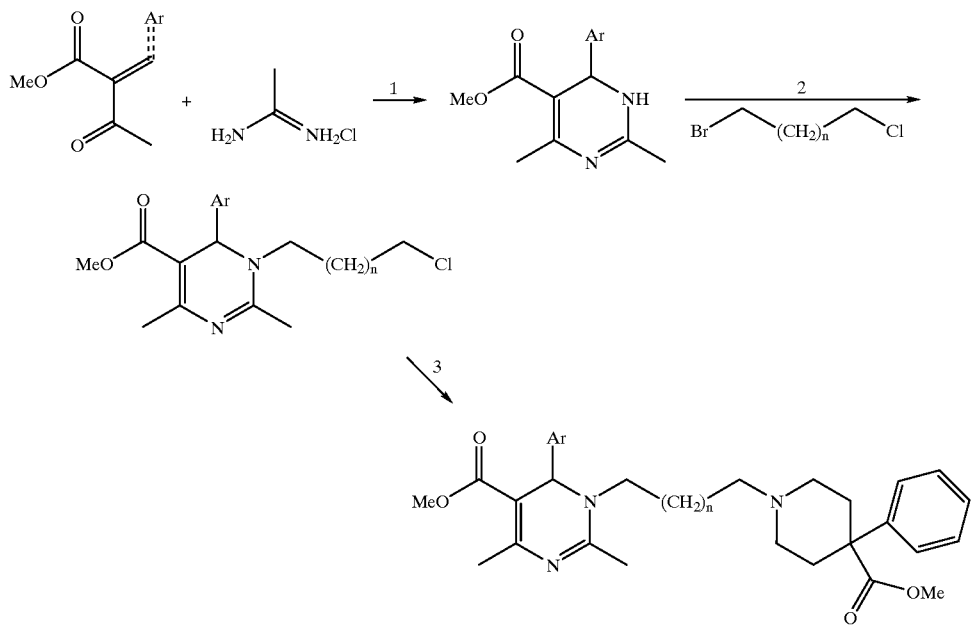
1. (a) t-BuOK, DMF, 0° C.; (b) TsOH•H₂O, DMF, 100–120° C.
2. NaH, THF, reflux.
3. 4-Methoxycarbonyl-4-phenylpiperidine, K₂CO₃, NaI, 1,4-dioxane, reflux.

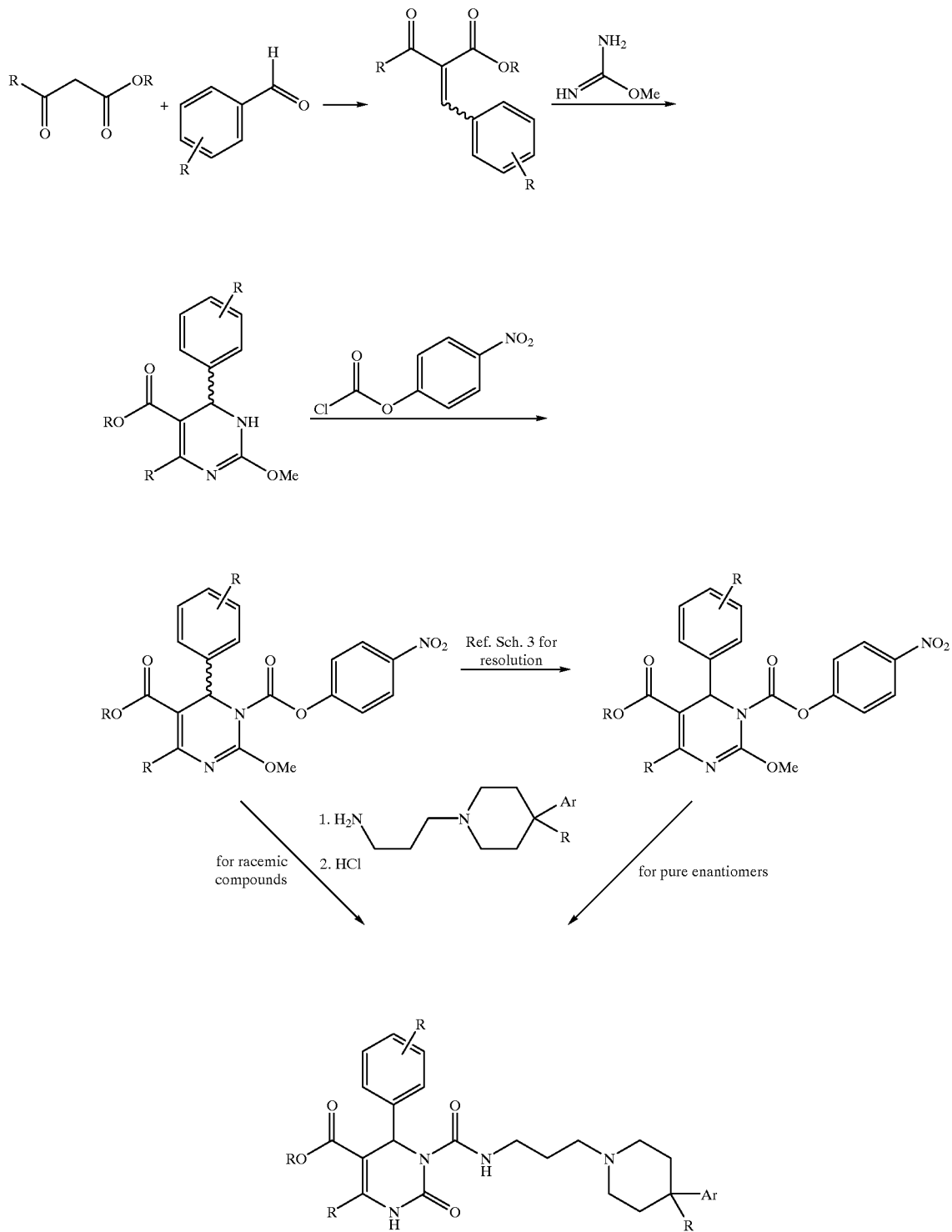

Scheme 11
Preparation of example 35.
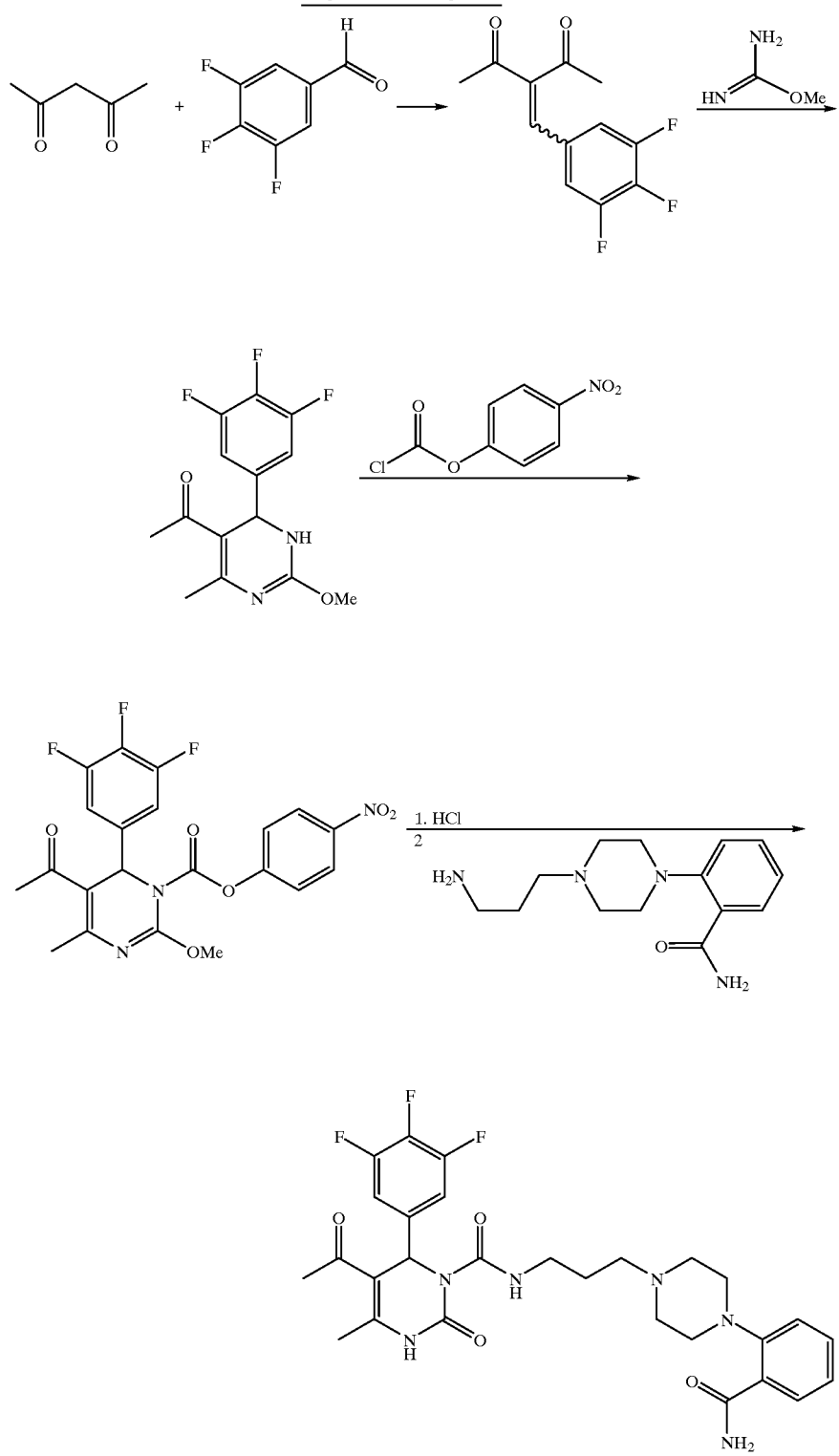

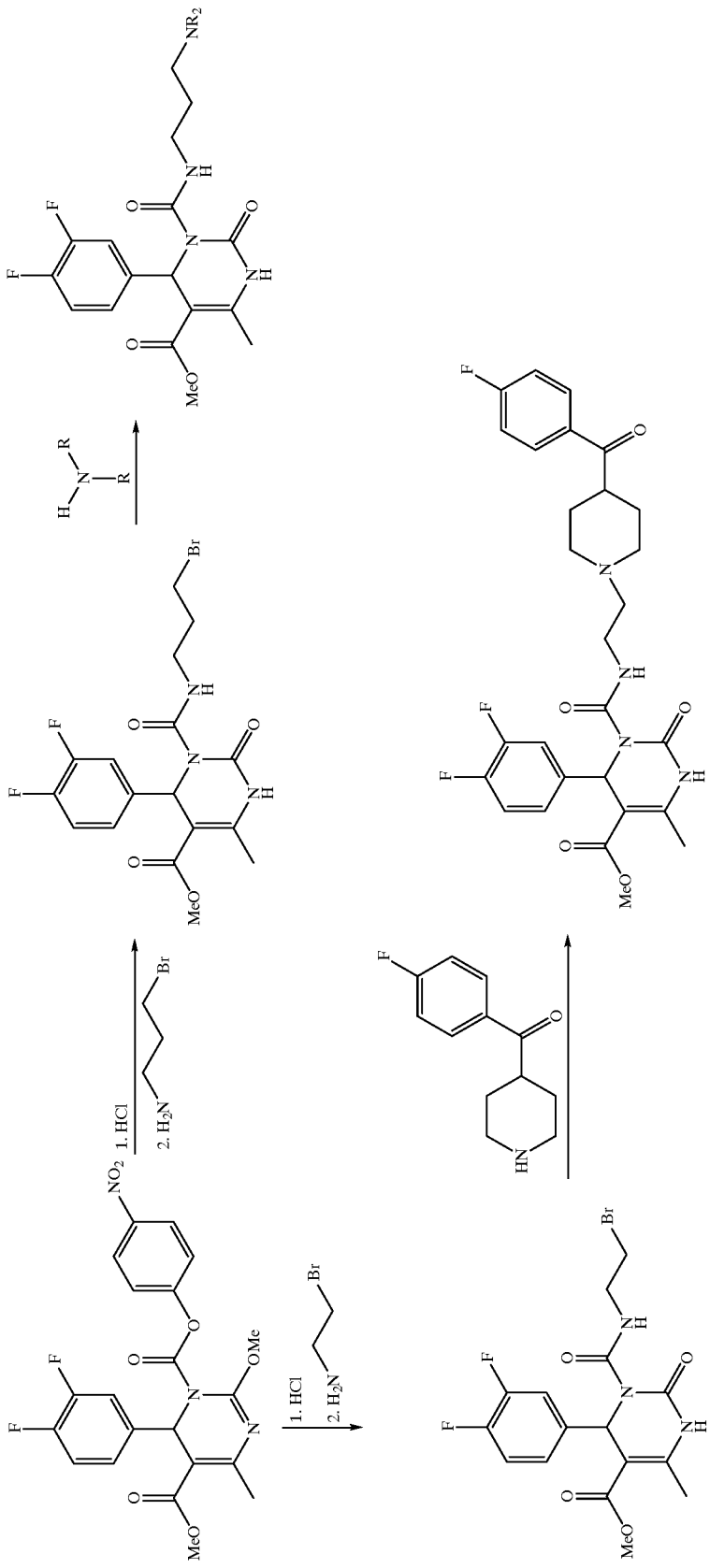

Scheme 13
Preparation of example 43 part-1
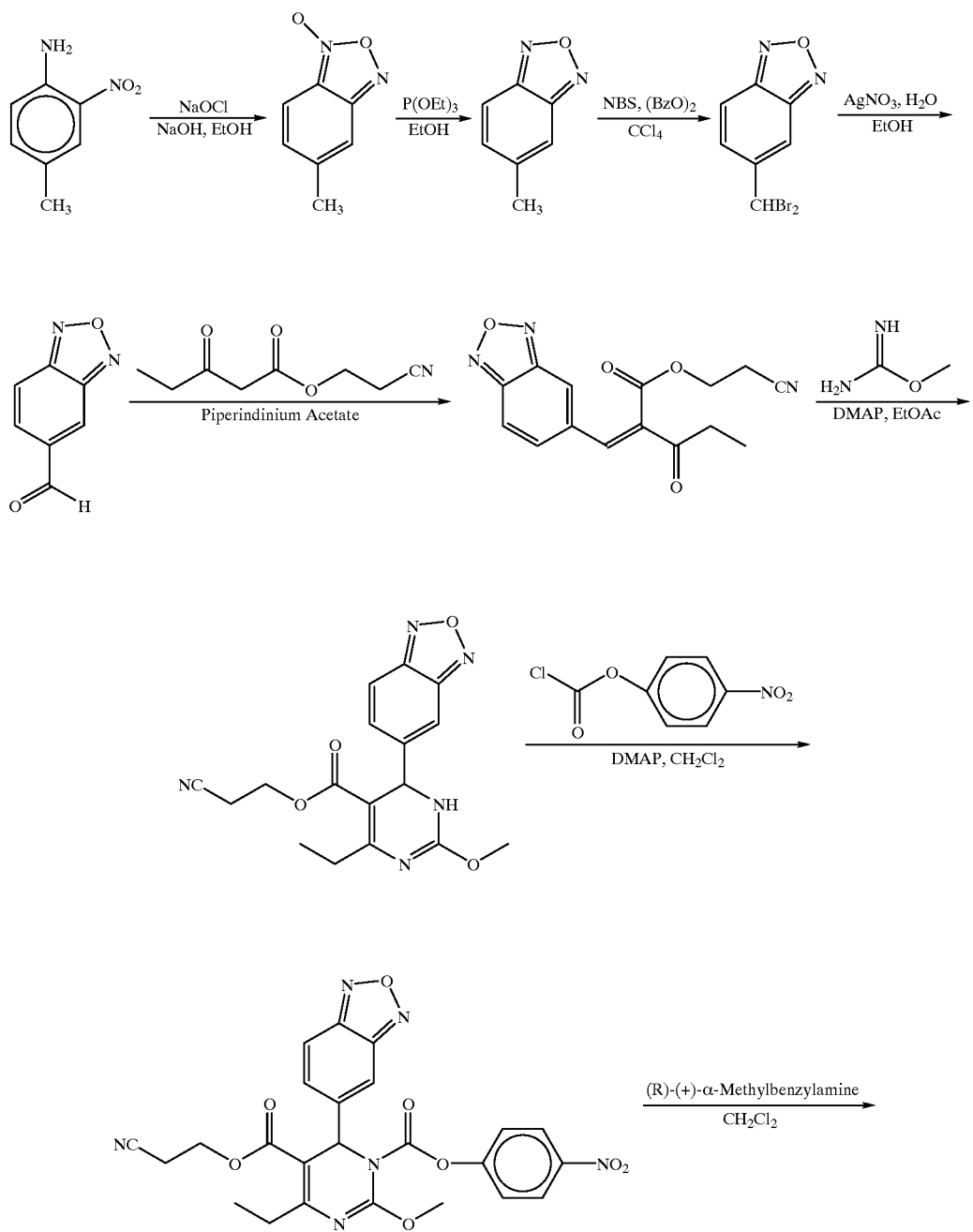

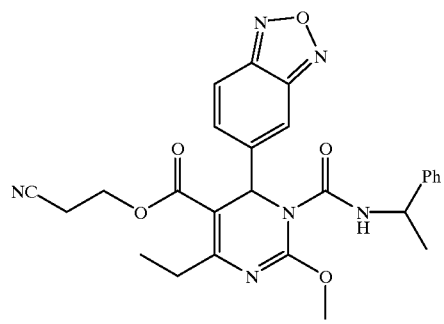
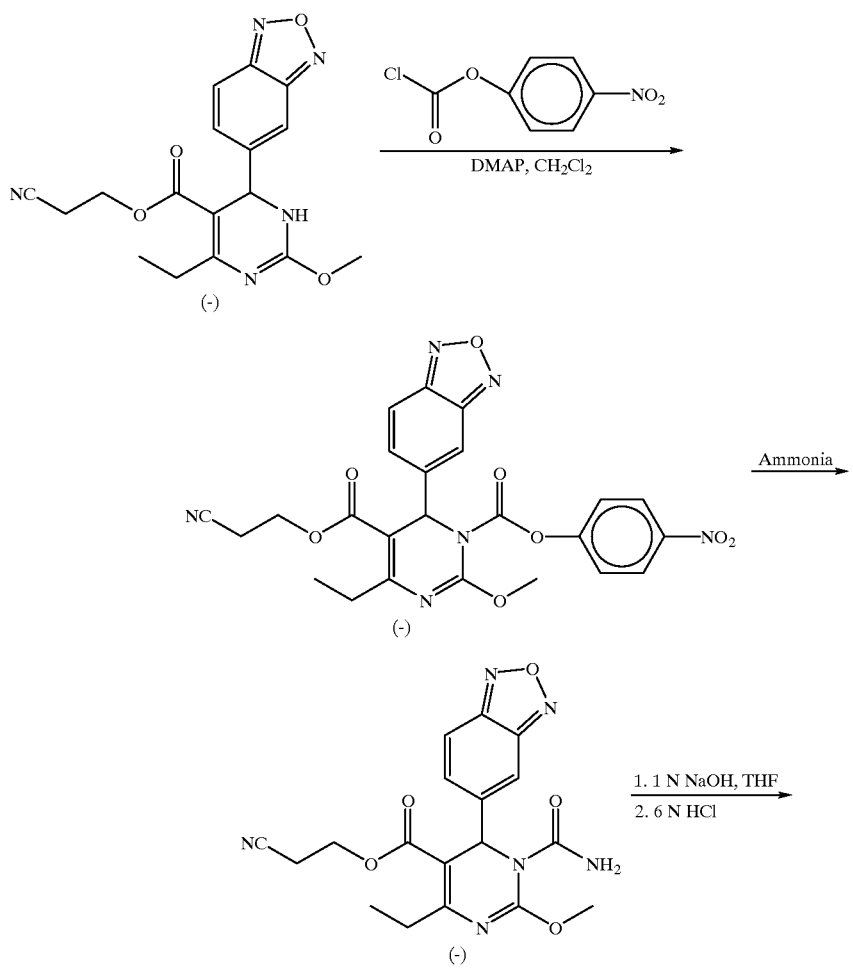
Scheme 13 (continued)
Preparation of example 43 part-2

-continued
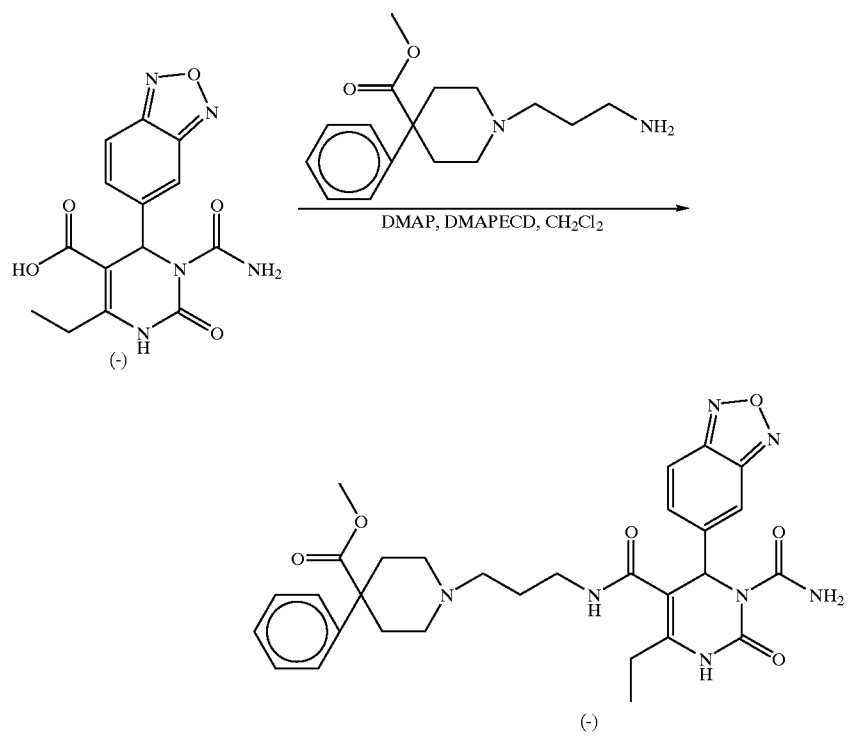
Scheme 14
Preparation of example 28 (part-1)
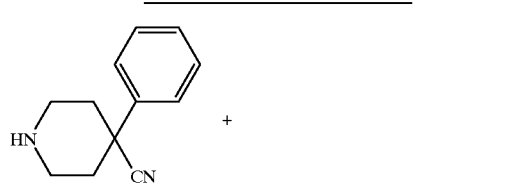
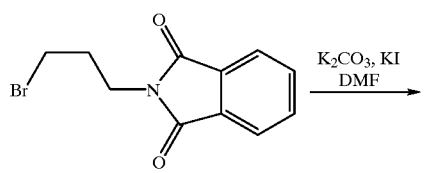
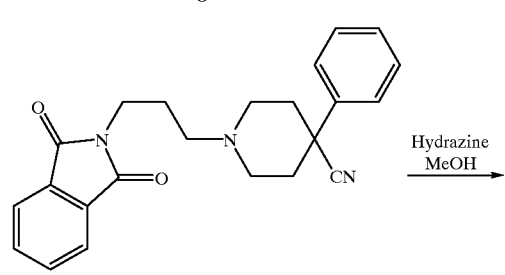
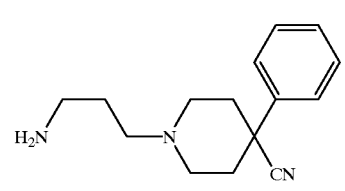
Scheme 14 (cont.)
Preparation of example 28 (part-2)
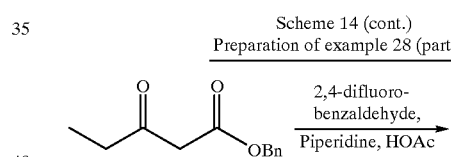
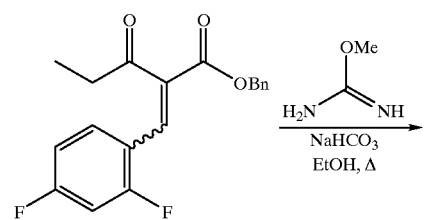
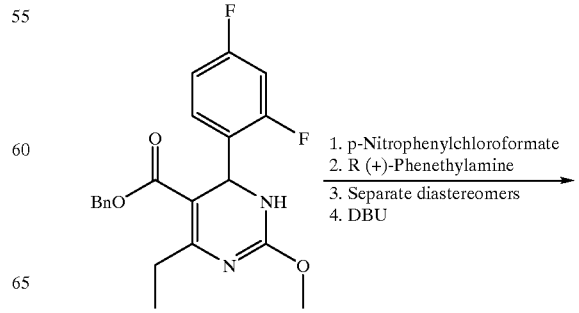

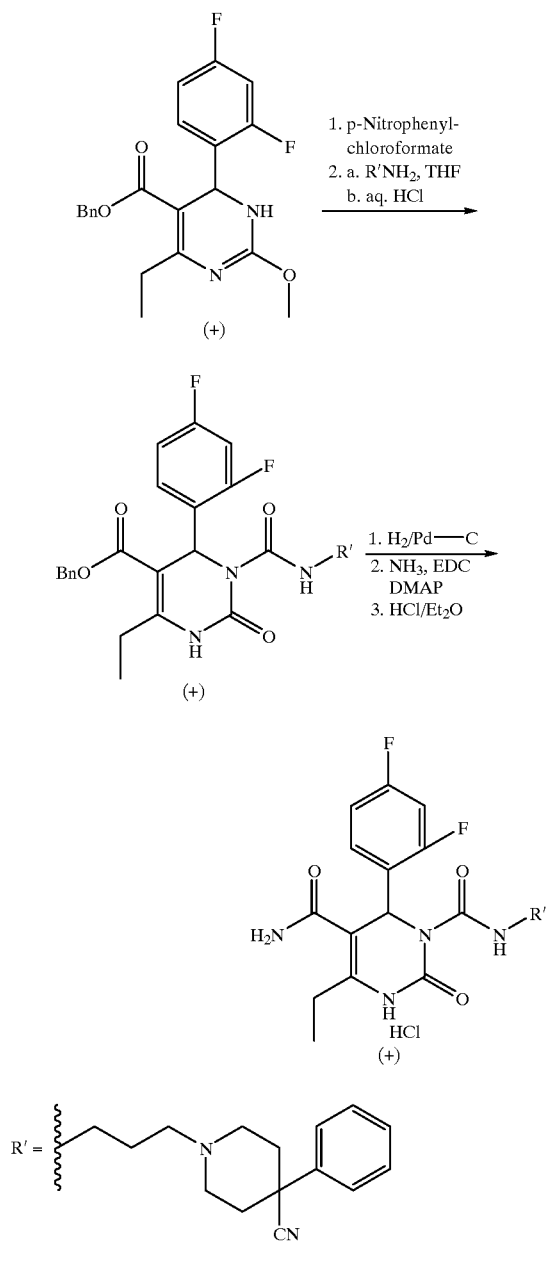
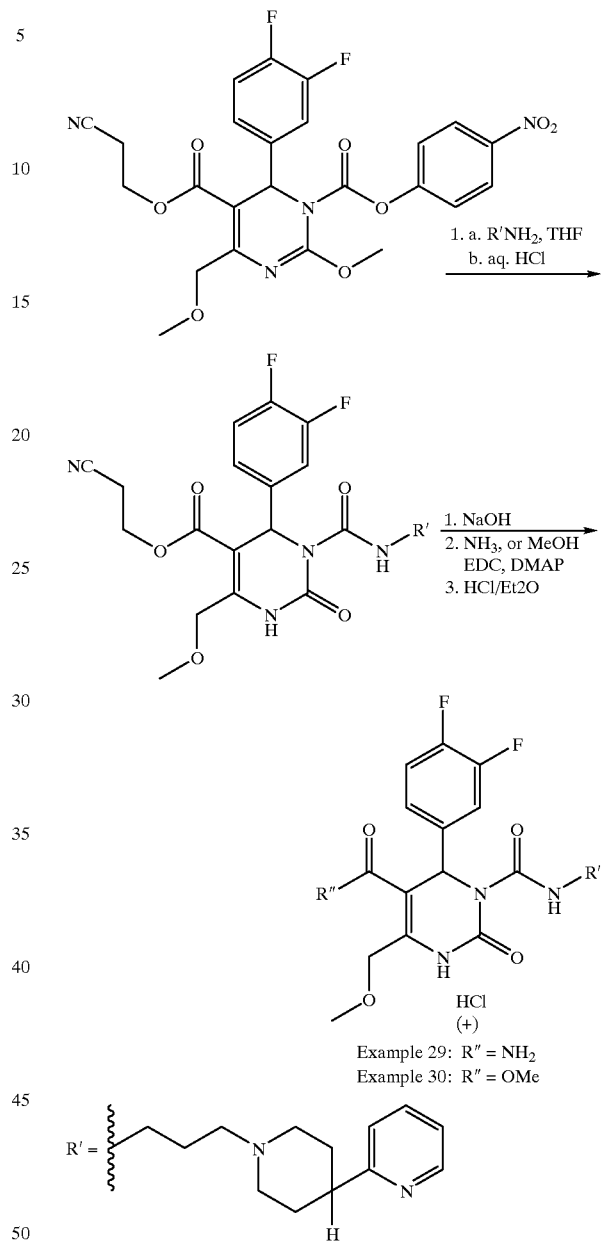
Scheme 15
Preparation of examples 29 and 30
Example 29: R″ = NH₂
Example 30: R″ = OMe
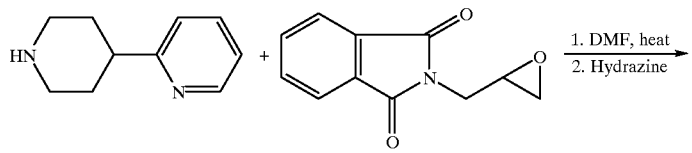
Scheme 16
Preparation of examples 25, 26, and 27
1. DMF, heat
2. Hydrazine

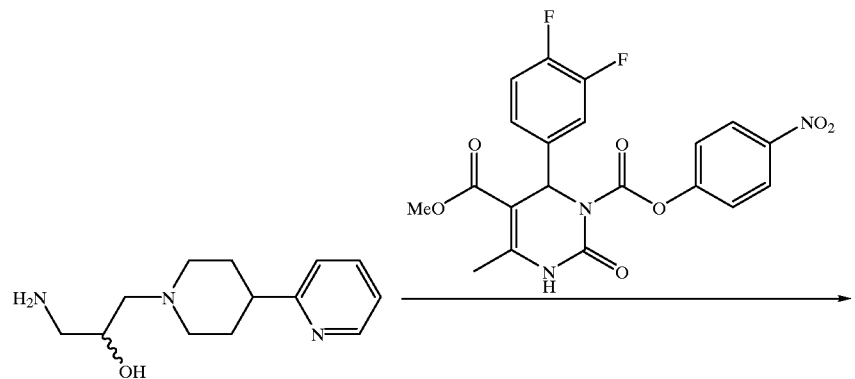
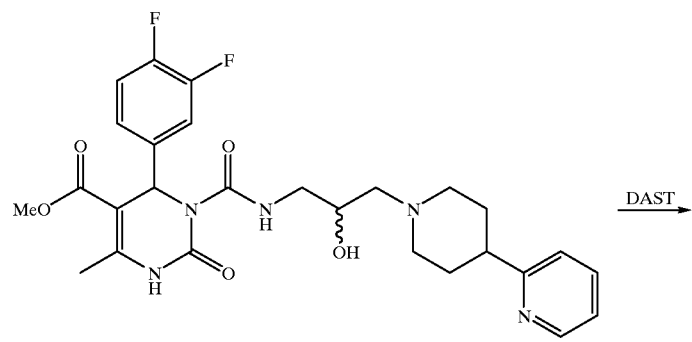
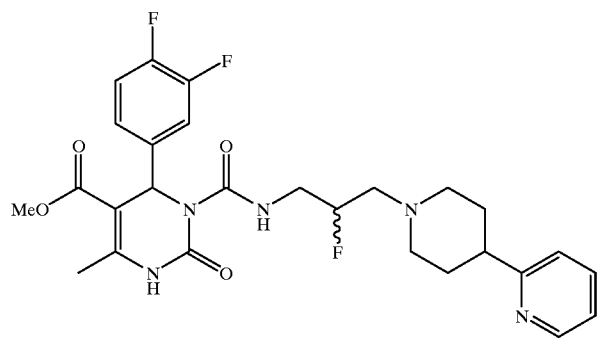

Scheme 17
Preparation of examples 31, 32, 33, and 34
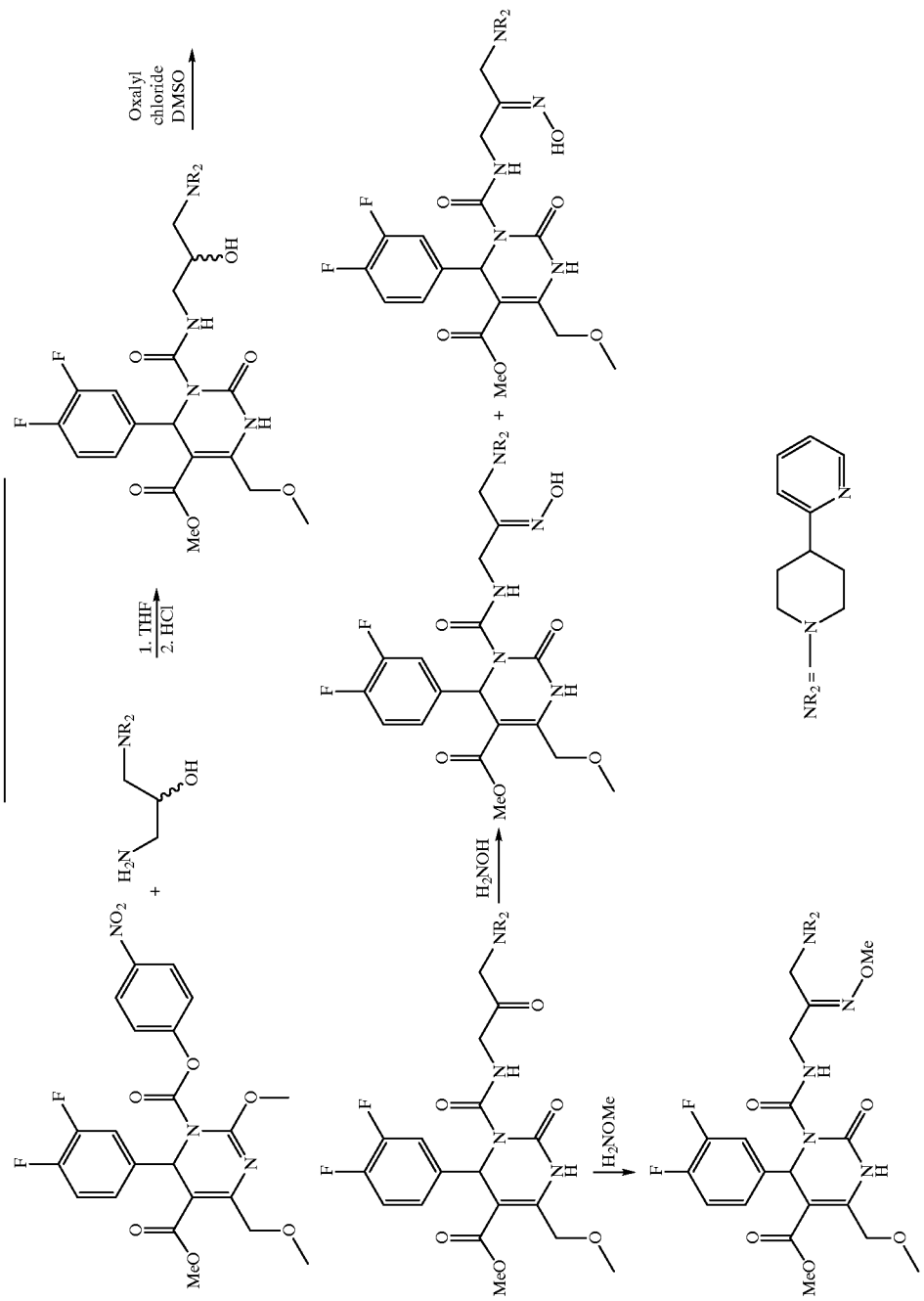

Scheme 18
Preparation of examples 39 and 40.
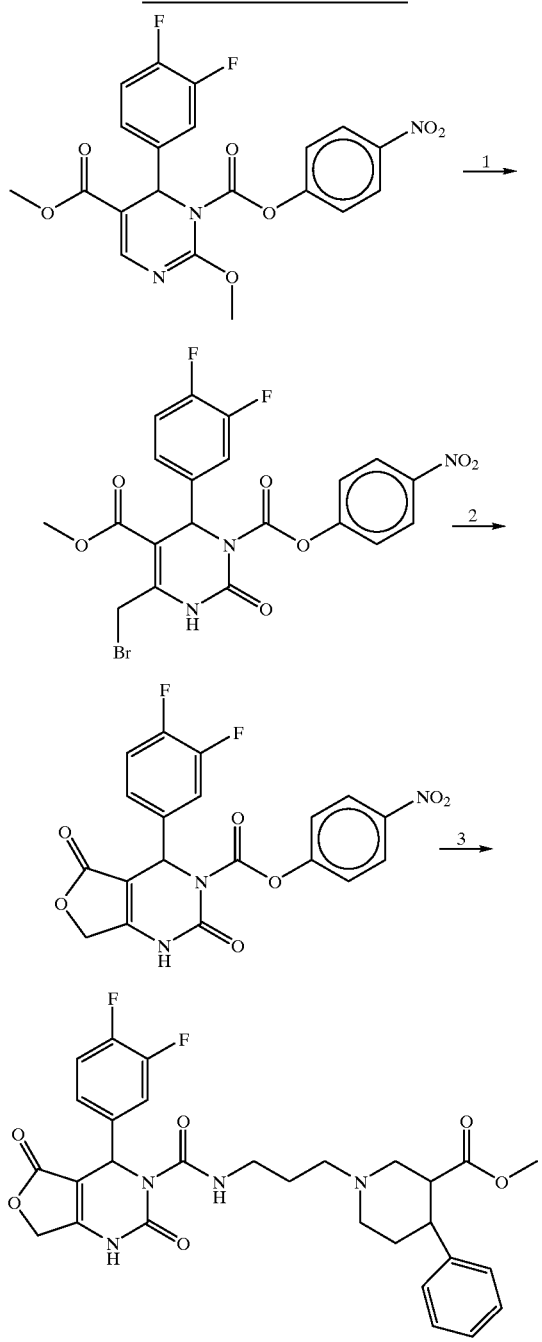
1. Br₂, CHCl₃, 0° C.
2. Neat 130° C.
3. H₂N-(propyl)-N-piperidine-4-(COOMe)(Ph)
Scheme 19
Preparation of example 38
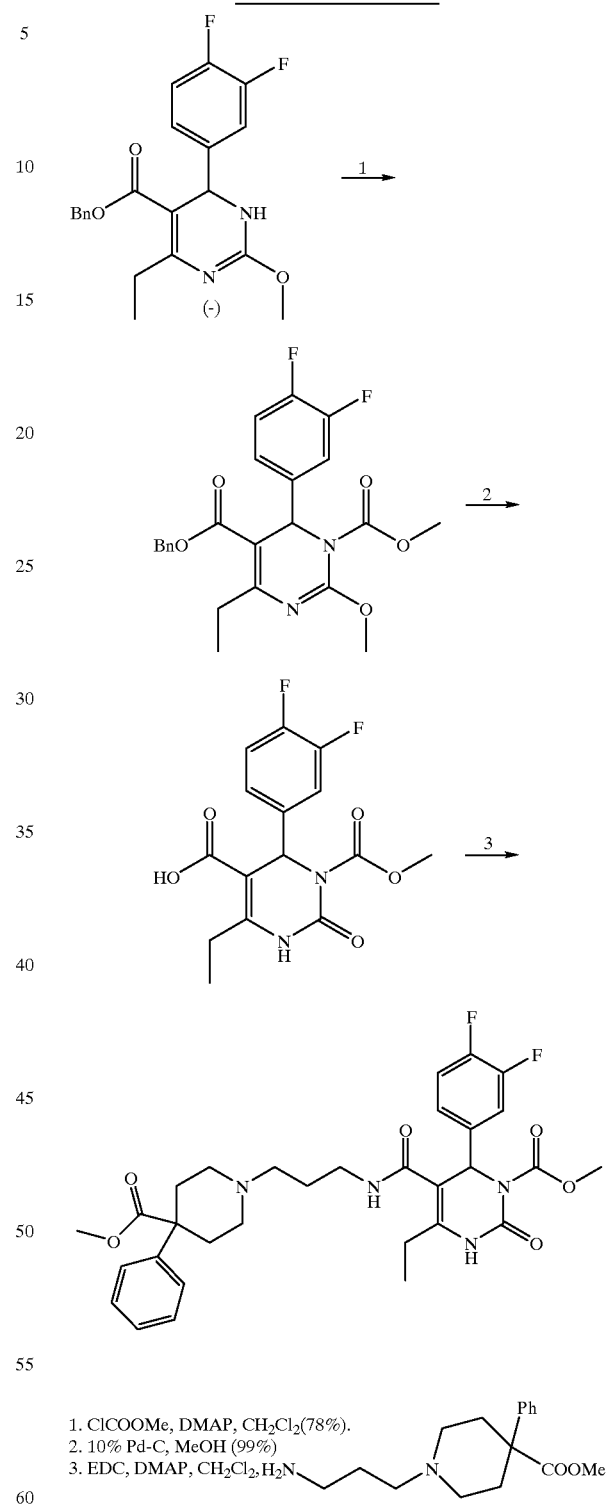
1. ClCOOMe, DMAP, CH₂Cl₂ (78%).
2. 10% Pd-C, MeOH (99%)
3. EDC, DMAP, CH₂Cl₂, H₂N-(propyl)-N-piperidine-4-(Ph)(COOMe)

Scheme 20
Preparation of examples 44 and 52.
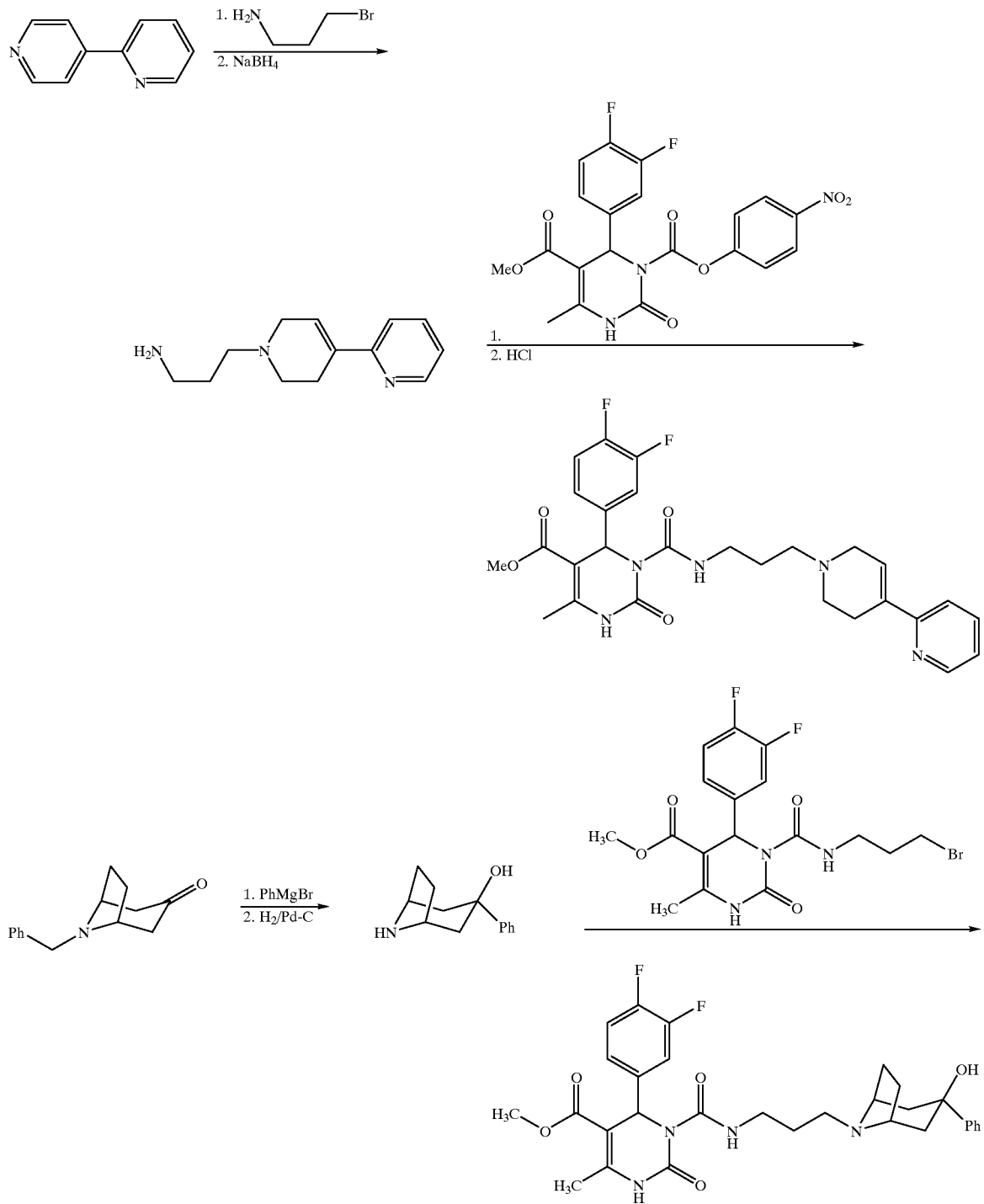

Scheme 21 (part-2)
Synthetic scheme for examples 55, 56, and 57

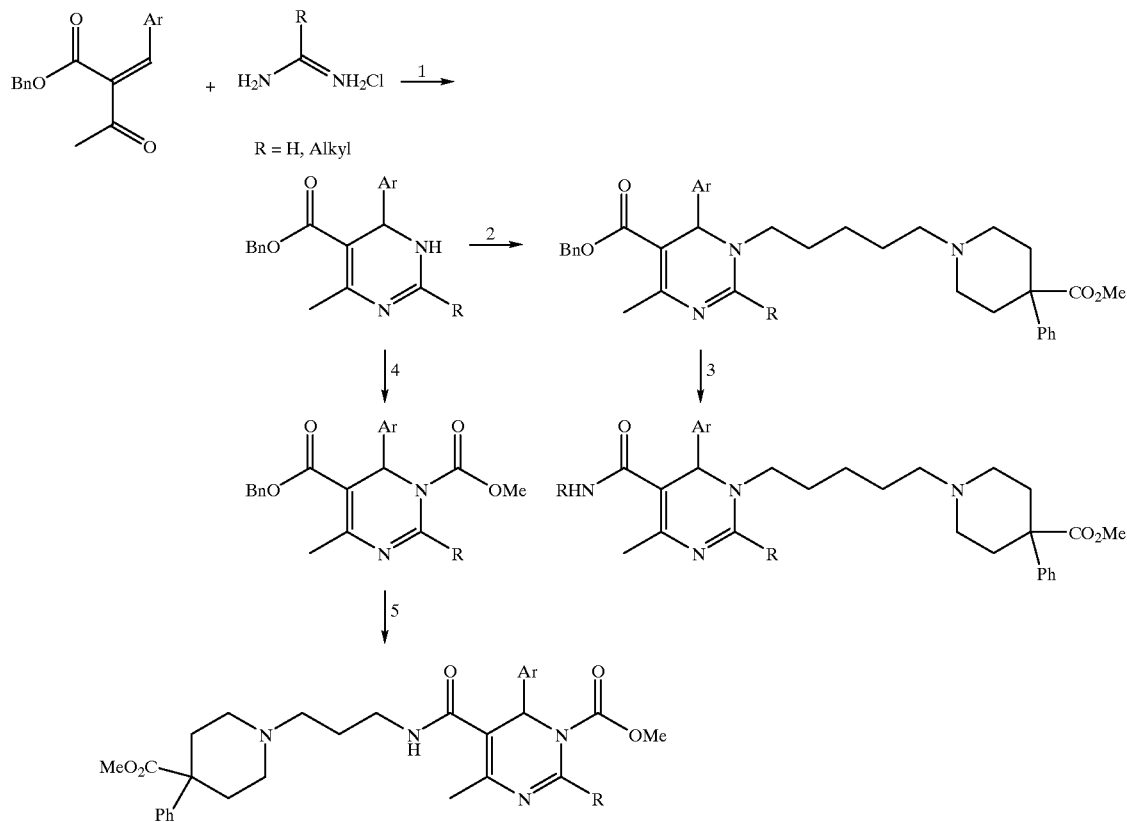

1. (a) KtBuO, DMF; (b) TsOH•H₂O, DMF, 100–110° C.
2. (a) NaH, THF, 1,5-dibromopentane; (b) 4-Methoxycarbonyl-4-phenylpiperidine, K₂CO₃, dioxane.
3. (a) H₂, Pd/C, MeOH. (b) CH₃NH₂, DMAPECD, CH₂Cl₂.
4. NaH, ClCO₂Me, THF.
5. (a) H₂, Pd/C, MeOH. (b) 3-(4-Methoxycarbonyl-4-phenylpiperidin-1-yl)propylamine, DMAPECD, CH₂Cl₂.

Scheme 21 (part-1)
Synthesis of (S)-(-)-2-methyl-1, 5-dibromopentane (Thurkauf et al. J. Org. Chem. 1987, 52, 5466–5467).

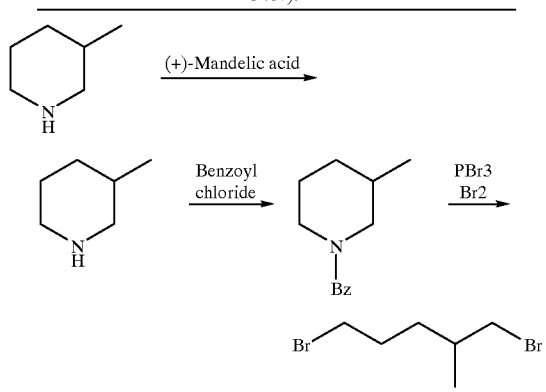

Scheme 22
Synthetic scheme for examples 62 and 63.

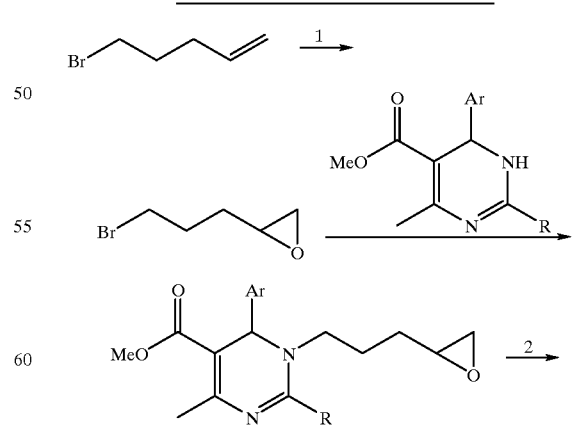

121                                                   122

-continued                                         wherein A is

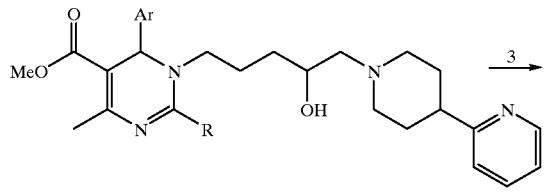

1. mCPBA, CH$_2$Cl$_2$.
2. 4-(2-Pyridyl) piperdine, dioxane.
3. Oxalyl chloride, DMSO, CH$_2$Cl$_2$.

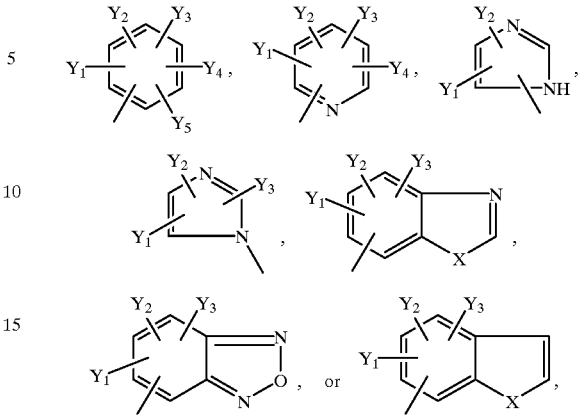

Scheme 23
Synthetic scheme for example 65

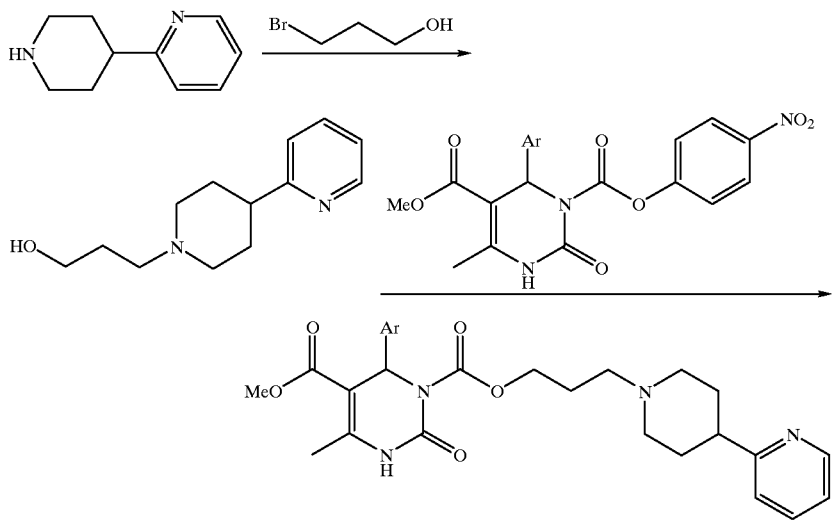

What is claimed is:
1. A compound having the structure:

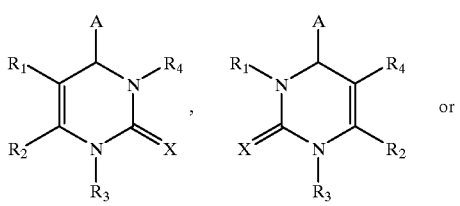

wherein each of $Y_1$, $Y_2$, $Y_3$, $Y_4$ and $Y_5$ is independently —H; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —F, —Cl, —Br, or —I; —NO$_2$; —N$_3$; —CN; —OR$_3$, —OCOR$_3$, —COR$_3$, —CONHR$_3$, —CON(R$_3$)$_2$, or —COOR$_3$; or any two of $Y_1$, $Y_2$, $Y_3$, $Y_4$ and $Y_5$ present on adjacent carbon atoms can constitute a methylenedioxy group;

wherein X is S; O; or NR$_3$;

wherein $R_1$ is —H; —NO$_2$; —CN; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —N(R$_3$)$_2$; —OR$_3$; —(CH$_2$)$_p$OR$_3$; —COR$_3$; —CO$_2$R$_3$; or —CON(R$_3$)$_2$;

wherein $R_2$ is —H; straight chained or branched $C_1$–$C_7$ alkyl, hydroxyalkyl, alkoxyalkyl, aminoalkyl, monofluoroalkyl or polyfluoroalkyl; straight chained or branched C₂–C₇ alkenyl or alkynyl; C₃–C₇ cycloalkyl, monofluorocycloalkyl, polyfluorocycloalkyl or cycloalkenyl; C₃–C₁₀ cycloalkyl-C₁–C₁₀-alkyl, C₃–C₁₀ cycloalkyl-C₁–C₁₀-monofluoroalkyl or C₃–C₁₀ cycloalkyl-C₁–C₁₀-polyfluoroalkyl; —CN; —CH₂XR₃, —CH₂X(CH₂)ₚNHR₃, —(CH₂)ₙNHR₃, —CH₂X(CH₂)ₚN(R₃)₂, —CH₂X(CH₂)ₚN₃, or —CH₂X(CH₂)ₚNHCXR₇; or —OR₃;

wherein each p is independently an integer from 1 to 7;

wherein each n is independently an integer from 0 to 5;

wherein each R₃ is independently —H; straight chained or branched C₁–C₇ alkyl, monofluoroalkyl or polyfluoroalkyl; straight chained or branched C₂–C₇ alkenyl or alkynyl; or C₃–C₇ cycloalkyl, monofluorocycloalkyl, polyfluorocycloalkyl or cycloalkenyl;

wherein R₄ is

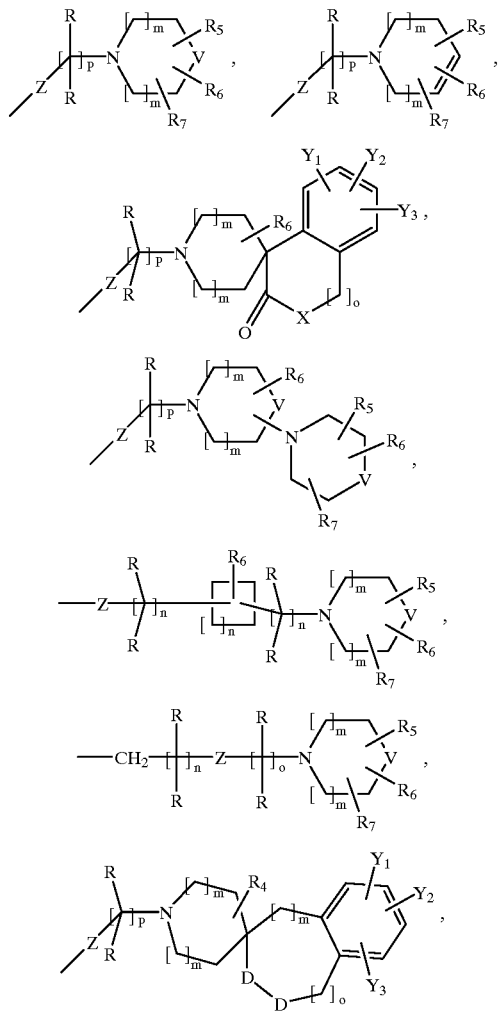

wherein R₄ in the immediately preceding structure is —H; straight chained or branched C₁–C₇ alkyl, monofluoroalkyl or polyfluoroalkyl, straight chained or branched C₂–C₇ alkenyl or alkynyl; or C₃–C₇ cycloakyl, monofluorocycloalkyl, polyfluorocycloalkyl or cycloalkenyl,

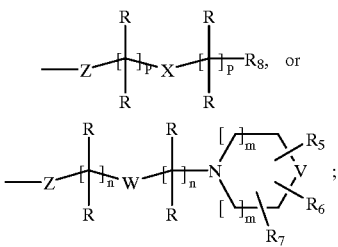

wherein Z is C₂–C₇ alkenylene or alkynylene; CH₂; O; CONR₃; S; SO; SO₂ ; or NR₃;

wherein each D is independently CH₂; O; S; NR₃; CO; or CS;

wherein W is C=O; C=NOR₃; or substituted or unsubstituted phenyl, pyridyl, thiophenyl, furanyl, pyrazinyl, pyrrolyl, naphthyl, indolyl, imidazolyl, benzofurazanyl, benzofuranyl or benzimidazolyl, wherein the phenyl, pyridyl, thiophenyl, furanyl, pyrazinyl, pyrrolyl, naphthyl, indolyl, imidazolyl, benzofurazanyl, benzofuranyl or benzimidazolyl is substituted with —H, —F, —Cl, —Br, —I, —NO₂, —CN, straight chained or branched C₁–C₇ alkyl, straight chained or branched C₁–C₇ monofluoroalkyl, straight chained or branched C₁–C₇ polyfluoroalkyl, straight chained or branched C₂–C₇ alkenyl, straight chained or branched C₂–C₇ alkynyl, C₃–C₇ cycloalkyl, C₃–C₇ monofluorocycloalkyl, C₃–C₇ polyfluorocycloalkyl, C₃–C₇ cycloalkenyl, —N(R₃)₂, —OR₃, —COR₃, —CO₂R₃, or —CON(R₃)₂;

wherein each V is independently O; S; CR₅R₇; C(R₇)₂; or NR₇;

wherein each m is independently an integer from 0 to 3;

wherein o is an integer from 1 to 3;

wherein each R is independently —H; —F; straight chained or branched C₁–C₇ alkyl, monofluoroalkyl or polyfluoroalkyl; straight chained or branched C₂–C₇ alkenyl or alkynyl; —N(R₃)₂; —NO₂; —CN; —CO₂R₃; or —OR₃;

wherein R₅ is —H; straight chained or branched C₁–C₇ alkyl, monofluoroalkyl or polyfluoroalkyl; straight chained or branched C₂–C₇ alkenyl or alkynyl; C₃–C₇ cycloalkyl, monofluorocycloalkyl, polyfluorocycloalkyl or cycloalkenyl; phenyl, thiophenyl, pyridyl, pyrrolyl, furanyl, imidazolyl or indolyl; or —COOR₃, —COR₃, —CONHR₃, —CN, or —OR₃;

wherein each R₆ is independently —H; straight chained or branched C₁–C₇ alkyl, hydroxyalkyl, aminoalkyl, alkoxyalkyl, monofluoroalkyl or polyfluoroalkyl; straight chained or branched C₂–C₇ alkenyl or alkynyl; C₃–C₇ cycloalkyl, monofluorocycloalkyl, polyfluorocycloalkyl or cycloalkenyl; or —OR₃;

wherein each R₇ is independently —H; substituted or unsubstituted benzyl, benzoyl, phenyl, pyridyl, thiophenyl, furanyl, pyrazinyl, pyrrolyl, naphthyl, indolyl, imidazolyl, benzofurazanyl, benzofuranyl, benzimidazolyl or 2-keto-1-benzimidazolinyl, wherein the benzyl, benzoyl, phenyl, pyridyl, thiophenyl, furanyl, pyrazinyl, pyrrolyl, naphthyl, indolyl, imidazolyl, benzofurazanyl, benzofuranyl, benzimidazolyl or 2-keto-1-benzimidazolinyl is substituted with —H, —F, —Cl, —Br, —I, —NO₂, —CN, straight chained or branched $C_1$–$C_7$ alkyl, straight chained or branched $C_1$–$C_7$ monofluoroalkyl, straight chained or branched $C_1$–$C_7$ polyfluoroalkyl, straight chained or branched $C_2$–$C_7$ alkenyl, straight chained or branched $C_2$–$C_7$ alkynyl, $C_3$–$C_7$ cycloalkyl, $C_3$–$C_7$ monofluorocycloalkyl, $C_3$–$C_7$ polyfluorocycloalkyl, $C_3$–$C_7$ cycloalkenyl, —N(R₃)₂, —OR₃, —COR₃, —CO₂R₃, or —CON(R₃)₂; substituted or unsubstituted straight chained or branched $C_1$–$C_7$ alkyl, monofluoroalkyl or polyfluoroalkyl; substituted or unsubstituted straight chained or branched $C_2$–$C_7$ alkenyl or alkynyl; or $C_3$–$C_7$ cycloalkyl or cycloalkenyl, wherein the alkyl, monofluoroalkyl, polyfluoroalkyl, alkenyl, alkynyl, cycloalkyl or cycloalkenyl is substituted with —H, phenyl, pyridyl, thiophenyl, furanyl, pyrazinyl, pyrrolyl, naphthyl, indolyl, imidazolyl, benzofurazanyl, benzofuranyl, or benzimidazolyl; and wherein $R_8$ is —H; substituted or unsubstituted benzyl, benzoyl, phenyl, pyridyl, thiophenyl, furanyl, pyrazinyl, pyrrolyl, naphthyl, indolyl, imidazolyl, benzofurazanyl, benzofuranyl, benzimidazolyl or 2-keto-1-benzimidazolinyl, wherein the benzyl, benzoyl, phenyl, pyridyl, thiophenyl, furanyl, pyrazinyl, pyrrolyl, naphthyl, indolyl, imidazolyl, benzofurazanyl, benzofuranyl, benzimidazolyl or 2-keto-1-benzimidazolinyl is substituted with —H, —F, —Cl, —Br, —I, —NO₂, —CN, straight chained or branched $C_1$–$C_7$ alkyl, straight chained or branched $C_1$–$C_7$ monofluoroalkyl, straight chained or branched $C_1$–$C_7$ polyfluoroalkyl, straight chained or branched $C_2$–$C_7$ alkenyl, straight chained or branched $C_2$–$C_7$ alkynyl, $C_3$–$C_7$ cycloalkyl, $C_3$–$C_7$ monofluorocycloalkyl, $C_3$–$C_7$ polyfluorocycloalkyl, $C_3$–$C_7$ cycloalkenyl, —N(R₃)₂, —OR₃, —COR₃, —CO₂R₃, or —CON(R₃)₂; substituted or unsubstituted straight chained or branched $C_1$–$C_7$ alkyl, monofluoroalkyl or polyfluoroalkyl; substituted or unsubstituted straight chained or branched $C_2$–$C_7$ alkenyl or alkynyl; or $C_3$–$C_7$ cycloalkyl or cycloalkenyl, wherein the alkyl, monofluoroalkyl, polyfluoroalkyl, alkenyl, alkynyl, cycloalkyl or cycloalkenyl is substituted with —H, phenyl, pyridyl, thiophenyl, furanyl, pyrazinyl, pyrrolyl, naphthyl, indolyl, imidazolyl, benzofurazanyl, benzofuranyl, benzimidazolyl, —N(R₃)₂, —NO₂, —CN, —CO₂R₃, —OR₃;

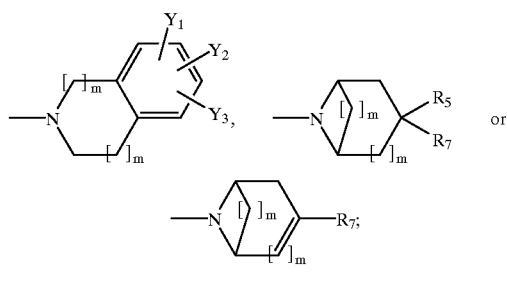

or a pharmaceutically acceptable salt thereof.

2. An enantiomer of the compound of claim 1.

3. An (−) enantiomer of the compound of claim 1.

4. The compound of claim 1 having the structure:

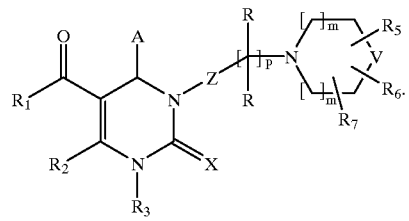

5. The compound of claim 1 having the structure:

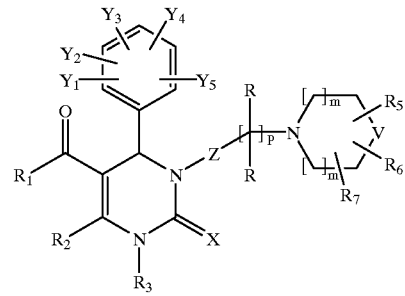

6. The compound of claim 5, having the structure:

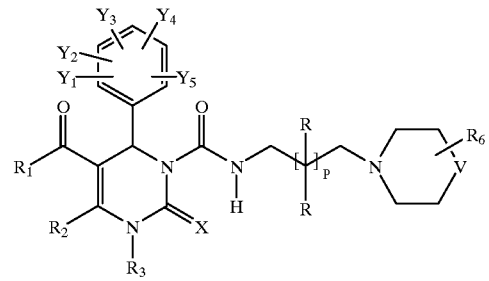

wherein V is selected from $CR_5R_7$ or NR, and p is selected from 1–3.

7. The compound of claim 6, wherein the compound is selected from the group consisting of:

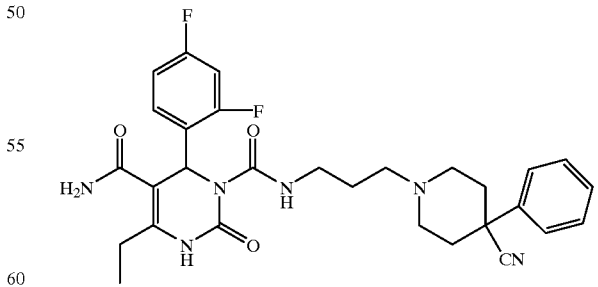

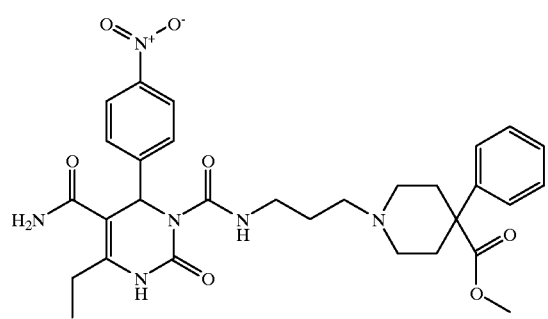
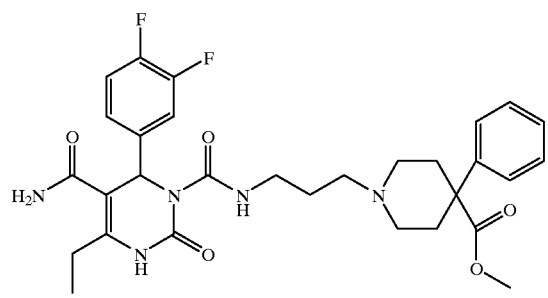
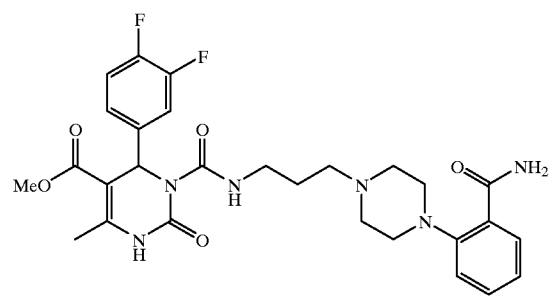
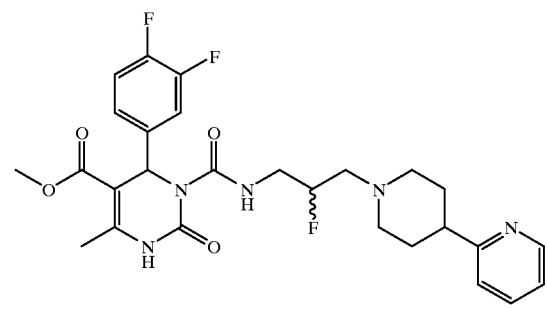
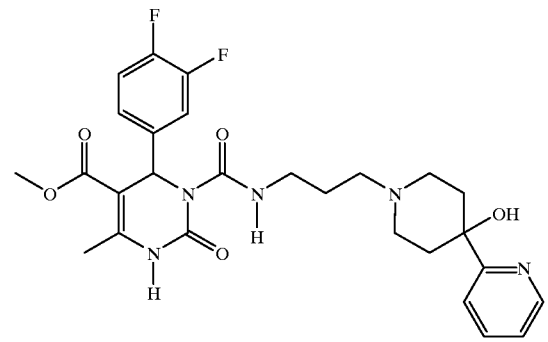
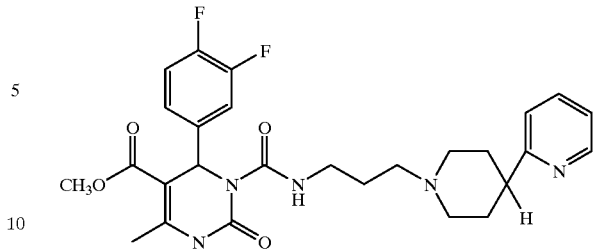
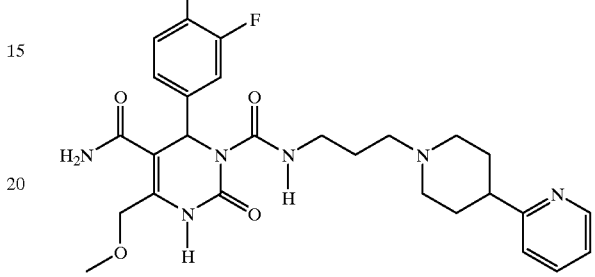
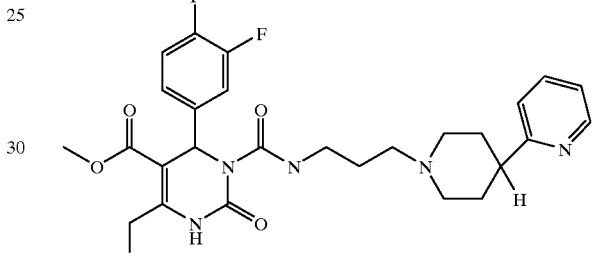
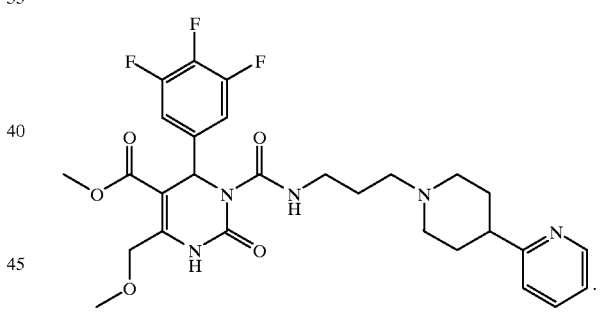
8. A compound according to claim 1, wherein the compound is:
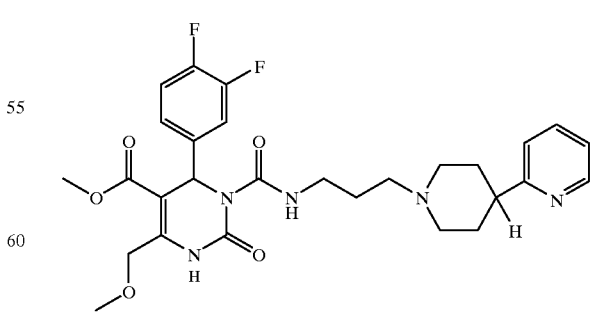

9. A compound according to claim 1, wherein the compound is (+)-5-Methoxycarbonyl-6-(3,4-difluorophenyl)-4-methoxymethyl-1-{N-[3-(4-(2-pyridyl)piperidin-1-yl)propyl]}carboxamido-2-oxo-1,2,3,6-tetrahydropyrimidine.

10. A compound according to claim 1, wherein the compound is 6-(3,4-Difluorophenyl)-4-methoxymethyl-1-{N-[3-(4-(2-pyridyl)piperidin-1-yl)propyl]}carboxamido-1,2,3,6-tetrahydro-2-oxypyrimidine-5-carboxylic acid.

11. A pharmaceutical composition comprising an amount of the compound of claim 1, 8, 9 or 10 effective to treat benign prostatic hyperplasia and a pharmaceutically acceptable carrier.

12. A pharmaceutical composition comprising an amount of the compound of claim 1, 8, 9 or 10 effective to relax lower urinary tract tissue and a pharmaceutically acceptable carrier.

13. A pharmaceutical composition comprising an amount of the compound of claim 1, 8, 9 or 10 effective to treat benign prostatic hyperplasia, an amount of finasteride effective to treat benign prostatic hyperplasia and a pharmaceutically acceptable carrier.

14. A pharmaceutical composition comprising an amount of the compound of claim 1, 8, 9 or 10 effective to relax lower urinary tract tissue, an amount of finasteride effective to relax lower urinary tract tissue and a pharmaceutically acceptable carrier.

15. A method of treating a subject suffereing from benign prostatic hyperplasia which comprises administering to the subject an amount of the compound of claim 1, 7, 8, 9 or 10 effective to treat benign prostatic hyperplasia.

16. A method of treating a subject suffering from benign prostatic hyperplasia which comprises administering to the subject an amount of the compound of claim 1, 8, 9, or 10 in combination with a 5 alpha-reductase inhibitor effective to treat benign prostatic hyperplasia.

17. The method of claim 16 wherein the 5-alpha reductase inhibitor is finasteride.

18. A method relaxing lower urinary tract tissue which comprises contacting the lower urinary tract tissue with an amount of the compound of claim 1, 8, 9 or 10 effective to relax lower urinary tract tissue.

19. The method of claim 18, wherein the lower urinary tract tissue is urethral smooth muscle.

20. A method of relaxing lower urinary tract tissue in a subject which comprises administering to the subject an amount of the compound of claim 1, 8, 9 or 10 effective to relax lower urinary tract tissue.

21. The method of claim 20, wherein lower urinary tract tissue is urethral smooth muscle.

\* \* \* \* \*